United States Patent
Ishikawa

(10) Patent No.: US 11,932,860 B2
(45) Date of Patent: Mar. 19, 2024

(54) METHOD FOR PRODUCING ALKALINE PHOSPHATASE, ALKALINE PHOSPHATASE OBTAINED USING SAID METHOD, AND VECTOR AND TRANSFORMANT FOR PRODUCTION THEREOF

(71) Applicant: Kikkoman Corporation, Chiba (JP)

(72) Inventor: Junya Ishikawa, Chiba (JP)

(73) Assignee: Kikkoman Corporation, Noda (JP)

( * ) Notice: Subject to any disclaimer, the term of this patent is extended or adjusted under 35 U.S.C. 154(b) by 610 days.

(21) Appl. No.: 16/652,805

(22) PCT Filed: Oct. 3, 2018

(86) PCT No.: PCT/JP2018/037026
§ 371 (c)(1),
(2) Date: Jun. 16, 2020

(87) PCT Pub. No.: WO2019/069977
PCT Pub. Date: Apr. 11, 2019

(65) Prior Publication Data
US 2020/0325485 A1 Oct. 15, 2020

(30) Foreign Application Priority Data
Oct. 3, 2017 (JP) ................. 2017-193624

(51) Int. Cl.
*C12N 15/80* (2006.01)
*C12N 1/14* (2006.01)
*C12R 1/665* (2006.01)
*C12R 1/685* (2006.01)
*C12R 1/69* (2006.01)

(52) U.S. Cl.
CPC .............. *C12N 15/80* (2013.01); *C12N 1/145* (2021.05); *C12R 2001/665* (2021.05); *C12R 2001/685* (2021.05); *C12R 2001/69* (2021.05); *C12Y 301/03001* (2013.01)

(58) Field of Classification Search
None
See application file for complete search history.

(56) References Cited

U.S. PATENT DOCUMENTS

| 5,707,853 A | 1/1998 | Millan |
| 5,766,912 A * | 6/1998 | Boel ....................... C12N 15/67 435/71.1 |
| 5,773,226 A | 6/1998 | Millan |
| 6,406,899 B1 * | 6/2002 | Hoelke ..................... C12N 9/16 435/320.1 |
| 2003/0096341 A1 | 5/2003 | Mueller et al. |
| 2006/0040345 A1 | 2/2006 | Hoesel et al. |
| 2018/0355022 A1 * | 12/2018 | Masakari ............... C12Q 1/006 |

FOREIGN PATENT DOCUMENTS

| JP | 10-276787 A | 10/1998 |
| JP | 11-332586 A | 12/1999 |
| JP | 3657895 B | 6/2005 |
| JP | 2008-005734 A | 1/2008 |
| JP | 4295386 B | 7/2009 |
| JP | 2011-087572 A | 5/2011 |
| JP | 2012-157315 A | 8/2012 |
| WO | WO 1993/018139 A | 9/1993 |
| WO | WO 2003/056004 A1 | 7/2003 |
| WO | WO 2004/083862 A | 9/2004 |
| WO | WO 2017/094776 A | 6/2017 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Bornscheuer et al. Curr Protoc Protein Sci. Nov. 2011;Chapter 26:Unit26.7. (Year: 2011).*
Yoshikuni et al. Curr Opin Chem Biol. Apr. 2007;11(2):233-9. (Year: 2007).*
Accession F1N6T5. May 3, 2011. (Year: 2011).*
Accession O77579. Nov. 1, 1998 (Year: 1998).*
Accession AF052226. Sep. 3, 1998 (Year: 1998).*
Accession AF052227. Sep. 3, 1998 (Year: 1998).*
Accession BDY52646. Jul. 27, 2017 (Year: 2017).*
Accession BDY52620. Jul. 27, 2017 (Year: 2017).*
International Search Report and Written Opinion dated Dec. 25, 2018 in connection with PCT/JP2018/037026.
Genbank Submission; NIH/NCBI, Accession No. KJK66304.1, alkPPC [Aspergillus parasiticus SU-1]. Mar. 18, 2015 [Retrieved on Dec. 7, 2018]. https://www.ncbi.nlm.nih.gov/protein/770309090, 1 page.
Genbank Submission; NIH/NCBI, Accession No. Q2UH22, Alkaline Phosphate. Nov. 28, 2016 [Retrieved on Dec. 7, 2018]. https://www.ncbi.nlm.nih.gov/protein/Q2UH22, 1 page.

* cited by examiner

Primary Examiner — Christian L Fronda
(74) Attorney, Agent, or Firm — Wolf, Greenfield & Sacks, P.C.

(57) ABSTRACT

The present invention provides a method for producing an alkaline phosphatase (ALP), the method including a step of: culturing an *Aspergillus* transformant capable of producing the ALP.

12 Claims, 2 Drawing Sheets

Specification includes a Sequence Listing.

[Figure 1]
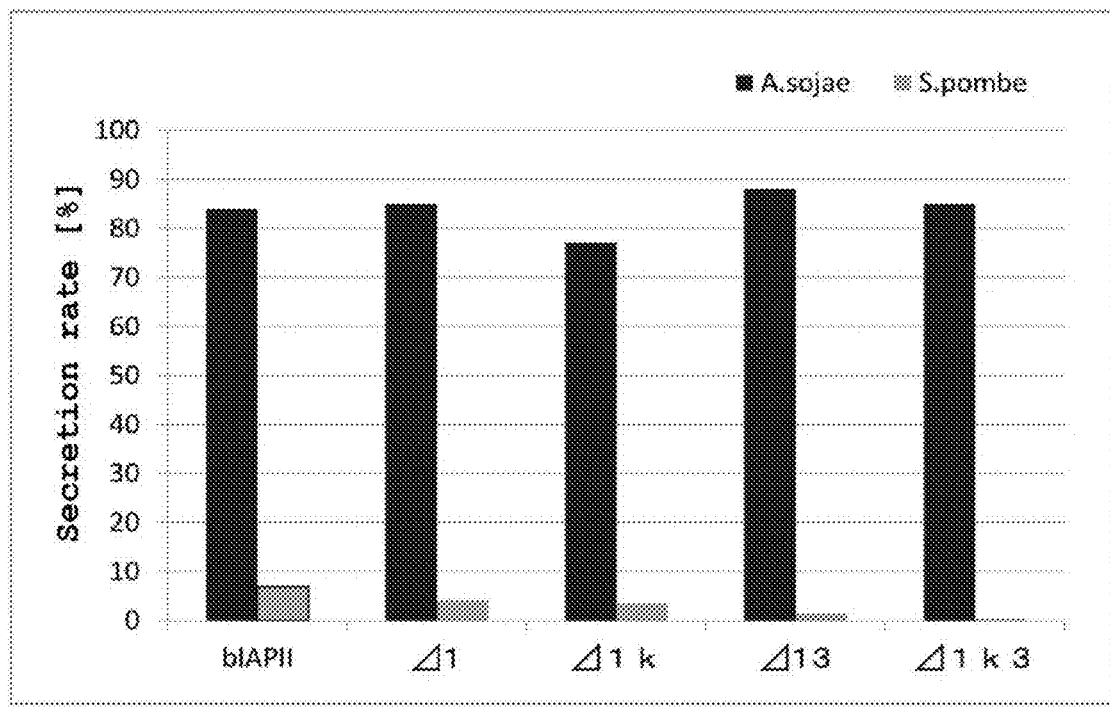
[Figure 2]
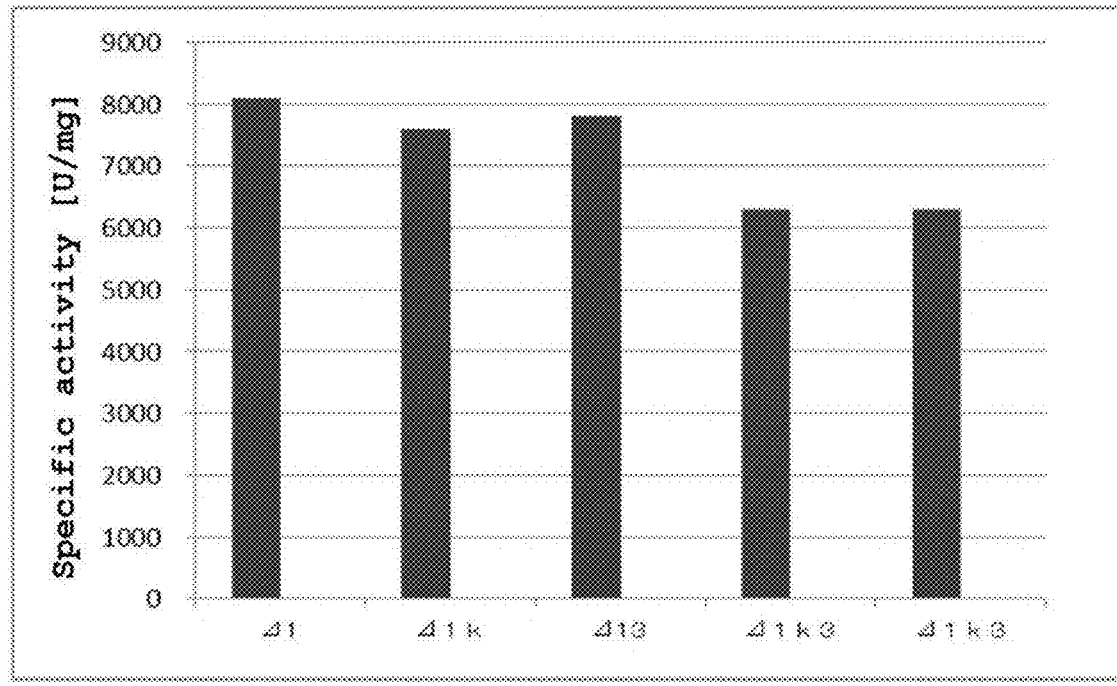

[Figure 3]
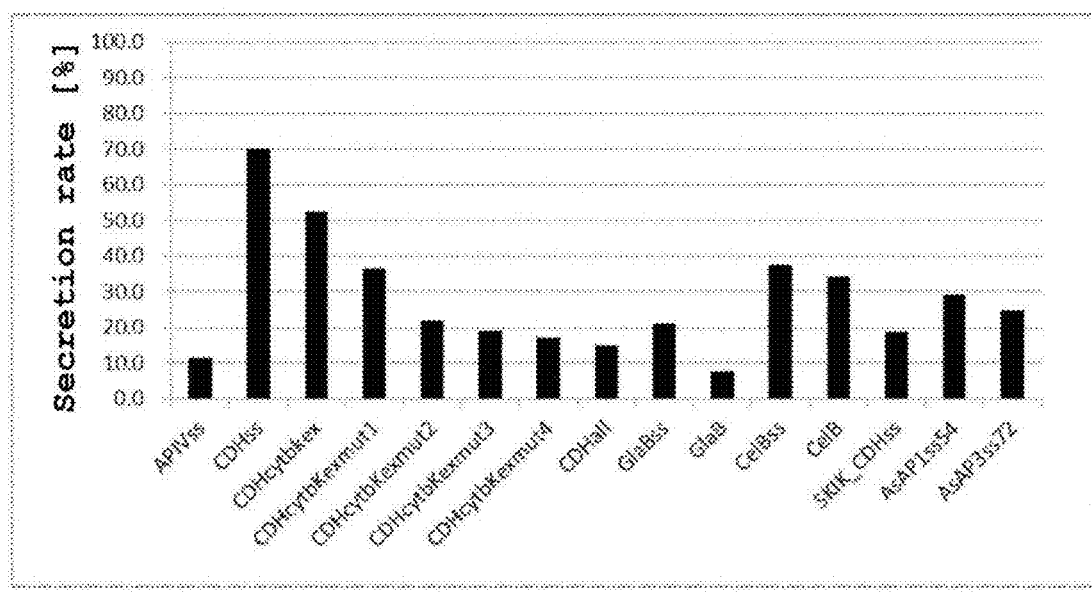

METHOD FOR PRODUCING ALKALINE PHOSPHATASE, ALKALINE PHOSPHATASE OBTAINED USING SAID METHOD, AND VECTOR AND TRANSFORMANT FOR PRODUCTION THEREOF

TECHNICAL FIELD

The present invention relates to a method for producing an alkaline phosphatase, an alkaline phosphatase obtained by using the method, and a vector and transformant for producing an alkaline phosphatase.

BACKGROUND ART

Alkaline phosphatase (hereinafter, abbreviated as ALP) is used, in the field of molecular biology, for dephosphorylation of DNA in gene recombination experiments or a label for antibodies in Western blotting experiments. In the field of industry, ALP is used as a labeling enzyme for immunological methods in clinical laboratory tests.

In order to label antibodies in an efficient and homogeneous manner, further, in order to obtain highly precise results of clinical laboratory tests by using antibodies labeled in such a manner (labeled antibodies), it is preferable that an antibody to be labeled itself be as homogeneous as possible, and the labeling enzyme itself be also as homogeneous as possible.

To homogenize a labeled antibody, for example, an operation is needed such that antibody molecules labeled, those not labeled, and excessive labeling enzyme molecules are separated by using a physical separation method to exclusively obtain the labeled antibody molecules in a post-process after a step of labeling an antibody. If the labeling enzyme itself in that operation is in a heterogeneous mixture or such a state in terms of molecular weight or the performance as an enzyme, the labeled antibody may have likewise a heterogenous molecular weight and performance as an enzyme.

With respect to molecular weight, exclusively obtaining labeled antibody molecules with a specific molecular weight in a stage of separation as a post-process is contemplated as a countermeasure; however, there is a limit to separation by molecular weight, even with such an approach. Moreover, the approach gives poor yields in obtaining a labeled antibody fraction of interest in a post-process, and hence there are still needs for enhancing the homogeneity of a labeling enzyme itself at an initial stage.

In addition, it has been known that there are multiple isoforms of ALP, and specific activity varies among them; for this reason, if an ALP composition consisting of a mixture of multiple isoforms, for example, having different specific activity properties is used as a labeling enzyme to label an antibody, the labeled antibody to be obtained will disadvantageously have heterogeneity in terms of activity. Also from this viewpoint, there are needs for enhancing the homogeneity of a labeling enzyme itself.

Examples of ALP conventionally used for preparation of labeled antibodies include ALP produced by extraction from the bovine intestinal tract. This ALP has been used for many years because of the high specific activity and thus of usefulness as a labeling enzyme; however, the ALP, which is derived from a mammal, is recognized to have a problem of difficulty in stable supply, because of restriction of import and export of the raw material due to infections such as mad cow disease and large-quality variation or the like caused by individual differences. Multiple isoforms of ALP are contained in the bovine intestinal tract, and in current circumstances every commercially available ALP product is inevitably a mixture containing multiple isoforms, even though the products are ones produced through extraction and purification. Accordingly, the ALP has a problem of being poor in homogeneity as an enzyme product, with regard to the object of labeling antibodies as a labeling enzyme as described above for use in clinical laboratory tests.

In view of the above recognition, examination has been previously made on various methods to obtain a more homogeneous ALP product. Disclosed as such a method is, for example, a method of recombinant expression of bovine intestinal tract-derived ALP in mammalian cells (e.g., see Patent Literatures 1 and 2). In this method, for example, if a gene encoding a specific isoform is selected and recombinant production is performed by using the gene alone, protein molecules to be expressed can be composed of the single specific isoform; thus, the method can eliminate heterogeneity in activity due to the coexistence of multiple isoforms having largely different specific activities.

Regarding the expression host, a method is known in which a yeast is employed as a host instead of mammalian cells to produce a huge amount of recombinant ALP (e.g., see Patent Literature 3). Further, a method has been proposed as a recombinant production method with a yeast, the method including performing deglycosylation treatment as a post-process after obtaining ALP produced by using a yeast as an expression host to obtain ALP with reduced glycan moieties (e.g., see Patent Literature 4).

CITATION LIST

Patent Literature

Patent Literature 1: International Publication No. WO 93/18139
Patent Literature 2: Japanese Patent No. 4295386
Patent Literature 3: Japanese Patent No. 3657895
Patent Literature 4: International Publication No. WO 2004/083862

SUMMARY OF INVENTION

Technical Problem

However, methods for producing a recombinant ALP derived from bovine intestinal tract as disclosed Patent Literatures 1 and 2 involve a problem of little ALP production, because CHO cells or the like as mammalian cells are used for the expression host.

In addition, use of a yeast for the expression host as disclosed in Patent Literature 3 leads to a problem of hyperglycosylation, specifically, excessive glycosylation occurs in a protein to be expressed. In fact, the degree of glycosylation in ALP formed through recombinant production using a yeast as a host is much more than that in ALP produced by extraction from the bovine intestinal tract, and moreover the ALP obtained is, disadvantageously, an enzyme with low glycan homogeneity because of the large number of glycan moieties heterogeneously added. The problem of heterogeneity of an enzyme can be disadvantageous not only in processes of enzymatic labeling of antibodies but also in using ALP for conjugate production or sensor applications, from the viewpoint of handling in various processes. Thus, the excessive glycosylation in ALP in the method of expressing with a yeast is considered to be unfavorable in an industrial sense.

Furthermore, although the ALP expression system using yeast cells as a host can be said to provide more production than in the case of expression using mammalian cells as a host, ALP produced is hardly secreted out of cells and accumulated in cells. Hence, needed to obtain ALP are processes of disrupting yeast cells and purifying ALP of interest from a mixture with all the other components in the cells, and improvement is still required also in terms of operational efficiency in the production process.

The deglycosylation treatment disclosed in Patent Literature 4, as a post-process for yeast-expressed ALP, can reduce the degree of glycosylation through enzymatic treatment, and is considered to be preferable in that it partially solves the problem that is inherent in yeast-expressed ALP and caused by the excessive glycosylation as disclosed in Patent Literature 3. In fact, however, cleavage of glycan moieties by enzymatic treatment is in a random manner, and it is difficult to perform deglycosylation treatment with necessary glycan moieties left uncleaved, and it is also difficult to achieve homogeneous cleavage for every process batch. Accordingly, it can be said that there is still a problem for continuous, reproducible supply of products in terms of homogeneity of the condition of glycosylation. In addition, there is a problem of need of additionally involving complicated processes of deglycosylation; specifically, in order to exclusively obtain deglycosylated ALP of interest, enzymatic treatment has to be additionally included as a post-process after purifying ALP, and thereafter deglycosylated ALP, incompletely deglycosylated ALP, and the enzyme for deglycosylation have to be further separated through a separation process such as gel filtration.

An object of the present invention is to provide: a method for producing an ALP to be used in recombinant ALP production, wherein the method enables production of a single isoform of an ALP with high productivity and much secretion without causing excessive and heterogeneous glycosylation; an ALP II or ALP IV obtained by using the method; and a vector and transformant for producing the ALP II or ALP IV.

Solution to Problem

In such circumstances, the present inventors diligently studied to achieve the object, and found that use of a method for producing an ALP, the method including the step of culturing an *Aspergillus* transformant capable of producing a glycosylated ALP, in particular, use of a method for producing an ALP, the method including culturing an *Aspergillus* transformant transformed with a vector for *Aspergillus* transformation, wherein the vector includes a nucleotide sequence encoding an amino acid sequence of a bovine tissue-derived ALP having a specific *Aspergillus* strain-derived secretory signal peptide on an N-terminal side of the bovine tissue-derived ALP, allows expression of a single isoform of an ALP with high productivity without causing excessive and heterogeneous glycosylation, and that the ALP expressed is very efficiently secreted out of cells of the *Aspergillus* transformant, thus completing the present invention.

Specifically, the present invention provides the followings.

[1]
A method for producing an alkaline phosphatase (ALP), the method comprising a step of culturing an *Aspergillus* transformant capable of producing an ALP.

[2]
The method for producing the ALP according to [1], wherein the ALP is an ALP including a mutation such that a part of N-linked glycosylation motifs is not glycosylated.

[3]
The method for producing the ALP according to [1] or [2], wherein the *Aspergillus* transformant includes a gene encoding an amino acid sequence of the ALP having an *Aspergillus* strain-derived secretory signal peptide selected from the group consisting of CDHss, CDHcytbkex, CDHcytbKexmut1, CDHcytbKexmut2, CDHcytbKexmut3, CDHcytbKexmut4, CDHall, GlaB, GlaBss, CelBss, CelB, SKIK_CDHss, AsAP1ss54, and AsAP3ss72 on an N-terminal side of the ALP.

[4]
The method for producing the ALP according to [1] or [2], wherein a nucleotide sequence encoding the ALP in the *Aspergillus* transformant includes a gene bound to a 5'-end side of the nucleotide sequence, the gene comprising any of the following nucleotide sequences (a) to (c):
(a) a nucleotide sequence set forth in any of SEQ ID NOs: 2 to 15;
(b) a nucleotide sequence consisting of a nucleotide sequence formed from a nucleotide sequence set forth in any of SEQ ID NOs: 2 to 15 with deletion, substitution, or addition of one or several nucleotides and encoding a secretory signal peptide having ALP secretion activity; and
(c) a nucleotide sequence having a homology of 90% or higher with a nucleotide sequence set forth in any of SEQ ID NOs: 2 to 15 and encoding a secretory signal peptide having ALP secretion activity; or
a gene consisting of a nucleotide sequence encoding any of the following secretory signal peptides (d) to (f):
(d) a secretory signal peptide consisting of an amino acid sequence set forth in any of SEQ ID NOs: 17 to 30;
(e) a secretory signal peptide consisting of an amino acid sequence formed from an amino acid sequence set forth in any of SEQ ID NOs: 17 to 30 with deletion, substitution, or addition of one or several amino acids and having ALP secretion activity; and
(f) a secretory signal peptide having a homology of 90% or higher with an amino acid sequence set forth in any of SEQ ID NOs: 17 to 30 and having ALP secretion activity.

The method for producing the ALP according to any one of [1] to [4], wherein the ALP is an ALP II or an ALP IV. [6]
The method for producing the ALP according to any one of [1] to [5], wherein the ALP includes any of the following proteins (i) to (iii):
(i) a protein consisting of an amino acid sequence set forth in SEQ ID NO: 31 or 32;
(ii) a protein formed from an amino acid sequence set forth in SEQ ID NO: 31 or 32 with deletion, substitution, or addition of one or several amino acids and having ALP activity; and
(iii) a protein having a homology of 90% or higher with an amino acid sequence set forth in SEQ ID NO: 31 or 32 and having activity with ALP activity; or
a protein encoded by any of the following nucleotide sequences (iv) to (vi):
(iv) a nucleotide sequence set forth in SEQ ID NO: 33 or 34;
(v) a nucleotide sequence formed from a nucleotide sequence set forth in SEQ ID NO: 33 or 34 with deletion, substitution, or addition of one or several nucleotides and encoding a protein having ALP activity; and
(vi) a nucleotide sequence having a homology of 90% or higher with a nucleotide sequence set forth in SEQ ID NO: 33 or 34 and encoding a protein having ALP activity.

[7]

The method for producing the ALP according to any one of [1] to [6], wherein the ALP is an ALP II including a mutation in one or two N-linked glycosylation motifs among three N-linked glycosylation motifs, with the N-linked glycosylation motif(s) including a mutation being not glycosylated.

[8]

The method for producing the ALP according to [7], wherein the mutation included in the N-linked glycosylation motif(s) in the ALP II is present at one or two positions of position 122, position 249, position 251, and position 410 in SEQ ID NO: 31.

[9]

The method for producing the ALP according to [7] or [8], wherein the mutation included in the N-linked glycosylation motif(s) in the ALP II is one or two of a mutation from Asn to Gln or Lys at position 122, a mutation from Asn to Gln, Asp, or His at position 249, a mutation from Thr to Cys at position 251, and a mutation from Asn to Gln or Lys at position 410 in SEQ ID NO: 31.

[10]

The method for producing the ALP according to any one of [1] to [9], wherein the *Aspergillus* transformant is a transformant of any of *Aspergillus sojae*, *Aspergillus oryzae* (Ahlburg) Cohn, *Aspergillus luchuensis*, *Aspergillus niger*, *Aspergillus nidulans*, *Aspergillus tamarii*, *Aspergillus kawachii*, *Aspergillus awamori*, *Aspergillus usamii*, and *Aspergillus saitoi*.

[11]

The method for producing the ALP according to any one of [1] to [10], further comprising steps of:

obtaining a secreted fraction from a culture of the *Aspergillus* transformant; and extracting the ALP from the secreted fraction.

[12]

A glycosylated alkaline phosphatase (ALP) II having a molecular weight of 80 to 150 kDa as measured by a gel filtration method.

[12-1]

The ALP II according to [12], wherein the ALP II has been isolated.

[13]

A vector for *Aspergillus* transformation, comprising a nucleotide sequence encoding an amino acid sequence of an ALP having an *Aspergillus* strain-derived secretory signal peptide selected from the group consisting of CDHss, CDHcytbkex, CDHcytbKexmut1, CDHcytbKexmut2, CDHcytbKexmut3, CDHcytbKexmut4, CDHall, GlaBss, CelBss, CelB, SKIK_CDHss, AsAP1ss54, and AsAP3ss72 on an N-terminal side of the ALP.

A vector for *Aspergillus* transformation, comprising a nucleotide sequence encoding an ALP, wherein the nucleotide sequence includes a gene bound to a 5'-end side of the nucleotide sequence, the gene comprising any of following nucleotide sequences (a) to (c):

(a) a nucleotide sequence set forth in any of SEQ ID NOs: 2 to 15;

(b) a nucleotide sequence consisting of a nucleotide sequence formed from a nucleotide sequence set forth in any of SEQ ID NOs: 2 to 15 with deletion, substitution, or addition of one or several nucleotides and encoding a secretory signal peptide having ALP secretion activity; and (c) a nucleotide sequence having a homology of 90% or higher with a nucleotide sequence set forth in any of SEQ ID NOs: 2 to 15 and encoding a secretory signal peptide having ALP secretion activity; or a gene consisting of a nucleotide sequence encoding any of the following secretory signal peptides (d) to (f):

(d) a secretory signal peptide consisting of an amino acid sequence set forth in any of SEQ ID NOs: 17 to 30;

(e) a secretory signal peptide consisting of an amino acid sequence formed from an amino acid sequence set forth in any of SEQ ID NOs: 17 to 30 with deletion, substitution, or addition of one or several amino acids and having ALP secretion activity; and (f) a secretory signal peptide having a homology of 90% or higher with an amino acid sequence set forth in any of SEQ ID NOs: 17 to 30 and having ALP secretion activity.

[15]

An *Aspergillus* transformant, obtained by transforming with the vector for *Aspergillus* transformation according to [13] or [14].

[16]

A glycosylated alkaline phosphatase obtained by using the method for producing an ALP according to any one of [1] to [11].

Advantageous Effects of Invention

The present invention provides a method for producing an ALP, wherein the method enables production of a single isoform of an ALP with high productivity and much secretion without causing excessive and heterogeneous glycosylation, and provides a novel ALP II, vector, and transformant, thus being industrially useful.

BRIEF DESCRIPTION OF DRAWINGS

FIG. 1 shows a graph for comparison between secretion rates calculated after measurement of ALP activity for different culture supernatant fractions and intracellular fractions in Example 3 and secretion rates calculated after measurement of ALP activity for a culture from yeast expression in Comparative Example.

FIG. 2 shows a graph of specific activities calculated after measurement of ALP activity for different types of purified bIAP II in Example 5.

FIG. 3 shows a graph of secretion rates calculated after measurement of ALP activity for different culture supernatant fractions and intracellular fractions in Example 10.

DESCRIPTION OF EMBODIMENTS

Hereinafter, the present invention will be described in detail.

The method of the present invention for producing an ALP (hereinafter, briefly referred to as the inventive production method) is a production method including the step of culturing an *Aspergillus* transformant (hereinafter, briefly referred to as the inventive transformant) capable of producing an ALP. More specifically, the inventive production method is a method for producing a bovine intestinal tract-derived ALP through recombinant expression, the method including the step of culturing the inventive transformant capable of producing a bovine intestinal tract-derived ALP.

The inventive production method differs from any of known ALP production methods at least in that an *Aspergillus* transformant capable of producing an ALP is used. Use of the inventive transformant as mentioned enables production of an ALP with a high secretion rate and high productivity.

The ALP may be a known ALP or an ALP newly obtained through searching, or an ALP obtained through modification to provide the ALP with altered physical or chemical characteristics by a gene engineering technique, mutagenesis treatment, or the like. Examples of known ALP include bovine (*Bos taurus*) intestinal tract-derived ALP [bIAP II; described in Manes et al., J. Biol. Chem., 273, No. 36, 23353-23360 (1998)].

The ALP may include a secretory signal peptide on the N-terminal side and a signal peptide with GPI (glycosylphosphatidylinositol) in the C-terminus. The signal peptide with GPI may be removed for secretory expression of the ALP, and the ALP may be used with the original secretory signal peptide left unremoved, and a host-derived secretory signal peptide may be used in place of the original secretory signal peptide of the ALP. After an ALP including the secretory signal peptide on the N-terminal side is expressed in the inventive transformant, the secretory signal peptide moiety is deleted in cells, and an ALP without the secretory signal peptide is then secreted from cells. In a certain embodiment, the secretory signal peptide may be a carrier protein including a peptide moiety having a function as a secretory signal peptide (hereinafter, also referred to as "secretory signal peptide moiety") on the N-terminal side. The carrier protein may include a linker (e.g., a Kex2-cleavable linker) linked to the C-terminus. In the present embodiment, the secretory signal peptide moiety may be the secretory signal peptide itself. The carrier protein is the whole of protein efficiently secreted by the host or a part on the N-terminal side thereof. A Kex2-cleavable linker is a peptide that includes at the C-terminus the cleavable motif KR (lysine-arginine dipeptide) for serine endopeptidase defined as the enzyme No. EC3.4.21.61. The peptide bond on the C-terminal side of the cleavable motif KR present in a protein sequence is decomposed by serine endopeptidases in the secretory pathway. After an ALP including on the N-terminal side a secretory signal peptide moiety consisting of a carrier protein and a Kex2-cleavable linker is expressed in the inventive transformant, the secretory signal peptide is removed in cells, and the resulting ALP including no secretory signal peptide is secreted from cells.

The ALP may be an isolated ALP, and examples of isolation methods include a step of extracting described later.

Examples of secretory signal peptides and carrier proteins that function in the inventive transformant include secretory proteins such as host-derived cellobiose dehydrogenase and cytochrome domain thereof, glucoamylase, endoglucanase, and alkaline phosphatase, and parts on the N-terminal side thereof (secretory signal peptide moieties).

The number of N-linked glycosylation motifs (an amino acid sequence of Asn-Xaa-Thr or Asn-Xaa-Ser; Xaa denotes an amino acid other than Pro) included in the amino acid sequence of ALP differs among its isoforms, and, for example, bIAP II includes three N-linked glycosylation motifs. The ALP in the present invention is required to be an ALP in which at least one N-linked glycosylation motif has been glycosylated, and in the case that two or more N-linked glycosylation motifs are originally present, the ALP may be an N-linked glycosylation motif-modified ALP modified so that the N-linked glycosylation motifs, with one of them excluded, are prevented from being N-glycosylated. Examples of the modification to prevent an N-linked glycosylation motif from being glycosylated include mutating the first Asn residue of an N-linked glycosylation motif into another amino acid, mutating the second Xaa residue into Pro, and mutating the third Thr/Ser residue into another amino acid.

Next, a method for obtaining a gene encoding the ALP for preparation of the inventive transformant or a DNA including the gene will be described in the following by taking bovine intestinal tract-derived ALP as an example.

To obtain a gene encoding the ALP to be used in the present invention, common gene cloning methods can be used. An example is as follows. A chromosomal DNA or mRNA is extracted from bovine intestinal tract cells by using a conventional method such as a method described in Current Protocols in Molecular Biology (WILEY Interscience, 1989). Further, a cDNA can be synthesized by using the mRNA as a template.

A library is prepared for the thus-obtained chromosomal DNA or cDNA.

Subsequently, an appropriate probe DNA is synthesized on the basis of the amino acid sequence of bovine intestinal tract-derived ALP, and with the probe DNA an appropriate primer DNA is prepared by using a method of screening from the library of the chromosomal DNA or cDNA or on the basis of the above amino acid sequence. DNAs including a gene fragment of interest are amplified by using appropriate polymerase chain reaction (PCR method) such as the 5'RACE method or 3'RACE method, and amplified products are linked together to obtain a DNA including the full-length gene of interest.

A preferred example of the thus-obtained gene encoding bovine intestinal tract-derived ALP is a bovine intestinal tract-derived ALP gene [bIAP I; Patent Literature 1 or Weissig et al., Bioche. J. 260, 503-508 (1993)], and a more preferred example thereof is a bovine intestinal tract-derived ALP gene of high specific activity [such as bIAP II; Patent Literature 2 or Manes et al., J. Biol. Chem., 273, No. 36, 23353-23360 (1998)]. The amino acid sequence of bovine intestinal tract-derived ALP is published, and hence the full-length gene can be obtained by synthesizing a polynucleotide encoding the full amino acid sequence with use of a DNA synthesizer and associating and then ligating the complementary strands, or by synthesizing a polynucleotide that is a part of the whole gene, partially associating the complementary strands, and amplifying the complementary portion with polymerase.

A preferred gene sequence is a DNA sequence optimized for codons so as to match up with the gene sequence for the ALP in terms of amino acid coding. Optimization for codons refers to optimization, for example, by causing silent mutation to each codon in the ALP gene sequence, that is, causing mutation over the DNA to enhance translation as demanded by the selected expression host, without any influence on amino acid coding. As with the case of conventional methods, it is preferred to clone such a gene in an appropriate vector selected in view of the host to be transformed.

A recombinant vector (recombinant DNA) including an ALP-encoding gene can be constructed by ligating a PCR amplification product including the ALP-encoding gene to an appropriate vector in such a manner that the ALP-encoding gene can be expressed. For example, such a recombinant vector can be constructed by cutting out a DNA fragment including an ALP-encoding gene with an appropriate restriction enzyme and linking the DNA fragment to a plasmid cleaved with an appropriate restriction enzyme, or alternatively, can be obtained by linking a DNA fragment including the gene with flanking sequences homologous to a plasmid at both ends to a plasmid-derived DNA fragment amplified through inverse PCR by using a commercially available recombinant vector preparation kit such as an In-Fusion HD Cloning Kit (Clontech Laboratories, Inc.). The appropriate vector includes a promotor that functions in the transformant, and may further include a terminator, a 5'-untranslated region, a 3'-untranslated region, an antibiotic-resistant gene, or an auxotrophic marker gene.

Next, the inventive transformant will be described.

By transforming or transducing an *Aspergillus* strain with an appropriate recombinant DNA obtained as described above, the inventive transformant can be obtained as an *Aspergillus* transformant including a recombinant DNA possessing an appropriately modified ALP gene fragment, though obtaining the inventive transformant is not limited to this fashion.

The *Aspergillus* strain in the present invention is not limited to a particular strain, and may be any strain belonging to the genus *Aspergillus*. Examples of the *Aspergillus* strain include strains of *Aspergillus sojae*, *Aspergillus oryzae* (Ahlburg) Cohn, *Aspergillus luchuensis*, *Aspergillus niger*, *Aspergillus nidulans*, *Aspergillus tamarii*, *Aspergillus kawachii*, *Aspergillus awamori*, *Aspergillus usamii*, and *Aspergillus saitoi*. Among these, strains of *Aspergillus sojae* and *Aspergillus oryzae* are preferred to obtain an ALP more reliably with a high secretion rate and high productivity.

In one embodiment of the present invention, the inventive transformant includes a gene encoding the amino acid sequence of the ALP having an *Aspergillus* strain-derived secretory signal peptide on the N-terminal side of the ALP. Examples of the *Aspergillus* strain-derived secretory signal peptide include CDHss, CDHcytbkex, CDHcytbKexmut1, CDHcytbKexmut2, CDHcytbKexmut3, CDHcytbKexmut4, CHDall, GlaBss, GlaB, CelBss, CelB, SKIK_CDHss, AsAP1ss54, and AsAP3ss72. To achieve more enhanced secretion, the *Aspergillus* strain-derived secretory signal peptide is preferably one selected from the group consisting of CDHss, CDHcytbkex, CDHcytbKexmut1, CDHcytbKexmut2, CDHcytbKexmut3, CDHcytbKexmut4, CDHall, GlaB, GlaBss, CelBss, CelB, SKIK_CDHss, AsAP1ss54, and AsAP3ss72, more preferably one selected from the group consisting of CDHss, CDHcytbkex, CDHcytbKexmut1, CDHcytbKexmut2, GlaB, GlaBss, CelBss, CelB, AsAP1ss54, and AsAP3ss72, even more preferably one selected from the group consisting of CDHss, CDHcytbkex, CDHcytbKexmut1, CelBss, and CelB, and particularly preferably one selected from the group consisting of CDHss and CDHcytbkex.

In the present embodiment, the amino acid sequence of the ALP having a secretory signal peptide on the N-terminal side of the ALP may be the amino acid sequence of the ALP having a secretory signal peptide directly bound to the N-terminal side of the ALP, or the amino acid sequence of the ALP having a secretory signal peptide moiety indirectly bound to the N-terminal side of the ALP, for example, via a linker (e.g., a carrier protein to the C-terminus of which a Kex2-cleavable linker is bound).

In one embodiment of the inventive transformant, a nucleotide sequence encoding the ALP includes a gene bound to the 5'-end side of the nucleotide sequence, the gene consisting of any of the following nucleotide sequences (a) to (c) bound thereto:
(a) a nucleotide sequence set forth in any of SEQ ID NOs: 2 to 15;
(b) a nucleotide sequence consisting of a nucleotide sequence formed from a nucleotide sequence set forth in any of SEQ ID NOs: 2 to 15 with deletion, substitution, or addition of one or several nucleotides and encoding a secretory signal peptide having ALP secretion activity; and
(c) a nucleotide sequence having a homology of 90% or higher, preferably of 95% or higher, more preferably of 98% or higher, particularly preferably of 99% or higher, with a nucleotide sequence set forth in any of SEQ ID NOs: 2 to 15 and encoding a secretory signal peptide having ALP secretion activity; or
a gene consisting of a nucleotide sequence encoding any of the following secretory signal peptides (d) to (f):
(d) a secretory signal peptide consisting of an amino acid sequence set forth in any of SEQ ID NOs: 17 to 30;
(e) a secretory signal peptide consisting of an amino acid sequence formed from an amino acid sequence set forth in any of SEQ ID NOs: 17 to 30 with deletion, substitution, or addition of one or several amino acids and having ALP secretion activity; and
(f) a secretory signal peptide having a homology of 90% or higher, preferably of 95% or higher, more preferably of 98% or higher, particularly preferably of 99% or higher, with an amino acid sequence set forth in any of SEQ ID NOs: 17 to 30 and having ALP secretion activity.

When the phrase "formed from . . . with deletion, substitution, or addition of one or several nucleotides" is used, the number of nucleotides deleted, substituted, or added is not limited to particular numbers, and may be any number that allows the resulting nucleotide sequence to encode a secretory signal peptide having ALP secretion activity. The term "several" here indicates an integer of two or more, preferably 2 to 20, more preferably 2 to 10, even more preferably 2 to 5, and further preferably 2, 3, or 4. The position of deletion, substitution, or addition in each nucleotide sequence may be any of the 5'-end, the 3'-end, and the intermediate positions, as long as the resulting nucleotide sequence is encoding a secretory signal peptide having ALP secretion activity.

The phrase "having a homology of Y % or higher with a nucleotide sequence set forth in SEQ ID NO: X" means that when two nucleotide sequences are aligned in such a manner that the degree of matching of the two nucleotide sequences is maximized (alignment), the ratio of the number of matching nucleotides to the total number of nucleotides in SEQ ID NO: X is Y % or higher.

When the phrase "formed from . . . with deletion, substitution, or addition of one or several amino acids" is used, the number of amino acids deleted, substituted, or added is not limited to particular numbers, and may be any number that allows the resulting secretory signal peptide to have secretion activity. The term "several" here indicates an integer of two or more, preferably 2 to 20, more preferably 2 to 10, even more preferably two to five, and further preferably two, three, or four. The position of deletion, substitution, or addition in each secretory signal peptide may be any of the N-terminus, the C-terminus, and the intermediate positions, as long as the resulting secretory signal peptide has ALP secretion activity.

The phrase "having a homology of Y % or higher with an amino acid sequence set forth in SEQ ID NO: X" means that when amino acid sequences of two secretory signal peptides are aligned in such a manner that the degree of matching of the two amino acid sequences is maximized (alignment), the ratio of the number of matching amino acids to the total number of amino acids in SEQ ID NO: X is Y % or higher.

The nucleotide sequence set forth in SEQ ID NO: 1 is a nucleotide sequence encoding a secretory signal peptide on the N-terminal side of bovine intestinal tract-derived alkaline phosphatase IV (bIAP IV) (bIAP IVss).

The nucleotide sequence set forth in SEQ ID NO: 2 is a nucleotide sequence encoding *Aspergillus* cellobiose dehydrogenase (CDH)-derived secretory signal peptide (CDHss).

The nucleotide sequence set forth in SEQ ID NO: 3 is a nucleotide sequence encoding a secretory signal peptide consisting of an *Aspergillus* CDH-derived cytochrome b domain as a carrier protein and a Kex2-cleavable linker (CDHcytbkex).

The nucleotide sequence set forth in SEQ ID NO: 4 is a nucleotide sequence encoding a secretory signal peptide consisting of an *Aspergillus* CDH-derived cytochrome b domain as a carrier protein and Kex2-cleavable linker mutant 1 (CDHcytbkexmut1).

The nucleotide sequence set forth in SEQ ID NO: 5 is a nucleotide sequence encoding a secretory signal peptide consisting of an *Aspergillus* CDH-derived cytochrome b domain as a carrier protein and Kex2-cleavable linker mutant 2 (CDHcytbkexmut2).

The nucleotide sequence set forth in SEQ ID NO: 6 is a nucleotide sequence encoding a secretory signal peptide consisting of an *Aspergillus* CDH-derived cytochrome b domain as a carrier protein and a Kex2-cleavable linker mutant 3 (CDHcytbkexmut3).

The nucleotide sequence set forth in SEQ ID NO: 7 is a nucleotide sequence encoding a secretory signal peptide consisting of an *Aspergillus* CDH-derived cytochrome b domain as a carrier protein and a Kex2-cleavable linker mutant 4 (CDHcytbkexmut4).

The nucleotide sequence set forth in SEQ ID NO: 8 is a nucleotide sequence encoding a secretory signal peptide carrier protein consisting of *Aspergillus* CDH as a carrier protein and a Kex2-cleavable linker (CDHall).

The nucleotide sequence set forth in SEQ ID NO: 9 is a nucleotide sequence encoding *Aspergillus* glucoamylase B-derived secretory signal peptide (GlaBss).

The nucleotide sequence set forth in SEQ ID NO: 10 is a nucleotide sequence encoding a secretory signal peptide consisting of *Aspergillus* glucoamylase B as a carrier protein and a Kex2-cleavable linker (GlaB).

The nucleotide sequence set forth in SEQ ID NO: 11 is a nucleotide sequence encoding *Aspergillus* endoglucanase-derived secretory signal peptide (CelBss).

The nucleotide sequence set forth in SEQ ID NO: 12 is a nucleotide sequence encoding a secretory signal peptide consisting of *Aspergillus* endoglucanase as a carrier protein and a Kex2-cleavable linker (CelB).

The nucleotide sequence set forth in SEQ ID NO: 13 is a nucleotide sequence encoding a secretory signal peptide formed by inserting an amino acid sequence of SKIK immediately after the start codon of *Aspergillus* CDH-derived secretory signal peptide (SKIK_CDHss).

The nucleotide sequence set forth in SEQ ID NO: 14 is a nucleotide sequence encoding *Aspergillus* ALP-derived secretory signal peptide 1 (AsAP1ss54).

The nucleotide sequence set forth in SEQ ID NO: 15 is a nucleotide sequence encoding *Aspergillus* ALP-derived secretory signal peptide 3 (AsAP1ss72).

The amino acid sequence set forth in SEQ ID NO: 16 is the amino acid sequence of a secretory signal peptide on the N-terminal side of bovine intestinal tract-derived alkaline phosphatase IV (bIAP IV) (bIAP IVss).

The amino acid sequence set forth in SEQ ID NO: 17 is the amino acid sequence of *Aspergillus* cellobiose dehydrogenase-derived secretory signal peptide (CDHss).

The amino acid sequence set forth in SEQ ID NO: 18 is the amino acid sequence of a secretory signal peptide consisting of an *Aspergillus* CDH-derived cytochrome b domain as a carrier protein and a Kex2-cleavable linker (CDHcytbkex).

The amino acid sequence set forth in SEQ ID NO: 19 is the amino acid sequence of a secretory signal peptide consisting of an *Aspergillus* CDH-derived cytochrome b domain as a carrier protein and Kex2-cleavable linker mutant 1 (CDHcytbkexmut1).

The amino acid sequence set forth in SEQ ID NO: 20 is the amino acid sequence of a secretory signal peptide consisting of an *Aspergillus* CDH-derived cytochrome b domain as a carrier protein and Kex2-cleavable linker mutant 2 (CDHcytbkexmut2).

The amino acid sequence set forth in SEQ ID NO: 21 is the amino acid sequence of a secretory signal peptide consisting of an *Aspergillus* CDH-derived cytochrome b domain as a carrier protein and a Kex2-cleavable linker mutant 3 (CDHcytbkexmut3).

The amino acid sequence set forth in SEQ ID NO: 22 is the amino acid sequence of a secretory signal peptide consisting of an *Aspergillus* CDH-derived cytochrome b domain as a carrier protein and a Kex2-cleavable linker mutant 4 (CDHcytbkexmut4).

The amino acid sequence set forth in SEQ ID NO: 23 is the amino acid sequence of a secretory signal peptide carrier protein consisting of *Aspergillus* CDH as a carrier protein and a Kex2-cleavable linker (CDHall).

The amino acid sequence set forth in SEQ ID NO: 24 is the amino acid sequence of *Aspergillus* glucoamylase B-derived secretory signal peptide (GlaBss)

The amino acid sequence set forth in SEQ ID NO: 25 is the amino acid sequence of a secretory signal peptide consisting of *Aspergillus* glucoamylase B as a carrier protein and a Kex2-cleavable sequence (GlaB).

The amino acid sequence set forth in SEQ ID NO: 26 is the amino acid sequence of *Aspergillus* endoglucanase-derived secretory signal peptide (CelBss).

The amino acid sequence set forth in SEQ ID NO: 27 is the amino acid sequence of a secretory signal peptide consisting of *Aspergillus* endoglucanase as a carrier protein and a Kex2-cleavable sequence (CelB).

The amino acid sequence set forth in SEQ ID NO: 28 is the amino acid sequence of a secretory signal peptide formed by inserting an amino acid sequence of SKIK immediately after the start codon of *Aspergillus* CDH-derived secretory signal peptide (SKIK_CDHss).

The amino acid sequence set forth in SEQ ID NO: 29 is the amino acid sequence of *Aspergillus* ALP-derived secretory signal peptide 1 (AsAP1ss54).

The amino acid sequence set forth in SEQ ID NO: 30 is the amino acid sequence of *Aspergillus* ALP-derived secretory signal peptide 3 (AsAP1ss72).

In recombinant expression of the ALP, functioning of secretory signal peptide to force extracellular secretion of the ALP is herein referred to as "ALP secretion activity". Examination of the ALP secretion activity of secretory signal peptide in the inventive transformant obtained can be performed, for example, as follows. The transformant is inoculated on a natural medium or synthesized medium containing a carbon source, a nitrogen source, inorganic salts, and so on that *Aspergillus* strains can assimilate to allow efficient culture of *Aspergillus* cell lines, and incubated with shaking culture at a temperature of 20 to 42° C., preferably of approximately 30° C., for 10 to 120 hours. Examples of the carbon source include saccharides such as glucose, fructose, and sucrose, and carbohydrates such as dextran and starch. Among these, dextran is preferred. Examples of the nitrogen source include yeast extract, peptone, and meat extract. Among these, yeast extract and peptone are preferred. Examples of the inorganic salts include magnesium phosphate, magnesium sulfate, and sodium chloride. Among these, magnesium sulfate is preferred. In addition, it is desirable to add magnesium ions and zinc ions, which are metal ions required for ALP activity, to the culture solution. Subsequently, the culture obtained is collected, and separated into a culture supernatant and a residue containing cells through centrifugal separation, centrifugation, or the like. The cells in the residue are disrupted, for example, by using a cell wall-lysing enzyme, a surfactant, a chemical agent such as EDTA, ultrasonication, or a multi-beads shocker, and centrifugal separation or the like is performed to afford a disrupted cells supernatant. The culture supernatant and disrupted cells supernatant obtained are used to measure ALP activity. In the present invention, if ALP activity is found for such a culture supernatant fraction, the case is determined as "having ALP secretion activity". Intensity of ALP secretion activity can be represented as a secretion rate according to the following expression:

Secretion rate=(Total activity of culture supernatant [$U$]/(Total activity of culture supernatant [$U$]+ Total activity of intracellular fraction [$U$])×100)

The ALP secretion activity of the inventive transformant is not limited to a particular secretion activity, but is preferably, for example, secretion activity equivalent to or higher than a secretion rate when AP IVss is used as secretory signal peptide as in Examples described later, more specifically, more preferably 10% or higher, even more preferably 20% or higher, and further preferably 30% or higher in a secretion rate measured in Examples described later.

In the described manner, the inventive transformant capable of ALP production can be obtained. The inventive transformant in one embodiment of the present invention includes a gene designed so that a part of N-linked glycosylation motifs of the ALP is not glycosylated.

More specifically, bovine intestinal tract-derived ALP isoform II (bIAP II or ALP II) includes a gene designed to include a mutation in one or two N-linked glycosylation motifs among three N-linked glycosylation motifs so that the N-linked glycosylation motif(s) including a mutation is/are not glycosylated. Even more specifically, the mutation included in the N-linked glycosylation motif(s) in the bovine intestinal tract-derived ALP II is present at one or two positions of position 122, position 249, position 251, and position 410 in SEQ ID NO: 31. Further specifically, the mutation included in the N-linked glycosylation motif(s) in the bovine intestinal tract-derived ALP II is one or two of a mutation from Asn to Gln or Lys at position 122, a mutation from Asn to Gln, Asp, or His at position 249, a mutation from Thr to Cys at position 251, and a mutation from Asn to Gln or Lys at position 410 in SEQ ID NO: 31.

Such a gene included in the inventive transformant is, in an example, a gene encoding a protein consisting of an amino acid sequence formed from SEQ ID NO: 31 with substitution of Asn with Gln at position 122 and Asn with Gln at position 410.

The inventive transformant in one embodiment of the present invention includes a gene designed to encode an ALP II or an ALP IV. A specific example of these types of ALP includes any of the following proteins (i) to (iii):
(i) a protein consisting of an amino acid sequence set forth in SEQ ID NO: 31 or 32;
(ii) a protein formed from an amino acid sequence set forth in SEQ ID NO: 31 or 32 with deletion, substitution, or addition of one or several amino acids and having ALP activity; and
(iii) a protein having a homology of 90% or higher, preferably of 95% or higher, more preferably of 98% or higher, particularly preferably of 99% or higher, with an amino acid sequence set forth in SEQ ID NO: 31 or 32 and having ALP activity; or a protein encoded by any of the following nucleotide sequences (iv) to (vi):
(iv) a nucleotide sequence set forth in SEQ ID NO: 33 or 34;
(v) a nucleotide sequence formed from a nucleotide sequence set forth in SEQ ID NO: 33 or 34 with deletion, substitution, or addition of one or several nucleotides and encoding a protein having ALP activity; and
(vi) a nucleotide sequence having a homology of 90% or higher, preferably of 95% or higher, more preferably of 98% or higher, particularly preferably of 99% or higher, with a nucleotide sequence set forth in SEQ ID NO: 33 or 34 and encoding a protein having ALP activity.

When the phrase "formed from . . . with deletion, substitution, or addition of one or several amino acids" is used, the number of amino acids deleted, substituted, or added is not limited to particular numbers, and may be any number that allows the resulting protein to have ALP activity. The term "several" here indicates an integer of two or more, preferably 2 to 20, more preferably 2 to 10, even more preferably two to five, and further preferably two, three, or four. The position of deletion, substitution, or addition in each protein may be any of the N-terminus, the C-terminus, and the intermediate positions, as long as the resulting protein has ALP activity.

The phrase "having a homology of Y % or higher with an amino acid sequence set forth in SEQ ID NO: X" means that when amino acid sequences of two proteins are aligned in such a manner that the degree of matching of the two amino acid sequences is maximized (alignment), the ratio of the number of matching amino acids to the total number of amino acids in SEQ ID NO: X is Y % or higher.

When the phrase "formed from . . . with deletion, substitution, or addition of one or several nucleotides" is used, the number of nucleotides deleted, substituted, or added is not limited to particular numbers, and may be any number that allows the resulting nucleotide sequence to encode a protein having ALP activity. The term "several" here indicates an integer of two or more, preferably 2 to 20, more preferably 2 to 10, even more preferably 2 to 5, and further preferably 2, 3, or 4. The position of deletion, substitution, or addition in each nucleotide sequence may be any of the 5'-end, the 3'-end, and the intermediate positions, as long as the resulting nucleotide sequence is encoding a protein having ALP activity.

The phrase "having a homology of Y % or higher with a nucleotide sequence set forth in SEQ ID NO: X" means that when two nucleotide sequences are aligned in such a manner that the degree of matching of the two nucleotide sequences is maximized (alignment), the ratio of the number of matching nucleotides to the total number of nucleotides in SEQ ID NO: X is Y % or higher.

To examine the ALP activity of the inventive transformant obtained, ALP activity is measured as described above for examination of ALP secretion activity.

The ALP activity of the inventive transformant is not limited to a particular activity, but is preferably, for example, activity equivalent to or higher than that of a secreted fraction obtained by culturing the wild-type strain before being transformed, more specifically, more preferably 10 (U/ml) or higher in an enzymatic activity value (U/ml), described later, in the secreted fraction.

The amino acid sequence set forth in SEQ ID NO: 31 is the amino acid sequence of bovine intestinal tract-derived alkaline phosphatase II (bIAP II).

The amino acid sequence set forth in SEQ ID NO: 32 is the amino acid sequence of bovine intestinal tract-derived alkaline phosphatase IV (bIAP IV).

The nucleotide sequence set forth in SEQ ID NO: 33 is a nucleotide sequence encoding bovine intestinal tract-derived alkaline phosphatase II (bIAP II).

The nucleotide sequence set forth in SEQ ID NO: 34 is a nucleotide sequence encoding bovine intestinal tract-derived alkaline phosphatase IV (bIAP IV).

Next, steps that the inventive production method can include will be described.

There is no limitation to the culture method in the step of culturing the inventive transformant, and the inventive mutant may be cultured by using any of solid culture methods and liquid culture methods; however, culturing with a liquid culture method is preferred.

An exemplary medium to be used for culturing the inventive transformant is one containing one or more nitrogen sources such as yeast extract, peptone, meat extract, corn steep liquor, and exudate of soybeans or wheat koji together with one or more of inorganic salts including potassium dihydrogen phosphate, dipotassium hydrogen phosphate, magnesium sulfate, ferric chloride, ferric sulfate, magnesium chloride, zinc chloride, cobalt chloride, and manganese sulfate, to which, as necessary, saccharide materials, vitamins, and so on are appropriately added.

Culturing is performed by using submerged culture with aeration and stirring, shaking culture, or the like preferably at 20 to 37° C., specifically at around 30° C., for 10 to 120 hours.

Bovine intestinal tract-derived ALP can be produced with the inventive production method, in which a culture is obtained through the step of culturing the inventive transformant in a medium, and from the culture bovine intestinal tract-derived ALP is collected. In the inventive production method, bovine intestinal tract-derived ALP can be collected from a culture of the inventive transformant by a common means of collecting an enzyme, and the inventive production method preferably further includes the steps of: obtaining a secreted fraction from a culture of the inventive transformant; and extracting bovine intestinal tract-derived ALP from the secreted fraction.

To obtain a secreted fraction from a culture of the inventive transformant, for example, it is suitable to remove an intracellular fraction from the culture, wherein an intracellular fraction is removed, for example, through an operation of filtration or centrifugal separation. The inventive transformant has a high secretion rate of bovine intestinal tract-derived ALP, and hence bovine intestinal tract-derived ALP tends to be abundantly present, rather than in the intracellular fraction, in the secreted fraction, from which bovine intestinal tract-derived ALP can be more easily extracted. Thus, bovine intestinal tract-derived ALP can be easily obtained from a culture with the inventive production method.

To extract bovine intestinal tract-derived ALP from the secreted fraction obtained, general methods used for purification of an enzyme can be used. It is preferred to perform any one of ammonium sulfate precipitation, organic solvent precipitation, ion-exchange chromatography, gel filtration chromatography, adsorption chromatography, electrophoresis, and so on singly, or perform any combination thereof as appropriate. Thereby, bovine intestinal tract-derived ALP can be extracted to such a degree that almost a single band appears in SDS-PAGE. In addition, it is also acceptable to appropriately combine such methods to prepare samples with different degrees of purification depending on applications.

Further, bovine intestinal tract-derived ALP may be collected from the intracellular fraction in the culture obtained through the step of culturing. In this case, it is preferred to wash cells in the culture or the intracellular fraction separated, and the resultant may be directly used, for which it is preferred to collect bovine intestinal tract-derived ALP from cells, for example, by using a method of breaking cells with use of any of various breaking means including ultrasonicators, French presses, and DYNO-MILLS, a method of lysing cell walls of cells with use of a cell wall-lysing enzyme, or a method of extracting the enzyme from cells with use of a surfactant such as Triton X-100.

The specific activity of the bovine intestinal tract-derived ALP of the present invention is preferably 6500 U/mg or higher. A primary example of methods for measuring specific activity of ALP is a method of measuring increase or decrease of coloring of a substrate converted through enzymatic reaction. The following shows, as an example, a method of measuring the increase of absorbance by p-nitrophenol generated from conversion of p-nitrophenylphosphoric acid. For enzyme titer, in measurement using p-nitrophenylphosphoric acid as a substrate, the amount of an enzyme to generate 1 μmol of p-nitrophenol per minute was defined as 1 U.

A. Preparation of Reagents (1) Reagent 1: 1.0 M $MgCl_2$ Solution

Dissolving 2.03 g $MgCl_2 \cdot 6H_2O$ in ion-exchanged water to reach a volume of 10 ml.

(2) Reagent 2: Diethanolamine (DEA) Buffer (Prepared at Time of Use)

Dissolving 52.2 g of DEA (Sigma-Aldrich Co. LLC) in 400 mL of ion-exchanged water, and adding 0.25 ml of $MgCl_2$ solution (reagent 1) thereto. Thereafter, warming to 37° C., then adjusting the pH to 9.8 with 2 N HCl, and adding ion-exchanged water to reach a volume of 500 ml.

(3) Reagent 3: 0.65 M p-Nitrophenylphosphoric Acid Solution

Dissolving 247 mg of p-nitrophenylphosphoric acid (Sigma-Aldrich Co. LLC) in 1 ml of ion-exchanged water.

(4) Diluted Enzyme Solution

Diluting with the DEA buffer (reagent 2) to attain an activity measurement of 0.10 to 0.20 U/ml.

B. Activity Measurement Method

Mixing together 2.90 ml of the DEA buffer (reagent 2) and 0.05 ml of the p-nitrophenylphosphoric acid solution (reagent 3), and warming the mixture at 37° C. for 5 minutes. Thereafter, adding 0.05 ml of the diluted enzyme solution and mixing the resultant, and then measuring the absorbance at 405 nm by using a spectrometer (U-3010, Hitachi High-Technologies Corporation). The change of absorbance at 405 nm per minute from 2 minutes to 4 minutes thereafter is used as a measurement (ΔODtest). Control solution (ΔODblank) is a solution prepared in the above-described manner except that 0.05 ml of the DEA buffer is added instead of the enzyme solution. Values calculated by using the following calculation formula were used as enzymatic activity values (U/ml).

$$U/\text{ml} = \frac{\Delta OD/\min(\Delta ODtest - \Delta ODblank)/3\,(\text{ml}) \times \text{Dilution ratio}}{18.2 \times 1.0 \times 0.05\,(\text{ml})}$$

18.2: millimolar molecular extinction coefficient under above measurement conditions (cm²/micromole), 1.0: optical path length (cm)

C. Calculation of Specific Activity

The absorbance of the enzyme solution at 280 nm was measured by using a spectrometer (U-3010, Hitachi High-Technologies Corporation) and the protein concentration (mg/ml) of the enzyme solution was calculated by using the relation 1.0 OD=1.0 mg/ml. The enzymatic activity value (U/ml) was divided by the protein concentration (mg/ml) to determine the specific activity (U/mg).

In the present invention, the molecular weight of the ALP II as measured by a gel filtration method is preferably 150 kDa or lower, more preferably 80 to 150 kDa, and even more preferably 90 to 135 kDa. Molecular weight to be measured by a gel filtration method is measured by using a method described later in Examples or a method according thereto.

The vector of the present invention for *Aspergillus* transformation in one embodiment includes a nucleotide sequence encoding an amino acid sequence of bovine intestinal tract-derived ALP having the above-described *Aspergillus* strain-derived secretory signal peptide on the N-terminal side of the bovine intestinal tract-derived ALP. The vector of the present invention for *Aspergillus* transformation in one embodiment includes a nucleotide sequence encoding bovine intestinal tract-derived ALP, wherein the nucleotide sequence includes a gene bound to the 5'-end side of the nucleotide sequence and consisting of above-described nucleotide sequence. The inventive transformant can be prepared by transforming with any of those vectors of the present invention for *Aspergillus* transformation.

Hereinafter, the present invention will be described in detail with reference to Examples.

EXAMPLES

Example 1. Preparation of DNA Construct Including Cdhss-Biap II Inserted Therein (1-1) Preparation of Plasmid for Constructs In the same manner as described in "[Example 1. Preparation of DNA construct inserted with gene AsEgtA, AsEgtB, or AsEgtC] (3) Construction of plasmid construct" in International Publication No. WO 2016/121285, Ptef, which is a promoter sequence of the elongation factor gene tef1, Talp, which is a terminator sequence of the alkaline protease gene alp, and pyrG, which is a transformation marker gene that complements uridine requirement, were linked to an In-Fusion Cloning Site present in a multicloning site of a pUC19 linearized Vector attached to an In-Fusion HD Cloning Kit (Clontech Laboratories, Inc.), preparing a plasmid for constructs.

(1-2) Preparation of Gene-Inserted DNA Construct

A DNA construct including a bIAP II, as a target gene, linked between Ptef and Talp of the plasmid for constructs was prepared as follows.

Inverse PCR was performed by using the plasmid for constructs obtained in the above as a template DNA, the PCR enzyme KOD-Plus-DNA Polymerase (TOYOBO CO., LTD.), a reaction reagent attached to the enzyme, and the apparatus T100™ Thermal Cycler (Bio-Rad Laboratories, Inc.) in accordance with a protocol accompanying the enzyme to obtain vector fragments of the plasmid for constructs. The primers used are shown below. The amplified vector fragments were separated in 1% (w/v) agarose gel, and purified by using a QIAquick Gel Extraction Kit (QIAGEN).

TABLE 1

| Talp1F | 5'GTACCAGGAGTACATTGGAGAGTTCTAC |
|---|---|
| Ptef-1R | 5'TTTGAAGGTGGTGCGAACTTTGTAG |

A CDHss-bIAP II-synthetic gene (SEQ ID NO: 37) was synthesized by outsourcing (GenScript), wherein a bovine intestinal tract-derived alkaline phosphatase II (bIAP II) gene was fused with *Aspergillus* cellobiose dehydrogenase-derived secretory signal peptide (CDHss), in place of the secretory signal peptide on the N-terminal side of bIAP II (SEQ ID NO: 36), and codon-optimized for *Aspergillus* strains. PCR was performed by using the thus-obtained CDHss-bIAP II-synthetic gene as a template DNA, the PCR enzyme KOD-Plus-DNA Polymerase (TOYOBO CO., LTD.), a reaction reagent attached to the enzyme, the apparatus T100™ Thermal Cycler (Bio-Rad Laboratories, Inc.) in accordance with a protocol accompanying the enzyme to obtain DNA fragments with the inserted gene. The primers used for amplification are shown below. In the sequences, sequences of lowercase letters are those to be added for linking to the plasmid for constructs (between Ptef and Talp). The amplified DNA fragments were separated in 1% (w/v) agarose gel, and purified by using a QIAquick Gel Extraction Kit (QIAGEN).

TABLE 2

| Ptef-CIAPIIFw | cgcaccaccttcaaaATGAAACTTGTCAAC |
|---|---|
| Talp-CIAPIIRv | atgtactcctggtacCTAGGCTGGGGCTGG |

The vector fragments and CDHss-bIAP II DNA fragments amplified as described above were linked together by using an In-Fusion HD Cloning Kit in accordance with a protocol accompanying the kit to afford a gene-inserted DNA construct including CDHss-bIAP II inserted therein (pbIAP II). The thus-obtained DNA construct included, from the upstream, a pUC19-derived DNA fragment, a DNA fragment of Ptef, a DNA fragment of CDHss, a DNA fragment of bIAP II, a DNA fragment of Talp, a DNA fragment of pyrG, and a pUC19-derived DNA fragment linked together. That is, a DNA construct including the sequences Ptef—CDHss-bIAP II—Talp—pyrG linked together in the order presented in an In-Fusion Cloning Site of a pUC19 linearized Vector (Clontech Laboratories, Inc.) was obtained.

Thereafter, in ice water, a solution of the DNA construct in a ¹⁄₁₀ volume to the volume of competent cells was mixed with the *Escherichia coli* competent cells ECOS Competent *E. coli* JM109 (NIPPON GENE CO., LTD.), and left to stand in the ice water for 5 minutes, and then treated at 42° C. for 45 seconds for transformation. Thereafter, the mixture was spread onto an LB (Luria-Bertani) plate containing 50 µg/ml ampicillin. The resultant was subjected to static culture at 37° C. overnight to form a colony.

The resulting colony was subjected to shaking culture in an LB liquid medium containing 50 µg/ml ampicillin at 37° C. overnight. The culture solution was centrifuged to collect cells. From the cells obtained, the plasmid DNA (DNA construct) was extracted by using a FastGene Plasmid Mini Kit (NIPPON Genetics Co., Ltd.) in accordance with a protocol accompanying the kit.

DNA nucleotide sequences inserted into the extracted plasmid DNA were determined to confirm that a DNA construct including CDHss-bIAP II inserted therein (DNA construct name: pbIAP II) was obtained.

(1-3) Preparation of N-Linked Glycosylation Motif-Modified ALP Gene-Inserted DNA Construct by Site-Specific Mutation To generate N-linked glycosylation motif-modified ALP_Asn122Gln (Δ1), inverse PCR was performed by using the gene-inserted DNA construct including CDHss-bIAP II inserted therein (pbIAP II) as a template, the PCR enzyme KOD-Plus-DNA Polymerase (TOYOBO CO., LTD.), a reaction reagent attached to the enzyme, and the apparatus T100™ Thermal Cycler (Bio-Rad Laboratories, Inc.) in accordance with a protocol accompanying the enzyme. The primers used are shown below. The amplified DNA fragments were separated in 1% (w/v) agarose gel, and purified by using a QIAquick Gel Extraction Kit (QIAGEN). The DNA fragments were linked by using an In-Fusion HD Cloning Kit in accordance with a protocol accompanying the kit to afford a gene-inserted DNA construct including CDHss-bIAP II inserted therein with the mutation Asn122Gln included in an N-linked glycosylation motif (pΔ1). Following this, site-specific mutations listed in the following table were sequentially introduced to afford different N-linked glycosylation motif-modified ALP gene-inserted DNA constructs.

TABLE 3

| Template | Primer sequence | Position of mutation | Mutation Introduced | DNA construct name |
|---|---|---|---|---|
| pbIAPII | Fw: AGGTACAACCAGT GTCAGACCACTAGAGGA Rv: ACACTGGTTGTAC CTAGCGGCAG | 122 | N→Q | pΔ1 |
| pbIAPII | Fw: AGGTACAACCAGT GTAAGACCACTAGAGGA Rv: ACACTGGTTGTAC CTAGCGGCAG | 122 | N→K | pΔ1k |
| pΔ1 | Fw: TCGAGGCCTGACG TGCAGGGTTCAACTAGT Rv: CACGTCAGGCCTC GATCCGCCACC | 410 | N→Q | pΔ13 |
| pΔ1k | Fw: TCGAGGCCTGACG TGCAGGGTTCAACTAGT Rv: CACGTCAGGCCTC GATCCGCCACC | 410 | N→Q | pΔ1k3 |

Example 2. Preparation of Transformed *Aspergillus sojae*

(2-1) *Aspergillus sojae* NBRC4239-Derived pyrG Disruptant

The gene-inserted DNA constructs were each precipitated in ethanol, and then dissolved in TE buffer and the concentration was adjusted to an intended concentration to prepare DNA solutions, which were used for transformation of an *Aspergillus sojae* NBRC4239-derived pyrG disruptant (a strain in which 48 bp in the upstream, 896 bp in the coding region, and 240 bp in the downstream of the pyrG gene deleted) in the following procedure.

(2-2) Transformation of *Aspergillus sojae* NBRC4239-Derived pyrG Disruptant

Conidia of the *Aspergillus sojae* NBRC4239-derived pyrG disruptant were inoculated on 100 ml of a polypeptone-dextrin liquid medium containing 20 mM uridine in a 500 ml-Erlenmeyer flask, and subjected to shaking culture at 30° C. for approximately 20 hours, and then cells were collected. Protoplasts were prepared from the collected cells. Transformation was performed by using a protoplast PEG method with the protoplasts obtained and 20 μg of a gene-inserted DNA construct, and the resultant was then incubated by using a Czapek-Dox minimal medium (Difco Laboratories; pH 6) containing 0.5% (w/v) agar and 1.2 M sorbitol at 30° C. for 5 days or longer, giving transformed *Aspergillus sojae* with colony-forming ability.

Once pyrG, a gene that complements uridine requirement, was introduced into the transformed *Aspergillus sojae* obtained, the transformed *Aspergillus sojae* became capable of growing in a uridine-free medium, and hence the transformed *Aspergillus sojae* was permitted to be selected as a strain including the gene of interest inserted therein.

Example 3. Various ALP Productions by Transformed *Aspergillus sojae*

Conidia of each of the transformed strains were inoculated on 1800 ml of a liquid medium (2% (w/v) HIPOLY-PEPTON (Nihon Pharmaceutical Co., Ltd.), 2% (w/v) Pinedex #2 (Matsutani Chemical Industry Co., Ltd.), 1% (w/v) yeast extract (Oriental Yeast Co., Ltd.), 0.25% (w/v) $KH_2PO_4$ (Wako Pure Chemical Industries, Ltd.), 0.25% (w/v) $K_2HPO_4$ (Wako Pure Chemical Industries, Ltd.), 0.05% (w/v) $MgSO_4 \cdot 7H_2O$ (Wako Pure Chemical Industries, Ltd.), 3 mM $MgCl_2$ (Wako Pure Chemical Industries, Ltd.), 0.1 mM $ZnCl_2$ (Wako Pure Chemical Industries, Ltd.); pH: not adjusted) in a 3 L-jar fermenter, and culture was initiated at 30° C. with a stirring rate of 250 rpm, which was changed to 500 rpm after 48 hours, and an aeration of 25 L/min under a pressure of 0.05 MPa, and continued for 5 days in total. Subsequently, the culture was separated through filtration with a Miracloth (Calbiochem), and the culture supernatant and cells were collected. The cells collected were washed with distilled water, and then sandwiched with a paper towel to squeeze out moisture, giving wet cells. The wet cells obtained were weighed, to which Tris buffer (20 mM Tris-HCl, pH 8.0, 3 mM $MgCl_2$, 0.1 mM $ZnCl_2$) was added to a concentration of 50 mg wet cells/ml. The resultant was homogenized, and a part thereof was placed together with zirconia beads in a 2 ml-screwcap vial, and twice subjected to crushing with a beads shocker (MS-100R, TOMY SEIKO CO., LTD.) for 20 seconds at 2500 rpm. Subsequently, centrifugation at 15000×g was performed for 5 minutes, and the resulting centrifuged supernatant was used as an intracellular fraction.

ALP activity measurement was carried out for the obtained culture supernatant fraction and intracellular fraction in accordance with the above description in "B. Activity measurement method" to calculate secretion rates (Total activity of culture supernatant [U]/(Total activity of culture supernatant [U]+Total activity of intracellular fraction [U])× 100) (FIG. 1).

Comparative Example. Various bIAP II Productions by Transformed *S. pombe*

A culture solution of the ALP-producing yeast *S. pombe* obtained in Example 5 in Japanese Patent Laid-Open No. 2008-5734 was prepared in the same manner, and the culture solution was centrifuged to separate into cells and a culture supernatant fraction. Subsequently, the cells were suspended in Tris buffer (10 mM Tris-HCl pH 7.0, 5 mM $MgCl_2$, 0.1 mM $ZnCl_2$) and crushed with a beads shocker to afford an intracellular fraction. The ALP activity measurement was carried out for the obtained culture supernatant fraction and intracellular fraction in the same manner as in Example 3 to calculate secretion rates (FIG. 1).

In the case of expression in the *Aspergillus A. sojae*, the secretion rate of each type of bIAP II (ALP name: bIAP II, Δ1, Δ1k, Δ13, and Δ1k3), which was expressed from the corresponding DNA construct (DNA construct name: pbIAP II, pΔ1, pΔ1k, pΔ13, and Δ1k3), was a very high value of 75% or higher. In the case of expression in the yeast *S. pombe*, in contrast, the secretion rate of bIAP II was about 7%. While the secretion rate decreased in the case of yeast expression as the number of N-linked glycosylation motifs reduced, the secretion rate was high for every case, regardless of the number of N-linked glycosylation motifs, in the case of *Aspergillus* expression.

Example 4. Purification of Each Type of ALP

The culture solution was centrifuged at 8000 rpm for 90 minutes to collect the supernatant, which was concentrated through the ultrafiltration membrane AIP-1010 (Asahi Kasei Corporation), and dialyzed with Tris buffer. The internal solution was collected and passed through a 0.45 μm filter (material: PES, Millipore Corporation), and the filtrate was collected. The sample was adsorbed on a Q-Sepharose Fast Flow (GE Healthcare) anion-exchange column chromatograph equilibrated with Tris buffer, and then subjected to gradient elution with Tris buffer containing 1 M NaCl. Ammonium sulfate was added to the eluate to a final concentration of 30%, and the resultant was passed through a 0.2 μm filter (material: PES, Millipore Corporation), and the filtrate was collected. Subsequently, the sample was adsorbed on a TOYO Pearl Butyl-650C (Tosoh Corporation) hydrophobic column chromatograph equilibrated with Tris buffer containing 30% ammonium sulfate, then subjected to gradient elution with Tris buffer, and concentrated by using the ultrafiltration membrane Amicon Ultra-15 (molecular weight cutoff: 30 kDa, Millipore Corporation). Subsequently, the concentrated product was fractionated and purified with a Hiload Superdex 200 pg (GE Healthcare) gel filtration column chromatograph equilibrated with Tris buffer.

Example 5. Measurement of Specific Activity

The ALP activity of each type of ALP purified was measured, the amount of protein was determined from the absorbance at 280 nm, and the specific activity was calculated (FIG. 2).

Each of bIAP II, Δ1, Δ1k, Δ13, and Δ1k3 obtained by *Aspergillus* expression exhibited a high specific activity of 6000 U/mg or higher.

Example 6. bIAP II Production by Transformed *Aspergillus oryzae*

Transformed *Aspergillus oryzae*-expressed bIAP II was prepared in the same procedures as in Examples 2 to 5, except that an *Aspergillus oryzae* RIB40 strain was used in place of the *Aspergillus sojae* NBRC4239 strain.

Example 7. Measurement of Molecular Weight

The molecular weight of each type of ALP purified was measured through gel filtration chromatography using HPLC (Agilent 1220 Infinity LC, Agilent Technologies). To a TSK-gel G3000SW (7.5 mm I.D.×30 cm, Tosoh Corporation) equilibrated with 100 mM phosphate buffer containing 0.1 M NaCl at pH 7.0, 50 μL of the purified ALP solution was applied, and eluted with the same buffer at a column temperature of 25° C. and a flow rate of 1 mL/min, and the absorbance at 280 nm was measured. A calibration curve was prepared by using molecular weight markers (MW-Marker proteins, Oriental Yeast Co., Ltd.), and the molecular weight of the purified ALP was calculated (Table 4). As controls, commercially available bovine intestinal tract-derived ALP from yeast recombinant expression (Alkaline Phosphatase recombinant highly active: Roche_ALP, F. Hoffmann-La Roche Ltd.), deglycosylated bovine intestinal tract-derived ALP from yeast recombinant expression (Alkaline Phosphatase recombinant highly active, Carbohydrate Reduced: Roche_ALP_CR, F. Hoffmann-La Roche Ltd.), and bovine intestinal tract extract-derived ALP with high specific activity (ALP13G, BBI Solutions) were used.

TABLE 4

<Number of glycosylation motifs and molecular weight (kDa) calculated through gel filtration for different types of ALP>

| ALP | Number of glycosylation motifs | Expression hosts | | |
|---|---|---|---|---|
| | | A. sojae | A. oryzae | S. pombe |
| bIAPII | 3 | 106 | 126 | 1100 |
| Δ1 | 2 | 110 | — | — |
| Δ1k | 2 | 116 | — | 440 |
| Δ13 | 1 | 92 | — | 120 |
| Δ1k3 | 1 | 84 | — | 120 |

The number of N-linked glycosylation motifs included in an amino acid sequence is three for bIAP II, two for Δ1 and Δ1k, and one for Δ13 and Δ1k3. The number of glycan molecules to be added to each type of ALP is expected to be proportional to the number of N-linked glycosylation motifs, and thus molecular weight is expected to increase in response to the number of glycan moieties. In fact, the molecular weights of bIAP II, Δ1k, and Δ13 and Δ1k3 expressed in the yeast *S. pombe* described in Japanese Patent Laid-Open No. 2008-5734 were 1100 kDa, 440 kDa, and 120 kDa, respectively (Table 5 in Japanese Patent Laid-Open No. 2008-5734), indicating that the molecular weight of ALP decreased in response to the reduction of the number of N-linked glycosylation motifs. Meanwhile, the same tendency was found for ALP obtained by expression in the *Aspergillus A. sojae*, and moreover the molecular weight of each type of ALP expressed in the *Aspergillus A. sojae* or *A. oryzae* was significantly lower than that of the corresponding ALP expressed in the yeast *S. pombe* with the same number of N-linked glycosylation motifs. The molecular weights of the commercially available bovine intestinal tract-derived ALP expressed in *Pichia* Patoris (Roche_ALP), deglycosylated Roche_ALP_CR, and bovine intestinal tract-derived ALP with specific activity (ALP13G; BBI Solutions) were 220 kDa, 145 kDa, and 131 kDa, respectively. The molecular weight of each type of ALP expressed in *Aspergillus* cells was lower than that of the corresponding, commercially available bovine intestinal tract-derived ALP.

Example 8. Preparation of DNA Constructs Including bIAP IV Inserted Therein with Different Secretory Signal Peptides Fused Therewith (8-1) Preparation of Plasmid for Constructs Plasmids for DNA constructs including bIAP IV inserted therein with different secretory signal peptides fused therewith were prepared in the same procedure as for the plasmid for DNA constructs including CDHss-bIAP II inserted therein in Example 1-1.

(8-2) Preparation of Bovine Intestinal Tract-Derived Alkaline Phosphatase IV (bIAP IV) Gene-Inserted DNA Construct DNA constructs including a bIAP IV gene, as a target gene, linked between Ptef and Talp of a plasmid for constructs was prepared as follows.

Inverse PCR was performed by using a plasmid for constructs obtained in the above as a template DNA, the PCR enzyme KOD-Plus-DNA Polymerase (TOYOBO CO., LTD.), a reaction reagent attached to the enzyme, and the apparatus T100™ Thermal Cycler (Bio-Rad Laboratories, Inc.) in accordance with a protocol accompanying the enzyme to obtain vector fragments of the plasmid for constructs. The primers used are shown below. The amplified vector fragments were separated in 1% (w/v) agarose gel, and purified by using a QIAquick Gel Extraction Kit (QIAGEN).

TABLE 5

| Talp1F | 5'GTACCAGGAGTACATTGGAGAGTTCTAC |
|---|---|
| Ptef-1R | 5'TTTGAAGGTGGTGCGAACTTTGTAG |

A bIAP IV-synthetic gene (SEQ ID NO: 60) was synthesized by outsourcing (GenScript), wherein a bovine intestinal tract-derived alkaline phosphatase IV (bIAP IV) gene (GenBank Accession No.: AAC33854) was codon-optimized for *Aspergillus* strains, and a region encoding a membrane-bound signal peptide on the C-terminal side was removed. PCR was performed by using the thus-obtained bIAP IV-synthetic gene as a template DNA, the PCR enzyme KOD-Plus-DNA Polymerase (TOYOBO CO., LTD.), a reaction reagent attached to the enzyme, the apparatus T100™ Thermal Cycler (Bio-Rad Laboratories, Inc.) in accordance with a protocol accompanying the enzyme to obtain DNA fragments with the bIAP IV-synthetic gene. The primers used for amplification are shown below. In the sequences, sequences of lowercase letters are those to be added for linking to the plasmid for constructs (between Ptef and Talp). The amplified DNA fragments were separated in 1% (w/v) agarose gel, and purified by using a QIAquick Gel Extraction Kit (QIAGEN).

TABLE 6

| Ptef-CIAPIVFw | cgcaccaccttcaaaATGCAGTGGGCCTGT |
|---|---|
| Talp-CIAPIVRv | atgtactcctggtacCTAACCCGAAGGGGC |

The vector fragments and bIAP IV-synthetic gene DNA fragments amplified as described above were linked together by using an In-Fusion HD Cloning Kit in accordance with a protocol accompanying the kit to afford a gene-inserted DNA construct with the bIAP IV-synthetic gene inserted therein (pbIAP IV). The thus-obtained DNA construct included, from the upstream, a pUC19-derived DNA fragment, a DNA fragment of Ptef, a bIAP IV-synthetic gene DNA fragment, a DNA fragment of Talp, a DNA fragment of pyrG, and a pUC19-derived DNA fragment. That is, a DNA construct including the sequences Ptef—bIAP IV—synthetic gene—Talp—pyrG linked together in the order presented in an In-Fusion Cloning Site of a pUC19 linearized Vector (Clontech Laboratories, Inc.) was obtained.

Thereafter, a solution of the DNA construct in a ¹⁄₁₀ volume to the volume of competent cells was mixed with the *Escherichia coli* competent cells ECOS Competent *E. coli* JM109 (NIPPON GENE CO., LTD.), and left to stand in the ice water for 5 minutes, and then treated at 42° C. for 45 seconds for transformation. Thereafter, the solution was spread onto an LB (Luria-Bertani) plate containing 50 µg/ml ampicillin. The resultant was subjected to static culture at 37° C. overnight to form a colony.

The resulting colony was subjected to shaking culture in an LB liquid medium containing 50 µg/ml ampicillin at 37° C. overnight. The culture solution was centrifuged to collect cells. From the cells obtained, the plasmid DNA (DNA construct) was extracted by using a FastGene Plasmid Mini Kit (NIPPON Genetics Co., Ltd.) in accordance with a protocol accompanying the kit.

DNA nucleotide sequences inserted into the extracted plasmid DNA were determined to confirm that a DNA construct including the bIAP IV-synthetic gene inserted therein (pbIAP IV) was obtained.

(8-3) Preparation of DNA Constructs Inserted with a Synthetic Gene of bIAP IV with Different Secretory Signal Peptides Prepared as follows were different DNA constructs including a synthetic gene of bIAP IV whose secretory signal peptide on the N-terminal side was replaced with any of secretory signal peptides listed in Table 3 (including a secretory signal peptide as a carrier protein fused with a Kex2-cleavable linker).

TABLE 7

| DNA construct name | Secretory signal peptide name |
|---|---|
| pbIAPIV | Bovine intestinal tract-derived alkaline phosphatase IV secretory signal peptide |
| pCDHss | *Aspergillus* cellobiose dehydrogenase secretory signal peptide |
| pCDHcytbkex | *Aspergillus* cellobiose dehydrogenase cytochrome b domain - Kex-cleavable linker |
| pCDHcytbkex mut1 | *Aspergillus* cellobiose dehydrogenase cytochrome b domain - Kex-cleavable linker mutant 1 |
| pCDHcytbkex mut2 | *Aspergillus* cellobiose dehydrogenase cytochrome b domain - Kex-cleavable linker mutant 2 |
| pCDHcytbkex mut3 | *Aspergillus* cellobiose dehydrogenase cytochrome b domain - Kex-cleavable linker mutant 3 |
| pCDHcytbkex mut4 | *Aspergillus* cellobiose dehydrogenase cytochrome b domain - Kex-cleavable linker mutant 4 |
| pCDHall | *Aspergillus* cellobiose dehydrogenase - Kex-cleavable linker |
| pGlaBss | *Aspergillus* glucoamylase B secretory signal peptide |
| pGlaB | *Aspergillus* glucoamylase B - Kex-cleavable linker |
| pCelBss | *Aspergillus* endoglucanase secretory signal peptide |
| pCelB | *Aspergillus* endoglucanase - Kex-cleavable linker |
| pSKIK_CDHss | Secretory signal peptide formed by inserting amino acid sequence of SKIK immediately after start codon of *Aspergillus* CDH-derived secretory signal peptide |
| pAsAP1ss | *Aspergillus* ALP-derived secretory signal peptide 1 |
| pAsAP3ss | *Aspergillus* ALP-derived secretory signal peptide 3 |

Inverse PCR was performed by using pbIAP IV as a template DNA, the PCR enzyme KOD-Plus-DNA Polymerase (TOYOBO CO., LTD.), a reaction reagent attached to the enzyme, and the apparatus T100™ Thermal Cycler (Bio-Rad Laboratories, Inc.) in accordance with a protocol accompanying the enzyme to obtain vector fragments of a plasmid for constructs with a nucleotide sequence encoding pbIAP IV free of secretory signal peptide. The primers used are shown below. The amplified vector fragments were separated in 1% (w/v) agarose gel, and purified by using a QIAquick Gel Extraction Kit (QIAGEN).

TABLE 8

| | |
|---|---|
| bIAPIV-1F | TTCATCCCAGCTGAGGAAGAGGATCC |
| Ptef-1R | TTTGAAGGTGGTGCGAACTTTG |

A chromosomal DNA was obtained through the same operations as in "[Example 1. Preparation of DNA construct inserted with gene AsEgtA, AsEgtB, or AsEgtC] in International Publication No. WO 2016/121285, (2) Extraction of chromosomal DNA of *Aspergillus sojae* NBRC4239 strain", and PCR was performed by using the chromosomal DNA as a template, the PCR enzyme KOD-Plus-DNA Polymerase (TOYOBO CO., LTD.), a reaction reagent attached to the enzyme, and the apparatus T100™ Thermal Cycler (Bio-Rad Laboratories, Inc.) in accordance with a protocol accompanying the enzyme. The primers used for amplification of genes for cellobiose dehydrogenase, glucoamylase B, and endoglucanase to serve as a carrier protein (cdh, glab, and celb) are shown in a table below. By using primers shown in the table below, DNA fragments each encoding an amino acid sequence (SEQ ID NO: 23, 25, or 27) in which a linker sequence (SEQ ID NO: 61) including a Kex2-cleavable sequence was linked to the C-terminus of the corresponding carrier protein were obtained. DNA fragments of the CDH gene, GlaB gene, and CelB gene amplified were separated in 1% (w/v) agarose gel, and purified by using a QIAquick Gel Extraction Kit (QIAGEN).

TABLE 9

| Gene | Primer |
|---|---|
| cdh | Fw: CGCACCACCTTCAAAATGAAGCTCGTTAAC<br>Rv: CTCAGCTGGGATGAAGCGCTTAGAGCCTCCACCGCCCAGC<br>GCAAGAATCTT |
| glab | Fw: CGCACCACCTTCAAAATGCGGAACAACTTT<br>Rv: CTCAGCTGGGATGAAGCGCTTAGAGCCTCCACCGCCCAC<br>GACCCAACAGT |
| celb | Fw: CGCACCACCTTCAAAATGATCTGGACACTC<br>Rv: CTCAGCTGGGATGAAGCGCTTAGAGCCTCCACCGCCATGC<br>CTGTAGGTAGA |

The DNA fragments of the CDH gene, GlaB gene, or CelB gene and vector fragments of the plasmid for constructs were linked together by using an In-Fusion HD Cloning Kit to afford gene-inserted DNA constructs including the CDH gene, GlaB gene, or CelB gene inserted therein (pCDHall, pGlaB, and pCelB). The thus-obtained DNA constructs each included, from the upstream, a pUC19-derived DNA fragment, a DNA fragment of Ptef, a DNA fragment of the corresponding carrier protein gene, a DNA fragment of the synthetic gene coding bIAP IV free of the secretory signal peptide, a DNA fragment of Talp, a DNA fragment of pyrG, and a pUC19-derived DNA fragment linked together. That is, DNA constructs (pCDHall, pGlaB, and pCelB) each including the sequences Ptef—corresponding carrier protein gene—nucleotide sequence encoding linker including Kex2-cleavable sequence—bIAP IV—synthetic gene free of nucleotide sequence encoding secretory signal peptide—Talp—pyrG linked together in the order presented in an In-Fusion Cloning Site of a pUC19 linearized Vector (Clontech Laboratories, Inc.) were obtained.

The *Escherichia coli* JM109 was transformed with each DNA construct obtained. Thereafter, the product was spread onto an LB (Luria-Bertani) plate containing 50 μg/ml ampicillin. The resultant was subjected to static culture at 37° C. overnight to form a colony.

The resulting colony was subjected to shaking culture in an LB liquid medium containing 50 μg/ml ampicillin at 37° C. overnight. The culture solution was centrifuged to collect cells. From the cells obtained, the plasmid DNA (DNA construct) was extracted by using a FastGene Plasmid Mini Kit (NIPPON Genetics Co., Ltd.) in accordance with a protocol accompanying the kit.

DNA nucleotide sequences inserted into each extracted plasmid DNA were determined to confirm that the DNA constructs (pCDHall, pGlaB, and pCelB) of interest were obtained.

Subsequently prepared in the following procedure was a DNA construct including a synthetic gene of bIAP IV with the secretory signal peptide replaced by a secretory signal peptide (SEQ ID NO: 18) consisting of an *Aspergillus sojae*-derived cellobiose dehydrogenase cytochrome b domain (CDHcytb) and a linker sequence (SEQ ID NO: 61) including a Kex2-cleavable sequence. Inverse PCR was performed by using pCDHall obtained in the above as a template DNA, the primers set forth in SEQ ID NOs: 71 and 72, the PCR enzyme KOD-Plus-DNA Polymerase (TOYOBO CO., LTD.), a reaction reagent attached to the enzyme, and the apparatus T100™ Thermal Cycler (Bio-Rad Laboratories, Inc.) in accordance with a protocol accompanying the enzyme to obtain constructed DNA fragments of CDHcytbkex-bIAP IV. The constructed DNA fragments of CDHcytbkex_bIAP IV were transformed in the *Escherichia coli* JM109 by using an In-Fusion HD Cloning Kit.

Plate culture was performed by using the above-described method and the resulting colony was cultured, and the plasmid DNA was then collected from cells. DNA nucleotide sequences inserted into the extracted plasmid DNA were determined to confirm that the DNA construct (pCDHcytbkex) was obtained.

Subsequently prepared in the following procedure was a DNA construct including a synthetic gene of bIAP IV with the secretory signal peptide replaced by that derived from *Aspergillus sojae* cellobiose dehydrogenase (CDHss; SEQ ID NO: 17). Inverse PCR was performed by using pCDHall obtained in the above as a template DNA, the primers set forth in SEQ ID NOs: 73 and 74, the PCR enzyme KOD-Plus-DNA Polymerase (TOYOBO CO., LTD.), a reaction reagent attached to the enzyme, and the apparatus T100™ Thermal Cycler (Bio-Rad Laboratories, Inc.) in accordance with a protocol accompanying the enzyme to obtain constructed DNA fragments of CDHss-bIAP IV. The constructed DNA fragments of CDHss_bIAP IV were transformed in the *Escherichia coli* JM109 by using an In-Fusion HD Cloning Kit.

Plate culture was performed by using the above-described method and the resulting colony was cultured, and the plasmid DNA was then collected from cells. DNA nucleotide sequences inserted into the extracted plasmid DNA were determined to confirm that the DNA construct (pCDHss) was obtained.

Subsequently prepared in the following procedure was a DNA construct including a synthetic gene of bIAP IV with the secretory signal peptide replaced by a secretory signal peptide (SKIK_CDHss; SEQ ID NO: 28) formed by inserting SKIK immediately after the starting methionine of *Aspergillus sojae* cellobiose dehydrogenase-derived secretory signal peptide (CDHss). Inverse PCR was performed by using pCDHss obtained in the above as a template DNA, the primers set forth in SEQ ID NOs: 75 and 76, the PCR enzyme KOD-Plus-DNA Polymerase (TOYOBO CO., LTD.), a reaction reagent attached to the enzyme, and the apparatus T100™ Thermal Cycler (Bio-Rad Laboratories, Inc.) in accordance with a protocol accompanying the enzyme to obtain constructed DNA fragments of SKIK_CDHss-bIAP IV. The constructed DNA fragments of SKIK_CDHss-bIAP IV were transformed in the *Escherichia coli* JM109 by using an In-Fusion HD Cloning Kit.

Plate culture was performed by using the above-described method and the resulting colony was cultured, and the plasmid DNA was then collected from cells. DNA nucleotide sequences inserted into the extracted plasmid DNA were determined to confirm that the DNA construct (pSKIK_CDHss) was obtained.

Subsequently prepared in the following procedure were DNA constructs each including a synthetic gene of bIAP IV with the secretory signal peptide replaced by a secretory signal peptide (any of SEQ ID NOs: 19 to 22) consisting of an *Aspergillus sojae*-derived cellobiose dehydrogenase cytochrome b domain (CDHcytb) and a linker sequence (any of SEQ ID NOs: 62 to 65) including any of Kex2-cleavable linker mutation 1 to 4. Inverse PCR was performed by using pCDHcytbkex obtained in the above as a template DNA, the primers set forth in SEQ ID NOs: 77 to 81, the PCR enzyme KOD-Plus-DNA Polymerase (TOYOBO CO., LTD.), a reaction reagent attached to the enzyme, and the apparatus T100™ Thermal Cycler (Bio-Rad Laboratories, Inc.) in accordance with a protocol accompanying the enzyme to obtain constructed DNA fragments of CDHcytbkexmut1_bIAP IV, CDHcytbkexmut2_bIAP IV, CDHcytbkexmut3_bIAP IV, and CDHcytbkexmut4_bIAP IV. The constructed DNA fragments obtained were transformed in the *Escherichia coli* JM109 by using an In-Fusion HD Cloning Kit.

Plate culture was performed by using the above-described method and the resulting colony was cultured, and the plasmid DNA was then collected from cells. DNA nucleotide sequences inserted into each extracted plasmid DNA were determined to confirm that the DNA constructs (pCDHcytbkexmut1, pCDHcytbkexmut2, pCDHcytbkexmut3, pCDHcytbkexmut4) were obtained.

Subsequently prepared in the following procedure was a DNA construct including a synthetic gene of bIAP IV with the secretory signal peptide replaced by that derived from *Aspergillus sojae* glucoamylase (SEQ ID NO: 24). Inverse PCR was performed by using pbIAP IV obtained above as a template DNA, the primers set forth in SEQ ID NOs: 82 and 83, the PCR enzyme KOD-Plus-DNA Polymerase (TOYOBO CO., LTD.), a reaction reagent attached to the enzyme, and the apparatus T100™ Thermal Cycler (Bio-Rad Laboratories, Inc.) in accordance with a protocol accompanying the enzyme to obtain constructed DNA fragments of GlaBss_bIAP IV. The constructed DNA fragments obtained were transformed in the *Escherichia coli* JM109 by using an In-Fusion HD Cloning Kit.

Plate culture was performed by using the above-described method and the resulting colony was cultured, and the plasmid DNA was then collected from cells. DNA nucleotide sequences inserted into the extracted plasmid DNA were determined to confirm that the DNA construct (pGlaBss) was obtained.

Subsequently prepared in the following procedure was a DNA construct including a synthetic gene of bIAP IV with the secretory signal peptide replaced by that derived from *Aspergillus sojae* endoglucanase (CelBss; SEQ ID NO: 26). Inverse PCR was performed by using pCelB obtained above as a template DNA, the primers set forth in SEQ ID NOs: 84 and 85, the PCR enzyme KOD-Plus-DNA Polymerase (TOYOBO CO., LTD.), a reaction reagent attached to the enzyme, and the apparatus T100™ Thermal Cycler (Bio-Rad Laboratories, Inc.) in accordance with a protocol accompanying the enzyme to obtain constructed DNA fragments of CelBss_bIAP IV. The constructed DNA fragments of CelBss_bIAP IV were transformed in the *Escherichia coli* JM109 by using an In-Fusion HD Cloning Kit.

Plate culture was performed by using the above-described method and the resulting colony was cultured, and the plasmid DNA was then collected from cells. DNA nucleotide sequences inserted into the extracted plasmid DNA were determined to confirm that the DNA construct (pCelBss) including a gene encoding CelBss inserted in the upstream of the bIAP IV gene was obtained.

Subsequently prepared in the following procedure were DNA constructs each including a synthetic gene of bIAP IV with the secretory signal peptide replaced by that derived from *Aspergillus sojae* alkaline phosphatase (any of SEQ ID NOs: 29 and 30). Inverse PCR was performed by using pbIAP IV obtained above as a template DNA, the PCR enzyme KOD-Plus-DNA Polymerase (TOYOBO CO., LTD.), the primers set forth in SEQ ID NOs: 86 to 89, a reaction reagent attached to the enzyme, and the apparatus T100™ Thermal Cycler (Bio-Rad Laboratories, Inc.) in accordance with a protocol accompanying the enzyme to obtain constructed DNA fragments of AsAP1ss_bIAP IV and AsAP3ss_bIAP IV. The constructed DNA fragments obtained were transformed in the *Escherichia coli* JM109 by using an In-Fusion HD Cloning Kit.

Plate culture was performed by using the above-described method, the resulting colony was cultured, and the plasmid DNA was collected from cells. DNA nucleotide sequences inserted into each extracted plasmid DNA were determined to confirm that the DNA constructs (pAsAP1ss54 and pAsAP3ss72) were obtained.

Example 9. Preparation of Transformed *Aspergillus sojae*

In accordance with the method described in Example 2, transformant strains of the *Aspergillus sojae* NBRC4239-derived pyrG disruptant were obtained by using the DNA constructs, obtained in Example 8, including a synthetic gene of bIAP IV inserted therein with different secretory signal peptides.

Example 10. Flusk Culture Test for Transformed *Aspergillus sojae*

Conidia of each of the transformed strains obtained in Example 9 were inoculated on 20 ml of a liquid medium (2% (w/v) HIPOLYPEPTON (Nihon Pharmaceutical Co., Ltd.), 2% (w/v) Pinedex #2 (Matsutani Chemical Industry Co., Ltd.), 1% (w/v) yeast extract (Oriental Yeast Co., Ltd.), 0.25% (w/v) $KH_2PO_4$ (Wako Pure Chemical Industries, Ltd.), 0.25% (w/v) $K_2HPO_4$ (Wako Pure Chemical Industries, Ltd.), 0.05% (w/v) $MgSO_4.7H_2O$ (Wako Pure Chemical Industries, Ltd.), 3 mM $MgCl_2$ (Wako Pure Chemical Industries, Ltd.), 0.1 mM $ZnCl_2$ (Wako Pure Chemical Industries, Ltd.); pH: not adjusted) in a 50 ml-Erlenmeyer flask, and culture was initiated at 30° C. with a stirring rate of 180 rpm, and continued for 3 days in total. Subsequently, the culture was separated through filtration with a Miracloth (Calbiochem), and the culture supernatant and cells were collected. The cells collected were washed with distilled water, and then sandwiched with a paper towel to squeeze out moisture, giving wet cells. The wet cells obtained were weighed, to which Tris buffer (20 mM Tris-HCl, pH 8.0, 3 mM $MgCl_2$, 0.1 mM $ZnCl_2$) was added to a concentration of 50 mg wet cells/ml. The resultant was homogenized, and a part thereof was placed together with zirconia beads in a 2 ml-screwcap vial, and twice subjected to crushing with a beads shocker (MS-100R, TOMY SEIKO CO., LTD.) for 20 seconds at 2500 rpm. Subsequently, centrifugation at 15000×g was performed for 5 minutes, and the resulting centrifuged supernatant was used as an intracellular fraction.

ALP activity measurement was carried out for the obtained culture supernatant fraction and intracellular fraction in accordance with the description in Japanese Patent Laid-Open No. 2008-5734 to calculate secretion rates (Total activity of culture supernatant [U]/(Total activity of culture supernatant [U]+Total activity of intracellular fraction [U])× 100) (FIG. 3).

TABLE

| SEQ ID NO: | Description | Sequence |
|---|---|---|
| 1 | Showing nucleotide sequence encoding bAP IVss | ATGCAGTGGGCCTGTGTGCTGCTGCTGCTGGGCCTGTGGCTACAGCTCTCCCTCACC |
| 2 | Showing nucleotide sequence encoding CDHss and including intron | ATGAAGCTCGTTAACCGTTTGCTCGCTTCATTCCTGTCAGCGAGCACCGGTGAGTGGTGGCCTATCGAGCTAATGTTGCTTCTCTTCGTCTGACTTTTCTTGGCAGTGTTGCAGTCATGCTGGGCT |
| 3 | Showing nucleotide sequence encoding CDHcytbkex | ATGAAGCTCGTTAACCGTTTGCTCGCTTCATTCCTGTCAGCGAGCACCGGTGAGTGGTGGCCTATCGAGCTAATGTTGCTTCTCTTCGTCTGACTTTTCTTGGCAGTGTTGCAGTCATGCTGGGCTCAGTCCGGCACACCGGTTGCCTACACGGATACTGAGACGGGCATCACGTTTGACACGTGGTCGGTACCTGCTGGTACGGGTACGGGTGGTCTCGTCTTCGGTGTAGCCCTGCCGGGTTCGGCATTGACCACCGATGCGACGGAGTTTATCGGTTACCTGGTGAGGATCTCGAGCTAATCATGACCGCTCTGAAGTGGCGCTAAACGTTCTAATGTTTCAAGCAATGTGCGTCCCAAAATGCCTCGTCCGCTGGCTGGTGTGGCATTTCCTTGGGTGGTGGCATGAACAACAATCTCTTGTTCTTGGCCTATCCGTACGAGGATACCATCTTGACCTCCCTGCGATTCGGCTCGGGCTATAGCATGCCCGGGGTCTATACCGGCAATGCCAACGTCACCCAGATTTCTTCAAGCATCAATGCCACTCACTTTACGTTGCTTTTCCGTTGCGAGAATTGTCTGACCTGGGACCAAGATGGTCAAACCGGAAACGCGACCACAAGCAAGGGTAGGTTAGTCCTGGGATGGGCACAGTCTACGGAGAGCCCGTCGAACCCGTCCTGTCCGGACAATATCAGCCTGGCGCAGCACGACAACCAGGGTATTATCTCAGCCACTCTGGATGAGAATGCAGCCAGTGAGTCCTACGAGGACTGGGTCAAGTTGGCTAATAAGACTGTTCCCGGGGACTGCTCCGGTGACGGTGGTGGCGGCAACGAGCCGACTCCTGTCCCTGTCCCTGACGGTGGCGGTGGAGGCTCTAAGCGC |
| 4 | Showing nucleotide sequence encoding CDHcytbkexmut1 | ATGAAGCTCGTTAACCGTTTGCTCGCTTCATTCCTGTCAGCGAGCACCGGTGAGTGGTGGCCTATCGAGCTAATGTTGCTTCTCTTCGTCTGACTTTTCTTGGCAGTGTTGCAGTCATGCTGGGCTCAGTCCGGCACACCGGTTGCCTACACGGATACTGAGACGGGCATCACGTTTGACACGTGGTCGGTACCTGCTGGTACGGGTACGGGTGGTCTCGTCTTCGGTGTAGCCCTGCCGGGTTCGGCATTGACCACCGATGCGACGGAGTTTATCGGTTACCTGGTGAGGATCTCGAGCTAATCATGACCGCTCTGAAGTGGCGCTAAACGTTCTAATGTTTCAAGCAATGTGCGTCCCAAAATGCCTCGTCCGCTGGCTGGTGTGGCATTTCCTTGGGTGGTGGCATGAACAACAATCTCTTGTTCTTGGCCTATCCGTACGAGGATACCATCTTGACCTCCCTGCGATTCGGCTCGGGCTATAGCATGCCCGGGGTCTATACCGGCAATGCCAACGTCACCCAGATTTCTTCAAGCATCAATGCCACTCACTTTACGTTGCTTTTCCGTTGCGAGAATTGTCTGACCTGGGACCAAGATGGTCAAACCGGAAACGCGACCACAAGCAAGGGTAGGTTAGTCCTGGGATGGGCACAGTCTACGGAGAGCCCGTCGAACCCGTCCTGTCCGGACAATATCAGCCTGGCGCAGCACGACAACCAGGGTATTATCTCAGCCACTCTGGATGAGAATGCAGCCAGTGAGTCCTACGAGGACTGGGTCAAGTTGGCTAATAAGACTGTTCCCGGGGACTGCTCCGGTGACGGTGGTGGCGGCAACGAGCCGACTCCTGTCCCTGTCCCTGACGGTGGCGGTGGACGCCATAAGCGC |
| 5 | Showing nucleotide sequence encoding CDHcytbkexmut2 | ATGAAGCTCGTTAACCGTTTGCTCGCTTCATTCCTGTCAGCGAGCACCGGTGAGTGGTGGCCTATCGAGCTAATGTTGCTTCTCTTCGTCTGACTTTTCTTGGCAGTGTTGCAGTCATGCTGGGCTCAGTCCGGCACACCGGTTGCCTACACGGATACTGAGACGGGCATCACGTTTGACACGTGGTCGGTACCTGCTGGTACGGGTACGGGTGGTCTCGTCTTCGGTGTAGCCCTGCCGGGTTCGGCATTGACCACCGATGCGACGGAGTTTATCGGTTACCTGGTGAGGATCTCGAGCTAATCATGACCGCTCTGAAGTGGCGCTAAACGTTCTAATGTTTCAAGCAATGTGCGTCCCAAAATGCCTCGTCCGCTGGCTGGTGTGGCATTTCCTTGGGTGGTGGCATGAACAACAATCTCTTGTTCTTGGCCTATCCGTACGAGGATACCATCTTGACCTCCCTGCGATTCGGCTCGGGCTATAGCATGCCCGGGGTCTATACCGGCAATGCCAACGTCACCCAGATTTCTTCAAGCATCAATGCCACTCACTTTACGTTGCTTTTCCGTTGCGAGAATTGTCTGACCTGGGACCAAGATGGTCAAACCGGAAACGCGACCACAAGCAAGGGTAGGTTAGTCCTGGGATGGGCACAGTCTACGGAGAGCCCGTCGAACCCGTCCTGTCCGGACAATATCAGCCTGGCGCAGCACGACAACCAGGGTATTATCTCAGCCACTCTGGATGAGAATGCAGCCAGTGAGTCC |

TABLE-continued

| SEQ ID NO: | Description | Sequence |
|---|---|---|
| | | TACGAGGACTGGGTCAAGTTGGCTAATAAGACTGTTCCCGGGGACTGCTCCGGTG ACGGTGGTGGCGGCAACGAGCCGACTCCTGTCCCTGTCCCTGACGGTGGCGGTGG ACCCCATAAGCGC |
| 6 | Showing nucleotide sequence encoding CDHcytbkexmut3 | ATGAAGCTCGTTAACCGTTTGCTCGCTTCATTCCTGTCAGCGAGCACCGGTGAGT GGTGGCCTATCGAGCTAATGTTGCTTCTCTTCGTCTGACTTTTCTTGGCAGTGTT GCAGTCATGCTGGGCTCAGTCCGGCACACCGGTTGCCTACACGGATACTGAGACG GGCATCACGTTTGACACGTGGTCGGTACCTGCTGGTACGGGTACGGGTGGTCTCG TCTTCGGTGTAGCCCTGCCGGGTTCGGCATTGACCACCGATGCGACGGAGTTTAT CGGTTACCTGGTGAGGATCTCGAGCTAATCATGACCGCTCTGAAGTGGCGCTAAA CGTTCTAATGTTTCAAGCAATGTGCGTCCCAAAATGCCTCGTCCGCTGGCTGGTG TGGCATTTCCTTGGGTGGTGGCATGAACAACAATCTCTTGTTCTTGGCCTATCCG TACGAGGATACCATCTTGACCTCCCTGCGATTCGGCTCGGGCTATAGCATGCCCG GGGTCTATACCGGCAATGCCAACGTCACCCAGATTTCTTCAAGCATCAATGCCAC TCACTTTACGTTGCTTTTCCGTTGCGAGAATTGTCTGACCTGGGACCAAGATGGT CAAACCGGAAACGCGACCACAAGCAAGGGTAGGTTAGTCCTGGGATGGGCACAGT CTACGGAGAGCCCGTCGAACCCGTCCTGTCCGGACAATATCAGCCTGGCGCAGCA CGACAACCAGGGTATTATCTCAGCCACTCTGGATGAGAATGCAGCCAGTGAGTCC TACGAGGACTGGGTCAAGTTGGCTAATAAGACTGTTCCCGGGGACTGCTCCGGTG ACGGTGGTGGCGGCAACGAGCCGACTCCTGTCCCTGTCCCTGACGGTGGCGGTGG ACAACGCCTGGTCAAGCGC |
| 7 | Showing nucleotide sequence encoding CDHcytbkexmut4 | ATGAAGCTCGTTAACCGTTTGCTCGCTTCATTCCTGTCAGCGAGCACCGGTGAGT GGTGGCCTATCGAGCTAATGTTGCTTCTCTTCGTCTGACTTTTCTTGGCAGTGTT GCAGTCATGCTGGGCTCAGTCCGGCACACCGGTTGCCTACACGGATACTGAGACG GGCATCACGTTTGACACGTGGTCGGTACCTGCTGGTACGGGTACGGGTGGTCTCG TCTTCGGTGTAGCCCTGCCGGGTTCGGCATTGACCACCGATGCGACGGAGTTTAT CGGTTACCTGGTGAGGATCTCGAGCTAATCATGACCGCTCTGAAGTGGCGCTAAA CGTTCTAATGTTTCAAGCAATGTGCGTCCCAAAATGCCTCGTCCGCTGGCTGGTG TGGCATTTCCTTGGGTGGTGGCATGAACAACAATCTCTTGTTCTTGGCCTATCCG TACGAGGATACCATCTTGACCTCCCTGCGATTCGGCTCGGGCTATAGCATGCCCG GGGTCTATACCGGCAATGCCAACGTCACCCAGATTTCTTCAAGCATCAATGCCAC TCACTTTACGTTGCTTTTCCGTTGCGAGAATTGTCTGACCTGGGACCAAGATGGT CAAACCGGAAACGCGACCACAAGCAAGGGTAGGTTAGTCCTGGGATGGGCACAGT CTACGGAGAGCCCGTCGAACCCGTCCTGTCCGGACAATATCAGCCTGGCGCAGCA CGACAACCAGGGTATTATCTCAGCCACTCTGGATGAGAATGCAGCCAGTGAGTCC TACGAGGACTGGGTCAAGTTGGCTAATAAGACTGTTCCCGGGGACTGCTCCGGTG ACGGTGGTGGCGGCAACGAGCCGACTCCTGTCCCTGTCCCTGACGGTGGCGGTGG AGTCGCAGTCGAAAAGCGC |
| 8 | Showing nucleotide sequence encoding CDHall | ATGAAGCTCGTTAACCGTTTGCTCGCTTCATTCCTGTCAGCGAGCACCGGTGAGT GGTGGCCTATCGAGCTAATGTTGCTTCTCTTCGTCTGACTTTTCTTGGCAGTGTT GCAGTCATGCTGGGCTCAGTCCGGCACACCGGTTGCCTACACGGATACTGAGACG GGCATCACGTTTGACACGTGGTCGGTACCTGCTGGTACGGGTACGGGTGGTCTCG TCTTCGGTGTAGCCCTGCCGGGTTCGGCATTGACCACCGATGCGACGGAGTTTAT CGGTTACCTGGTGAGGATCTCGAGCTAATCATGACCGCTCTGAAGTGGCGCTAAA CGTTCTAATGTTTCAAGCAATGTGCGTCCCAAAATGCCTCGTCCGCTGGCTGGTG TGGCATTTCCTTGGGTGGTGGCATGAACAACAATCTCTTGTTCTTGGCCTATCCG TACGAGGATACCATCTTGACCTCCCTGCGATTCGGCTCGGGCTATAGCATGCCCG GGGTCTATACCGGCAATGCCAACGTCACCCAGATTTCTTCAAGCATCAATGCCAC TCACTTTACGTTGCTTTTCCGTTGCGAGAATTGTCTGACCTGGGACCAAGATGGT CAAACCGGAAACGCGACCACAAGCAAGGGTAGGTTAGTCCTGGGATGGGCACAGT CTACGGAGAGCCCGTCGAACCCGTCCTGTCCGGACAATATCAGCCTGGCGCAGCA CGACAACCAGGGTATTATCTCAGCCACTCTGGATGAGAATGCAGCCAGTGAGTCC TACGAGGACTGGGTCAAGTTGGCTAATAAGACTGTTCCCGGGGACTGCTCCGGTG ACGGTGGTGGCGGCAACGAGCCGACTCCTGTCCCTGTCCCTGACGGTGCTACATA CGACTATATTGTCGTCGGTGGAGGTGCCGGGGGTATCCCTGTCGCCGATCGGCTG AGTGAGGCTGGACACAGTGTTCTCCTGATCGAGAAAGGTCCTCCTTCCTCGGGAC GCTGGGGTGGCACCATGAAGCCCAGCTGGCTGGATGATACCAACCTGACGCGATT TGATGTCCCTGGGCTGTGCAACCAGATCTGGGTCGACTCCAACGGTATCGCCTGC AGTGACACCGATCAGATGGCAGGTTGTGTGCTGGGTGGAGGCACCGCCGTCAACG CAGGATTGTGGTGGAAGGTAAGCCGTGCCCAGATGCCATGTTCGGATCCATCACT GACAATGTCCAGCCAAATCCCGTTGACTGGGACTACAACTTCCCCGAGGGATGGC AGTCGTCCGACATGCAGGCTGCCGCGGACCGCGTGTTCTCGCGGATCCCTGGAAC CACAACCCCCTCCACCGATGGAAAGCTTTATTACCAACAAGGAGCCGATATACTG TTAAATGGCTTGCAATCCGCCGGATGGTCATCCGTCACCCTCAACGATGTCCCGG CCCAGAAAACCAAGACCTTTGGCCACGCACCATTCATGTTCTCTGGAGGTGAGCG CGGAGGGCCCATGGGACGTATCTGGTGTCGGCGAGCGAGAGAGATAATTTTGCC CGCTGGTCGAACACGACTGTGAAGAGGGTTGTTCGTGAAGGCGGACGTATCACCG GAGTTGAGGTCGAGGCGACCCTCGATGGTGGCTACGCGGGTACCGTCAATGTAAC TGCCAATACGGGTCGAGTCATTCTTTCTGCAGGAACTTTTGGAACGCCCAAGGTC CTTATGAGAAGTACGCTTCGTTGGATGATATTGTTAGGGAGTTATTGCTAATGGC GTATAGGTGGTATCGGCCCGAAGGACCAGCTGTCCATCGTGAAGAGCTCAACTGA TGGAGAGACAATGATTGCCGAATCTGAGTGGATCGAACTTCCGGTTGGCGAGAAC TTGGTCGATCATGTCAATGTGAGTGCCAAGTGGACCGGGGAGGCTACTACTATGC TAATAGGATGCTTACAGACTGATGTTGTGGTGACCCACCCTGATGTTGTCTTCTA |

TABLE-continued

| SEQ ID NO: | Description | Sequence |
|---|---|---|
| | | TGATTTCAAAGCGGCATACAAGACCCCCATCGAGAGTGATGCGACGAGCTATCTG<br>AGTATGTAGTAATGCTTCGAAGGACAGTCCAGCACTAACTTGCGTAGACGATCGC<br>ACCGGGATTTTCGCCCAGGCTGCGCCTAACATTGGTCCTATGTAAGTTGCCCGTC<br>TACCAAACACGTCATGGTACTAACGCCTGTAGAATCTTCGACGAAGTCACCGGCT<br>CTGATGGCATTAAACGACAGATACAGTGGACTGCTCGTGTGGAAGGCGGCCACGA<br>CACGCCTGACGACGTACGTTGACTCCTAAGTGAAAGATTAGTGCAATATATTAA<br>CCGTGCTGTAGACGCCATGACCATCAGCCAATACCTCGGCCGCGGCTCAACCTCG<br>CGTGGCCGCATGACCATTACCGCAGGACTGGACACGGTGGTCTCGACGCTGCCAT<br>TCCTACGGGACGAGAGCGACGTTAATGCTGTAATCCAGGGAATCCAGAACCTGAA<br>GATGGCCCTGAACGGGACAGGATTTACCTGGAACTACCCTGCTCGGAACACTTCC<br>ATTGCCGAGTTTGTCAATACTGTGAGTGCTGATTTCTGGAAGGATGTTCGACGTA<br>ACTGACACTGATAGATGCCAATCACTGCCGGAACACGCCGAGCTAATCACTGGAT<br>GGGTGAGTTATGAATCTGCTTTTTAAAATTTCGTCGCTAATTGTTATAGGAACCT<br>GCAAAATAGGTACAGATGATGGCCGTACTGGAGGTAGCGCCGTTGTTGATTTGAA<br>TACGAAGGTCTATGGAACGGACAACCTGTTCGTCGTGGATGCTAGTATCTTCCCG<br>GGTATGATCACGTCCAATCCTTCGGCTTACATTGTTACGGTCGCGGAGCATGCAG<br>CTGAAAAGATTCTTGCGCTGGGCGGTGGAGGCTCTAAGCGC |
| 9 | Showing nucleotide sequence encoding GlaBss | ATGCGGAACAACTTTCTTTTTTCCCTCAATGCCATTGCTGGCGCTGTCGCG |
| 10 | Showing nucleotide sequence encoding GlaB | ATGCGGAACAACTTTCTTTTTTCCCTCAATGCCATTGCTGGCGCTGTCGCGCATC<br>CGTCGTTCCCTGTCCATAAGAGGCAGTCGGATGTCAACGCCTTCATTGAGACACA<br>GACACCCATCGCCAAACAGGGCGTCCTCAATAATATCGGCGCTGATGGCAAGCTT<br>GTAGAGGGGGCTGCCGCGGGTATTGTTGTAGCCTCCCCATCCAAGAGTAATCCCG<br>ACTGTTCGTACAATCCTACCCTCTAAACCGCTTAATACGACCATAGAACTAATTA<br>TATTTAGACTTCTATACCTGGACGCGCGACGCTGGCCTCACCATGGAAGAAGTGA<br>TAGAGCAATTCATCGGGGGAGACGCGACTCTCGAGTCTACAATCCAGAATTATGT<br>TGACTCTCAAGCGAAGCAGCAGGCAGTCTCCAACCCATCAGGCAGCCTGTCGGAT<br>GGCTCGGGTCTTGCTGAACCCAAGTTTTACGTCAACATCTCTCAATTCACCGATT<br>CTTGGGGCCGACCCCAGCGCGACGGGCCAGCTTTACGTGCTTCCGCCTTGATCGC<br>ATATGGCAACTCCCTGATCGCCAGCGACAAGCAATCTGTTGTCAAAGCCAACATC<br>TGGCCAATTGTCCAGAATGACTTGTCTTACGTGGGTCAATACTGGAACCAGACCG<br>GGTTTGATCTTTGGGAAGAGGTTCAGGGCAGCTCCTTCTTCACTGTTGCTGTACA<br>GCACAAGGCCTTGGTGGAGGGCGACGCGTTTGCGAAGGCACTCGGAGAGGAATGC<br>CAGGCGTGCTCCGTGGCGCCGCAAATCCTCTGCCATCTTCAGGATTTCTGGAATG<br>GGTCCGCTGTTATTTCTAACTTACAAACCAGTGGGCGCAGTGGACTGGATGCCAA<br>CTCGCTTTTGGGTTCCATCCATACTTTTGACCCAGCTGCTGCTTGTGATGATACA<br>ACGTTCCAACCCTGCTCCTCTCGGGCTCTGTCAAACCATAAGCTTGTGGTGGACT<br>CTTTCCGGTCGGTCTACGGTATCAACAACGGACGTGGAGCAGGAAAGGCCGCAGC<br>AGTGGGCCGTTACGCAGAGGACACCTATCAGGGAGGCAATCCATGGTTGGTACTC<br>TGTCTCATTGATTCCAAGGCTAAACTAATGAATAATAGGTATCTTACCACTCTG<br>GTCGCTGCGGAATTGCTCTACGACGCCTTGTATCAATGGGACAAACAAGGTCAAG<br>TGAACGTCACCGAAACTTCCCTTCCCTTCTTCAAGGACCTCTCCAGCAATGTCAC<br>GACCGGATCCTACGCCAAGTCTTCCTCAGCCTACGAGTCCCTTACAAGCGCTGTC<br>AAGACCTACGCAGACGGCTTCATCTCCGTTGTCCAGGAGTATACTCCTGATGGCG<br>GTGCTCTGGCCGAGCAGTACAGTCGGGACCAGGGCACCCCAGTTTCGGCATCCGA<br>TCTGACTTGGTCTTATGCAGCTTTCTTGAGTGCTGTTGGGAGACGAAACGGCACT<br>GTCCCTGCTAGCTGGGGCTCTTCCACGGCCAACGCAGTTCCAAGCCAATGTTCGG<br>GGGGTACAGTTTCTGGAAGTTACACTACCCCAACTGTTGGGTCGTGGGCGGTGG<br>AGGCTCTAAGCGc |
| 11 | Showing nucleotide sequence encoding CelBss | ATGATCTGGACACTCGCTCCCTTTGTGGCACTCCTGCCACTGGTAACGGCT |
| 12 | Showing nucleotide sequence encoding CelB | ATGATCTGGACACTCGCTCCCTTTGTGGCACTCCTGCCACTGGTAACGGCTCAAC<br>AGGTGGGAACTACAGCGGACGCCCATCCCAGACTCACCACGTATAAATGTACTTC<br>ACAGAACGGCTGCACGAGGCAGAACACCTCAGTCGTCCTTGATGCAGCAACCCAT<br>TTTATCCACAAAAAAGGAACACAAACATCCTGCACCAACAGCAACGGCTTGGACA<br>CTTCCATTTGTCCGGACAAACAGACCTGCGCGGACAACTGTGTCGTTGATGGGAT<br>CACGGACTACGCTAGCTACGGCGTCCAGACGAAGAATGACACATTGACCCTTCAC<br>CAATATCTGCAAACTGGCAATGAAACAAAGTCCGTGTCACCGCGTGTCTACCTCC<br>TCGCTGAAGACGGAGAGAACTATTCCATGCTGCAACTCCTGAATCAGGAATTCAC<br>CTTCGATGTCGACGCCTCTACCCTCGTCTGCGGCATGAATGGTGCTCTATATCTC<br>TCTGAAATGGAGGCTTCGGGCGGAAAGAGTTCCCTAAATCAAGCGGGAGCCAAAT<br>ACGGAACCGGTTACTGTGATGCCCAATGCTACACCACGCCTTGGATCAACGGCGA<br>AGGCAACACCGAGAGTGTCGGCTCCTGCTGTCAGGAAATGGATATTTGGGAAGCC<br>AACGCCCGAGCAACAGGGCTTACACCGCACCCTTGCAACACAACCGGTTTGTACG<br>AGTGCAGCGGCTCGGGATGCGGAGACTCCGGGGTCTGTGACAAGTCCGGCTGTGG<br>ATTCAACCCATATGGCCTAGGTGCAAAGGACTACTACGGTTACGGCCTCAAGGTC<br>AACACCAACGAGACATTCACGGTCGTAACCCAGTTCCTCACAAGCGATAACACGA<br>CATCGGGCCAGCTCAGCGAAATCCGCCGTCTCTACATCCAGAACGGCCAGGTTAT<br>TCAAAATGCTGCCGTCACCTCAGGAGGAAAAACTGTCGACTCAATCACAAAGGAT<br>TTCTGCAGCGGTGAAGGAAGTGCCCTTCAACCGACTTGGCGGCCTCGAGGAAATGG |

TABLE-continued

| SEQ ID NO: | Description | Sequence |
|---|---|---|
| | | GCCACGCCTTGGGCCGCGGCATGGTTCTTGCGCTCAGTGTCTGGAACGACGCAGG<br>CTCATTCATGCAATGGCTTGATGGGGGCAGCGCAGGACCGTGCAGCGCGACGGAG<br>GGAGACCCGGCGTTGATCGAGAAGTTGTATCCGGATACTCATGTGAAGTTTTCCA<br>AGATCCGGTGGGAGATATTGGATCTACCTACAGGCATGGCGGTGGAGGCTCTAA<br>GCGC |
| 13 | Showing nucleotide sequence encoding SKIK_CDHss | ATGTCCAAGATCAAGAAGCTCGTTAACCGTTTGCTCGCTTCATTCCTGTCAGCGA<br>GCACCGGTGAGTGGTGGCCTATCGAGCTAATGTTGCTTCTCTTCGTCTGACTTTT<br>CTTGGCAGTGTTGCAGTCATGCTGGGCT |
| 14 | Showing nucleotide sequence encoding AsAP1ss54 | ATGAGGTTCCTCTCAATTGTAGGTGCGGCGCTCTTCGCTTCCAGCGCTGTTGCC |
| 15 | Showing nucleotide sequence encoding AsAP3ss72 | ATGCATATCCGCACTGCCATCACCGCGGGCGCGGCCCTTGTCCAGACTGCAGTTG<br>CAGCTTCTGTTCAGGCA |
| 16 | Showing amino acid sequence of bIap IVss | MQWACVLLLLGLWLQLSLT |
| 17 | Showing amino acid sequence of CDHss | MKLVNRLLASFLSASTVLQSCWA |
| 18 | Showing amino acid sequence of CDHcytbkex | MKLVNRLLASFLSASTVLQSCWAQSGTPVAYTDTETGITFDTWSVPAGTGTGGLV<br>FGVALPGSALTTDATEFIGYLQCASQNASSAGWCGISLGGGMNNNLLFLAYPYED<br>TILTSLRFGSGYSMPGVYTGNANVTQISSSINATHFTLLFRCENCLTWDQDGQTG<br>NATTSKGRLVLGWAQSTESPSNPSCPDNISLAQHDNQGIISATLDENAASESYED<br>WVKLANKTVPGDCSGDGGGGNEPTPVPVPDGGGGGSKR |
| 19 | Showing amino acid sequence of CDHcytbkexmut1 | MKLVNRLLASFLSASTVLQSCWAQSGTPVAYTDTETGITFDTWSVPAGTGTGGLV<br>FGVALPGSALTTDATEFIGYLQCASQNASSAGWCGISLGGGMNNNLLFLAYPYED<br>TILTSLRFGSGYSMPGVYTGNANVTQISSSINATHFTLLFRCENCLTWDQDGQTG<br>NATTSKGRLVLGWAQSTESPSNPSCPDNISLAQHDNQGIISATLDENAASESYED<br>WVKLANKTVPGDCSGDGGGGNEPTPVPVPDGGGGRHKR |
| 20 | Showing amino acid sequence of CDHcytbkexmut2 | MKLVNRLLASFLSASTVLQSCWAQSGTPVAYTDTETGITFDTWSVPAGTGTGGLV<br>FGVALPGSALTTDATEFIGYLQCASQNASSAGWCGISLGGGMNNNLLFLAYPYED<br>TILTSLRFGSGYSMPGVYTGNANVTQISSSINATHFTLLFRCENCLTWDQDGQTG<br>NATTSKGRLVLGWAQSTESPSNPSCPDNISLAQHDNQGIISATLDENAASESYED<br>WVKLANKTVPGDCSGDGGGGNEPTPVPVPDGGGGPHKR |
| 21 | Showing amino acid sequence of CDHcytbkexmut3 | MKLVNRLLASFLSASTVLQSCWAQSGTPVAYTDTETGITFDTWSVPAGTGTGGLV<br>FGVALPGSALTTDATEFIGYLQCASQNASSAGWCGISLGGGMNNNLLFLAYPYED<br>TILTSLRFGSGYSMPGVYTGNANVTQISSSINATHFTLLFRCENCLTWDQDGQTG<br>NATTSKGRLVLGWAQSTESPSNPSCPDNISLAQHDNQGIISATLDENAASESYED<br>WVKLANKTVPGDCSGDGGGGNEPTPVPVPDGGGGQRLVKR |
| 22 | Showing amino acid sequence of CDHcytbkexmut4 | MKLVNRLLASFLSASTVLQSCWAQSGTPVAYTDTETGITFDTWSVPAGTGTGGLV<br>FGVALPGSALTTDATEFIGYLQCASQNASSAGWCGISLGGGMNNNLLFLAYPYED<br>TILTSLRFGSGYSMPGVYTGNANVTQISSSINATHFTLLFRCENCLTWDQDGQTG<br>NATTSKGRLVLGWAQSTESPSNPSCPDNISLAQHDNQGIISATLDENAASESYED<br>WVKLANKTVPGDCSGDGGGGNEPTPVPVPDGGGGVAVEKR |
| 23 | Showing amino acid sequence of CDHall | MKLVNRLLASFLSASTVLQSCWAQSGTPVAYTDTETGITFDTWSVPAGTGTGGLV<br>FGVALPGSALTTDATEFIGYLQCASQNASSAGWCGISLGGGMNNNLLFLAYPYED<br>TILTSLRFGSGYSMPGVYTGNANVTQISSSINATHFTLLFRCENCLTWDQDGQTG<br>NATTSKGRLVLGWAQSTESPSNPSCPDNISLAQHDNQGIISATLDENAASESYED<br>WVKLANKTVPGDCSGDGGGGNEPTPVPVPDGATYDYIVVGGGAGGIPVADRLSEA<br>GHSVLLIEKGPPSSGRWGGTMKPSWLDDTNLTRFDVPGLCNQIWVDSNGIACSDT<br>DQMAGCVLGGGTAVNAGLWWKPNPVDWDYNFPEGWQSSDMQAAADRVFSRIPGTT<br>TPSTDGKLYYQQGADILLNGLQSAGWSSVTLNDVPAQKTKTFGHAPFMFSGGERG<br>GPMGTYLVSASERDNFARWSNTTVKRVVREGGRITGVEVEATLDGGYAGTVNVTA<br>NTGRVILSAGTFGTPKVLMRSGIGPKDQLSIVKSSTDGETMIAESEWIELPVGEN<br>LVDHVNTDVVVTHPDVVFYDFKAAYKTPIESDATSYLNDRTGIFAQAAPNIGPII<br>FDEVTGSGDGIKRQTQWTARVEGGHDTPDGHAMTISQYLGRGSTSRGRMTITAGLD<br>TVVSTLPFLRDESDVNAVIQGIQNLKMALNGTGFTWNYPARNTSIAEFVNTMPIT<br>AGTRRANHWMGTCKIGTDDGRTGGSAVVDLNTKVYGTDNLFVVDASIFPGMITSN<br>PSAYIVTVAEHAAEKILALGGGGSKR |
| 24 | Showing amino acid sequence of GlaBss | MRNNFLFSLNATAGAVA |

TABLE-continued

| SEQ ID NO: | Description | Sequence |
|---|---|---|
| 25 | Showing amino acid sequence of GlaB | MRNNLLFSLNATAGAVAHPSFPIHKRQSDLNAFIEAQTPIAKQGVLNNIGADGKL VEGAAAGIVVASPSKSNPDYFYTWTRDAGLTMEEVIEQFIGGDATLESTIQNYVD SQANEQAVSNPSGGLSDGSGLAEPKFYVNISQFTDSWGRPQRDGPALRASALIAY GNSLISSDKQSVVKANIWPIVQNDLSYVGQYWNQTGFDLWEEVQGSSFFTVAVQH KALVEGDAFAKALGEECQACSVAPQILCHLQDFWNGSAVLSNLPTNGRSGLDTNS LLGSIHTFDPAAACDDTTFQPCSSRALSNHKLVVDSFRSVYGINNGRGAGKAAAV GPYAEDTYQGGNPWYLTTLVAAELLYDALYQWDKQGQVNVTETSLPFFKDLSSNV TTGSYAKSSSAYESLTSAVKTYADGFISVVQEYTPDDGALAEQYSRDQGTPVSAS DLTWSYAAFLSAVGRRNGTVPASWGSSTANAVPSQCSGGTVSGSYTTPTVGSWGG GGSKR |
| 26 | Showing amino acid sequence of CelBss | MIWTLAPFVALLPLVTA |
| 27 | Showing amino acid sequence of CelB | MIWTLAPFVALLPLVTAQQVGTTADAHPRLTTYKCTSQNGCTRQNTSVVLDAATH FIHKKGTQTSCTNSNGLDTSICPDKQTCADNCVVDGITDYASYGVQTKNDTLTLH QYLQTGNETKSVSPRVYLLAEDGENYSMLQLLNQEFTFDVDASTLVCGMNGALYL SEMEASGGKSSLNQAGAKYGTGYCDAQCYTTPWINGEGNTESVGSCCQEMDIWEA NARATGLTPHPCNTTGLYECSGSGCGDSGVCDKSGCGFNPYGLGAKDYYGYGLKV NTNETFTVVTQFLTSDNTTSGQLSEIRRLYIQNGQVIQNAAVTSGGKTVDSITKD FCSGEGSAFNRLGGLEEMGHALGRGMVLALSVWNDAGSFMQWLDGGSAGPCSATE GDPALIEKLYPDTHVKFSKIRWGDIGSTYRHGGGGSKR |
| 28 | Showing amino acid sequence of SKIK_CDHss | MSKIKKLVNRLLASFLSASTVLQSCWA |
| 29 | Showing amino acid sequence of AsAP1ss54 | MRFLSIVGAALFASSAVA |
| 30 | Showing amino acid sequence of ASAP3ss72 | MHIRTAITAGAALVQTAVAASVQA |
| 31 | Showing amino acid sequence of ALP II free of secretion signal and C-terminus signal | LIPAEEENPAFWNRQAAQALDVAKKLQPIQTAAKNVILFLGDGMGVPTVTATRIL KGQMNGKLGPETPLAMDQFPYVALSKTYNVDRQVPDSAGTATAYLCGVKGNYRTI GVSAAARYNQCNTTRGNEVTSVINRAKKAGKAVGVVTTTRVQHASPAGAYAHTVN RNWYSDADLPADAQKNGCQDIAAQLVYNMDIDVILGGGRMYMFPEGTPDPEYPDD ASVNGVRKDKQNLVQEWQAKHQGAQYVWNRTALLQAADDSSVTHLMGLFEPADMK YNVQQDHTKDPTLAEMTEAALQVLSRNPRGFYLFVEGGRIDHGHHDGKAYMALTE AIMFDNAIAKANELTSELDTLILVTADHSHVFSFGGYTLRGTSIFGLAPGKALDS KSYTSILYGNGPGYALGGGSRPDVNGSTSEEPSYRQQAAVPLASETHGGEDVAVF ARGPQAHLVHGVQEETFVAHIMAFAGCVEPYTDCNLPAPA |
| 32 | Showing amino acid sequence of ALP IV free of secretion signal and C-terminus signal | FIPAEEEDPAFWNRQAAQALDVAKKLQPIQTAAKNVILFLGDGMGVPTVTATRIL KGQMNGKLGPETPLAMDQFPYVALSKTYNVDRQVPDSAGTATAYLCGVKGNYKTI GVSAAARYNQCNTTSGNEVTSVMNRAKKAGKSVGVVTTSRVQHASPAGAYAHTVN RNWYSDADLPADAQTYGCQDIATQLVNNMDIDVILGGGRMYMFPEGTPDPEYPYD VNQTGVRKDKRNLVQEWQAKHQGAQYVWNRTELLQAANDPSVTHLMGLFEPADMK YNVQQDPTKDPTLEEMTEAALQVLSRNPQGFYLFVEGGRIDHGHHEGKAYMALTD TVMFDNAIAKANELTSELDTLILATADHSHVFSFGGYTLRGTSIFGLAPSKASDN KSYTSILYGNGPGYVLGGGLRPDVNDSISEDPSYRQQAAVPLSSESHGGEDVAVF ARGPQAHLVHGVQEETFVAHVMAFAGCVEPYTDCNLPAPSG |
| 33 | Showing nucleotide sequence encoding ALP II | CTCATCCCAGCTGAAGAGGAAAACCCGGCCTTCTGGAACAGGCAGGCTGCCCAAG CTCTGGACGTGGCCAAGAAGCTCCAGCCTATCCAAACGGCCGCTAAGAACGTCAT CCTCTTCTTGGGAGATGGCATGGGCGTGCCAACAGTCACTGCCACTCGTATCCTT AAGGGCCAAATGAACGGAAAGTTGGGCCCAGAGACTCCTCTGGCTATGGACCAGT TCCCATACGTGGCCCTGTCGAAGACATACAACGTTGACCGTCAAGTGCCGGATTC CGCTGGAACAGCCACCGCTTACCTCTGCGGCGTCAAGGGAAACTACCGCACAATC GGCGTTTCCGCTGCCGCTAGGTACAACCAGTGTAACACCACTAGAGGAAACGAGG TTACCTCTGTGATCAACCGTGCTAAGAAGGCTGGCAAGGCCGTTGGCGTGGTCAC AACCACTAGAGTGCAGCACGCTTCTCCCGCCGGTGCTTACGCCCACACCGTCAAC CGCAACTGGTACAGCGACGCCGATCTGCCTGCTGACGCCCAGAAGAACGGCTGCC AAGACATCGCCGCTCAGTTGGTCTACAACATGGACATCGATGTTATCCTGGGAGG TGGCAGGATGTACATGTTCCCCGAGGGAACTCCCGACCCTGAATACCCTGACGAT GCTTCCGTCAACGGTGTTAGAAAGGATAAGCAGAACCTGGTCCAGGAGTGGCAAG CTAAGCACCAGGGAGCCCAATACGTTTGGAACCGTACAGCTCTGCTCCAGGCCGC TGACGATTCCTCTGTGACCCACTTGATGGGTCTGTTCGAACCGCTGACATGAAG TACAACGTCCAGCAAGACCACACTAAAGATCCTACACTGGCCGAGATGACTGAAG CCGCTCTCCAGGTTTTGTCCCGTAACCCCCGTGGTTTCTACCTCTTCGTGGAGGG AGGTCGCATCGACCACGGTCACCACGACGGCAAGGCTTACATGGCTTTGACAGAA GCTATCATGTTCGACAACGCTATCGCCAAGGCTAACGAGCTGACAAGCGAACTCG ACACCCTGATCCTCGTGACTGCCGATCACTCCCACGTCTTCTCTTTCGGCGGATA |

TABLE-continued

| SEQ ID NO: | Description | Sequence |
|---|---|---|
| | | CACCCTGAGGGGCACTTCAATCTTCGGCCTCGCTCCTGGAAAGGCCTTGGACTCT AAGAGCTACACCTCAATCCTGTACGGAAACGGTCCCGGCTACGCTCTCGGTGGCG GATCGAGGCCTGACGTGAACGGTTCAACTAGTGAGGAACCAAGCTACAGACAGCA AGCCGCTGTCCCGTTGGCCTCAGAGACTCACGGTGGCGAAGACGTTGCTGTGTTC GCCCGTGGTCCACAAGCTCACCTGGTGCACGGCGTCCAGGAAGAAACCTTCGTGG CCCACATCATGGCCTTCGCTGGTTGTGTCGAGCCTTACACCGACTGCAACCTCCC AGCCCCAGCC |
| 34 | Showing nucleotide sequence encoding ALP IV | TTCATCCCAGCTGAGGAAGAGGATCCTGCTTTCTGGAACCGTCAGGCTGCTCAGG CTCTTGACGTTGCCAAGAAGTTGCAGCCAATCCAGACCGCCGCTAAGAATGTCAT CCTCTTCCTGGGCGATGGTATGGGAGTCCCGACCGTGACTGCTACCCGCATCCTC AAGGGCCAGATGAATGGAAAGCTCGGCCCAGAAACCCCGCTGGCTATGGACCAGT TCCCTTACGTGGCCCTGTCGAAGACTTATAACGTTGATCGTCAAGTCCCTGACTC TGCTGGTACTGCTACCGCCTACCTTTGCGGTGTGAAGGGAAATTATAAGACCATC GGCGTTTCCGCCGCTGCCCGGTATAACCAGTGTAATACCACTTCTGGTAACGAGG TTACTAGCGTCATGAATCGGGCTAAGAAGGCCGGCAAGTCTGTTGGTGTCGTGAC CACTTCGCGCGTCCAGCATGCTTCCCCTGCTGGAGCCTACGCTCACACCGTCAAC CGCAATTGGTATAGCGATGCTGACCTGCCCGCCGATGCTCAGACCTACGGCTGCC AGGACATCGCCACTCAGCTCGTCAACAATATGGATATCGACGTGATCCTGGGAGG CGGTCGTATGTATATGTTCCCTGAAGGTACCCCTGATCCCGAGTACCCCTATGAC GTGAACCAGACTGGAGTTCGGAAGGACAAGCGCAATCTTGTGCAGGAATGGCAGG CTAAGCATCAGGGTGCCCAGTACGTTTGGAACCGCACCGAGCTCCTGCAGGCTGC CAATGATCCATCGGTCACTCACCTCATGGGACTGTTCGAACCGGCCGACATGAAG TATAACGTGCAGCAGGATCCTACTAAGGACCCCACCCCTTGAAGAGATGACCGAGG CTGCCCTTCAGGTTTTGTCCCGGAATCCACAGGGCTTCTACTTGTTCGTCGAGGG CGGCCGCATCGATCATGGACATCACGAGGGCAAGGCTTATATGGCCCTCACTGAT ACCGTTATGTTCGACAACGCCATCGCTAAGGCCAATGAACTCACTTCGGAGCTGG ATACCCTTATCTTGGCTACTGCCGACCATTCGCACGTCTTCTCCTTCGGTGGATA CACTCTTCGTGGTACCTCCATCTTCGGATTGGCTCCTTCCAAGGCCTCTGACAAC AAGAGCTACACCTCGATCCTGTATGGCAATGGTCCTGGATACGTCCTTGGCGGTG GATTGCGTCCCGATGTGAACGACAGCATCTCGGAGGATCCATCTTATCGGCAGCA GGCTGCCGTCCCGTTGTCCTCTGAAAGCCATGGCGGTGAGGATGTGGCTGTTTTC GCTCGTGGACCACAGGCTCATTTGGTGCACGCGTTCAGGAAGAGACCTTCGTCG CCCACGTGATGGCTTTTGCGGGTTGCGTTGAGCCCTATACTGACTGTAACTTGCC AGCCCCTTCGGGT |
| 35 | Showing nucleotide sequence encoding AP IIss | ATGCAAGGTGCTTGTGTTTTATTACTTCTTGGTTTACATTTACAATTATCTTTAG GT |
| 36 | Showing amino acid sequence of AP IIss | MQGACVLLLLGLHLQLSLG |
| 37 | Showing nucleotide sequence of CDHss-bIAP II | ATGAAACTTGTCAACCGTCTGCTGGCTTCGTTCTTGTCCGCATCCACCGTTCTCC AGTCGTGCTGGGCTCTCATCCCAGCTGAAGAGGAAAACCCGGCCTTCTGGAACAG GCAGGCTGCCCAAGCTCTGGACGTGGCCAAGAAGCTCCAGCCTATCCAAACGGCC GCTAAGAACGTCATCCTCTTCTTGGGAGATGGCATGGGCGTGCCAACAGTCACTG CCACTCGTATCCTTAAGGGCCAAATGAACGGAAAGTTGGGCCCAGAGACTCCTCT GGCTATGGACCAGTTCCCATACGTGGCCCTGTCGAAGACATACAACGTTGACCGT CAAGTGCCGGATTCCGCTGGAACAGCCACCGCTTACCTCTGCGGCGTCAAGGGAA ACTACCGCACAATCGGCGTTTCCGCTGCCGCTAGGTACAACCAGTGTAACACCAC TAGAGGAAACGAGGTTACCTCTGTGATCAACCGTGCTAAGAAGGCTGGCAAGGCC GTTGGCGTGGTCACAACCACTAGAGTGCAGCACGCTTCTCCCGCCGGTGCTTACG CCCACACCGTCAACCGCAACTGGTACAGCGACGCCGATCTGCCTGCTGACGCCCA GAAGAACGGCTGCCAAGACATCGCCGCTCAGTTGGTCTACAACATGGACATCGAT GTTATCCTGGGAGGTGGCAGGATGTACATGTTCCCCGAGGGAACTCCCGACCCTG AATACCCTGACGATGCTTCCGTCAACGGTGTTAGAAAGGATAAGCAGAACCTGGT CCAGGAGTGGCAAGCTAAGCACCAGGGAGCCCAATACGTTTGGAACCGTACAGCT CTGCTCCAGGCCGCTGACGATTCCTCTGTGACCCACTTGATGGGTCTGTTCGAAC CCGCTGACATGAAGTACAACGTCCAGCAAGACCACACTAAAGATCCTACACTGGC CGAGATGACTGAAGCCGCTCTCCAGGTTTTGTCCCGTAACCCCCGTGGTTTCTAC CTCTTCGTGGAGGGAGGTCGCATCGACCACGGTCACCACGACGGCAAGGCTTACA TGGCTTTGACAGAAGCTATCATGTTCGACAACGCTATCGCCAAGGCTAACGAGCT GACAAGCGAACTCGACACCCTGATCCTCGTGACTGCCGATCACTCCCACGTCTTC TCTTTCGGCGGATACACCCTGAGGGGCACTTCAATCTTCGGCCTCGCTCCTGGAA AGGCCTTGGACTCTAAGAGCTACACCTCAATCCTGTACGGAAACGGTCCCGGCTA CGCTCTCGGTGGCGGATCGAGGCCTGACGTGAACGGTTCAACTAGTGAGGAACCA AGCTACAGACAGCAAGCCGCTGTCCCGTTGGCCTCAGAGACTCACGGTGGCGAAG ACGTTGCTGTGTTCGCCCGTGGTCCACAAGCTCACCTGGTGCACGGCGTCCAGGA AGAAACCTTCGTGGCCCACATCATGGCCTTCGCTGGTTGTGTCGAGCCTTACACC GACTGCAACCTCCCAGCCCCAGCC |
| 38 | Showing nucleotide sequence of Talp1F | GTACCAGGAGTACATTGGAGAGTTCTAC |

| SEQ ID NO: | Description | Sequence |
|---|---|---|
| 39 | Showing nucleotide sequence of Ptef-1R | TTTGAAGGTGGTGCGAACTTTGTAG |
| 40 | Showing nucleotide sequence of Ptef-CIAP IIFw | cgcaccaccttcaaaATGAAACTTGTCAAC |
| 41 | Showing nucleotide sequence of Talp-CIAP IIRv | atgtactcctggtacCTAGGCTGGGGCTGG |
| 42 | Showing nucleotide sequence of pΔ1Fw | AGGTACAACCAGTGTCAGACCACTAGAGGA |
| 43 | Showing nucleotide sequence of pΔ1Rv | ACACTGGTTGTACCTAGCGGCAG |
| 44 | Showing nucleotide sequence of pΔ1kFw | AGGTACAACCAGTGTAAGACCACTAGAGGA |
| 45 | Showing nucleotide sequence of pΔ1kRv | ACACTGGTTGTACCTAGCGGCAG |
| 46 | Showing nucleotide sequence of pΔ13Fw | TCGAGGCCTGACGTGCAGGGTTCAACTAGT |
| 47 | Showing nucleotide sequence of pΔ13Rv | CACGTCAGGCCTCGATCCGCCACC |
| 48 | Showing nucleotide sequence of PΔ1k3Fw | TCGAGGCCTGACGTGCAGGGTTCAACTAGT |
| 49 | Showing nucleotide sequence of PΔ1k3Rv | CACGTCAGGCCTCGATCCGCCACC |
| 50 | Showing nucleotide sequence of DNA construct Δ1 | ATGAAACTTGTCAACCGTCTGCTGGCTTCGTTCTTGTCCGCATCCACCGTTCTCC AGTCGTGCTGGGCTCTCATCCCAGCTGAAGAGGAAAACCCGGCCTTCTGGAACAG GCAGGCTGCCCAAGCTCTGGACGTGGCCAAGAAGCTCCAGCCTATCCAAACGGCC GCTAAGAACGTCATCCTCTTCTTGGGAGATGGCATGGGCGTGCCAACAGTCACTG CCACTCGTATCCTTAAGGGCCAAATGAACGGAAAGTTGGGCCCAGAGACTCCTCT GGCTATGGACCAGTTCCCATACGTGGCCCTGTCGAAGACATACAACGTTGACCGT CAAGTGCCGGATTCCGCTGGAACAGCCACCGCTTACCTCTGCGGCGTCAAGGGAA ACTACCGCACAATCGGCGTTTCCGCTGCCGCTAGGTACAACCAGTGTCAGACCAC TAGAGGAAACGAGGTTACCTCTGTGATCAACCGTGCTAAGAAGGCTGGCAAGGCC GTTGGCGTGGTCACAACCACTAGAGTGCAGCACGCTTCTCCCGCCGGTGCTTACG CCCACACCGTCAACCGCAACTGGTACAGCGACGCCGATCTGCCTGCTGACGCCCA GAAGAACGGCTGCCAAGACATCGCCGCTCAGTTGGTCTACAACATGGACATCGAT GTTATCCTGGGAGGTGGCAGGATGTACATGTTCCCCGAGGGAACTCCCGACCCTG AATACCCTGACGATGCTTCCGTCAACGGTGTTAGAAAGGATAAGCAGAACCTGGT CCAGGAGTGGCAAGCTAAGCACCAGGGAGCCCAATACGTTTGGAACCGTACAGCT CTGCTCCAGGCCGCTGACGATTCCTCTGTGACCCACTTGATGGGTCTGTTCGAAC CCGCTGACATGAAGTACAACGTCCAGCAAGACCACACTAAAGATCCTACACTGGC CGAGATGACTGAAGCCGCTCTCCAGGTTTTGTCCCGTAACCCCCGTGGTTTCTAC CTCTTCGTGGAGGGAGGTCGCATCGACCACGGTCACCACGACGGCAAGGCTTACA TGGCTTTGACAGAAGCTATCATGTTCGACAACGCTATCGCCAAGGCTAACGAGCT GACAAGCGAACTCGACACCCTGATCCTCGTGACTGCCGATCACTCCCACGTCTTC TCTTTCGGCGGATACACCCTGAGGGGCACTTCAATCTTCGGCCTCGCTCCTGGAA AGGCCTTGGACTCTAAGAGCTACACCTCAATCCTGTACGAAACGGTCCCGGCTA CGCTCTCGGTGGCGGATCGAGGCCTGACGTGAACGGTTCAACTAGTGAGGAACCA AGCTACAGACAGCAAGCCGCTGTCCCGTTGGCCTCAGAGACTCACGGTGGCGAAG ACGTTGCTGTGTTCGCCCGTGGTCCACAAGCTCACCTGGTGCACGGCGTCCAGGA AGAAACCTTCGTGGCCCACATCATGGCCTTCGCTGGTTGTGTCGAGCCTTACACC GACTGCAACCTCCCAGCCCCAGCCTAG |
| 51 | Showing nucleotide sequence of DNA construct Δ1k | ATGAAACTTGTCAACCGTCTGCTGGCTTCGTTCTTGTCCGCATCCACCGTTCTCC AGTCGTGCTGGGCTCTCATCCCAGCTGAAGAGGAAAACCCGGCCTTCTGGAACAG GCAGGCTGCCCAAGCTCTGGACGTGGCCAAGAAGCTCCAGCCTATCCAAACGGCC GCTAAGAACGTCATCCTCTTCTTGGGAGATGGCATGGGCGTGCCAACAGTCACTG CCACTCGTATCCTTAAGGGCCAAATGAACGGAAAGTTGGGCCCAGAGACTCCTCT GGCTATGGACCAGTTCCCATACGTGGCCCTGTCGAAGACATACAACGTTGACCGT CAAGTGCCGGATTCCGCTGGAACAGCCACCGCTTACCTCTGCGGCGTCAAGGGAA ACTACCGCACAATCGGCGTTTCCGCTGCCGCTAGGTACAACCAGTGTAAGACCAC TAGAGGAAACGAGGTTACCTCTGTGATCAACCGTGCTAAGAAGGCTGGCAAGGCC |

| SEQ ID NO: | Description | Sequence |
|---|---|---|
| | | GTTGGCGTGGTCACAACCACTAGAGTGCAGCACGCTTCTCCCGCCGGTGCTTACG<br>CCCACACCGTCAACCGCAACTGGTACAGCGACGCCGATCTGCCTGCTGACGCCCA<br>GAAGAACGGCTGCCAAGACATCGCCGCTCAGTTGGTCTACAACATGGACATCGAT<br>GTTATCCTGGGAGGTGGCAGGATGTACATGTTCCCCGAGGGAACTCCCGACCCTG<br>AATACCCTGACGATGCTTCCGTCAACGGTGTTAGAAAGGATAAGCAGAACCTGGT<br>CCAGGAGTGGCAAGCTAAGCACCAGGGAGCCCAATACGTTTGGAACCGTACAGCT<br>CTGCTCCAGGCCGCTGACGATTCCTCTGTGACCCACTTGATGGGTCTGTTCGAAC<br>CCGCTGACATGAAGTACAACGTCCAGCAAGACCACACTAAAGATCCTACACTGGC<br>CGAGATGACTGAAGCCGCTCTCCAGGTTTTGTCCCGTAACCCCCGTGGTTTCTAC<br>CTCTTCGTGGAGGGAGGTCGCATCGACCACGGTCACCACGACGGCAAGGCTTACA<br>TGGCTTTGACAGAAGCTATCATGTTCGACAACGCTATCGCCAAGGCTAACGAGCT<br>GACAAGCGAACTCGACACCCTGATCCTCGTGACTGCCGATCACTCCCACGTCTTC<br>TCTTTCGGCGGATACACCCTGAGGGGCACTTCAATCTTCGGCCTCGCTCCTGGAA<br>AGGCCTTGGACTCTAAGAGCTACACCTCAATCCTGTACGGAAACGGTCCCGGCTA<br>CGCTCTCGGTGGCGGATCGAGGCCTGACGTGAACGGTTCAACTAGTGAGGAACCA<br>AGCTACAGACAGCAAGCCGCTGTCCCGTTGGCCTCAGAGACTCACGGTGGCGAAG<br>ACGTTGCTGTGTTCGCCCGTGGTCCACAAGCTCACCTGGTGCACGGCGTCCAGGA<br>AGAAACCTTCGTGGCCCACATCATGGCCTTCGCTGGTTGTGTCGAGCCTTACACC<br>GACTGCAACCTCCCAGCCCCAGCCTAG |
| 52 | Showing nucleotide sequence of DNA construct Δ13 | ATGAAACTTGTCAACCGTCTGCTGGCTTCGTTCTTGTCCGCATCCACCGTTCTCC<br>AGTCGTGCTGGGCTCTCATCCCAGCTGAAGAGGAAAACCCGGCCTTCTGGAACAG<br>GCAGGCTGCCCAAGCTCTGGACGTGGCCAAGAAGCTCCAGCCTATCCAAACGGCC<br>GCTAAGAACGTCATCCTCTTCTTGGGAGATGGCATGGGCGTGCCAACAGTCACTG<br>CCACTCGTATCCTTAAGGGCCAAATGAACGGAAAGTTGGGCCCAGAGACTCCTCT<br>GGCTATGGACCAGTTCCCATACGTGGCCCTGTCGAAGACATACAACGTTGACCGT<br>CAAGTGCCGGATTCCGCTGGAACAGCCACCGCTTACCTCTGCGGCGTCAAGGGAA<br>ACTACCGCACAATCGGCGTTTCCGCTGCCGCTAGGTACAACCAGTGTCAGACCAC<br>TAGAGGGAAACGAGGTTACCTCTGTGATCAACCGTGCTAAGAAGGCTGGCAAGGCC<br>GTTGGCGTGGTCACAACCACTAGAGTGCAGCACGCTTCTCCCGCCGGTGCTTACG<br>CCCACACCGTCAACCGCAACTGGTACAGCGACGCCGATCTGCCTGCTGACGCCCA<br>GAAGAACGGCTGCCAAGACATCGCCGCTCAGTTGGTCTACAACATGGACATCGAT<br>GTTATCCTGGGAGGTGGCAGGATGTACATGTTCCCCGAGGGAACTCCCGACCCTG<br>AATACCCTGACGATGCTTCCGTCAACGGTGTTAGAAAGGATAAGCAGAACCTGGT<br>CCAGGAGTGGCAAGCTAAGCACCAGGGAGCCCAATACGTTTGGAACCGTACAGCT<br>CTGCTCCAGGCCGCTGACGATTCCTCTGTGACCCACTTGATGGGTCTGTTCGAAC<br>CCGCTGACATGAAGTACAACGTCCAGCAAGACCACACTAAAGATCCTACACTGGC<br>CGAGATGACTGAAGCCGCTCTCCAGGTTTTGTCCCGTAACCCCCGTGGTTTCTAC<br>CTCTTCGTGGAGGGAGGTCGCATCGACCACGGTCACCACGACGGCAAGGCTTACA<br>TGGCTTTGACAGAAGCTATCATGTTCGACAACGCTATCGCCAAGGCTAACGAGCT<br>GACAAGCGAACTCGACACCCTGATCCTCGTGACTGCCGATCACTCCCACGTCTTC<br>TCTTTCGGCGGATACACCCTGAGGGGCACTTCAATCTTCGGCCTCGCTCCTGGAA<br>AGGCCTTGGACTCTAAGAGCTACACCTCAATCCTGTACGGAAACGGTCCCGGCTA<br>CGCTCTCGGTGGCGGATCGAGGCCTGACGTGCAGGGTTCAACTAGTGAGGAACCA<br>AGCTACAGACAGCAAGCCGCTGTCCCGTTGGCCTCAGAGACTCACGGTGGCGAAG<br>ACGTTGCTGTGTTCGCCCGTGGTCCACAAGCTCACCTGGTGCACGGCGTCCAGGA<br>AGAAACCTTCGTGGCCCACATCATGGCCTTCGCTGGTTGTGTCGAGCCTTACACC<br>GACTGCAACCTCCCAGCCCCAGCCTAG |
| 53 | Showing nucleotide sequence of DNA construct Δ1k3 | ATGAAACTTGTCAACCGTCTGCTGGCTTCGTTCTTGTCCGCATCCACCGTTCTCC<br>AGTCGTGCTGGGCTCTCATCCCAGCTGAAGAGGAAAACCCGGCCTTCTGGAACAG<br>GCAGGCTGCCCAAGCTCTGGACGTGGCCAAGAAGCTCCAGCCTATCCAAACGGCC<br>GCTAAGAACGTCATCCTCTTCTTGGGAGATGGCATGGGCGTGCCAACAGTCACTG<br>CCACTCGTATCCTTAAGGGCCAAATGAACGGAAAGTTGGGCCCAGAGACTCCTCT<br>GGCTATGGACCAGTTCCCATACGTGGCCCTGTCGAAGACATACAACGTTGACCGT<br>CAAGTGCCGGATTCCGCTGGAACAGCCACCGCTTACCTCTGCGGCGTCAAGGGAA<br>ACTACCGCACAATCGGCGTTTCCGCTGCCGCTAGGTACAACCAGTGTAAGACCAC<br>TAGAGGGAAACGAGGTTACCTCTGTGATCAACCGTGCTAAGAAGGCTGGCAAGGCC<br>GTTGGCGTGGTCACAACCACTAGAGTGCAGCACGCTTCTCCCGCCGGTGCTTACG<br>CCCACACCGTCAACCGCAACTGGTACAGCGACGCCGATCTGCCTGCTGACGCCCA<br>GAAGAACGGCTGCCAAGACATCGCCGCTCAGTTGGTCTACAACATGGACATCGAT<br>GTTATCCTGGGAGGTGGCAGGATGTACATGTTCCCCGAGGGAACTCCCGACCCTG<br>AATACCCTGACGATGCTTCCGTCAACGGTGTTAGAAAGGATAAGCAGAACCTGGT<br>CCAGGAGTGGCAAGCTAAGCACCAGGGAGCCCAATACGTTTGGAACCGTACAGCT<br>CTGCTCCAGGCCGCTGACGATTCCTCTGTGACCCACTTGATGGGTCTGTTCGAAC<br>CCGCTGACATGAAGTACAACGTCCAGCAAGACCACACTAAAGATCCTACACTGGC<br>CGAGATGACTGAAGCCGCTCTCCAGGTTTTGTCCCGTAACCCCCGTGGTTTCTAC<br>CTCTTCGTGGAGGGAGGTCGCATCGACCACGGTCACCACGACGGCAAGGCTTACA<br>TGGCTTTGACAGAAGCTATCATGTTCGACAACGCTATCGCCAAGGCTAACGAGCT<br>GACAAGCGAACTCGACACCCTGATCCTCGTGACTGCCGATCACTCCCACGTCTTC<br>TCTTTCGGCGGATACACCCTGAGGGGCACTTCAATCTTCGGCCTCGCTCCTGGAA<br>AGGCCTTGGACTCTAAGAGCTACACCTCAATCCTGTACGGAAACGGTCCCGGCTA<br>CGCTCTCGGTGGCGGATCGAGGCCTGACGTGCAGGGTTCAACTAGTGAGGAACCA<br>AGCTACAGACAGCAAGCCGCTGTCCCGTTGGCCTCAGAGACTCACGGTGGCGAAG |

| SEQ ID NO: | Description | Sequence |
|---|---|---|
| | | ACGTTGCTGTGTTCGCCCGTGGTCCACAAGCTCACCTGGTGCACGGCGTCCAGGA AGAAACCTTCGTGGCCCACATCATGGCCTTCGCTGGTTGTGTCGAGCCTTACACC GACTGCAACCTCCCAGCCCCAGCCTAG |
| 54 | Showing amino acid sequence of bIAP IIΔ1 | MKLVNRLLASFLSASTVLQSCWALIPAEEENPAFWNRQAAQALDVAKKLQPIQTA AKNVILFLGDGMGVPTVTATRILKGQMNGKLGPETPLAMDQFPYVALSKTYNVDR QVPDSAGTATAYLCGVKGNYRTIGVSAAARYNQCQTTRGNEVTSVINRAKKAGKA VGVVTTTRVQHASPAGAYAHTVNRNWYSDADLPADAQKNGCQDIAAQLVYNMDID VILGGGRMYMFPEGTPDPEYPDDASVNGVRKDKQNLVQEWQAKHQGAQYVWNRTA LLQAADDSSVTHLMGLFEPADMKYNVQQDHTKDPTLAEMTEAALQVLSRNPRGFY LFVEGGRIDHGHHDGKAYMALTEAIMFDNATAKANELTSELDTLILVTADHSHVF SFGGYTLRGTSIFGLAPGKALDSKSYTSILYGNGPGYALGGGSRPDVNGSTSEEP SYRQQAAVPLASETHGGEDVAVFARGPQAHLVHGVQEETFVAHIMAFAGCVEPYT DCNLPAPA |
| 55 | Showing amino acid sequence of bIap IIΔ1k | MKLVNRLLASFLSASTVLQSCWALIPAEEENPAFWNRQAAQALDVAKKLQPIQTA AKNVILFLGDGMGVPTVTATRILKGQMNGKLGPETPLAMDQFPYVALSKTYNVDR QVPDSAGTATAYLCGVKGNYRTIGVSAAARYNQCKTTRGNEVTSVINRAKKAGKA VGVVTTTRVQHASPAGAYAHTVNRNWYSDADLPADAQKNGCQDIAAQLVYNMDID VILGGGRMYMFPEGTPDPEYPDDASVNGVRKDKQNLVQEWQAKHQGAQYVWNRTA LLQAADDSSVTHLMGLFEPADMKYNVQQDHTKDPTLAEMTEAALQVLSRNPRGFY LFVEGGRIDHGHHDGKAYMALTEAIMFDNAIAKANELTSELDTLILVTADHSHVF SFGGYTLRGTSIFGLAPGKALDSKSYTSILYGNGPGYALGGGSRPDVNGSTSEEP SYRQQAAVPLASETHGGEDVAVFARGPQAHLVHGVQEETFVAHIMAFAGCVEPYT DCNLPAPA |
| 56 | Showing amino acid sequence of bIap IIΔ13 | MKLVNRLLASFLSASTVLQSCWALIPAEEENPAFWNRQAAQALDVAKKLQPIQTA AKNVILFLGDGMGVPTVTATRILKGQMNGKLGPETPLAMDQFPYVALSKTYNVDR QVPDSAGTATAYLCGVKGNYRTIGVSAAARYNQCKTTRGNEVTSVINRAKKAGKA VGVVTTTRVQHASPAGAYAHTVNRNWYSDADLPADAQKNGCQDIAAQLVYNMDID VILGGGRMYMFPEGTPDPEYPDDASVNGVRKDKQNLVQEWQAKHQGAQYVWNRTA LLQAADDSSVTHLMGLFEPADMKYNVQQDHTKDPTLAEMTEAALQVLSRNPRGFY LFVEGGRIDHGHHDGKAYMALTEAIMFDNATAKANELTSELDTLILVTADHSHVF SFGGYTLRGTSIFGLAPGKALDSKSYTSILYGNGPGYALGGGSRPDVQGSTSEEP SYRQQAAVPLASETHGGEDVAVFARGPQAHLVHGVQEETFVAHIMAFAGCVEPYT DCNLPAPA |
| 57 | Showing amino acid sequence of bIap TTΔ1k3 | MKLVNRLLASELSASTVLQSCWALIPAEEENPAFWNRQAAQALDVAKKLQPIQTA AKNVILFLGDGMGVPTVTATRILKGQMNGKLGPETPLAMDQFPYVALSKTYNVDR QVPDSAGTATAYLCGVKGNYRTIGVSAAARYNQCKTTRGNEVTSVINRAKKAGKA VGVVTTTRVQHASPAGAYAHTVNRNWYSDADLPADAQKNGCQDTAAQLVYNMDID VILGGGRMYMFPEGTPDPEYPDDASVNGVRKDKQNLVQEWQAKHQGAQYVWNRTA LLQAADDSSVTHLMGLFEPADMKYNVQQDHTKDPTLAEMTEAALQVLSRNPRGFY LFVEGGRIDHGHHDGKAYMALTEAIMEDNAIAKANELTSELDTLILVTADHSHVF SFGGYTLRGTSIFGLAPGKALDSKSYTSILYGNGPGYALGGGSRPDVQGSTSEEP SYRQQAAVPLASETHGGEDVAVFARGPQAHLVHGVQEETFVAHIMAFAGCVEPYT DCNLPAPA |
| 58 | Showing nucleotide sequence of Ptef-CTAP IVFw | cgcaccaccttcaaaATGCAGTGGGCCTGT |
| 59 | Showing nucleotide sequence of Talp-CTAP IVRv | atgtactcctggtacCTAACCCGAAGGGGC |
| 60 | Showing nucleotide sequence of bIap IV-synthetic gene | ATGCAGTGGGCCTGTGTGCTGCTGCTGGGCCTGTGGCTACAGCTCTCCCTCA CCTTCATCCCAGCTGAGGAAGAGGATCCTGCTTTCTGGAACCGTCAGGCTGCTCA GGCTCTTGACGTTGCCAAGAAGTTGCAGCCAATCCAGACCGCCGCTAAGAATGTC ATCCTCTTCCTGGGCGATGGTATGGGAGTCCCGACCGTGACTGCTACCCGCATCC TCAAGGGCCAGATGAATGGAAAGCTCGGCCCAGAAACCCCGCTGGCTATGGACCA GTTCCCTTACGTGGCCCTGTCGAAGACTTATAACGTTGATCGTCAAGTCCCTGAC TCTGCTGGTACTGCTACCGCCTACCTTTGCGGTGTGAAGGGAAATTATAAGACCA TCGGCGTTTCCGCCGCTGCCCGGTATAACCAGTGTAATACCACTTCTGGTAACGA GGTTACTAGCGTCATGAATCGGGCTAAGAAGGCCGGCAAGTCTGTTGGTGTCGTG ACCACTTCGCGCGTCCAGCATGCTTCCCCTGCTGGAGCCTACGCTCACACCGTCA ACCGCAATTGGTATAGCGATGCTGACCTGCCCGCCGATGCTCAGACCTACGGCTG CCAGGACATCGCCACTCAGCTCGTCAACAATATGGATATCGACGTGATCCTGGGA GGCGGTGTATGTATATGTTCCCTGAAGGTACCCCTGATCCCGAGTACCCCTATG ACGTGAACCAGACTGGAGTTCGGAAGGACAAGCGCAATCTTGTGCAGGAATGGCA GGCTAAGCATCAGGGTGCCCAGTACGTTTGGAACCGCACCGAGCTCCTGCAGGCT GCCAATGATCCATCGGTCACTCACCTCATGGGACTGTTCGAACCGGCCGACATGA AGTATAACGTGCAGCAGGATCCTACTAAGGACCCCACCCTTGAAGAGATGACCGA GGCTGCCCTTCAGGTTTTGTCCCGGAATCCACAGGGCTTCTACTTGTTCGTCGAG GGCGGCCGCATCGATCATGGACATCACGAGGGCAAGGCTTATATGGCCCTCACTG ATACCGTTATGTTCGACAACGCCATCGCTAAGGCCAATGAACTCACTTCGGGAGCT |

TABLE-continued

| SEQ ID NO: | Description | Sequence |
|---|---|---|
| | | GGATACCCTTATCTTGGCTACTGCCGACCATTCGCACGTCTTCTCCTTCGGTGGA TACACTCTTCGTGGTACCTCCATCTTCGGATTGGCTCCTTCCAAGGCCTCTGACA ACAAGAGCTACACCTCGATCCTGTATGGCAATGGTCCTGGATACGTCCTTGGCGG TGGATTGCGTCCCGATGTGAACGACAGCATCTCGGAGGATCCATCTTATCGGCAG CAGGCTGCCGTCCCGTTGTCCTCTGAAAGCCATGGCGGTGAGGATGTGGCTGTTT TCGCTCGTGGACCACAGGCTCATTTGGTGCACGGCGTTCAGGAAGAGACCTTCGT CGCCCACGTGATGGCTTTTGCGGGTTGCGTTGAGCCCTATACTGACTGTAACTTG CCAGCCCCTTCGGGT |
| 61 | Showing amino acid sequence of linker Kex including Kex2-recognition sequence | GGGGSKR |
| 62 | Showing amino acid sequence of linker Kexmut1 including Kex2-recognition sequence | GGGRHKR |
| 63 | Showing amino acid sequence of linker Kexmut2 including Kex2-recognition sequence | GGGPHKR |
| 64 | Showing amino acid sequence of linker Kexmut3 including Kex2-recognition sequence | GGGQRLVKR |
| 65 | Showing amino acid sequence of linker Kexmut4 including Kex2-recognition sequence | GGGVAVEKR |
| 66 | Showing nucleotide sequence encoding linker Kex including Kex2-recognition sequence | GGCGGTGGAGGCTCTAAGCGC |
| 67 | Showing nucleotide sequence encoding linker Kexmut1 including Kex2-recognition sequence | GGCGGTGGACGCCATAAGCGC |
| 68 | Showing nucleotide sequence encoding linker Kexmut2 including Kex2-recognition sequence | GGCGGTGGACCCCATAAGCGC |
| 69 | Showing nucleotide sequence encoding linker Kexmut3 including Kex2-recognition sequence | GGCGGTGGACAACGCCTGGTCAAGCGC |
| 70 | Showing nucleotide sequence encoding linker Kexmut4 including Kex2-recognition sequence | GGCGGTGGAGTCGCAGTCGAAAAGCGC |

TABLE-continued

| SEQ ID NO: | Description | Sequence |
|---|---|---|
| 71 | Showing nucleotide sequence of primer Kex Fw | GGCGGTGGAGGCTCTAAGCGCTTCA |
| 72 | Showing nucleotide sequence of primer Cytbb rev | AGAGCCTCCACCGCCACCGTCAGGGACAGG |
| 73 | Showing nucleotide sequence of primer bIAP IV-1F | TTCATCCCAGCTGAGGAAGAGGATCC |
| 74 | Showing nucleotide sequence of primer CDHssrev | CTCAGCTGGGATGAAAGCCCAGCATGACTG |
| 75 | Showing nucleotide sequence of primer SKIK Fw | CGCACCACCTTCAAAATGTCCAAGATCAAGAAGCTCGTTAACCGT |
| 76 | Showing nucleotide sequence of primer Ptef-1R | TTTGAAGGTGGTGCGAACTTTGTAG |
| 77 | Showing nucleotide sequence of primer Kexmut1F | GACGGTGGCGGTGGACGCCATAAGCGCTTCATCCCA |
| 78 | Showing nucleotide sequence of primer Kexmut2F | GACGGTGGCGGTGGACCCCATAAGCGCTTCATCCCA |
| 79 | Showing nucleotide sequence of primer Kexmut3F | GACGGTGGCGGTGGACAACGCCTGGTCAAGCGCTTCATCCCA |
| 80 | Showing nucleotide sequence of primer Kexmut4F | GACGGTGGCGGTGGAGTCGCAGTCGAAAAGCGCTTCATCCCA |
| 81 | Showing nucleotide sequence of primer KexmutRv | TCCACCGCCACCGTCAGGGA |
| 82 | Showing nucleotide sequence of primer GlaBssF | AACTTTCTTTTTTCCCTCAATGCCATTGCTGGCGCTGTCGCGTTCATCCCAGCTGAG |
| 83 | Showing nucleotide sequence of primer GlaBssRv | GGAAAAAAGAAAGTTGTTCCGCATTTTGAAGGTGGTGCG |
| 84 | Showing nucleotide sequence of primer CelBssF | CCACTGGTAACGGCTTTCATCCCAGCTGAG |
| 85 | Showing nucleotide sequence of primer CelBssRv | AGCCGTTACCAGTGGCAGGAGTGCC |
| 86 | Showing nucleotide sequence of primer AsAP1ss54F | TAGGTGCGGCGCTCTTCGCTTCCAGCGCTGTTGCCTTCATCCCAGCTGAG |
| 87 | Showing nucleotide sequence of primer AsAP1ss54R | AGAGCGCCGCACCTACAATTGAGAGGAACCTCATTTTGAAGGTGGTGCG |
| 88 | Showing nucleotide sequence of primer AsAP3ss72F | CCCTTGTCCAGACTGCAGTTGCAGCTTCTGTTCAGGCATTCATCCCAGCTGAG |
| 89 | Showing nucleotide sequence of primer AsAP3ss72R | CAGTCTGGACAAGGGCCGCGCCCGCGGTGATGGCAGTGCGGATATGCATTTTGAAGGTGGTGCG |

| SEQ ID NO: | Description | Sequence |
|---|---|---|
| 90 | Showing nucleotide sequence of bIAP IV-synthetic gene | ATGCAGTGGGCCTGTGTGCTGCTGCTGCTGGGCCTGTGGCTACAGCTCTCCCTCA CCTTCATCCCAGCTGAGGAAGAGGATCCTGCTTTCTGGAACCGTCAGGCTGCTCA GGCTCTTGACGTTGCCAAGAAGTTGCAGCCAATCCAGACCGCCGCTAAGAATGTC ATCCTCTTCCTGGGCGATGGTATGGGAGTCCCGACCGTGACTGCTACCCGCATCC TCAAGGGCCAGATGAATGGAAAGCTCGGCCCAGAAACCCCGCTGGCTATGGACCA GTTCCCTTACGTGGCCCTGTCGAAGACTTATAACGTTGATCGTCAAGTCCCTGAC TCTGCTGGTACTGCTACCGCCTACCTTTGCGGTGTGAAGGGAAATTATAAGACCA TCGGCGTTTCCGCCGCTGCCCGGTATAACCAGTGTAATACCACTTCTGGTAACGA GGTTACTAGCGTCATGAATCGGGCTAAGAAGGCCGGCAAGTCTGTTGGTGTCGTG ACCACTTCGCGCGTCCAGCATGCTTCCCCTGCTGGAGCCTACGCTCACACCGTCA ACCGCAATTGGTATAGCGATGCTGACCTGCCCGCCGATGCTCAGACCTACGGCTG CCAGGACATCGCCACTCAGCTCGTCAACAATATGGATATCGACGTGATCCTGGGA GGCGGTCGTATGTATATGTTCCCTGAAGGTACCCCTGATCCCGAGTACCCCTATG ACGTGAACCAGACTGGAGTTCGGAAGGACAAGCGCAATCTTGTGCAGGAATGGCA GGCTAAGCATCAGGGTGCCCAGTACGTTTGGAACCGCACCGAGCTCCTGCAGGCT GCCAATGATCCATCGGTCACTCACCTCATGGGACTGTTCGAACCGGCCGACATGA AGTATAACGTGCAGCAGGATCCTACTAAGGACCCCACCCTTGAAGAGATGACCGA GGCTGCCCTTCAGGTTTTGTCCCGGAATCCACAGGGCTTCTACTTGTTCGTCGAG GGCGGCCGCATCGATCATGGACATCACGAGGGCAAGGCTTATATGGCCCTCACTG ATACCGTTATGTTCGACAACGCCATCGCTAAGGCCAATGAACTCACTTCGGAGCT GGATACCCTTATCTTGGCTACTGCCGACCATTCGCACGTCTTCTCCTTCGGTGGA TACACTCTTCGTGGTACCTCCATCTTCGGATTGGCTCCTTCCAAGGCCTCTGACA ACAAGAGCTACACCTCGATCCTGTATGGCAATGGTCCTGGATACGTCCTTGGCGG TGGATTGCGTCCCGATGTGAACGACAGCATCTCGGAGGATCCATCTTATCGGCAG CAGGCTGCCGTCCCGTTGTCCTCTGAAAGCCATGGCGGTGAGGATGTGGCTGTTT TCGCTCGTGGACCACAGGCTCATTTGGTGCACGGCGTTCAGGAAGAGACCTTCGT CGCCCACGTGATGGCTTTTGCGGGTTGCGTTGAGCCCTATACTGACTGTAACTTG CCAGCCCCTTCGGGT |
| 91 | Showing nucleotide sequence encoding CDHss_bAP IV | ATGAAGCTCGTTAACCGTTTGCTCGCTTCATTCCTGTCAGCGAGCACCGGTGAGT GGTGGCCTATCGAGCTAATGTTGCTTCTCTTCGTCTGACTTTTCTTGGCAGTGTT GCAGTCATGCTGGGCTTTCATCCCAGCTGAGGAAGAGGATCCTGCTTTCTGGAAC CGTCAGGCTGCTCAGGCTCTTGACGTTGCCAAGAAGTTGCAGCCAATCCAGACCG CCGCTAAGAATGTCATCCTCTTCCTGGGCGATGGTATGGGAGTCCCGACCGTGAC TGCTACCCGCATCCTCAAGGGCCAGATGAATGGAAAGCTCGGCCCAGAAACCCCG CTGGCTATGGACCAGTTCCCTTACGTGGCCCTGTCGAAGACTTATAACGTTGATC GTCAAGTCCCTGACTCTGCTGGTACTGCTACCGCCTACCTTTGCGGTGTGAAGGG AAATTATAAGACCATCGGCGTTTCCGCCGCTGCCCGGTATAACCAGTGTAATACC ACTTCTGGTAACGAGGTTACTAGCGTCATGAATCGGGCTAAGAAGGCCGGCAAGT CTGTTGGTGTCGTGACCACTTCGCGCGTCCAGCATGCTTCCCCTGCTGGAGCCTA CGCTCACACCGTCAACCGCAATTGGTATAGCGATGCTGACCTGCCCGCCGATGCT CAGACCTACGGCTGCCAGGACATCGCCACTCAGCTCGTCAACAATATGGATATCG ACGTGATCCTGGGAGGCGGTCGTATGTATATGTTCCCTGAAGGTACCCCTGATCC CGAGTACCCCTATGACGTGAACCAGACTGGAGTTCGGAAGGACAAGCGCAATCTT GTGCAGGAATGGCAGGCTAAGCATCAGGGTGCCCAGTACGTTTGGAACCGCACCG AGCTCCTGCAGGCTGCCAATGATCCATCGGTCACTCACCTCATGGGACTGTTCGA ACCGGCCGACATGAAGTATAACGTGCAGCAGGATCCTACTAAGGACCCCACCCTT GAAGAGATGACCGAGGCTGCCCTTCAGGTTTTGTCCCGGAATCCACAGGGCTTCT ACTTGTTCGTCGAGGGCGGCCGCATCGATCATGGACATCACGAGGGCAAGGCTTA TATGGCCCTCACTGATACCGTTATGTTCGACAACGCCATCGCTAAGGCCAATGAA CTCACTTCGGAGCTGGATACCCTTATCTTGGCTACTGCCGACCATTCGCACGTCT TCTCCTTCGGTGGATACACTCTTCGTGGTACCTCCATCTTCGGATTGGCTCCTTC CAAGGCCTCTGACAACAAGAGCTACACCTCGATCCTGTATGGCAATGGTCCTGGA TACGTCCTTGGCGGTGGATTGCGTCCCGATGTGAACGACAGCATCTCGGAGGATC CATCTTATCGGCAGCAGGCTGCCGTCCCGTTGTCCTCTGAAAGCCATGGCGGTGA GGATGTGGCTGTTTTCGCTCGTGGACCACAGGCTCATTTGGTGCACGGCGTTCAG GAAGAGACCTTCGTCGCCCACGTGATGGCTTTTGCGGGTTGCGTTGAGCCCTATA CTGACTGTAACTTGCCAGCCCCTTCGGGT |
| 92 | Showing nucleotide sequence encoding CDHcytbkex_bAP IV | ATGAAGCTCGTTAACCGTTTGCTCGCTTCATTCCTGTCAGCGAGCACCGGTGAGT GGTGGCCTATCGAGCTAATGTTGCTTCTCTTCGTCTGACTTTTCTTGGCAGTGTT GCAGTCATGCTGGGCTCAGTCCGGCACCGTTGCCTACACGGATACTGAGACG GGCATCACGTTTGACACGGTCGGTACCTGCTGGTACGGGTACGGGTGGTCTCG TCTTCGGTGTAGCCCTGCCGGGTTCGGCATTGACCACCGATGCGACGGAGTTTAT CGGTTACCTGGTGAGGATCTCGAGCTAATCATGACCGCTCTGAAGTGGCGCTAAA CGTTCTAATGTTTCAAGCAATGTGCGTCCCAAAATGCCTCGTCCGCTGGCTGGTG TGGCATTTCCTTGGGTGGTGGCATGAACAACAATCTCTTGTTCTTGGCCTATCCG TACGAGGATACCATCTTGACCTCCCTGCGATTCGGCTCGGGCTATAGCATGCCCG GGGTCTATACCGGCAATGCCAACGTCACCCAGATTTCTTCAAGCATCAATGCCAC TCACTTTACGTTGCTTTTCCGTTGCGAGAATTGTCTGGACCAAGATGGT CAAACCGGAAACGCGACCACAAGCAAGGGTAGGTTAGTCCTGGGATGGGCACAGT CTACGGAGAGCCCGTCGAACCCGTCCTGTCCGGACAATATCAGCCTGGCGCAGCA CGACAACCAGGGTATTATCTCAGCCACTCTGGATGAGAATGCAGCCAGTGAGTCC TACGAGGACTGGGTCAAGTTGGCTAATAAGACTGTTCCCGGGGACTGCTCCGGTG ACGGTGGTGGCGGCAACGAGCCGACTCCTGTCCCTGTCCCTGACGGTGGCGGTGG |

TABLE-continued

| SEQ ID NO: | Description | Sequence |
|---|---|---|
| | | AGGCTCTAAGCGCTTCATCCCAGCTGAGGAAGAGGATCCTGCTTTCTGGAACCGT<br>CAGGCTGCTCAGGCTCTTGACGTTGCCAAGAAGTTGCAGCCAATCCAGACCGCCG<br>CTAAGAATGTCATCCTCTTCCTGGGCGATGGTATGGGAGTCCCGACCGTGACTGC<br>TACCCGCATCCTCAAGGGCCAGATGAATGGAAAGCTCGGCCCAGAAACCCCGCTG<br>GCTATGGACCAGTTCCCTTACGTGGCCCTGTCGAAGACTTATAACGTTGATCGTC<br>AAGTCCCTGACTCTGCTGGTACTGCTACCGCCTACCTTTGCGGTGTGAAGGGAAA<br>TTATAAGACCATCGGCGTTTCCGCCGCTGCCCGGTATAACCAGTGTAATACCACT<br>TCTGGTAACGAGGTTACTAGCGTCATGAATCGGGCTAAGAAGGCCGGCAAGTCTG<br>TTGGTGTCGTGACCACTTCGCGCGTCCAGCATGCTTCCCCTGCTGGAGCCTACGC<br>TCACACCGTCAACCGCAATTGGTATAGCGATGCTGACCTGCCCGCCGATGCTCAG<br>ACCTACGGCTGCCAGGACATCGCCACTCAGCTCGTCAACAATATGGATATCGACG<br>TGATCCTGGGAGGCGGTCGTATGTATATGTTCCCTGAAGGTACCCCTGATCCCGA<br>GTACCCCTATGACGTGAACCAGACTGGAGTTCGGAAGGACAAGCGCAATCTTGTG<br>CAGGAATGGCAGGCTAAGCATCAGGGTGCCCAGTACGTTTGGAACCGCACCGAGC<br>TCCTGCAGGCTGCCAATGATCCATCGGTCACTCACCTCATGGGACTGTTCGAACC<br>GGCCGACATGAAGTATAACGTGCAGCAGGATCCTACTAAGGACCCCACCCTTGAA<br>GAGATGACCGAGGCTGCCCTTCAGGTTTTGTCCCGGAATCCACAGGGCTTCTACT<br>TGTTCGTCGAGGGCGGCCGCATCGATCATGGACATCACGAGGGCAAGGCTTATAT<br>GGCCCTCACTGATACCGTTATGTTCGACAACGCCATCGCTAAGGCCAATGAACTC<br>ACTTCGGAGCTGGATACCCTTATCTTGGCTACTGCCGACCATTCGCACGTCTTCT<br>CCTTCGGTGGATACACTCTTCGTGGTACCTCCATCTTCGGATTGGCTCCTTCCAA<br>GGCCTCTGACAACAAGAGCTACACCTCGATCCTGTATGGCAATGGTCCTGGATAC<br>GTCCTTGGCGGTGGATTGCGTCCCGATGTGAACGACAGCATCTCGGAGGATCCAT<br>CTTATCGGCAGCAGGCTGCCGTCCCGTTGTCCTCTGAAAGCCATGGCGGTGAGGA<br>TGTGGCTGTTTTCGCTCGTGGACCACAGGCTCATTTGGTGCACGGCGTTCAGGAA<br>GAGACCTTCGTCGCCCACGTGATGGCTTTTGCGGGTTGCGTTGAGCCCTATACTG<br>ACTGTAACTTGCCAGCCCCTTCGGGT |
| 93 | Showing nucleotide sequence encoding CDHcytbKexmut1_bAP IV | ATGAAGCTCGTTAACCGTTTGCTCGCTTCATTCCTGTCAGCGAGCACCGGTGAGT<br>GGTGGCCTATCGAGCTAATGTTGCTTCTCTTCGTCTGACTTTTCTTGGCAGTGTT<br>GCAGTCATGCTGGGCTCAGTCCGGCACACCGGTTGCCTACACGGATACTGAGACG<br>GGCATCACGTTTGACACGTGGTCGGTACCTGCTGGTACGGGTACGGGTGGTCTCG<br>TCTTCGGTGTAGCCCTGCCGGGTTCGGCATTGACCACCGATGCGACGGAGTTTAT<br>CGGTTACCTGGTGAGGATCTCGAGCTAATCATGACCGCTCTGAAGTGGCGCTAAA<br>CGTTCTAATGTTTCAAGCAATGTGCGTCCCAAAATGCCTCGTCCGCTGGCTGGTG<br>TGGCATTTCCTTGGGTGGTGGCATGAACAACAATCTCTTGTTCTTGGCCTATCCG<br>TACGAGGATACCATCTTGACCTCCCTGCGATTCGGCTCGGGCTATAGCATGCCCG<br>GGGTCTATACCGGCAATGCCAACGTCACCCAGATTTCTTCAAGCATCAATGCCAC<br>TCACTTTACGTTGCTTTTCCGTTGCGAGAATTGTCTGACCTGGGACCAAGATGGT<br>CAAACCGGAAACGCGACCACAAGCAAGGGTAGGTTAGTCCTGGGATGGGCACAGT<br>CTACGGAGAGCCCGTCGAACCCGTCCTGTCCGGACAATATCAGCCTGGCGCAGCA<br>CGACAACCAGGGTATTATCTCAGCCACTCTGGATGAGAATGCAGCCAGTGAGTCC<br>TACGAGGACTGGGTCAAGTTGGCTAATAAGACTGTTCCCGGGGACTGCTCCGGTG<br>ACGGTGGTGGCGGCAACGAGCCGACTCCTGTCCCTGTCCCTGACGGTGGCGGTGG<br>ACGCCATAAGCGCTTCATCCCAGCTGAGGAAGAGGATCCTGCTTTCTGGAACCGT<br>CAGGCTGCTCAGGCTCTTGACGTTGCCAAGAAGTTGCAGCCAATCCAGACCGCCG<br>CTAAGAATGTCATCCTCTTCCTGGGCGATGGTATGGGAGTCCCGACCGTGACTGC<br>TACCCGCATCCTCAAGGGCCAGATGAATGGAAAGCTCGGCCCAGAAACCCCGCTG<br>GCTATGGACCAGTTCCCTTACGTGGCCCTGTCGAAGACTTATAACGTTGATCGTC<br>AAGTCCCTGACTCTGCTGGTACTGCTACCGCCTACCTTTGCGGTGTGAAGGGAAA<br>TTATAAGACCATCGGCGTTTCCGCCGCTGCCCGGTATAACCAGTGTAATACCACT<br>TCTGGTAACGAGGTTACTAGCGTCATGAATCGGGCTAAGAAGGCCGGCAAGTCTG<br>TTGGTGTCGTGACCACTTCGCGCGTCCAGCATGCTTCCCCTGCTGGAGCCTACGC<br>TCACACCGTCAACCGCAATTGGTATAGCGATGCTGACCTGCCCGCCGATGCTCAG<br>ACCTACGGCTGCCAGGACATCGCCACTCAGCTCGTCAACAATATGGATATCGACG<br>TGATCCTGGGAGGCGGTCGTATGTATATGTTCCCTGAAGGTACCCCTGATCCCGA<br>GTACCCCTATGACGTGAACCAGACTGGAGTTCGGAAGGACAAGCGCAATCTTGTG<br>CAGGAATGGCAGGCTAAGCATCAGGGTGCCCAGTACGTTTGGAACCGCACCGAGC<br>TCCTGCAGGCTGCCAATGATCCATCGGTCACTCACCTCATGGGACTGTTCGAACC<br>GGCCGACATGAAGTATAACGTGCAGCAGGATCCTACTAAGGACCCCACCCTTGAA<br>GAGATGACCGAGGCTGCCCTTCAGGTTTTGTCCCGGAATCCACAGGGCTTCTACT<br>TGTTCGTCGAGGGCGGCCGCATCGATCATGGACATCACGAGGGCAAGGCTTATAT<br>GGCCCTCACTGATACCGTTATGTTCGACAACGCCATCGCTAAGGCCAATGAACTC<br>ACTTCGGAGCTGGATACCCTTATCTTGGCTACTGCCGACCATTCGCACGTCTTCT<br>CCTTCGGTGGATACACTCTTCGTGGTACCTCCATCTTCGGATTGGCTCCTTCCAA<br>GGCCTCTGACAACAAGAGCTACACCTCGATCCTGTATGGCAATGGTCCTGGATAC<br>GTCCTTGGCGGTGGATTGCGTCCCGATGTGAACGACAGCATCTCGGAGGATCCAT<br>CTTATCGGCAGCAGGCTGCCGTCCCGTTGTCCTCTGAAAGCCATGGCGGTGAGGA<br>TGTGGCTGTTTTCGCTCGTGGACCACAGGCTCATTTGGTGCACGGCGTTCAGGAA<br>GAGACCTTCGTCGCCCACGTGATGGCTTTTGCGGGTTGCGTTGAGCCCTATACTG<br>ACTGTAACTTGCCAGCCCCTTCGGGT |

TABLE-continued

| SEQ ID NO: | Description | Sequence |
|---|---|---|
| 94 | Showing nucleotide sequence encoding CDHcytbKexmut2_bAP IV | ATGAAGCTCGTTAACCGTTTGCTCGCTTCATTCCTGTCAGCGAGCACCGGTGAGT GGTGGCCTATCGAGCTAATGTTGCTTCTCTTCGTCTGACTTTTCTTGGCAGTGTT GCAGTCATGCTGGGCTCAGTCCGGCACACCGGTTGCCTACACGGATACTGAGACG GGCATCACGTTTGACACGTGGTCGGTACCTGCTGGTACGGGTACGGGTGGTCTCG TCTTCGGTGTAGCCCTGCCGGGTTCGGCATTGACCACCGATGCGACGGAGTTTAT CGGTTACCTGGTGAGGATCTCGAGCTAATCATGACCGCTCTGAAGTGGCGCTAAA CGTTCTAATGTTTCAAGCAATGTGCGTCCCAAAATGCCTCGTCCGCTGGCTGGTG TGGCATTTCCTTGGGTGGTGGCATGAACAACAATCTCTTGTTCTTGGCCTATCCG TACGAGGATACCATCTTGACCTCCCTGCGATTCGGCTCGGGCTATAGCATGCCCG GGGTCTATACCGGCAATGCCAACGTCACCCAGATTTCTTCAAGCATCAATGCCAC TCACTTTACGTTGCTTTTCCGTTGCGAGAATTGTCTGACCTGGGACCAAGATGGT CAAACCGGAAACGCGACCACAAGCAAGGGTAGGTTAGTCCTGGGATGGGCACAGT CTACGGAGAGCCCGTCGAACCCGTCCTGTCCGGACAATATCAGCCTGGCGCAGCA CGACAACCAGGGTATTATCTCAGCCACTCTGGATGAGAATGCAGCCAGTGAGTCC TACGAGGACTGGGTCAAGTTGGCTAATAAGACTGTTCCCGGGGACTGCTCCGGTG ACGGTGGTGGCGGCAACGAGCCGACTCCTGTCCCTGTCCCTGACGGTGGCGGTGG ACCCCATAAGCGCTTCATCCCAGCTGAGGAAGAGGATCCTGCTTTCTGGAACCGT CAGGCTGCTCAGGCTCTTGACGTTGCCAAGAAGTTGCAGCCAATCCAGACCGCCG CTAAGAATGTCATCCTCTTCCTGGGCGATGGTATGGGAGTCCCGACCGTGACTGC TACCCGCATCCTCAAGGGCCAGATGAATGGAAAGCTCGGCCCAGAAACCCCGCTG GCTATGGACCAGTTCCCTTACGTGGCCCTGTCGAAGACTTATAACGTTGATCGTC AAGTCCCTGACTCTGCTGGTACTGCTACCGCCTACCTTTGCGGTGTGAAGGGAAA TTATAAGACCATCGGCGTTTCCGCCGCTGCCCGGTATAACCAGTGTAATACCACT TCTGGTAACGAGGTTACTAGCGTCATGAATCGGGCTAAGAAGGCCGGCAAGTCTG TTGGTGTCGTGACCACTTCGCGCGTCCAGCATGCTTCCCCTGCTGGAGCCTACGC TCACACCGTCAACCGCAATTGGTATAGCGATGCTGACCTGCCCGCCGATGCTCAG ACCTACGGCTGCCAGGACATCGCCACTCAGCTCGTCAACAATATGGATATCGACG TGATCCTGGGAGGCGGTCGTATGTATATGTTCCCTGAAGGTACCCCTGATCCCGA GTACCCCTATGACGTGAACCAGACTGGAGTTCGGAAGGACAAGCGCAATCTTGTG CAGGAATGGCAGGCTAAGCATCAGGGTGCCCAGTACGTTTGGAACCGCACCGAGC TCCTGCAGGCTGCCAATGATCCATCGGTCACTCACCTCATGGGACTGTTCGAACC GGCCGACATGAAGTATAACGTGCAGCAGGATCCTACTAAGGACCCCACCCTTGAA GAGATGACCGAGGCTGCCCTTCAGGTTTTGTCCCGGAATCCACAGGGCTTCTACT TGTTCGTCGAGGGCGGCCGCATCGATCATGGACATCACGAGGGCAAGGCTTATAT GGCCCTCACTGATACCGTTATGTTCGACAACGCCATCGCTAAGGCCAATGAACTC ACTTCGGAGCTGGATACCCTTATCTTGGCTACTGCCGACCATTCGCACGTCTTCT CCTTCGGTGGATACACTCTTCGTGGTACCTCCATCTTCGGATTGGCTCCTTCCAA GGCCTCTGACAACAAGAGCTACACCTCGATCCTGTATGGCAATGGTCCTGGATAC GTCCTTGGCGGTGGATTGCGTCCCGATGTGAACGACAGCATCTCGGAGGATCCAT CTTATCGGCAGCAGGCTGCCGTCCCGTTGTCCTCTGAAAGCCATGGCGGTGAGGA TGTGGCTGTTTTCGCTCGTGGACCACAGGCTCATTTGGTGCACGGCGTTCAGGAA GAGACCTTCGTCGCCCACGTGATGGCTTTTGCGGGTTGCGTTGAGCCCTATACTG ACTGTAACTTGCCAGCCCCTTCGGGT |
| 95 | Showing nucleotide sequence encoding CDHcytbKexmut3_bAP IV | ATGAAGCTCGTTAACCGTTTGCTCGCTTCATTCCTGTCAGCGAGCACCGGTGAGT GGTGGCCTATCGAGCTAATGTTGCTTCTCTTCGTCTGACTTTTCTTGGCAGTGTT GCAGTCATGCTGGGCTCAGTCCGGCACACCGGTTGCCTACACGGATACTGAGACG GGCATCACGTTTGACACGTGGTCGGTACCTGCTGGTACGGGTACGGGTGGTCTCG TCTTCGGTGTAGCCCTGCCGGGTTCGGCATTGACCACCGATGCGACGGAGTTTAT CGGTTACCTGGTGAGGATCTCGAGCTAATCATGACCGCTCTGAAGTGGCGCTAAA CGTTCTAATGTTTCAAGCAATGTGCGTCCCAAAATGCCTCGTCCGCTGGCTGGTG TGGCATTTCCTTGGGTGGTGGCATGAACAACAATCTCTTGTTCTTGGCCTATCCG TACGAGGATACCATCTTGACCTCCCTGCGATTCGGCTCGGGCTATAGCATGCCCG GGGTCTATACCGGCAATGCCAACGTCACCCAGATTTCTTCAAGCATCAATGCCAC TCACTTTACGTTGCTTTTCCGTTGCGAGAATTGTCTGACCTGGGACCAAGATGGT CAAACCGGAAACGCGACCACAAGCAAGGGTAGGTTAGTCCTGGGATGGGCACAGT CTACGGAGAGCCCGTCGAACCCGTCCTGTCCGGACAATATCAGCCTGGCGCAGCA CGACAACCAGGGTATTATCTCAGCCACTCTGGATGAGAATGCAGCCAGTGAGTCC TACGAGGACTGGGTCAAGTTGGCTAATAAGACTGTTCCCGGGGACTGCTCCGGTG ACGGTGGTGGCGGCAACGAGCCGACTCCTGTCCCTGTCCCTGACGGTGGCGGTGG ACAACGCCTGGTCAAGCGCTTCATCCCAGCTGAGGAAGAGGATCCTGCTTTCTGG AACCGTCAGGCTGCTCAGGCTCTTGACGTTGCCAAGAAGTTGCAGCCAATCCAGA CCGCCGCTAAGAATGTCATCCTCTTCCTGGGCGATGGTATGGGAGTCCCGACCGT GACTGCTACCCGCATCCTCAAGGGCCAGATGAATGGAAAGCTCGGCCCAGAAACC CCGCTGGCTATGGACCAGTTCCCTTACGTGGCCCTGTCGAAGACTTATAACGTTG ATCGTCAAGTCCCTGACTCTGCTGGTACTGCTACCGCCTACCTTTGCGGTGTGAA GGGAAATTATAAGACCATCGGCGTTTCCGCCGCTGCCCGGTATAACCAGTGTAAT ACCACTTCTGGTAACGAGGTTACTAGCGTCATGAATCGGGCTAAGAAGGCCGGCA AGTCTGTTGGTGTCGTGACCACTTCGCGCGTCCAGCATGCTTCCCCTGCTGGAGC CTACGCTCACACCGTCAACCGCAATTGGTATAGCGATGCTGACCTGCCCGCCGAT GCTCAGACCTACGGCTGCCAGGACATCGCCACTCAGCTCGTCAACAATATGGATA TCGACGTGATCCTGGGAGGCGGTCGTATGTATATGTTCCCTGAAGGTACCCCTGA TCCCGAGTACCCCTATGACGTGAACCAGACTGGAGTTCGGAAGGACAAGCGCAAT CTTGTGCAGGAATGGCAGGCTAAGCATCAGGGTGCCCAGTACGTTTGGAACCGCA CCGAGCTCCTGCAGGCTGCCAATGATCCATCGGTCACTCACCTCATGGGACTGTT |

| SEQ ID NO: | Description | Sequence |
|---|---|---|
| | | CGAACCGGCCGACATGAAGTATAACGTGCAGCAGGATCCTACTAAGGACCCCACC<br>CTTGAAGAGATGACCGAGGCTGCCCTTCAGGTTTTGTCCCGGAATCCACAGGGCT<br>TCTACTTGTTCGTCGAGGGCGGCCGCATCGATCATGGACATCACGAGGGCAAGGC<br>TTATATGGCCCTCACTGATACCGTTATGTTCGACAACGCCATCGCTAAGGCCAAT<br>GAACTCACTTCGGAGCTGGATACCCTTATCTTGGCTACTGCCGACCATTCGCACG<br>TCTTCTCCTTCGGTGGATACACTCTTCGTGGTACCTCCATCTTCGGATTGGCTCC<br>TTCCAAGGCCTCTGACAACAAGAGCTACACCTCGATCCTGTATGGCAATGGTCCT<br>GGATACGTCCTTGGCGGTGGATTGCGTCCCGATGTGAACGACAGCATCTCGGAGG<br>ATCCATCTTATCGGCAGCAGGCTGCCGTCCCGTTGTCCTCTGAAAGCCATGGCGG<br>TGAGGATGTGGCTGTTTTCGCTCGTGGACCACAGGCTCATTTGGTGCACGGCGTT<br>CAGGAAGAGACCTTCGTCGCCCACGTGATGGCTTTTGCGGGTTGCGTTGAGCCCT<br>ATACTGACTGTAACTTGCCAGCCCTTCGGGT |
| 96 | Showing nucleotide sequence encoding CDHcytbKexmut4_bAP IV | ATGAAGCTCGTTAACCGTTTGCTCGCTTCATTCCTGTCAGCGAGCACCGGTGAGT<br>GGTGGCCTATCGAGCTAATGTTGCTTCTCTTCGTCTGACTTTTCTTGGCAGTGTT<br>GCAGTCATGCTGGGCTCAGTCCGGCACACCGGTTGCCTACACGGATACTGAGACG<br>GGCATCACGTTTGACACGTGGTCGGTACCTGCTGGTACGGGTACGGGTGGTCTCG<br>TCTTCGGTGTAGCCCTGCCGGGTTCGGCATTGACCACCGATGCGACGGAGTTTAT<br>CGGTTACCTGGTGAGGATCTCGAGCTAATCATGACCGCTCTGAAGTGGCGCTAAA<br>CGTTCTAATGTTTCAAGCAATGTGCGTCCCAAAATGCCTCGTCCGCTGGCTGGTG<br>TGGCATTTCCTTGGGTGGTGGCATGAACAACAATCTCTTGTTCTTGGCCTATCCG<br>TACGAGGATACCATCTTGACCTCCCTGCGATTCGGCTCGGGCTATAGCATGCCCG<br>GGGTCTATACCGGCAATGCCAACGTCACCCAGATTCTTCAAGCATCAATGCCAC<br>TCACTTTACGTTGCTTTTCCGTTGCGAGAATTGTCTGACCTGGGACCAAGATGGT<br>CAAACCGGAAACGCGACCACAAGCAAGGGTAGGTTAGTCCTGGGATGGGCACAGT<br>CTACGGAGAGCCCGTCGAACCCGTCCTGTCCGGACAATATCAGCCTGGCGCAGCA<br>CGACAACCAGGGTATTATCTCAGCCACTCTGGATGAGAATGCAGCCAGTGAGTCC<br>TACGAGGACTGGGTCAAGTTGGCTAATAAGACTGTTCCCGGGGACTGCTCCGGTG<br>ACGGTGGTGGCGGCAACGAGCCGACTCCTGTCCCTGTCCCTGACGGTGGCGGTGG<br>AGTCGCAGTCGAAAAGCGCTTCATCCCAGCTGAGGAAGAGGATCCTGCTTTCTGG<br>AACCGTCAGGCTGCTCAGGCTCTTGACGTTGCCAAGAAGTTGCAGCCAATCCAGA<br>CCGCCGCTAAGAATGTCATCCTCTTCCTGGGCGATGGTATGGGAGTCCCGACCGT<br>GACTGCTACCCGCATCCTCAAGGGCCAGATGAATGGAAAGCTCGGCCCAGAAACC<br>CCGCTGGCTATGGACCAGTTCCCTTACGTGGCCCTGTCGAAGACTTATAACGTTG<br>ATCGTCAAGTCCCTGACTCTGCTGGTACTGCTACCGCCTACCTTTGCGGTGTGAA<br>GGGAAATTATAAGACCATCGGCGTTTCCGCCGCTGCCCGGTATAACAGTGTAAT<br>ACCACTTCTGGTAACGAGGTTACTAGCGTCATGAATGGGCTAAGAAGGCCGGCA<br>AGTCTGTTGGTGTCGTGACCACTTCGCGCGTCCAGCATGCTTCCCCTGCTGGAGC<br>CTACGCTCACACCGTCAACCGCAATTGGTATAGCGATGCTGACCTGCCCGCCGAT<br>GCTCAGACCTACGGCTGCCAGGACATCGCCACTCAGCTCGTCAACAATATGGATA<br>TCGACGTGATCCTGGGAGGCGGTCGTATGTATATGTTCCCTGAAGGTACCCCTGA<br>TCCCGAGTACCCCTATGACGTGAACCAGACTGGAGTTCGGAAGGACAAGCGCAAT<br>CTTGTGCAGGAATGGCAGGCTAAGCATCAGGGTGCCCAGTACGTTTGGAACCGCA<br>CCGAGCTCCTGCAGGCTGCCAATGATCCATCGGTCACTCACCTCATGGGACTGTT<br>CGAACCGGCCGACATGAAGTATAACGTGCAGCAGGATCCTACTAAGGACCCCACC<br>CTTGAAGAGATGACCGAGGCTGCCCTTCAGGTTTTGTCCCGGAATCCACAGGGCT<br>TCTACTTGTTCGTCGAGGGCGGCCGCATCGATCATGGACATCACGAGGGCAAGGC<br>TTATATGGCCCTCACTGATACCGTTATGTTCGACAACGCCATCGCTAAGGCCAAT<br>GAACTCACTTCGGAGCTGGATACCCTTATCTTGGCTACTGCCGACCATTCGCACG<br>TCTTCTCCTTCGGTGGATACACTCTTCGTGGTACCTCCATCTTCGGATTGGCTCC<br>TTCCAAGGCCTCTGACAACAAGAGCTACACCTCGATCCTGTATGGCAATGGTCCT<br>GGATACGTCCTTGGCGGTGGATTGCGTCCCGATGTGAACGACAGCATCTCGGAGG<br>ATCCATCTTATCGGCAGCAGGCTGCCGTCCCGTTGTCCTCTGAAAGCCATGGCGG<br>TGAGGATGTGGCTGTTTTCGCTCGTGGACCACAGGCTCATTTGGTGCACGGCGTT<br>CAGGAAGAGACCTTCGTCGCCCACGTGATGGCTTTTGCGGGTTGCGTTGAGCCCT<br>ATACTGACTGTAACTTGCCAGCCCTTCGGGT |
| 97 | Showing nucleotide sequence encoding CDHall_bIAP IV | ATGAAGCTCGTTAACCGTTTGCTCGCTTCATTCCTGTCAGCGAGCACCGGTGAGT<br>GGTGGCCTATCGAGCTAATGTTGCTTCTCTTCGTCTGACTTTTCTTGGCAGTGTT<br>GCAGTCATGCTGGGCTCAGTCCGGCACACCGGTTGCCTACACGGATACTGAGACG<br>GGCATCACGTTTGACACGTGGTCGGTACCTGCTGGTACGGGTACGGGTGGTCTCG<br>TCTTCGGTGTAGCCCTGCCGGGTTCGGCATTGACCACCGATGCGACGGAGTTTAT<br>CGGTTACCTGGTGAGGATCTCGAGCTAATCATGACCGCTCTGAAGTGGCGCTAAA<br>CGTTCTAATGTTTCAAGCAATGTGCGTCCCAAAATGCCTCGTCCGCTGGCTGGTG<br>TGGCATTTCCTTGGGTGGTGGCATGAACAACAATCTCTTGTTCTTGGCCTATCCG<br>TACGAGGATACCATCTTGACCTCCCTGCGATTCGGCTCGGGCTATAGCATGCCCG<br>GGGTCTATACCGGCAATGCCAACGTCACCCAGATTCTTCAAGCATCAATGCCAC<br>TCACTTTACGTTGCTTTTCCGTTGCGAGAATTGTCTGACCTGGGACCAAGATGGT<br>CAAACCGGAAACGCGACCACAAGCAAGGGTAGGTTAGTCCTGGGATGGGCACAGT<br>CTACGGAGAGCCCGTCGAACCCGTCCTGTCCGGACAATATCAGCCTGGCGCAGCA<br>CGACAACCAGGGTATTATCTCAGCCACTCTGGATGAGAATGCAGCCAGTGAGTCC<br>TACGAGGACTGGGTCAAGTTGGCTAATAAGACTGTTCCCGGGGACTGCTCCGGTG<br>ACGGTGGTGGCGGCAACGAGCCGACTCCTGTCCCTGTCCCTGACGGTGCTACATA<br>CGACTATATTGTCGTCGGTGGAGGTGCCGGGGGTATCCCTGTCGCCGATCGGCTG<br>AGTGAGGCTGGACACAGTGTTCTCCTGATCGAGAAGGTCCTCCTTCCTCGGGAC<br>GCTGGGGTGGCACCATGAAGCCCAGCTGGCTGGATGATACCAACCTGACGCGATT |

TABLE-continued

| SEQ ID NO: | Description | Sequence |
|---|---|---|
| | | TGATGTCCCTGGGCTGTGCAACCAGATCTGGGTCGACTCCAACGGTATCGCCTGC<br>AGTGACACCGATCAGATGGCAGGTTGTGTGCTGGGTGGAGGCACCGCCGTCAACG<br>CAGGATTGTGGTGGAAGGTAAGCCGTGCCCAGATGCCATGTTCGGATCCATCACT<br>GACAATGTCCAGCCAAATCCCGTTGACTGGGACTACAACTTCCCCGAGGGATGGC<br>AGTCGTCCGACATGCAGGCTGCCGCGGACCGCGTGTTCTCGCGGATCCCTGGAAC<br>CACAACCCCCTCCACCGATGGAAAGCTTTATTACCAACAAGGAGCCGATATACTG<br>TTAAATGGCTTGCAATCCGCCGGATGGTCATCCGTCACCCTCAACGATGTCCCGG<br>CCCAGAAAACCAAGACCTTTGGCCACGCACCATTCATGTTCTCTGGAGGTGAGCG<br>CGGAGGGCCCATGGGGACGTATCTGGTGTCGGCGAGCGAGAGAGATAATTTTGCC<br>CGCTGGTCGAACACGACTGTGAAGAGGGTTGTTCGTGAAGGCGGACGTATCACCG<br>GAGTTGAGGTCGAGGCGACCCTCGATGGTGGCTACGCGGGTACCGTCAATGTAAC<br>TGCCAATACGGGTCGAGTCATTCTTTCTGCAGGAACTTTTGGAACGCCCAAGGTC<br>CTTATGAGAAGTACGCTTCGTTGGATGATATTGTTAGGGAGTTATTGCTAATGGC<br>GTATAGGTGGTATCGGCCCGAAGGACCAGCTGTCCATCGTGAAGAGCTCAACTGA<br>TGGAGAGACAATGATTGCCGAATCTGAGTGGATCGAACTTCCGGTTGGCGAGAAC<br>TTGGTCGATCATGTCAATGTGAGTGCCAAGTGGACCGGGGAGGCTACTACTATGC<br>TAATAGGATGCTTACAGACTGATGTTGTGGTGACCCACCCTGATGTTGTCTTCTA<br>TGATTTCAAAGCGGCATACAAGACCCCCATCGAGAGTGATGCGACGAGCTATCTG<br>AGTATGTAGTAATGCTTCGAAGGACAGTCCAGCACTAACTTGCGTAGACGATCGC<br>ACCGGGATTTTCGCCCAGGCTGCGCCTAACATTGGTCCTATGTAAGTTGCCCGTC<br>TACCAAACACGTCATGGTACTAACGCCTGTAGAATCTTCGACGAAGTCACCGGCT<br>CTGATGGCATTAAACGACAGATACAGTGGACTGCTCGTGTGGAAGGCGGCCACGA<br>CACGCCTGACGGACGTACGTTGACTCCTAAGTGAAAGATTAGTGCAATATATTAA<br>CCGTGCTGTAGACGCCATGACCATCAGCCAATACCTCGGCCGCGGCTCAACCTCG<br>CGTGGCCGCATGACCATTACCGCAGGACTGGACACGGTGGTCTCGACGCTGCCAT<br>TCCTACGGGACGAGAGCGACGTTAATGCTGTAATCCAGGGAATCCAGAACCTGAA<br>GATGCCCTGAACGGGACAGGATTTACCTGGAACTACCCTGCTCGGAACACTTCC<br>ATTGCCGAGTTTGTCAATACTGTGAGTGCTGATTTCTGGAAGGATGTTCGACGTA<br>ACTGACACTGATAGATGCCAATCACTGCCGGAACACGCCGAGCTAATCACTGGAT<br>GGGTGAGTTATGAATCTGCTTTTTAAAATTTCGTCGCTAATTGTTATAGGAACCT<br>GCAAAATAGGTACAGATGATGGCCGTACTGGAGGTAGCGCCGTTGTTGATTTGAA<br>TACGAAGGTCTATGGAACGGACAACCTGTTCGTCGTGGATGCTAGTATCTTCCCG<br>GGTATGATCACGTCCAATCCTTCGGCTTACATTGTTACGGTCGCGGAGCATGCAG<br>CTGAAAAGATTCTTGCGCTGGGCGGTGGAGGCTCTAAGCGCTTCATCCCAGCTGA<br>GGAAGAGGATCCTGCTTTCTGGAACCGTCAGGCTGCTCAGGCTCTTGACGTTGCC<br>AAGAAGTTGCAGCCAATCCAGACCGCCGCTAAGAATGTCATCCTCTTCCTGGGCG<br>ATGGTATGGGAGTCCCGACCGTGACTGCTACCCGCATCCTCAAGGGCCAGATGAA<br>TGGAAAGCTCGGCCCAGAAACCCCGCTGGCTATGGACCAGTTCCCTTACGTGGCC<br>CTGTCGAAGACTTATAACGTTGATCGTCAAGTCCCTGACTCTGCTGGTACTGCTA<br>CCGCCTACCTTTGCGGTGTGAAGGGAAATTATAAGACCATCGGCGTTTCCGCCGC<br>TGCCCGGTATAACCAGTGTAATACCACTTCTGGTAACGAGGTTACTAGCGTCATG<br>AATCGGGCTAAGAAGGCCGGCAAGTCTGTTGGTGTCGTGACCACTTCGCGCGTCC<br>AGCATGCTTCCCCTGCTGGAGCCTACGCTCACACCGTCAACCGCAATTGGTATAG<br>CGATGCTGACCTGCCCGCCGATGCTCAGACCTACGGCTGCCAGGACATCGCCACT<br>CAGCTCGTCAACAATATGGATATCGACGTGATCCTGGGAGGCGGTCGTATGTATA<br>TGTTCCCTGAAGGTACCCCTGATCCCGAGTACCCCTATGACGTGAACCAGACTGG<br>AGTTCGGAAGGACAAGCGCAATCTTGTGCAGGAATGGCAGGCTAAGCATCAGGGT<br>GCCCAGTACGTTTGGAACCGCACCGAGCTCCTGCAGGCTGCCAATGATCCATCGG<br>TCACTCACCTCATGGGACTG |
| | | TTCGAACCGGCCGACATGAAGTATAACGTGCAGCAGGATCCTACTAAGGACCCCA<br>CCCTTGAAGAGATGACCGAGGCTGCCCTTCAGGTTTTGTCCCGGAATCCACAGGG<br>CTTCTACTTGTTCGTCGAGGGCGGCCGCATCGATCATGGACATCACGAGGGCAAG<br>GCTTATATGGCCCTCACTGATACCGTTATGTTCGACAACGCCATCGCTAAGGCCA<br>ATGAACTCACTTCGGAGCTGGATACCCTTATCTTGGCTACTGCCGACCATTCGCA<br>CGTCTTCTCCTTCGGTGGATACACTCTTCGTGGTACCTCCATCTTCGGATTGGCT<br>CCTTCCAAGGCCTCTGACAACAAGAGCTACACCTCGATCCTGTATGGCAATGGTC<br>CTGGATACGTCCTTGGCGGTGGATTGCGTCCCGATGTGAACGACAGCATCTCGGA<br>GGATCCATCTTATCGGCAGCAGGCTGCCGTCCCGTTGTCCTCTGAAAGCCATGGC<br>GGTGAGGATGTGGCTGTTTTCGCTCGTGGACCACAGGCTCATTTGGTGCACGGCG<br>TTCAGGAAGAGACCTTCGTCGCCCACGTGATGGCTTTTGCGGGTTGCGTTGAGCC<br>CTATACTGACTGTAACTTGCCAGCCCCTTCGGGT |
| 98 | Showing nucleotide sequence encoding GlaBss_bIAP IV | ATGCGGAACAACTTTCTTTTTTCCCTCAATGCCATTGCTGGCGCTGTCGCGTTCA<br>TCCCAGCTGAGGAAGAGGATCCTGCTTTCTGGAACCGTCAGGCTGCTCAGGCTCT<br>TGACGTTGCCAAGAAGTTGCAGCCAATCCAGACCGCCGCTAAGAATGTCATCCTC<br>TTCCTGGGCGATGGTATGGGAGTCCCGACCGTGACTGCTACCCGCATCCTCAAGG<br>GCCAGATGAATGGAAAGCTCGGCCCAGAAACCCCGCTGGCTATGGACCAGTTCCC<br>TTACGTGGCCCTGTCGAAGACTTATAACGTTGATCGTCAAGTCCCTGACTCTGCT<br>GGTACTGCTACCGCCTACCTTTGCGGTGTGAAGGGAAATTATAAGACCATCGGCG<br>TTTCCGCCGCTGCCCGGTATAACCAGTGTAATACCACTTCTGGTAACGAGGTTAC<br>TAGCGTCATGAATCGGGCTAAGAAGGCCGGCAAGTCTGTTGGTGTCGTGACCACT<br>TCGCGCGTCCAGCATGCTTCCCCTGCTGGAGCCTACGCTCACACCGTCAACCGCA<br>ATTGGTATAGCGATGCTGACCTGCCCGCCGATGCTCAGACCTACGGCTGCCAGGA<br>CATCGCCACTCAGCTCGTCAACAATATGGATATCGACGTGATCCTGGGAGGCGGT<br>CGTATGTATATGTTCCCTGAAGGTACCCCTGATCCCGAGTACCCCTATGACGTGA |

| SEQ ID NO: | Description | Sequence |
|---|---|---|
| | | ACCAGACTGGAGTTCGGAAGGACAAGCGCAATCTTGTGCAGGAATGGCAGGCTAA<br>GCATCAGGGTGCCCAGTACGTTTGGAACCGCACCGAGCTCCTGCAGGCTGCCAAT<br>GATCCATCGGTCACTCACCTCATGGGACTGTTCGAACCGGCCGACATGAAGTATA<br>ACGTGCAGCAGGATCCTACTAAGGACCCCACCCTTGAAGAGATGACCGAGGCTGC<br>CCTTCAGGTTTTGTCCCGGAATCCACAGGGCTTCTACTTGTTCGTCGAGGGCGGC<br>CGCATCGATCATGGACATCACGAGGGCAAGGCTTATATGGCCCTCACTGATACCG<br>TTATGTTCGACAACGCCATCGCTAAGGCCAATGAACTCACTTCGGAGCTGGATAC<br>CCTTATCTTGGCTACTGCCGACCATTCGCACGTCTTCTCCTTCGGTGGATACACT<br>CTTCGTGGTACCTCCATCTTCGGATTGGCTCCTTCCAAGGCCTCTGACAACAAGA<br>GCTACACCTCGATCCTGTATGGCAATGGTCCTGGATACGTCCTTGGCGGTGGATT<br>GCGTCCCGATGTGAACGACAGCATCTCGGAGGATCCATCTTATCGGCAGCAGGCT<br>GCCGTCCCGTTGTCCTCTGAAAGCCATGGCGGTGAGGATGTGGCTGTTTTCGCTC<br>GTGGACCACAGGCTCATTTGGTGCACGGCGTTCAGGAAGAGACCTTCGTCGCCCA<br>CGTGATGGCTTTTGCGGGTTGCGTTGAGCCCTATACTGACTGTAACTTGCCAGCC<br>CCTTCGGGT |
| 99 | Showing nucleotide sequence encoding CelBss_bIAP IV | ATGATCTGGACACTCGCTCCCTTTGTGGCACTCCTGCCACTGGTAACGGCTTTCA<br>TCCCAGCTGAGGAAGAGGATCCTGCTTTCTGGAACCGTCAGGCTGCTCAGGCTCT<br>TGACGTTGCCAAGAAGTTGCAGCCAATCCAGACCGCCGCTAAGAATGTCATCCTC<br>TTCCTGGGCGATGGTATGGGAGTCCCGACCGTGACTGCTACCCGCATCCTCAAGG<br>GCCAGATGAATGGAAAGCTCGGCCCAGAAACCCCGCTGGCTATGGACCAGTTCCC<br>TTACGTGGCCCTGTCGAAGACTTATAACGTTGATCGTCAAGTCCCTGACTCTGCT<br>GGTACTGCTACCGCCTACCTTTGCGGTGTGAAGGGAAATTATAAGACCATCGGCG<br>TTTCCGCCGCTGCCCGGTATAACCAGTGTAATACCACTTCTGGTAACGAGGTTAC<br>TAGCGTCATGAATCGGGCTAAGAAGGCCGGCAAGTCTGTTGGTGTCGTGACCACT<br>TCGCGCGTCCAGCATGCTTCCCCTGCTGGAGCCTACGCTCACACCGTCAACCGCA<br>ATTGGTATAGCGATGCTGACCTGCCCGCCGATGCTCAGACCTACGGCTGCCAGGA<br>CATCGCCACTCAGCTCGTCAACAATATGGATATCGACGTGATCCTGGGAGGCGGT<br>CGTATGTATATGTTCCCTGAAGGTACCCCTGATCCCGAGTACCCCTATGACGTGA<br>ACCAGACTGGAGTTCGGAAGGACAAGCGCAATCTTGTGCAGGAATGGCAGGCTAA<br>GCATCAGGGTGCCCAGTACGTTTGGAACCGCACCGAGCTCCTGCAGGCTGCCAAT<br>GATCCATCGGTCACTCACCTCATGGGACTGTTCGAACCGGCCGACATGAAGTATA<br>ACGTGCAGCAGGATCCTACTAAGGACCCCACCCTTGAAGAGATGACCGAGGCTGC<br>CCTTCAGGTTTTGTCCCGGAATCCACAGGGCTTCTACTTGTTCGTCGAGGGCGGC<br>CGCATCGATCATGGACATCACGAGGGCAAGGCTTATATGGCCCTCACTGATACCG<br>TTATGTTCGACAACGCCATCGCTAAGGCCAATGAACTCACTTCGGAGCTGGATAC<br>CCTTATCTTGGCTACTGCCGACCATTCGCACGTCTTCTCCTTCGGTGGATACACT<br>CTTCGTGGTACCTCCATCTTCGGATTGGCTCCTTCCAAGGCCTCTGACAACAAGA<br>GCTACACCTCGATCCTGTATGGCAATGGTCCTGGATACGTCCTTGGCGGTGGATT<br>GCGTCCCGATGTGAACGACAGCATCTCGGAGGATCCATCTTATCGGCAGCAGGCT<br>GCCGTCCCGTTGTCCTCTGAAAGCCATGGCGGTGAGGATGTGGCTGTTTTCGCTC<br>GTGGACCACAGGCTCATTTGGTGCACGGCGTTCAGGAAGAGACCTTCGTCGCCCA<br>CGTGATGGCTTTTGCGGGTTGCGTTGAGCCCTATACTGACTGTAACTTGCCAGCC<br>CCTTCGGGT |
| 100 | Showing nucleotide sequence encoding CelB_bIAP IV | ATGATCTGGACACTCGCTCCCTTTGTGGCACTCCTGCCACTGGTAACGGCTCAAC<br>AGGTGGGAACTACAGCGGACGCCCATCCCAGACTCACCACGTATAAATGTACTTC<br>ACAGAACGGCTGCACGAGGCAGAACACCTCAGTCGTCCTTGATGCAGCAACCCAT<br>TTTATCCACAAAAAAGGAACACAAACATCCTGCACCAACAGCAACGGCTTGGACA<br>CTTCCATTTGTCCGACAAACAGACCTGCGCGGACAACTGTGTCGTTGATGGGAT<br>CACGGACTACGCTAGCTACGGCGTCCAGACGAAGAATGACACATTGACCCTTCAC<br>CAATATCTGCAAACTGGCAATGAAACAAAGTCCGTGTCACCGCGTGTCTACCTCC<br>TCGCTGAAGACGGAGAGAACTATTCCATGCTGCAACTCCTGAATCAGGAATTCAC<br>CTTCGATGTCGACGCCTCTACCCTCGTCTGCGGCATGAATGGTGCTCTATATCTC<br>TCTGAAATGGAGGCTTCGGGCGGAAAGAGTTCCCTAAATCAAGCGGGAGCCAAAT<br>ACGGAACCGGTTACTGTGATGCCCAATGCTACACCACGCCTTGGATCAACGGCGA<br>AGGCAACACCGAGAGTGTCGGCTCCTGCTGTCAGGAAATGGATATTTGGAAGCC<br>AACGCCCGAGCAACAGGGCTTACACCGCACCCTTGCAACACAACCGGTTTGTACG<br>AGTGCAGCGGCTCGGGATGCGGAGACTCCGGGGTCTGTGACAAGTCCGGCTGTGG<br>ATTCAACCCATATGGCCTAGGTGCAAAGGACTACTACGGTTACGGCCTCAAGGTC<br>AACACCAACGAGACATTCACGGTCGTAACCCAGTTCCTCACAAGCGATAACACGA<br>CATCGGGCCAGCTCAGCGAAATCCGCCGTCTCTACATCCAGAACGGCCAGGTTAT<br>TCAAAATGTGCCGTCACCTCAGGAGGAAAACTGTGACTCAATCACAAAGGAT<br>TTCTGCAGCGGTGAAGGAAGTGCCTTCAACCGACTTGGCGGCCTCGAGGAAATGG<br>GCCACGCCTTGGGCCGCGGCATGGTTCTTGCGCTCAGTGTCTGGAACGACGCAGG<br>CTCATTCATGCAATGGCTTGATGGGGCAGCGCAGGACCGTGCAGCGCGACGGAG<br>GGAGACCCGGCGTTGATCGAGAAGTTGTATCCGGATACTCATGTGAAGTTTTCCA<br>AGATCCGGTGGGGAGATATTGGATCTACCTACAGGCATGGCGGTGGAGGCTCTAA<br>GCGCTTCATCCCAGCTGAGGAAGAGGATCCTGCTTTTCTGGAACCGTCAGGCTGCT<br>CAGGCTCTTGACGTTGCCAAGAAGTTGCAGCCAATCCAGACCGCCGCTAAGAATG<br>TCATCCTCTTCCTGGGCGATGGTATGGGAGTCCCGACCGTGACTGCTACCCGCAT<br>CCTCAAGGGCCAGATGAATGGAAAGCTCGGCCCAGAAACCCCGCTGGCTATGGAC<br>CAGTTCCCTTACGTGGCCCTGTCGAAGACTTATAACGTTGATCGTCAAGTCCCTG<br>ACTCTGCTGGTACTGCTACCGCCTACCTTTGCGGTGTGAAGGGAAATTATAAGAC<br>CATCGGCGTTTCCGCCGCTGCCCGGTATAACCAGTGTAATACCACTTCTGGTAAC<br>GAGGTTACTAGCGTCATGAATCGGGCTAAGAAGGCCGGCAAGTCTGTTGGTGTCG |

| SEQ ID NO: | Description | Sequence |
|---|---|---|
| | | TGACCACTTCGCGCGTCCAGCATGCTTCCCCTGCTGGAGCCTACGCTCACACCGT<br>CAACCGCAATTGGTATAGCGATGCTGACCTGCCCGCCGATGCTCAGACCTACGGC<br>TGCCAGGACATCGCCACTCAGCTCGTCAACAATATGGATATCGACGTGATCCTGG<br>GAGGCGGTCGTATGTATATGTTCCCTGAAGGTACCCCTGATCCCGAGTACCCCTA<br>TGACGTGAACCAGACTGGAGTTCGGAAGGACAAGCGCAATCTTGTGCAGGAATGG<br>CAGGCTAAGCATCAGGGTGCCCAGTACGTTTGGAACCGCACCGAGCTCCTGCAGG<br>CTGCCAATGATCCATCG<br>GTCACTCACCTCATGGGACTGTTCGAACCGGCCGACATGAAGTATAACGTGCAGC<br>AGGATCCTACTAAGGACCCCACCCTTGAAGAGATGACCGAGGCTGCCCTTCAGGT<br>TTTGTCCCGGAATCCACAGGGCTTCTACTTGTTCGTCGAGGGCGGCCGCATCGAT<br>CATGGACATCACGAGGGCAAGGCTTATATGGCCCTCACTGATACCGTTATGTTCG<br>ACAACGCCATCGCTAAGGCCAATGAACTCACTTCGGAGCTGGATACCCTTATCTT<br>GGCTACTGCCGACCATTCGCACGTCTTCTCCTTCGGTGGATACACTCTTCGTGGT<br>ACCTCCATCTTCGGATTGGCTCCTTCCAAGGCCTCTGACAACAAGAGCTACACCT<br>CGATCCTGTATGGCAATGGTCCTGGATACGTCCTTGGCGGTGGATTGCGTCCCGA<br>TGTGAACGACAGCATCTCGGAGGATCCATCTTATCGGCAGCAGGCTGCCGTCCCG<br>TTGTCCTCTGAAAGCCATGGCGGTGAGGATGTGGCTGTTTTCGCTCGTGGACCAC<br>AGGCTCATTTGGTGCACGGCGTTCAGGAAGAGACCTTCGTCGCCCACGTGATGGC<br>TTTTGCGGGTTGCGTTGAGCCCTATACTGACTGTAACTTGCCAGCCCCTTCGGGT |
| 101 | Showing nucleotide sequence encoding SKIK_CDHss_bIAP IV | ATGTCCAAGATCAAGAAGCTCGTTAACCGTTTGCTCGCTTCATTCCTGTCAGCGA<br>GCACCGGTGAGTGGTGGCCTATCGAGCTAATGTTGCTTCTCTTCGTCTGACTTTT<br>CTTGGCAGTGTTGCAGTCATGCTGGGCTTTCATCCCAGCTGAGGAAGAGGATCCT<br>GCTTTCTGGAACCGTCAGGCTGCTCAGGCTCTTGACGTTGCCAAGAAGTTGCAGC<br>CAATCCAGACCGCCGCTAAGAATGTCATCCTCTTCCTGGGCGATGGTATGGGAGT<br>CCCGACCGTGACTGCTACCCGCATCCTCAAGGGCCAGATGAATGGAAAGCTCGGC<br>CCAGAAACCCCGCTGGCTATGACCAGTTCCCTTACGTGGCCCTGTCGAAGACTT<br>ATAACGTTGATCGTCAAGTCCCTGACTCTGCTGGTACTGCTACCGCCTACCTTTG<br>CGGTGTGAAGGGAAATTATAAGACCATCGGCGTTTCCGCCGCTGCCCGGTATAAC<br>CAGTGTAATACCACTTCTGGTAACGAGGTTACTAGCGTCATGAATCGGGCTAAGA<br>AGGCCGGCAAGTCTGTTGGTGTCGTGACCACTTCGCGCGTCCAGCATGCTTCCCC<br>TGCTGGAGCCTACGCTCACACCGTCAACCGCAATTGGTATAGCGATGCTGACCTG<br>CCCGCCGATGCTCAGACCTACGGCTGCCAGGACATCGCCACTCAGCTCGTCAACA<br>ATATGGATATCGACGTGATCCTGGGAGGCGGTCGTATGTATATGTTCCCTGAAGG<br>TACCCCTGATCCCGAGTACCCCTATGACGTGAACCAGACTGGAGTTCGGAAGGAC<br>AAGCGCAATCTTGTGCAGGAATGGCAGGCTAAGCATCAGGGTGCCCAGTACGTTT<br>GGAACCGCACCGAGCTCCTGCAGGCTGCCAATGATCCATCGGTCACTCACCTCAT<br>GGGACTGTTCGAACCGGCCGACATGAAGTATAACGTGCAGCAGGATCCTACTAAG<br>GACCCCACCCTTGAAGAGATGACCGAGGCTGCCCTTCAGGTTTTGTCCCGGAATC<br>CACAGGGCTTCTACTTGTTCGTCGAGGGCGGCCGCATCGATCATGGACATCACGA<br>GGGCAAGGCTTATATGGCCCTCACTGATACCGTTATGTTCGACAACGCCATCGCT<br>AAGGCCAATGAACTCACTTCGGAGCTGGATACCCTTATCTTGGCTACTGCCGACC<br>ATTCGCACGTCTTCTCCTTCGGTGGATACACTCTTCGTGGTACCTCCATCTTCGG<br>ATTGGCTCCTTCCAAGGCCTCTGACAACAAGAGCTACACCTCGATCCTGTATGGC<br>AATGGTCCTGGATACGTCCTTGGCGGTGGATTGCGTCCCGATGTGAACGACAGCA<br>TCTCGGAGGATCCATCTTATCGGCAGCAGGCTGCCGTCCCGTTGTCCTCTGAAAG<br>CCATGGCGGTGAGGATGTGGCTGTTTTCGCTCGTGGACCACAGGCTCATTTGGTG<br>CACGGCGTTCAGGAAGAGACCTTCGTCGCCCACGTGATGGCTTTTGCGGGTTGCG<br>TTGAGCCCTATACTGACTGTAACTTGCCAGCCCCTTCGGGT |
| 102 | Showing nucleotide sequence encoding AsAP1ss54_bIAP IV | ATGAGGTTCCTCTCAATTGTAGGTGCGGCGCTCTTCGCTTCCAGCGCTGTTGCCT<br>TCATCCCAGCTGAGGAAGAGGATCCTGCTTTCTGGAACCGTCAGGCTGCTCAGGC<br>TCTTGACGTTGCCAAGAAGTTGCAGCCAATCCAGACCGCCGCTAAGAATGTCATC<br>CTCTTCCTGGGCGATGGTATGGGAGTCCCGACCGTGACTGCTACCCGCATCCTCA<br>AGGGCCAGATGAATGGAAAGCTCGGCCCAGAAACCCCGCTGGCTATGACCAGTT<br>CCCTTACGTGGCCCTGTCGAAGACTTATAACGTTGATCGTCAAGTCCCTGACTCT<br>GCTGGTACTGCTACCGCCTACCTTTGCGGTGTGAAGGGAAATTATAAGACCATCG<br>GCGTTTCCGCCGCTGCCCGGTATAACCAGTGTAATACCACTTCTGGTAACGAGGT<br>TACTAGCGTCATGAATCGGGCTAAGAAGGCCGGCAAGTCTGTTGGTGTCGTGACC<br>ACTTCGCGCGTCCAGCATGCTTCCCCTGCTGGAGCCTACGCTCACACCGTCAACC<br>GCAATTGGTATAGCGATGCTGACCTGCCCGCCGATGCTCAGACCTACGGCTGCCA<br>GGACATCGCCACTCAGCTCGTCAACAATATGGATATCGACGTGATCCTGGGAGGC<br>GGTCGTATGTATATGTTCCCTGAAGGTACCCCTGATCCCGAGTACCCCTATGACG<br>TGAACCAGACTGGAGTTCGGAAGGACAAGCGCAATCTTGTGCAGGAATGGCAGGC<br>TAAGCATCAGGGTGCCCAGTACGTTTGGAACCGCACCGAGCTCCTGCAGGCTGCC<br>AATGATCCATCGGTCACTCACCTCATGGGACTGTTCGAACCGGCCGACATGAAGT<br>ATAACGTGCAGCAGGATCCTACTAAGGACCCCACCCTTGAAGAGATGACCGAGGC<br>TGCCCTTCAGGTTTTGTCCCGGAATCCACAGGGCTTCTACTTGTTCGTCGAGGGC<br>GGCCGCATCGATCATGGACATCACGAGGGCAAGGCTTATATGGCCCTCACTGATA<br>CCGTTATGTTCGACAACGCCATCGCTAAGGCCAATGAACTCACTTCGGAGCTGGA<br>TACCCTTATCTTGGCTACTGCCGACCATTCGCACGTCTTCTCCTTCGGTGGATAC<br>ACTCTTCGTGGTACCTCCATCTTCGGATTGGCTCCTTCCAAGGCCTCTGACAACA<br>AGAGCTACACCTCGATCCTGTATGGCAATGGTCCTGGATACGTCCTTGGCGGTGG<br>ATTGCGTCCCGATGTGAACGACAGCATCTCGGAGGATCCATCTTATCGGCAGCAG<br>GCTGCCGTCCCGTTGTCCTCTGAAAGCCATGGCGGTGAGGATGTGGCTGTTTTCG |

| SEQ ID NO: | Description | Sequence |
|---|---|---|
| | | CTCGTGGACCACAGGCTCATTTGGTGCACGGCGTTCAGGAAGAGACCTTCGTCGC<br>CCACGTGATGGCTTTTGCGGGTTGCGTTGAGCCCTATACTGACTGTAACTTGCCA<br>GCCCCTTCGGGT |
| 103 | Showing nucleotide sequence encoding AsAP3ss72_bIAP IV | ATGCATATCCGCACTGCCATCACCGCGGGCGCGGCCCTTGTCCAGACTGCAGTTG<br>CAGCTTCTGTTCAGGCATTCATCCCAGCTGAGGAAGAGGATCCTGCTTTCTGGAA<br>CCGTCAGGCTGCTCAGGCTCTTGACGTTGCCAAGAAGTTGCAGCCAATCCAGACC<br>GCCGCTAAGAATGTCATCCTCTTCCTGGGCGATGGTATGGGAGTCCCGACCGTGA<br>CTGCTACCCGCATCCTCAAGGGCCAGATGAATGGAAAGCTCGGCCCAGAAACCCC<br>GCTGGCTATGGACCAGTTCCCTTACGTGGCCCTGTCGAAGACTTATAACGTTGAT<br>CGTCAAGTCCCTGACTCTGCTGGTACTGCTACCGCCTACCTTTGCGGTGTGAAGG<br>GAAATTATAAGACCATCGGCGTTTCCGCCGCTGCCCGGTATAACCAGTGTAATAC<br>CACTTCTGGTAACGAGGTTACTAGCGTCATGAATCGGGCTAAGAAGGCCGGCAAG<br>TCTGTTGGTGTCGTGACCACTTCGCGCGTCCAGCATGCTTCCCCTGCTGGAGCCT<br>ACGCTCACACCGTCAACCGCAATTGGTATAGCGATGCTGACCTGCCCGCCGATGC<br>TCAGACCTACGGCTGCCAGGACATCGCCACTCAGCTCGTCAACAATATGGATATC<br>GACGTGATCCTGGGAGGCGGTCGTATGTATATGTTCCCTGAAGGTACCCCTGATC<br>CCGAGTACCCCTATGACGTGAACCAGACTGGAGTTCGGAAGGACAAGCGCAATCT<br>TGTGCAGGAATGGCAGGCTAAGCATCAGGGTGCCCAGTACGTTTGGAACCGCACC<br>GAGCTCCTGCAGGCTGCCAATGATCCATCGGTCACTCACCTCATGGGACTGTTCG<br>AACCGGCCGACATGAAGTATAACGTGCAGCAGGATCCTACTAAGGACCCCCACCCT<br>TGAAGAGATGACCGAGGCTGCCCTTCAGGTTTTGTCCCGGAATCCACAGGGCTTC<br>TACTTGTTCGTCGAGGGCGGCCGCATCGATCATGGACATCACGAGGGCAAGGCTT<br>ATATGGCCCTCACTGATACCGTTATGTTCGACAACGCCATCGCTAAGGCCAATGA<br>ACTCACTTCGGAGCTGGATACCCTTATCTTGGCTACTGCCGACCATTCGCACGTC<br>TTCTCCTTCGGTGGATACACTCTTCGTGGTACCTCCATCTTCGGATTGGCTCCTT<br>CCAAGGCCTCTGACAACAAGAGCTACACCTCGATCCTGTATGGCAATGGTCCTGG<br>ATACGTCCTTGGCGGTGGATTGCGTCCCGATGTGAACGACAGCATCTCGGAGGAT<br>CCATCTTATCGGCAGCAGGCTGCCGTCCCGTTGTCCTCTGAAAGCCATGGCGGTG<br>AGGATGTGGCTGTTTTCGCTCGTGGACCACAGGCTCATTTGGTGCACGGCGTTCA<br>GGAAGAGACCTTCGTCGCCCACGTGATGGCTTTTGCGGGTTGCGTTGAGCCCTAT<br>ACTGACTGTAACTTGCCAGCCCCTTCGGGT |
| 104 | Showing amino acid sequence of bIAP IV without region encoding membrane-bound signal peptide in C-terminus side | MQWACVLLLLGLWLQLSLTFIPAEEEDPAFWNRQAAQALDVAKKLQPIQTAAKNV<br>ILFLGDGMGVPTVTATRILKGQMNGKLGPETPLAMDQFPYVALSKTYNVDRQVPD<br>SAGTATAYLCGVKGNYKTIGVSAAARYNQCNTTSGNEVTSVMNRAKKAGKSVGVV<br>TTSRVQHASPAGAYAHTVNRNWYSDADLPADAQTYGCQDIATQLVNNMDIDVILG<br>GGRMYMFPEGTPDPEYPYDVNQTGVRKDKRNLVQEWQAKHQGAQYVWNRTELLQA<br>ANDPSVTHLMGLFEPADMKYNVQQDPTKDPTLEEMTEAALQVLSRNPQGFYLFVE<br>GGRIDHGHHEGKAYMALTDTVMFDNATAKANELTSELDTLILATADHSHVFSFGG<br>YTLRGTSIFGLAPSKASDNKSYTSILYGNGPGYVLGGGLRPDVNDSISEDPSYRQ<br>QAAVPLSSESHGGEDVAVFARGPQAHLVHGVQEETFVAHVMAFAGCVEPYTDCNL<br>PAPSG |
| 105 | Showing amino acid sequence of CDHss_bAP IV | MKLVNRLLASFLSASTVLQSCWAFIPAEEEDPAFWNRQAAQALDVAKKLQPIQTA<br>AKNVILFLGDGMGVPTVTATRILKGQMNGKLGPETPLAMDQFPYVALSKTYNVDR<br>QVPDSAGTATAYLCGVKGNYKTIGVSAAARYNQCNTTSGNEVTSVMNRAKKAGKS<br>VGVVTTSRVQHASPAGAYAHTVNRNWYSDADLPADAQTYGCQDIATQLVNNMDID<br>VILGGGRMYMFPEGTPDPEYPYDVNQTGVRKDKRNLVQEWQAKHQGAQYVWNRTE<br>LLQAANDPSVTHLMGLFEPADMKYNVQQDPTKDPTLEEMTEAALQVLSRNPQGFY<br>LFVEGGRIDHGHHEGKAYMALTDTVMFDNATAKANELTSELDTLILATADHSHVF<br>SFGGYTLRGTSIFGLAPSKASDNKSYTSILYGNGPGYVLGGGLRPDVNDSISEDP<br>SYRQQAAVPLSSESHGGEDVAVFARGPQAHLVHGVQEETFVAHVMAFAGCVEPYT<br>DCNLPAPSG |
| 106 | Showing amino acid sequence of CDHcytbkex_bAP IV | MKLVNRLLASFLSASTVLQSCWAQSGTPVAYTDTETGITFDTWSVPAGTGTGGLV<br>FGVALPGSALTTDATEFIGYLQCASQNASSAGWCGISLGGGMNNNLLFLAYPYED<br>TILTSLRFGSGYSMPGVYTGNANVTQISSSINATHFTLLFRCENCLTWDQDGQTG<br>NATTSKGRLVLGWAQSTESPSNPSCPDNISLAQHDNQGIISATLDENAASESYED<br>WVKLANKTVPGDCSGDGGGNEPTPVPVPDGGGGGSKRFIPAEEEDPAFWNRQAA<br>QALDVAKKLQPIQTAAKNVILFLGDGMGVPTVTATRILKGQMNGKLGPETPLAMD<br>QFPYVALSKTYNVDRQVPDSAGTATAYLCGVKGNYKTIGVSAAARYNQCNTTSGN<br>EVTSVMNRAKKAGKSVGVVTTSRVQHASPAGAYAHTVNRNWYSDADLPADAQTYG<br>CQDIATQLVNNMDIDVILGGGRMYMFPEGTPDPEYPYDVNQTGVRKDKRNLVQEW<br>QAKHQGAQYVWNRTELLQAANDPSVTHLMGLFEPADMKYNVQQDPTKDPTLEEMT<br>EAALQVLSRNPQGFYLFVEGGRIDHGHHEGKAYMALTDTVMFDNATAKANELTSE<br>LDTLILATADHSHVFSFGGYTLRGTSIFGLAPSKASDNKSYTSILYGNGPGYVLG<br>GGLRPDVNDSISEDPSYRQQAAVPLSSESHGGEDVAVFARGPQAHLVHGVQEETF<br>VAHVMAFAGCVEPYTDCNLPAPSG |
| 107 | Showing amino acid sequence of CDHcytbKexmut1_bAP IV | MKLVNRLLASFLSASTVLQSCWAQSGTPVAYTDTETGITFDTWSVPAGTGTGGLV<br>FGVALPGSALTTDATEFIGYLQCASQNASSAGWCGISLGGGMNNNLLFLAYPYED<br>TILTSLRFGSGYSMPGVYTGNANVTQISSSINATHFTLLFRCENCLTWDQDGQTG<br>NATTSKGRLVLGWAQSTESPSNPSCPDNISLAQHDNQGIISATLDENAASESYED<br>WVKLANKTVPGDCSGDGGGNEPTPVPVPDGGGGRHKRFIPAEEEDPAFWNRQAA<br>QALDVAKKLQPIQTAAKNVILFLGDGMGVPTVTATRILKGQMNGKLGPETPLAMD |

TABLE-continued

| SEQ ID NO: | Description | Sequence |
|---|---|---|
| | | QFPYVALSKTYNVDRQVPDSAGTATAYLCGVKGNYKTIGVSAAARYNQCNTTSGN EVTSVMNRAKKAGKSVGVVTTSRVQHASPAGAYAHTVNRNWYSDADLPADAQTYG CQDIATQLVNNMDIDVILGGGRMYMFPEGTPDPEYPYDVNQTGVRKDKRNLVQEW QAKHQGAQYVWNRTELLQAANDPSVTHLMGLFEPADMKYNVQQDPTKDPTLEEMT EAALQVLSRNPQGFYLFVEGGRIDHGHHEGKAYMALTDTVMFDNATAKANELTSE LDTLILATADHSHVFSFGGYTLRGTSIFGLAPSKASDNKSYTSILYGNGPGYVLG GGLRPDVNDSISEDPSYRQQAAVPLSSESHGGEDVAVFARGPQAHLVHGVQEETF VAHVMAFAGCVEPYTDCNLPAPSG |
| 108 | Showing amino acid sequence of CDHcytbKexmut2_bAP IV | MKLVNRLLASFLSASTVLQSCWAQSGTPVAYTDTETGITFDTWSVPAGTGTGGLV FGVALPGSALTTDATEFIGYLQCASQNASSAGWCGISLGGGMNNNLLFLAYPYED TILTSLRFGSGYSMPGVYTGNANVTQISSSINATHFTLLFRCENCLTWDQDGQTG NATTSKGRLVLGWAQSTESPSNPSCPDNISLAQHDNQGIISATLDENAASESYED WVKLANKTVPGDCSGDGGGGNEPTPVPVPDGGGGPHKRFIPAEEEDPAFWNRQAA QALDVAKKLQPIQTAAKNVILFLGDGMGVPTVTATRILKGQMNGKLGPETPLAMD QFPYVALSKTYNVDRQVPDSAGTATAYLCGVKGNYKTIGVSAAARYNQCNTTSGN EVTSVMNRAKKAGKSVGVVTTSRVQHASPAGAYAHTVNRNWYSDADLPADAQTYG CQDIATQLVNNMDIDVILGGGRMYMFPEGTPDPEYPYDVNQTGVRKDKRNLVQEW QAKHQGAQYVWNRTELLQAANDPSVTHLMGLFEPADMKYNVQQDPTKDPTLEEMT EAALQVLSRNPQGFYLFVEGGRIDHGHHEGKAYMALTDTVMFDNATAKANELTSE LDTLILATADHSHVFSFGGYTLRGTSIFGLAPSKASDNKSYTSILYGNGPGYVLG GGLRPDVNDSISEDPSYRQQAAVPLSSESHGGEDVAVFARGPQAHLVHGVQEETF VAHVMAFAGCVEPYTDCNLPAPSG |
| 109 | Showing amino acid sequence of CDHcytbKexmut3_bAP IV | MKLVNRLLASFLSASTVLQSCWAQSGTPVAYTDTETGITFDTWSVPAGTGTGGLV FGVALPGSALTTDATEFIGYLQCASQNASSAGWCGISLGGGMNNNLLFLAYPYED TILTSLRFGSGYSMPGVYTGNANVTQISSSINATHFTLLFRCENCLTWDQDGQTG NATTSKGRLVLGWAQSTESPSNPSCPDNISLAQHDNQGIISATLDENAASESYED WVKLANKTVPGDCSGDGGGGNEPTPVPVPDGGGGQRLVKRFIPAEEEDPAFWNRQ AAQALDVAKKLQPIQTAAKNVILFLGDGMGVPTVTATRILKGQMNGKLGPETPLA MDQFPYVALSKTYNVDRQVPDSAGTATAYLCGVKGNYKTIGVSAAARYNQCNTTS GNEVTSVMNRAKKAGKSVGVVTTSRVQHASPAGAYAHTVNRNWYSDADLPADAQT YGCQDIATQLVNNMDIDVILGGGRMYMFPEGTPDPEYPYDVNQTGVRKDKRNLVQ EWQAKHQGAQYVWNRTELLQAANDPSVTHLMGLFEPADMKYNVQQDPTKDPTLEE MTEAALQVLSRNPQGFYLFVEGGRIDHGHHEGKAYMALTDTVMFDNAIAKANELT SELDTLILATADHSHVFSFGGYTLRGTSIFGLAPSKASDNKSYTSILYGNGPGYV LGGGLRPDVNDSISEDPSYRQQAAVPLSSESHGGEDVAVFARGPQAHLVHGVQEE TFVAHVMAFAGCVEPYTDCNLPAPSG |
| 110 | Showing amino acid sequence of CDHcytbKexmut4_bAP IV | MKLVNRLLASFLSASTVLQSCWAQSGTPVAYTDTETGITFDTWSVPAGTGTGGLV FGVALPGSALTTDATEFIGYLQCASQNASSAGWCGISLGGGMNNNLLFLAYPYED TILTSLRFGSGYSMPGVYTGNANVTQISSSINATHFTLLFRCENCLTWDQDGQTG NATTSKGRLVLGWAQSTESPSNPSCPDNISLAQHDNQGIISATLDENAASESYED WVKLANKTVPGDCSGDGGGGNEPTPVPVPDGGGGVAVEKRFIPAEEEDPAFWNRQ AAQALDVAKKLQPIQTAAKNVILFLGDGMGVPTVTATRILKGQMNGKLGPETPLA MDQFPYVALSKTYNVDRQVPDSAGTATAYLCGVKGNYKTIGVSAAARYNQCNTTS GNEVTSVMNRAKKAGKSVGVVTTSRVQHASPAGAYAHTVNRNWYSDADLPADAQT YGCQDIATQLVNNMDIDVILGGGRMYMFPEGTPDPEYPYDVNQTGVRKDKRNLVQ EWQAKHQGAQYVWNRTELLQAANDPSVTHLMGLFEPADMKYNVQQDPTKDPTLEE MTEAALQVLSRNPQGFYLFVEGGRIDHGHHEGKAYMALTDTVMFDNATAKANELT SELDTLILATADHSHVFSFGGYTLRGTSIFGLAPSKASDNKSYTSILYGNGPGYV LGGGLRPDVNDSISEDPSYRQQAAVPLSSESHGGEDVAVFARGPQAHLVHGVQEE TFVAHVMAFAGCVEPYTDCNLPAPSG |
| 111 | Showing amino acid sequence of CDHall_bIAP IV | MKLVNRLLASFLSASTVLQSCWAQSGTPVAYTDTETGITFDTWSVPAGTGTGGLV FGVALPGSALTTDATEFIGYLQCASQNASSAGWCGISLGGGMNNNLLFLAYPYED TILTSLRFGSGYSMPGVYTGNANVTQISSSINATHFTLLFRCENCLTWDQDGQTG NATTSKGRLVLGWAQSTESPSNPSCPDNISLAQHDNQGIISATLDENAASESYED WVKLANKTVPGDCSGDGGGGNEPTPVPVPDGATYDYIVVGGGAGGIPVADRLSEA GHSVLLIEKGPPSSGRWGGTMKPSWLDDTNLTRFDVPGLCNQIWVDSNGIACSDT DQMAGCVLGGGTAVNAGLWWKPNPVDWDYNFPEGWQSSDMQAAADRVFSRIPGTT TPSTDGKLYYQQGADILLNGLQSAGWSSVTLNDVPAQKTKTFGHAPFMFSGGERG GPMGTYLVSASERDNFARWSNTTVKRVVREGGRITGVEVEATLDGGYAGTVNVTA NTGRVILSAGTFGTPKVLMRSGIGPKDQLSIVKSSTDGETMIAESEWIELPVGEN LVDHVNTDVVVTHPDVVFYDFKAAYKTPIESDATSYLNDRTGIFAQAAPNIGPII FDEVTGSDGIKRQTQWTARVEGGHDTPDGHAMTISQYLGRGSTSRGRMTITAGLD TVVSTLPFLRDESDVNAVIQGIQNLKMALNGTGFTWNYPARNTSIAEFVNTMPIT AGTRRANHWMGTCKIGTDDGRTGGSAVVDLNTKVYGTDNLFVVDASIFPGMITSN PSAYIVTVAEHAAEKILALGGGGSKRFIPAEEEDPAFWNRQAAQALDVAKKLQPI QTAAKNVILFLGDGMGVPTVTATRILKGQMNGKLGPETPLAMDQFPYVALSKTYN VDRQVPDSAGTATAYLCGVKGNYKTIGVSAAARYNQCNTTSGNEVTSVMNRAKKA GKSVGVVTTSRVQHASPAGAYAHTVNRNWYSDADLPADAQTYGCQDIATQLVNNM DIDVILGGGRMYMFPEGTPDPEYPYDVNQTGVRKDKRNLVQEWQAKHQGAQYVWN RTELLQAANDPSVTHLMGLFEPADMKYNVQQDPTKDPTLEEMTEAALQVLSRNPQ GFYLFVEGGRIDHGHHEGKAYMALTDTVMFDNAIAKANELTSELDTLILATADHS HVFSFGGYTLRGTSIFGLAPSKASDNKSYTSILYGNGPGYVLGGGLRPDVNDSIS |

| SEQ ID NO: | Description | Sequence |
|---|---|---|
| | | EDPSYRQQAAVPLSSESHGGEDVAVFARGPQAHLVHGVQEETFVAHVMAFAGCVE PYTDCNLPAPSG |
| 112 | Showing amino acid sequence of GlaBss_bIAP IV | MRNNFLFSLNAIAGAVAFIPAEEEDPAFWNRQAAQALDVAKKLQPIQTAAKNVIL FLGDGMGVPTVTATRILKGQMNGKLGPETPLAMDQFPYVALSKTYNVDRQVPDSA GTATAYLCGVKGNYKTIGVSAAARYNQCNTTSGNEVTSVMNRAKKAGKSVGVVTT SRVQHASPAGAYAHTVNRNWYSDADLPADAQTYGCQDIATQLVNNMDIDVILGGG RMYMFPEGTPDPEYPYDVNQTGVRKDKRNLVQEWQAKHQGAQYVWNRTELLQAAN DPSVTHLMGLFEPADMKYNVQQDPTKDPTLEEMTEAALQVLSRNPQGFYLFVEGG RIDHGHHEGKAYMALTDTVMFDNAIAKANELTSELDTLILATADHSVFSFGGYT LRGTSIFGLAPSKASDNKSYTSILYGNGPGYVLGGGLRPDVNDSISEDPSYRQQA AVPLSSESHGGEDVAVFARGPQAHLVHGVQEETFVAHVMAFAGCVEPYTDCNLPA PSG |
| 113 | Showing amino acid sequence of CelBss_bIAP IV | MIWTLAPFVALLPLVTAFIPAEEEDPAFWNRQAAQALDVAKKLQPIQTAAKNVIL FLGDGMGVPTVTATRILKGQMNGKLGPETPLAMDQFPYVALSKTYNVDRQVPDSA GTATAYLCGVKGNYKTIGVSAAARYNQCNTTSGNEVTSVMNRAKKAGKSVGVVTT SRVQHASPAGAYAHTVNRNWYSDADLPADAQTYGCQDIATQLVNNMDIDVILGGG RMYMFPEGTPDPEYPYDVNQTGVRKDKRNLVQEWQAKHQGAQYVWNRTELLQAAN DPSVTHLMGLFEPADMKYNVQQDPTKDPTLEEMTEAALQVLSRNPQGFYLFVEGG RIDHGHHEGKAYMALTDTVMFDNAIAKANELTSELDTLILATADHSVFSFGGYT LRGTSIFGLAPSKASDNKSYTSILYGNGPGYVLGGGLRPDVNDSISEDPSYRQQA AVPLSSESHGGEDVAVFARGPQAHLVHGVQEETFVAHVMAFAGCVEPYTDCNLPA PSG |
| 114 | Showing amino acid sequence of CelB_bIap IV | MIWTLAPFVALLPLVTAQQVGTTADAHPRLTTYKCTSQNGCTRQNTSVVLDAATH FIHKKGTQTSCTNSNGLDTSICPDKQTCADNCVVDGITDYASYGVQTKNDTLTLH QYLQTGNETKSVSPRVYLLAEDGENYSMLQLLNQEFTFDVDASTLVCGMNGALYL SEMEASGGKSSLNQAGAKYGTGYCDAQCYTTPWINGEGNTESVGSCCQEMDIWEA NARATGLTPHPCNTTGLYECSGSGCGDSGVCDKSGCFNPYGLGAKDYYGYGLKV NTNETFTVVTQFLTSDNTTSGQLSEIRRLYIQNGQVIQNAAVTSGGKTVDSITKD FCSGEGSAFNRLGGLEEMGHALGRGMVLALSVWNDAGSFMQWLDGGSAGPCSATE GDPALIEKLYPDTHVKFSKIRWGDIGSTYRHGGGGSKRFIPAEEEDPAFWNRQAA QALDVAKKLQPIQTAAKNVILFLGDGMGVPTVTATRILKGQMNGKLGPETPLAMD QFPYVALSKTYNVDRQVPDSAGTATAYLCGVKGNYKTIGVSAAARYNQCNTTSGN EVTSVMNRAKKAGKSVGVVTTSRVQHASPAGAYAHTVNRNWYSDADLPADAQTYG CQDIATQLVNNMDIDVILGGGRMYMFPEGTPDPEYPYDVNQTGVRKDKRNLVQEW QAKHQGAQYVWNRTELLQAANDPSVTHLMGLFEPADMKYNVQQDPTKDPTLEEMT EAALQVLSRNPQGFYLFVEGGRIDHGHHEGKAYMALTDTVMFDNATAKANELTSE LDTLILATADHSHVFSFGGYTLRGTSIFGLAPSKASDNKSYTSILYGNGPGYVLG GGLRPDVNDSISEDPSYRQQAAVPLSSESHGGEDVAVFARGPQAHLVHGVQEETF VAHVMAFAGCVEPYTDCNLPAPSG |
| 115 | Showing amino acid sequence of SKIK_CDHss_bIAP IV | MSKIKKLVNRLLASFLSASTVLQSCWAFIPAEEEDPAFWNRQAAQALDVAKKLQP IQTAAKNVILFLGDGMGVPTVTATRILKGQMNGKLGPETPLAMDQFPYVALSKTY NVDRQVPDSAGTATAYLCGVKGNYKTIGVSAAARYNQCNTTSGNEVTSVMNRAKK AGKSVGVVTTSRVQHASPAGAYAHTVNRNWYSDADLPADAQTYGCQDIATQLVNN MDIDVILGGGRMYMFPEGTPDPEYPYDVNQTGVRKDKRNLVQEWQAKHQGAQYVW NRTELLQAANDPSVTHLMGLFEPADMKYNVQQDPTKDPTLEEMTEAALQVLSRNP QGFYLFVEGGRIDHGHHEGKAYMALTDTVMFDNAIAKANELTSELDTLILATADH SHVFSFGGYTLRGTSIFGLAPSKASDNKSYTSILYGNGPGYVLGGGLRPDVNDSI SEDPSYRQQAAVPLSSESHGGEDVAVFARGPQAHLVHGVQEETFVAHVMAFAGCV EPYTDCNLPAPSG |
| 116 | Showing amino acid sequence of AsAP1ss54_bIAP IV | MRFLSIVGAALFASSAVAFIPAEEEDPAFWNRQAAQALDVAKKLQPIQTAAKNVI LFLGDGMGVPTVTATRILKGQMNGKLGPETPLAMDQFPYVALSKTYNVDRQVPDS AGTATAYLCGVKGNYKTIGVSAAARYNQCNTTSGNEVTSVMNRAKKAGKSVGVVT TSRVQHASPAGAYAHTVNRNWYSDADLPADAQTYGCQDIATQLVNNMDIDVILGG GRMYMFPEGTPDPEYPYDVNQTGVRKDKRNLVQEWQAKHQGAQYVWNRTELLQAA NDPSVTHLMGLFEPADMKYNVQQDPTKDPTLEEMTEAALQVLSRNPQGFYLFVEG GRIDHGHHEGKAYMALTDTVMFDNAIAKANELTSELDTLILATADHSVFSFGGY TLRGTSIFGLAPSKASDNKSYTSILYGNGPGYVLGGGLRPDVNDSISEDPSYRQQ AAVPLSSESHGGEDVAVFARGPQAHLVHGVQEETFVAHVMAFAGCVEPYTDCNLP APSG |
| 117 | Showing amino acid sequence of AsAP3ss72_bIAP IV | MHIRTAITAGAALVQTAVAASVQAFIPAEEEDPAFWNRQAAQALDVAKKLQPIQT AAKNVILFLGDGMGVPTVTATRILKGQMNGKLGPETPLAMDQFPYVALSKTYNVD RQVPDSAGTATAYLCGVKGNYKTIGVSAAARYNQCNTTSGNEVTSVMNRAKKAGK SVGVVTTSRVQHASPAGAYAHTVNRNWYSDADLPADAQTYGCQDIATQLVNNMDI DVILGGGRMYMFPEGTPDPEYPYDVNQTGVRKDKRNLVQEWQAKHQGAQYVWNRT ELLQAANDPSVTHLMGLFEPADMKYNVQQDPTKDPTLEEMTEAALQVLSRNPQGF YLFVEGGRIDHGHHEGKAYMALTDTVMFDNATAKANELTSELDTLILATADHSHV FSFGGYTLRGTSIFGLAPSKASDNKSYTSILYGNGPGYVLGGGLRPDVNDSISED PSYRQQAAVPLSSESHGGEDVAVFARGPQAHLVHGVQEETFVAHVMAFAGCVEPY TDCNLPAPSG |

TABLE-continued

| SEQ ID NO: | Description | Sequence |
|---|---|---|
| 118 | Showing nucleotide sequence encoding CDHss and including no intron | ATGAAACTTGTCAACCGTCTGCTGGCTTCGTTCTTGTCCGCATCCACCGTTCTCC AGTCGTGCTGGGCT |

The present application claims priority to Japanese Patent Application No. 2017-193624 filed on Oct. 3, 2017, and the contents are incorporated herein by reference.

INDUSTRIAL APPLICABILITY

The present invention provides a method for producing an ALP, wherein the method enables production of a single isoform of an ALP with high productivity and much secretion without causing excessive and heterogeneous glycosylation, and provides a novel ALP II, vector, and transformant, thus being industrially useful.

The invention claimed is:

1. A method for producing an alkaline phosphatase (ALP), comprising:
   transforming an *Aspergillus* host with a vector comprising an open reading frame encoding an ALP and an *Aspergillus* strain-derived N-terminal secretory signal peptide,
   culturing the *Aspergillus* host in appropriate culture medium and culture conditions to produce the ALP, and
   wherein the amino acid sequence of the ALP comprises 90% or greater homology with either of the amino acid sequences set forth in SEQ ID NOs: 31 or 32 and has an amino acid substitution at position 122, 249, 251 and/or 410, and decreased protein glycosylation levels compared to a wild-type ALP, and wherein the Asn at position 122 is a substitution to Gln or Lys, the Asn at position 249 is a substitution to Gln, Asp or His, the Thr at position 251 is a substitution to Cys, and the Asn at position 410 is a substitution to Gln or Lys.

2. The method of claim 1, wherein the *Aspergillus* strain-derived N-terminal secretory signal peptide is selected from the group consisting of CDHss, CDHcytbkex, CDHcytbKexmut1, CDHcytbKexmut2, CDHcytbKexmut3, CDHcytbKexmut4, CDHall, GlaB, GlaBss, CelBss, CelB, SKIK_CDHss, AsAP1ss54, and AsAP3ss72.

3. The method of claim 1, wherein the *Aspergillus* host comprises:
   (i) a nucleotide sequence comprising a gene encoding for ALP and, on its 5' end, the nucleotide sequence set forth in SEQ ID NO: 2; or
   (ii) a nucleotide sequence encoding a secretory signal peptide with the amino acid sequence set forth in SEQ ID NO: 17.

4. The method of claim 1, wherein the ALP is an ALP II or an ALP IV.

5. The method of claim 1, wherein the ALP is an ALP II comprising at least one mutation in at least one N-linked glycosylation motif wherein the at least one mutation causes the at least one N-linked glycosylation motif to be unable to be glycosylated.

6. The method of claim 1, wherein the *Aspergillus* host is a transformant of any of: *Aspergillus sojae, Aspergillus oryzae, Aspergillus luchuensis, Aspergillus niger, Aspergillus nidulans, Aspergillus tamarii, Aspergillus kawachii, Aspergillus awamori, Aspergillus usamii*, and *Aspergillus saitoi*.

7. The method of claim 1, further comprising:
   (a) obtaining a secreted fraction from a culture of the *Aspergillus* host; and
   (b) extracting the ALP from the secreted fraction.

8. A vector for *Aspergillus* transformation, comprising:
   (a) an open reading frame encoding an alkaline phosphatase (ALP); and
   (b) an *Aspergillus* strain-derived N-terminal secretory signal peptide,
   wherein the ALP comprises 90% or greater homology with either of the amino acid sequences set forth in SEQ ID NOs: 31 or 32 and has an amino acid substitution at position 122, 249, 251 and/or 410, wherein the Asn at position 122 is a substitution to Gln or Lys, the Asn at position 249 is a substitution to Gln, Asp or His, the Thr at position 251 is a substitution to Cys, and the Asn at position 410 is a substitution to Gln or Lys,
   wherein the *Aspergillus* strain-derived N-terminal secretory signal peptide is 5' to the open reading frame encoding the ALP and comprises 90% or greater homology with any one of the sequences set forth in SEQ ID NOs: 2 to 15, and
   wherein the ALP has decreased protein glycosylation levels compared to a wild-type ALP.

9. An *Aspergillus* transformant, obtained by transforming with the vector for *Aspergillus* transformation according to claim 8.

10. The method of claim 1, wherein the amino acid sequence of the ALP consists of either of the amino acid sequences set forth in SEQ ID NOs: 31 or 32.

11. The method of claim 1, wherein the amino acid sequence of the ALP comprises at least one functional deletion, substitution, and/or addition mutation in either of the amino acid sequences set forth in SEQ ID NOs: 31 or 32.

12. The vector of claim 8, wherein the *Aspergillus* strain-derived N-terminal secretory signal peptide comprises at least one functional deletion, substitution and/or addition mutation in any one of the nucleotide sequences set forth in SEQ ID NOs: 2 to 15.

\* \* \* \* \*

```
                       SEQUENCE LISTING

<160> NUMBER OF SEQ ID NOS: 118

<210> SEQ ID NO 1
<211> LENGTH: 57
<212> TYPE: DNA
<213> ORGANISM: Bos taurus (bovine intestinal)

<400> SEQUENCE: 1
atgcagtggg cctgtgtgct gctgctgctg ggcctgtggc tacagctctc cctcacc          57

<210> SEQ ID NO 2
<211> LENGTH: 126
<212> TYPE: DNA
<213> ORGANISM: Artificial Sequence
<220> FEATURE:
<223> OTHER INFORMATION: CDHss including intron

<400> SEQUENCE: 2
atgaagctcg ttaaccgttt gctcgcttca ttcctgtcag cgagcaccgg tgagtggtgg       60
cctatcgagc taatgttgct tctcttcgtc tgactttttct tggcagtgtt gcagtcatgc     120
tgggct                                                                126

<210> SEQ ID NO 3
<211> LENGTH: 893
<212> TYPE: DNA
<213> ORGANISM: Artificial Sequence
<220> FEATURE:
<223> OTHER INFORMATION: CDHcytbkex

<400> SEQUENCE: 3
atgaagctcg ttaaccgttt gctcgcttca ttcctgtcag cgagcaccgg tgagtggtgg       60
cctatcgagc taatgttgct tctcttcgtc tgactttttct tggcagtgtt gcagtcatgc     120
tgggctcagt ccggcacacc ggttgcctac acgatactg agacgggcat cacgtttgac      180
acgtggtcgg tacctgctgg tacgggtacg ggtggtctcg tcttcggtgt agccctgccg     240
ggttcggcat tgaccaccga tgcgacggag tttatcggtt acctggtgag gatctcgagc    300
taatcatgac cgctctgaag tggcgctaaa cgttctaatg tttcaagcaa tgtgcgtccc    360
```

```
aaaatgcctc gtccgctggc tggtgtggca tttccttggg tggtggcatg aacaacaatc    420
tcttgttctt ggcctatccg tacgaggata ccatcttgac ctccctgcga ttcggctcgg    480
gctatagcat gcccggggtc tataccggca atgccaacgt cacccagatt tcttcaagca    540
tcaatgccac tcactttacg ttgcttttcc gttgcgagaa ttgtctgacc tgggaccaag    600
atggtcaaac cggaaacgcg accacaagca agggtaggtt agtcctggga tgggcacagt    660
ctacggagag cccgtcgaac ccgtcctgtc cggacaatat cagcctggcg cagcacgaca    720
accagggtat tatctcagcc actctggatg agaatgcagc cagtgagtcc tacgaggact    780
gggtcaagtt ggctaataag actgttcccg gggactgctc cggtgacggt ggtggcggca    840
acgagccgac tcctgtccct gtccctgacg gtggcggtgg aggctctaag cgc           893
```

<210> SEQ ID NO 4
<211> LENGTH: 893
<212> TYPE: DNA
<213> ORGANISM: Artificial Sequence
<220> FEATURE:
<223> OTHER INFORMATION: CDHcytbKexmut1

<400> SEQUENCE: 4

```
atgaagctcg ttaaccgttt gctcgcttca ttcctgtcag cgagcaccgg tgagtggtgg     60
cctatcgagc taatgttgct tctcttcgtc tgacttttct tggcagtgtt gcagtcatgc    120
tgggctcagt ccggcacacc ggttgcctac acggatactg agacgggcat cacgtttgac    180
acgtggtcgg tacctgctgg tacgggtacg ggtggtctcg tcttcggtgt agccctgccg    240
ggttcggcat tgaccaccga tgcgacggag tttatcggtt acctggtgag gatctcgagc    300
taatcatgac cgctctgaag tggcgctaaa cgttctaatg tttcaagcaa tgtgcgtccc    360
aaaatgcctc gtccgctggc tggtgtggca tttccttggg tggtggcatg aacaacaatc    420
tcttgttctt ggcctatccg tacgaggata ccatcttgac ctccctgcga ttcggctcgg    480
gctatagcat gcccggggtc tataccggca atgccaacgt cacccagatt tcttcaagca    540
tcaatgccac tcactttacg ttgcttttcc gttgcgagaa ttgtctgacc tgggaccaag    600
atggtcaaac cggaaacgcg accacaagca agggtaggtt agtcctggga tgggcacagt    660
ctacggagag cccgtcgaac ccgtcctgtc cggacaatat cagcctggcg cagcacgaca    720
accagggtat tatctcagcc actctggatg agaatgcagc cagtgagtcc tacgaggact    780
gggtcaagtt ggctaataag actgttcccg gggactgctc cggtgacggt ggtggcggca    840
acgagccgac tcctgtccct gtccctgacg gtggcggtgg acgccataag cgc           893
```

<210> SEQ ID NO 5
<211> LENGTH: 893
<212> TYPE: DNA
<213> ORGANISM: Artificial Sequence
<220> FEATURE:
<223> OTHER INFORMATION: CDHcytbKexmut2

<400> SEQUENCE: 5

```
atgaagctcg ttaaccgttt gctcgcttca ttcctgtcag cgagcaccgg tgagtggtgg     60
cctatcgagc taatgttgct tctcttcgtc tgacttttct tggcagtgtt gcagtcatgc    120
tgggctcagt ccggcacacc ggttgcctac acggatactg agacgggcat cacgtttgac    180
acgtggtcgg tacctgctgg tacgggtacg ggtggtctcg tcttcggtgt agccctgccg    240
ggttcggcat tgaccaccga tgcgacggag tttatcggtt acctggtgag gatctcgagc    300
taatcatgac cgctctgaag tggcgctaaa cgttctaatg tttcaagcaa tgtgcgtccc    360
```

```
aaaatgcctc gtccgctggc tggtgtggca tttccttggg tggtggcatg aacaacaatc      420
tcttgttctt ggcctatccg tacgaggata ccatcttgac ctcccctgcga ttcggctcgg     480 gctatagcat gcccggggtc tataccggca atgccaacgt cacccagatt tcttcaagca     540
tcaatgccac tcactttacg ttgcttttcc gttgcgagaa ttgtctgacc tgggaccaag     600
atggtcaaac cggaaacgcg accacaagca agggtaggtt agtcctggga tgggcacagt    660
ctacggagag cccgtcgaac ccgtcctgtc cggacaatat cagcctggcg cagcacgaca    720
accagggtat tatctcagcc actctggatg agaatgcagc cagtgagtcc tacgaggact    780
gggtcaagtt ggctaataag actgttcccg gggactgctc cggtgacggt ggtggcggca    840
acgagccgac tcctgtccct gtccctgacg gtggcggtgg accccataag cgc           893
```

<210> SEQ ID NO 6
<211> LENGTH: 899
<212> TYPE: DNA
<213> ORGANISM: Artificial Sequence
<220> FEATURE:
<223> OTHER INFORMATION: CDHcytbKexmut3

<400> SEQUENCE: 6

```
atgaagctcg ttaaccgttt gctcgcttca ttcctgtcag cgagcaccgg tgagtggtgg      60
cctatcgagc taatgttgct tctcttcgtc tgacttttct tggcagtgtt gcagtcatgc    120
tgggctcagt ccggcacacc ggttgcctac acggatactg agacgggcat cacgtttgac    180
acgtggtcgg tacctgctgg tacgggtacg ggtggtctcg tcttcggtgt agccctgccg    240
ggttcggcat tgaccaccga tgcgacggag tttatcggtt acctggtgag gatctcgagc    300
taatcatgac cgctctgaag tggcgctaaa cgttctaatg tttcaagcaa tgtgcgtccc    360
aaaatgcctc gtccgctggc tggtgtggca tttccttggg tggtggcatg aacaacaatc    420
tcttgttctt ggcctatccg tacgaggata ccatcttgac ctcccctgcga ttcggctcgg    480 gctatagcat gcccggggtc tataccggca atgccaacgt cacccagatt tcttcaagca    540
tcaatgccac tcactttacg ttgcttttcc gttgcgagaa ttgtctgacc tgggaccaag    600
atggtcaaac cggaaacgcg accacaagca agggtaggtt agtcctggga tgggcacagt    660
ctacggagag cccgtcgaac ccgtcctgtc cggacaatat cagcctggcg cagcacgaca    720
accagggtat tatctcagcc actctggatg agaatgcagc cagtgagtcc tacgaggact    780
gggtcaagtt ggctaataag actgttcccg gggactgctc cggtgacggt ggtggcggca    840
acgagccgac tcctgtccct gtccctgacg gtggcggtgg acaacgcctg gtcaagcgc    899
```

<210> SEQ ID NO 7
<211> LENGTH: 899
<212> TYPE: DNA
<213> ORGANISM: Artificial Sequence
<220> FEATURE:
<223> OTHER INFORMATION: CDHcytbKexmut4

<400> SEQUENCE: 7

```
atgaagctcg ttaaccgttt gctcgcttca ttcctgtcag cgagcaccgg tgagtggtgg      60
cctatcgagc taatgttgct tctcttcgtc tgacttttct tggcagtgtt gcagtcatgc    120
tgggctcagt ccggcacacc ggttgcctac acggatactg agacgggcat cacgtttgac    180
acgtggtcgg tacctgctgg tacgggtacg ggtggtctcg tcttcggtgt agccctgccg    240
ggttcggcat tgaccaccga tgcgacggag tttatcggtt acctggtgag gatctcgagc    300
```

```
taatcatgac cgctctgaag tggcgctaaa cgttctaatg tttcaagcaa tgtgcgtccc    360
aaaatgcctc gtccgctggc tggtgtggca tttccttggg tggtggcatg aacaacaatc    420
tcttgttctt ggcctatccg tacgaggata ccatcttgac ctccctgcga ttcggctcgg    480
gctatagcat gcccggggtc tataccggca atgccaacgt cacccagatt tcttcaagca    540
tcaatgccac tcactttacg ttgcttttcc gttgcgagaa ttgtctgacc tgggaccaag    600
atggtcaaac cggaaacgcg accacaagca agggtaggtt agtcctggga tgggcacagt    660
ctacggagag cccgtcgaac ccgtcctgtc cggacaatat cagcctggcg cagcacgaca    720
accagggtat tatctcagcc actctggatg agaatgcagc cagtgagtcc tacgaggact    780
gggtcaagtt ggctaataag actgttcccg gggactgctc cggtgacggt ggtggcggca    840
acgagccgac tcctgtccct gtccctgacg gtggcggtgg agtcgcagtc gaaaagcgc    899
```

<210> SEQ ID NO 8
<211> LENGTH: 2901
<212> TYPE: DNA
<213> ORGANISM: Artificial Sequence
<220> FEATURE:
<223> OTHER INFORMATION: CDHall

<400> SEQUENCE: 8

```
atgaagctcg ttaaccgttt gctcgcttca ttcctgtcag cgagcaccgg tgagtggtgg     60
cctatcgagc taatgttgct tctcttcgtc tgacttttct tggcagtgtt gcagtcatgc    120
tgggctcagt ccggcacacc ggttgcctac acggatactg agacgggcat cacgtttgac    180
acgtggtcgg tacctgctgg tacgggtacg ggtggtctcg tcttcggtgt agccctgccg    240
ggttcggcat tgaccaccga tgcgacggag tttatcggtt acctggtgag gatctcgagc    300
taatcatgac cgctctgaag tggcgctaaa cgttctaatg tttcaagcaa tgtgcgtccc    360
aaaatgcctc gtccgctggc tggtgtggca tttccttggg tggtggcatg aacaacaatc    420
tcttgttctt ggcctatccg tacgaggata ccatcttgac ctccctgcga ttcggctcgg    480
gctatagcat gcccggggtc tataccggca atgccaacgt cacccagatt tcttcaagca    540
tcaatgccac tcactttacg ttgcttttcc gttgcgagaa ttgtctgacc tgggaccaag    600
atggtcaaac cggaaacgcg accacaagca agggtaggtt agtcctggga tgggcacagt    660
ctacggagag cccgtcgaac ccgtcctgtc cggacaatat cagcctggcg cagcacgaca    720
accagggtat tatctcagcc actctggatg agaatgcagc cagtgagtcc tacgaggact    780
gggtcaagtt ggctaataag actgttcccg gggactgctc cggtgacggt ggtggcggca    840
acgagccgac tcctgtccct gtccctgacg gtgctacata cgactatatt gtcgtcggtg    900
gaggtgccgg gggtatccct gtcgccgatc ggctgagtga ggctgacac agtgttctcc    960 tgatcgagaa aggtcctcct tcctcgggac gctggggtgg caccatgaag cccagctggc   1020
tggatgatac caacctgacg cgatttgatg tccctgggct gtgcaaccag atctgggtcg   1080
actccaacgg tatcgcctgc agtgacaccg atcagatggc aggttgtgtg ctgggtggag   1140
gcaccgccgt caacgcagga ttgtggtgga aggtaagccg tgcccagatg ccatgttcgg   1200
atccatcact gacaatgtcc agccaaatcc cgttgactgg gactacaact tccccgaggg   1260
atggcagtcg tccgacatgc aggctgccgc ggaccgcgtg ttctcgcgga tccctggaac   1320
cacaaccccc tccaccgatg gaaagcttta ttaccaacaa ggagccgata tactgttaaa   1380
tggcttgcaa tccgccggat ggtcatccgt caccctcaac gatgtcccgg cccagaaaac   1440
caagaccttt ggccacgcac cattcatgtt ctctggaggt gagcgcggag ggcccatggg   1500
```

| | | |
|---|---|---|
| gacgtatctg gtgtcggcga gcgagagaga taattttgcc cgctggtcga acacgactgt | 1560 | |
| gaagagggtt gttcgtgaag gcggacgtat caccggagtt gaggtcgagg cgaccctcga | 1620 | |
| tggtggctac gcgggtaccg tcaatgtaac tgccaatacg ggtcgagtca ttctttctgc | 1680 | |
| aggaactttt ggaacgccca aggtccttat gagaagtacg cttcgttgga tgatattgtt | 1740 | |
| agggagttat tgctaatggc gtataggtgg tatcggcccg aaggaccagc tgtccatcgt | 1800 | |
| gaagagctca actgatggag agacaatgat tgccgaatct gagtggatcg aacttccggt | 1860 | |
| tggcgagaac ttggtcgatc atgtcaatgt gagtgccaag tggaccgggg aggctactac | 1920 | |
| tatgctaata ggatgcttac agactgatgt tgtggtgacc cacctgatg ttgtcttcta | 1980 | |
| tgatttcaaa gcggcataca agaccccat cgagagtgat gcgacgagct atctgagtat | 2040 | |
| gtagtaatgc ttcgaaggac agtccagcac taacttgcgt agacgatcgc accgggattt | 2100 | |
| tcgcccaggc tgcgcctaac attggtccta tgtaagttgc ccgtctacca aacacgtcat | 2160 | |
| ggtactaacg cctgtagaat cttcgacgaa gtcaccggct ctgatggcat taaacgacag | 2220 | |
| atacagtgga ctgctcgtgt ggaaggcggc cacgacacgc ctgacggacg tacgttgact | 2280 | |
| cctaagtgaa agattagtgc aatatattaa ccgtgctgta gacgccatga ccatcagcca | 2340 | |
| atacctcggc cgcggctcaa cctcgcgtgg ccgcatgacc attaccgcag gactggacac | 2400 | |
| ggtggtctcg acgctgccat tcctacggga cgagagcgac gttaatgctg taatccaggg | 2460 | |
| aatccagaac ctgaagatgg ccctgaacgg gacaggattt acctggaact accctgctcg | 2520 | |
| gaacacttcc attgccgagt ttgtcaatac tgtgagtgct gatttctgga aggatgttcg | 2580 | |
| acgtaactga cactgataga tgccaatcac tgccggaaca cgccgagcta atcactggat | 2640 | |
| gggtgagtta tgaatctgct ttttaaaatt tcgtcgctaa ttgttatagg aacctgcaaa | 2700 | |
| ataggtacag atgatggccg tactggaggt agcgccgttg ttgatttgaa tacgaaggtc | 2760 | |
| tatgaacgg acaacctgtt cgtcgtggat gctagtatct tcccgggtat gatcacgtcc | 2820 | |
| aatccttcgg cttacattgt tacggtcgcg gagcatgcag ctgaaaagat tcttgcgctg | 2880 | |
| ggcggtggag gctctaagcg c | 2901 | |

<210> SEQ ID NO 9
<211> LENGTH: 51
<212> TYPE: DNA
<213> ORGANISM: Artificial Sequence
<220> FEATURE:
<223> OTHER INFORMATION: GlaBss

<400> SEQUENCE: 9

| | | |
|---|---|---|
| atgcggaaca actttctttt ttccctcaat gccattgctg gcgctgtcgc g | 51 | |

<210> SEQ ID NO 10
<211> LENGTH: 1608
<212> TYPE: DNA
<213> ORGANISM: Artificial Sequence
<220> FEATURE:
<223> OTHER INFORMATION: GlaB

<400> SEQUENCE: 10

| | | |
|---|---|---|
| atgcggaaca actttctttt ttccctcaat gccattgctg gcgctgtcgc gcatccgtcg | 60 | |
| ttccctgtcc ataagaggca gtcggatgtc aacgccttca ttgagacaca gacacccatc | 120 | |
| gccaaacagg gcgtccctca ataatatcggc gctgatggca agcttgtaga gggggctgcc | 180 | |
| gcgggtattg ttgtagccctc cccatccaag agtaatcccg actgttcgta caatcctacc | 240 | |

```
ctctaaaccg cttaatacga ccatagaact aattatattt agacttctat acctggacgc      300
gcgacgctgg cctcaccatg gaagaagtga tagagcaatt catcggggga gacgcgactc      360
tcgagtctac aatccagaat tatgttgact ctcaagcgaa gcagcaggca gtctccaacc      420
catcaggcag cctgtcggat ggctcgggtc ttgctgaacc caagttttac gtcaacatct      480
ctcaattcac cgattcttgg ggccgacccc agcgcgacgg gccagcttta cgtgcttccg      540
ccttgatcgc atatggcaac tccctgatcg ccagcgacaa gcaatctgtt gtcaaagcca      600
acatctggcc aattgtccag aatgacttgt cttacgtggg tcaatactgg aaccagaccg      660
ggtttgatct ttgggaagag gttcagggca gctccttctt cactgttgct gtacagcaca      720
aggccttggt ggagggcgac gcgtttgcga aggcactcgg agaggaatgc caggcgtgct      780
ccgtggcgcc gcaaatcctc tgccatcttc aggattctg gaatgggtcc gctgttattt       840
ctaacttaca aaccagtggg cgcagtggac tggatgccaa ctcgcttttg ggttccatcc      900 atactttga cccagctgct gcttgtgatg atacaacgtt ccaaccctgc tcctctcggg       960
ctctgtcaaa ccataagctt gtggtggact ctttccggtc ggtctacggt atcaacaacg     1020
gacgtggagc aggaaaggcc gcagcagtgg gccgttacgc agaggacacc tatcagggag     1080
gcaatccatg gttggtactc tgtctcattg attccaaggc ttaaactaat gaataatagg     1140
tatcttacca ctctggtcgc tgcggaattg ctctacgacg ccttgtatca atgggacaaa     1200
caaggtcaag tgaacgtcac cgaaacttcc cttcccttct tcaaggacct ctccagcaat     1260
gtcacgaccg gatcctacgc caagtcttcc tcagcctacg agtcccttac aagcgctgtc     1320
aagacctacg cagacggctt catctccgtt gtccaggagt atactcctga tggcggtgct     1380
ctggccgagc agtacagtcg ggaccagggc accccagttt cggcatccga tctgacttgg     1440
tcttatgcag ctttcttgag tgctgttggg agacgaaacg gcactgtccc tgctagctgg     1500
ggctcttcca cggccaacgc agttccaagc caatgttcgg ggggtacagt ttctggaagt     1560
tacactaccc caactgttgg gtcgtggggc ggtggaggct ctaagcgc                   1608

<210> SEQ ID NO 11
<211> LENGTH: 51
<212> TYPE: DNA
<213> ORGANISM: Artificial Sequence
<220> FEATURE:
<223> OTHER INFORMATION: CelBss

<400> SEQUENCE: 11
atgatctgga cactcgctcc ctttgtggca ctcctgccac tggtaacggc t                51

<210> SEQ ID NO 12
<211> LENGTH: 1269
<212> TYPE: DNA
<213> ORGANISM: Artificial Sequence
<220> FEATURE:
<223> OTHER INFORMATION: CelB

<400> SEQUENCE: 12
atgatctgga cactcgctcc ctttgtggca ctcctgccac tggtaacggc tcaacaggtg       60
ggaactacag cggacgccca tcccagactc accacgtata aatgtacttc acagaacggc      120
tgcacgaggc agaacaccct cagtcgtcct tgatgcagca acccattttat ccacaaaaaa     180 ggaacacaaa catcctgcac caacagcaac ggcttggaca cttccatttg tccggacaaa     240
cagacctgcg cggacaactg tgtcgttgat gggatcacgg actacgctag ctacggcgtc     300
cagacgaaga atgacacatt gacccttcac caatatctgc aaactggcaa tgaaacaaag     360
```

```
tccgtgtcac cgcgtgtcta cctcctcgct gaagacggag agaactattc catgctgcaa    420
ctcctgaatc aggaattcac cttcgatgtc gacgcctcta ccctcgtctg cggcatgaat    480
ggtgctctat atctctctga aatggaggct tcgggcggaa agagttccct aaatcaagcg    540
ggagccaaat acggaaccgg ttactgtgat gcccaatgct acaccacgcc ttggatcaac    600
ggcgaaggca acaccgagag tgtcggctcc tgctgtcagg aaatggatat tgggaagcc     660 aacgcccgag caacagggct acaccgcac ccttgcaaca caaccggttt gtacgagtgc     720
agcggctcgg gatgcggaga ctccggggtc tgtgacaagt ccggctgtgg attcaaccca    780
tatggcctag gtgcaaagga ctactacggt tacggcctca aggtcaacac caacgagaca    840
ttcacggtcg taacccagtt cctcacaagc gataacacga catcgggcca gctcagcgaa    900
atccgccgtc tctacatcca gaacggccag gttattcaaa atgctgccgt cacctcagga    960
ggaaaaactg tcgactcaat cacaaaggat ttctgcagcg gtgaaggaag tgccttcaac   1020
cgacttggcg gcctcgagga atgggccac gccttgggcc gcggcatggt tcttgcgctc    1080
agtgtctgga acgacgcagg ctcattcatg caatggcttg atgggggcag cgcaggaccg   1140
tgcagcgcga cggagggaga cccggcgttg atcgagaagt tgtatccgga tactcatgtg   1200
aagttttcca agatccggtg gggagatatt ggatctacct acaggcatgg cggtggaggc   1260
tctaagcgc                                                           1269

<210> SEQ ID NO 13
<211> LENGTH: 138
<212> TYPE: DNA
<213> ORGANISM: Artificial Sequence
<220> FEATURE:
<223> OTHER INFORMATION: SKIK_CDHss

<400> SEQUENCE: 13
atgtccaaga tcaagaagct cgttaaccgt ttgctcgctt cattcctgtc agcgagcacc     60
ggtgagtggt ggcctatcga gctaatgttg cttctcttcg tctgactttt cttggcagtg    120
ttgcagtcat gctgggct                                                  138

<210> SEQ ID NO 14
<211> LENGTH: 54
<212> TYPE: DNA
<213> ORGANISM: Artificial Sequence
<220> FEATURE:
<223> OTHER INFORMATION: AsAP1ss54

<400> SEQUENCE: 14
atgaggttcc tctcaattgt aggtgcggcg ctcttcgctt ccagcgctgt tgcc           54

<210> SEQ ID NO 15
<211> LENGTH: 72
<212> TYPE: DNA
<213> ORGANISM: Artificial Sequence
<220> FEATURE:
<223> OTHER INFORMATION: AsAP3ss72

<400> SEQUENCE: 15
atgcatatcc gcactgccat caccgcgggc gcggcccttg tccagactgc agttgcagct     60
tctgttcagg ca                                                        72

<210> SEQ ID NO 16
<211> LENGTH: 19
<212> TYPE: PRT
```

<213> ORGANISM: Bos taurus (bovine intestinal)

<400> SEQUENCE: 16

Met Gln Trp Ala Cys Val Leu Leu Leu Gly Leu Trp Leu Gln Leu
1               5                   10                  15

Ser Leu Thr

<210> SEQ ID NO 17
<211> LENGTH: 23
<212> TYPE: PRT
<213> ORGANISM: Artificial Sequence
<220> FEATURE:
<223> OTHER INFORMATION: CDHss

<400> SEQUENCE: 17

Met Lys Leu Val Asn Arg Leu Leu Ala Ser Phe Leu Ser Ala Ser Thr
1               5                   10                  15

Val Leu Gln Ser Cys Trp Ala
            20

<210> SEQ ID NO 18
<211> LENGTH: 258
<212> TYPE: PRT
<213> ORGANISM: Artificial Sequence
<220> FEATURE:
<223> OTHER INFORMATION: CDHcytbkex

<400> SEQUENCE: 18

Met Lys Leu Val Asn Arg Leu Leu Ala Ser Phe Leu Ser Ala Ser Thr
1               5                   10                  15

Val Leu Gln Ser Cys Trp Ala Gln Ser Gly Thr Pro Val Ala Tyr Thr
            20                  25                  30

Asp Thr Glu Thr Gly Ile Thr Phe Asp Thr Trp Ser Val Pro Ala Gly
        35                  40                  45

Thr Gly Thr Gly Gly Leu Val Phe Gly Val Ala Leu Pro Gly Ser Ala
    50                  55                  60

Leu Thr Thr Asp Ala Thr Glu Phe Ile Gly Tyr Leu Gln Cys Ala Ser
65                  70                  75                  80

Gln Asn Ala Ser Ser Ala Gly Trp Cys Gly Ile Ser Leu Gly Gly Gly
                85                  90                  95

Met Asn Asn Asn Leu Leu Phe Leu Ala Tyr Pro Tyr Glu Asp Thr Ile
            100                 105                 110

Leu Thr Ser Leu Arg Phe Gly Ser Gly Tyr Ser Met Pro Gly Val Tyr
        115                 120                 125

Thr Gly Asn Ala Asn Val Thr Gln Ile Ser Ser Ser Ile Asn Ala Thr
    130                 135                 140

His Phe Thr Leu Leu Phe Arg Cys Glu Asn Cys Leu Thr Trp Asp Gln
145                 150                 155                 160

Asp Gly Gln Thr Gly Asn Ala Thr Thr Ser Lys Gly Arg Leu Val Leu
                165                 170                 175

Gly Trp Ala Gln Ser Thr Glu Ser Pro Ser Asn Pro Ser Cys Pro Asp
            180                 185                 190

Asn Ile Ser Leu Ala Gln His Asp Asn Gln Gly Ile Ile Ser Ala Thr
        195                 200                 205

Leu Asp Glu Asn Ala Ala Ser Glu Ser Tyr Glu Asp Trp Val Lys Leu
    210                 215                 220

Ala Asn Lys Thr Val Pro Gly Asp Cys Ser Gly Asp Gly Gly Gly Gly
225                 230                 235                 240

Asn Glu Pro Thr Pro Val Pro Val Pro Asp Gly Gly Gly Gly Ser
            245             250             255

Lys Arg

<210> SEQ ID NO 19
<211> LENGTH: 258
<212> TYPE: PRT
<213> ORGANISM: Artificial Sequence
<220> FEATURE:
<223> OTHER INFORMATION: CDHcytbKexmut1

<400> SEQUENCE: 19

Met Lys Leu Val Asn Arg Leu Leu Ala Ser Phe Leu Ser Ala Ser Thr
1               5                   10                  15

Val Leu Gln Ser Cys Trp Ala Gln Ser Gly Thr Pro Val Ala Tyr Thr
            20                  25                  30

Asp Thr Glu Thr Gly Ile Thr Phe Asp Thr Trp Ser Val Pro Ala Gly
        35                  40                  45

Thr Gly Thr Gly Gly Leu Val Phe Gly Val Ala Leu Pro Gly Ser Ala
    50                  55                  60

Leu Thr Thr Asp Ala Thr Glu Phe Ile Gly Tyr Leu Gln Cys Ala Ser
65                  70                  75                  80

Gln Asn Ala Ser Ser Ala Gly Trp Cys Gly Ile Ser Leu Gly Gly Gly
                85                  90                  95

Met Asn Asn Asn Leu Leu Phe Leu Ala Tyr Pro Tyr Glu Asp Thr Ile
            100                 105                 110

Leu Thr Ser Leu Arg Phe Gly Ser Gly Tyr Ser Met Pro Gly Val Tyr
        115                 120                 125

Thr Gly Asn Ala Asn Val Thr Gln Ile Ser Ser Ile Asn Ala Thr
    130                 135                 140

His Phe Thr Leu Leu Phe Arg Cys Glu Asn Cys Leu Thr Trp Asp Gln
145                 150                 155                 160

Asp Gly Gln Thr Gly Asn Ala Thr Thr Ser Lys Gly Arg Leu Val Leu
                165                 170                 175

Gly Trp Ala Gln Ser Thr Glu Ser Pro Ser Asn Pro Ser Cys Pro Asp
            180                 185                 190

Asn Ile Ser Leu Ala Gln His Asp Asn Gln Gly Ile Ile Ser Ala Thr
        195                 200                 205

Leu Asp Glu Asn Ala Ala Ser Glu Ser Tyr Glu Asp Trp Val Lys Leu
    210                 215                 220

Ala Asn Lys Thr Val Pro Gly Asp Cys Ser Asp Gly Gly Gly Gly
225                 230                 235                 240

Asn Glu Pro Thr Pro Val Pro Val Pro Asp Gly Gly Gly Gly Arg His
            245                 250                 255

Lys Arg

<210> SEQ ID NO 20
<211> LENGTH: 258
<212> TYPE: PRT
<213> ORGANISM: Artificial Sequence
<220> FEATURE:
<223> OTHER INFORMATION: CDHcytbKexmut2

<400> SEQUENCE: 20

Met Lys Leu Val Asn Arg Leu Leu Ala Ser Phe Leu Ser Ala Ser Thr
1               5                   10                  15

```
Val Leu Gln Ser Cys Trp Ala Gln Ser Gly Thr Pro Val Ala Tyr Thr
            20                  25                  30

Asp Thr Glu Thr Gly Ile Thr Phe Asp Thr Trp Ser Val Pro Ala Gly
        35                  40                  45

Thr Gly Thr Gly Gly Leu Val Phe Gly Val Ala Leu Pro Gly Ser Ala
    50                  55                  60

Leu Thr Thr Asp Ala Thr Glu Phe Ile Gly Tyr Leu Gln Cys Ala Ser
65                  70                  75                  80

Gln Asn Ala Ser Ser Ala Gly Trp Cys Gly Ile Ser Leu Gly Gly Gly
                85                  90                  95

Met Asn Asn Asn Leu Leu Phe Leu Ala Tyr Pro Tyr Glu Asp Thr Ile
            100                 105                 110

Leu Thr Ser Leu Arg Phe Gly Ser Gly Tyr Ser Met Pro Gly Val Tyr
        115                 120                 125

Thr Gly Asn Ala Asn Val Thr Gln Ile Ser Ser Ile Asn Ala Thr
    130                 135                 140

His Phe Thr Leu Leu Phe Arg Cys Glu Asn Cys Leu Thr Trp Asp Gln
145                 150                 155                 160

Asp Gly Gln Thr Gly Asn Ala Thr Thr Ser Lys Gly Arg Leu Val Leu
                165                 170                 175

Gly Trp Ala Gln Ser Thr Glu Ser Pro Ser Asn Pro Ser Cys Pro Asp
            180                 185                 190

Asn Ile Ser Leu Ala Gln His Asp Asn Gln Gly Ile Ile Ser Ala Thr
        195                 200                 205

Leu Asp Glu Asn Ala Ala Ser Glu Ser Tyr Glu Asp Trp Val Lys Leu
    210                 215                 220

Ala Asn Lys Thr Val Pro Gly Asp Cys Ser Gly Asp Gly Gly Gly
225                 230                 235                 240

Asn Glu Pro Thr Pro Val Pro Val Pro Asp Gly Gly Gly Pro His
                245                 250                 255

Lys Arg

<210> SEQ ID NO 21
<211> LENGTH: 260
<212> TYPE: PRT
<213> ORGANISM: Artificial Sequence
<220> FEATURE:
<223> OTHER INFORMATION: CDHcytbKexmut3

<400> SEQUENCE: 21

Met Lys Leu Val Asn Arg Leu Leu Ala Ser Phe Leu Ser Ala Ser Thr
1               5                   10                  15

Val Leu Gln Ser Cys Trp Ala Gln Ser Gly Thr Pro Val Ala Tyr Thr
            20                  25                  30

Asp Thr Glu Thr Gly Ile Thr Phe Asp Thr Trp Ser Val Pro Ala Gly
        35                  40                  45

Thr Gly Thr Gly Gly Leu Val Phe Gly Val Ala Leu Pro Gly Ser Ala
    50                  55                  60

Leu Thr Thr Asp Ala Thr Glu Phe Ile Gly Tyr Leu Gln Cys Ala Ser
65                  70                  75                  80

Gln Asn Ala Ser Ser Ala Gly Trp Cys Gly Ile Ser Leu Gly Gly Gly
                85                  90                  95

Met Asn Asn Asn Leu Leu Phe Leu Ala Tyr Pro Tyr Glu Asp Thr Ile
            100                 105                 110

Leu Thr Ser Leu Arg Phe Gly Ser Gly Tyr Ser Met Pro Gly Val Tyr
```

```
            115                 120                 125
Thr Gly Asn Ala Asn Val Thr Gln Ile Ser Ser Ile Asn Ala Thr
            130                 135                 140
His Phe Thr Leu Leu Phe Arg Cys Glu Asn Cys Leu Thr Trp Asp Gln
145                 150                 155                 160
Asp Gly Gln Thr Gly Asn Ala Thr Thr Ser Lys Gly Arg Leu Val Leu
                165                 170                 175
Gly Trp Ala Gln Ser Thr Glu Ser Pro Ser Asn Pro Ser Cys Pro Asp
                180                 185                 190
Asn Ile Ser Leu Ala Gln His Asp Asn Gln Gly Ile Ile Ser Ala Thr
                195                 200                 205
Leu Asp Glu Asn Ala Ala Ser Glu Ser Tyr Glu Asp Trp Val Lys Leu
            210                 215                 220
Ala Asn Lys Thr Val Pro Gly Asp Cys Ser Gly Asp Gly Gly Gly
225                 230                 235                 240
Asn Glu Pro Thr Pro Val Pro Val Pro Asp Gly Gly Gly Gln Arg
                245                 250                 255
Leu Val Lys Arg
            260

<210> SEQ ID NO 22
<211> LENGTH: 260
<212> TYPE: PRT
<213> ORGANISM: Artificial Sequence
<220> FEATURE:
<223> OTHER INFORMATION: CDHcytbKexmut4

<400> SEQUENCE: 22

Met Lys Leu Val Asn Arg Leu Leu Ala Ser Phe Leu Ser Ala Ser Thr
1               5                   10                  15
Val Leu Gln Ser Cys Trp Ala Gln Ser Gly Thr Pro Val Ala Tyr Thr
                20                  25                  30
Asp Thr Glu Thr Gly Ile Thr Phe Asp Thr Trp Ser Val Pro Ala Gly
            35                  40                  45
Thr Gly Thr Gly Gly Leu Val Phe Gly Val Ala Leu Pro Gly Ser Ala
        50                  55                  60
Leu Thr Thr Asp Ala Thr Glu Phe Ile Gly Tyr Leu Gln Cys Ala Ser
65                  70                  75                  80
Gln Asn Ala Ser Ser Ala Gly Trp Cys Gly Ile Ser Leu Gly Gly Gly
                85                  90                  95
Met Asn Asn Asn Leu Leu Phe Leu Ala Tyr Pro Tyr Glu Asp Thr Ile
                100                 105                 110
Leu Thr Ser Leu Arg Phe Gly Ser Gly Tyr Ser Met Pro Gly Val Tyr
            115                 120                 125
Thr Gly Asn Ala Asn Val Thr Gln Ile Ser Ser Ile Asn Ala Thr
            130                 135                 140
His Phe Thr Leu Leu Phe Arg Cys Glu Asn Cys Leu Thr Trp Asp Gln
145                 150                 155                 160
Asp Gly Gln Thr Gly Asn Ala Thr Thr Ser Lys Gly Arg Leu Val Leu
                165                 170                 175
Gly Trp Ala Gln Ser Thr Glu Ser Pro Ser Asn Pro Ser Cys Pro Asp
                180                 185                 190
Asn Ile Ser Leu Ala Gln His Asp Asn Gln Gly Ile Ile Ser Ala Thr
                195                 200                 205
Leu Asp Glu Asn Ala Ala Ser Glu Ser Tyr Glu Asp Trp Val Lys Leu
```

```
            210                 215                 220
Ala Asn Lys Thr Val Pro Gly Asp Cys Ser Gly Asp Gly Gly Gly
225                 230                 235                 240

Asn Glu Pro Thr Pro Val Pro Val Pro Asp Gly Gly Gly Val Ala
                245                 250                 255

Val Glu Lys Arg
            260

<210> SEQ ID NO 23
<211> LENGTH: 796
<212> TYPE: PRT
<213> ORGANISM: Artificial Sequence
<220> FEATURE:
<223> OTHER INFORMATION: CDHa11

<400> SEQUENCE: 23

Met Lys Leu Val Asn Arg Leu Leu Ala Ser Phe Leu Ser Ala Ser Thr
1               5                   10                  15

Val Leu Gln Ser Cys Trp Ala Gln Ser Gly Thr Pro Val Ala Tyr Thr
                20                  25                  30

Asp Thr Glu Thr Gly Ile Thr Phe Asp Thr Trp Ser Val Pro Ala Gly
            35                  40                  45

Thr Gly Thr Gly Gly Leu Val Phe Gly Val Ala Leu Pro Gly Ser Ala
        50                  55                  60

Leu Thr Thr Asp Ala Thr Glu Phe Ile Gly Tyr Leu Gln Cys Ala Ser
65                  70                  75                  80

Gln Asn Ala Ser Ser Ala Gly Trp Cys Gly Ile Ser Leu Gly Gly Gly
                85                  90                  95

Met Asn Asn Asn Leu Leu Phe Leu Ala Tyr Pro Tyr Glu Asp Thr Ile
            100                 105                 110

Leu Thr Ser Leu Arg Phe Gly Ser Gly Tyr Ser Met Pro Gly Val Tyr
        115                 120                 125

Thr Gly Asn Ala Asn Val Thr Gln Ile Ser Ser Ser Ile Asn Ala Thr
    130                 135                 140

His Phe Thr Leu Leu Phe Arg Cys Glu Asn Cys Leu Thr Trp Asp Gln
145                 150                 155                 160

Asp Gly Gln Thr Gly Asn Ala Thr Thr Ser Lys Gly Arg Leu Val Leu
                165                 170                 175

Gly Trp Ala Gln Ser Thr Glu Ser Pro Ser Asn Pro Ser Cys Pro Asp
            180                 185                 190

Asn Ile Ser Leu Ala Gln His Asp Asn Gln Gly Ile Ile Ser Ala Thr
        195                 200                 205

Leu Asp Glu Asn Ala Ala Ser Glu Ser Tyr Glu Asp Trp Val Lys Leu
    210                 215                 220

Ala Asn Lys Thr Val Pro Gly Asp Cys Ser Gly Asp Gly Gly Gly Gly
225                 230                 235                 240

Asn Glu Pro Thr Pro Val Pro Val Pro Asp Gly Ala Thr Tyr Asp Tyr
                245                 250                 255

Ile Val Val Gly Gly Gly Ala Gly Gly Ile Pro Val Ala Asp Arg Leu
            260                 265                 270

Ser Glu Ala Gly His Ser Val Leu Leu Ile Glu Lys Gly Pro Pro Ser
        275                 280                 285

Ser Gly Arg Trp Gly Gly Thr Met Lys Pro Ser Trp Leu Asp Asp Thr
    290                 295                 300

Asn Leu Thr Arg Phe Asp Val Pro Gly Leu Cys Asn Gln Ile Trp Val
```

```
            305                 310                 315                 320
Asp Ser Asn Gly Ile Ala Cys Ser Asp Thr Asp Gln Met Ala Gly Cys
                325                 330                 335

Val Leu Gly Gly Gly Thr Ala Val Asn Ala Gly Leu Trp Trp Lys Pro
                340                 345                 350

Asn Pro Val Asp Trp Asp Tyr Asn Phe Pro Glu Gly Trp Gln Ser Ser
                355                 360                 365

Asp Met Gln Ala Ala Asp Arg Val Phe Ser Arg Ile Pro Gly Thr
    370                 375                 380

Thr Thr Pro Ser Thr Asp Gly Lys Leu Tyr Gln Gln Gly Ala Asp
385                 390                 395                 400

Ile Leu Leu Asn Gly Leu Gln Ser Ala Gly Trp Ser Ser Val Thr Leu
                405                 410                 415

Asn Asp Val Pro Ala Gln Lys Thr Lys Thr Phe Gly His Ala Pro Phe
                420                 425                 430

Met Phe Ser Gly Gly Glu Arg Gly Gly Pro Met Gly Thr Tyr Leu Val
                435                 440                 445

Ser Ala Ser Glu Arg Asp Asn Phe Ala Arg Trp Ser Asn Thr Thr Val
                450                 455                 460

Lys Arg Val Val Arg Glu Gly Gly Arg Ile Thr Gly Val Glu Val Glu
465                 470                 475                 480

Ala Thr Leu Asp Gly Gly Tyr Ala Gly Thr Val Asn Val Thr Ala Asn
                485                 490                 495

Thr Gly Arg Val Ile Leu Ser Ala Gly Thr Phe Gly Thr Pro Lys Val
                500                 505                 510

Leu Met Arg Ser Gly Ile Gly Pro Lys Asp Gln Leu Ser Ile Val Lys
                515                 520                 525

Ser Ser Thr Asp Gly Glu Thr Met Ile Ala Glu Ser Glu Trp Ile Glu
                530                 535                 540

Leu Pro Val Gly Glu Asn Leu Val Asp His Val Asn Thr Asp Val Val
545                 550                 555                 560

Val Thr His Pro Asp Val Val Phe Tyr Asp Phe Lys Ala Ala Tyr Lys
                565                 570                 575

Thr Pro Ile Glu Ser Asp Ala Thr Ser Tyr Leu Asn Asp Arg Thr Gly
                580                 585                 590

Ile Phe Ala Gln Ala Ala Pro Asn Ile Gly Pro Ile Ile Phe Asp Glu
                595                 600                 605

Val Thr Gly Ser Asp Gly Ile Lys Arg Gln Ile Gln Trp Thr Ala Arg
                610                 615                 620

Val Glu Gly Gly His Asp Thr Pro Asp Gly His Ala Met Thr Ile Ser
625                 630                 635                 640

Gln Tyr Leu Gly Arg Gly Ser Thr Ser Arg Gly Arg Met Thr Ile Thr
                645                 650                 655

Ala Gly Leu Asp Thr Val Val Ser Thr Leu Pro Phe Leu Arg Asp Glu
                660                 665                 670

Ser Asp Val Asn Ala Val Ile Gln Gly Ile Gln Asn Leu Lys Met Ala
                675                 680                 685

Leu Asn Gly Thr Gly Phe Thr Trp Asn Tyr Pro Ala Arg Asn Thr Ser
                690                 695                 700

Ile Ala Glu Phe Val Asn Thr Met Pro Ile Thr Ala Gly Thr Arg Arg
705                 710                 715                 720

Ala Asn His Trp Met Gly Thr Cys Lys Ile Gly Thr Asp Asp Gly Arg
                725                 730                 735
```

-continued

```
Thr Gly Gly Ser Ala Val Val Asp Leu Asn Thr Lys Val Tyr Gly Thr
            740                 745                 750

Asp Asn Leu Phe Val Val Asp Ala Ser Ile Phe Pro Gly Met Ile Thr
            755                 760                 765

Ser Asn Pro Ser Ala Tyr Ile Val Thr Val Ala Glu His Ala Ala Glu
            770                 775                 780

Lys Ile Leu Ala Leu Gly Gly Gly Ser Lys Arg
785                 790                 795

<210> SEQ ID NO 24
<211> LENGTH: 17
<212> TYPE: PRT
<213> ORGANISM: Artificial Sequence
<220> FEATURE:
<223> OTHER INFORMATION: GlaBss

<400> SEQUENCE: 24

Met Arg Asn Asn Phe Leu Phe Ser Leu Asn Ala Ile Ala Gly Ala Val
1               5                   10                  15

Ala

<210> SEQ ID NO 25
<211> LENGTH: 500
<212> TYPE: PRT
<213> ORGANISM: Artificial Sequence
<220> FEATURE:
<223> OTHER INFORMATION: GlaB

<400> SEQUENCE: 25

Met Arg Asn Asn Leu Leu Phe Ser Leu Asn Ala Ile Ala Gly Ala Val
1               5                   10                  15

Ala His Pro Ser Phe Pro Ile His Lys Arg Gln Ser Asp Leu Asn Ala
            20                  25                  30

Phe Ile Glu Ala Gln Thr Pro Ile Ala Lys Gln Gly Val Leu Asn Asn
            35                  40                  45

Ile Gly Ala Asp Gly Lys Leu Val Glu Gly Ala Ala Ala Gly Ile Val
        50                  55                  60

Val Ala Ser Pro Ser Lys Ser Asn Pro Asp Tyr Phe Tyr Thr Trp Thr
65                  70                  75                  80

Arg Asp Ala Gly Leu Thr Met Glu Glu Val Ile Glu Gln Phe Ile Gly
                85                  90                  95

Gly Asp Ala Thr Leu Glu Ser Thr Ile Gln Asn Tyr Val Asp Ser Gln
            100                 105                 110

Ala Asn Glu Gln Ala Val Ser Asn Pro Ser Gly Gly Leu Ser Asp Gly
            115                 120                 125

Ser Gly Leu Ala Glu Pro Lys Phe Tyr Val Asn Ile Ser Gln Phe Thr
        130                 135                 140

Asp Ser Trp Gly Arg Pro Gln Arg Asp Gly Pro Ala Leu Arg Ala Ser
145                 150                 155                 160

Ala Leu Ile Ala Tyr Gly Asn Ser Leu Ile Ser Ser Asp Lys Gln Ser
                165                 170                 175

Val Val Lys Ala Asn Ile Trp Pro Ile Val Gln Asn Asp Leu Ser Tyr
            180                 185                 190

Val Gly Gln Tyr Trp Asn Gln Thr Gly Phe Asp Leu Trp Glu Glu Val
        195                 200                 205

Gln Gly Ser Ser Phe Phe Thr Val Ala Val Gln His Lys Ala Leu Val
    210                 215                 220
```

```
Glu Gly Asp Ala Phe Ala Lys Ala Leu Gly Glu Cys Gln Ala Cys
225                 230                 235                 240

Ser Val Ala Pro Gln Ile Leu Cys His Leu Gln Asp Phe Trp Asn Gly
                245                 250                 255

Ser Ala Val Leu Ser Asn Leu Pro Thr Asn Gly Arg Ser Gly Leu Asp
            260                 265                 270

Thr Asn Ser Leu Leu Gly Ser Ile His Thr Phe Asp Pro Ala Ala Ala
        275                 280                 285

Cys Asp Asp Thr Thr Phe Gln Pro Cys Ser Ser Arg Ala Leu Ser Asn
    290                 295                 300

His Lys Leu Val Val Asp Ser Phe Arg Ser Val Tyr Gly Ile Asn Asn
305                 310                 315                 320

Gly Arg Gly Ala Gly Lys Ala Ala Val Gly Pro Tyr Ala Glu Asp
                325                 330                 335

Thr Tyr Gln Gly Gly Asn Pro Trp Tyr Leu Thr Thr Leu Val Ala Ala
            340                 345                 350

Glu Leu Leu Tyr Asp Ala Leu Tyr Gln Trp Asp Lys Gln Gly Gln Val
        355                 360                 365

Asn Val Thr Glu Thr Ser Leu Pro Phe Phe Lys Asp Leu Ser Ser Asn
370                 375                 380

Val Thr Thr Gly Ser Tyr Ala Lys Ser Ser Ala Tyr Glu Ser Leu
385                 390                 395                 400

Thr Ser Ala Val Lys Thr Tyr Ala Asp Gly Phe Ile Ser Val Val Gln
                405                 410                 415

Glu Tyr Thr Pro Asp Gly Gly Ala Leu Ala Glu Gln Tyr Ser Arg Asp
                420                 425                 430

Gln Gly Thr Pro Val Ser Ala Ser Asp Leu Thr Trp Ser Tyr Ala Ala
            435                 440                 445

Phe Leu Ser Ala Val Gly Arg Arg Asn Gly Thr Val Pro Ala Ser Trp
        450                 455                 460

Gly Ser Ser Thr Ala Asn Ala Val Pro Ser Gln Cys Ser Gly Gly Thr
465                 470                 475                 480

Val Ser Gly Ser Tyr Thr Thr Pro Thr Val Gly Ser Trp Gly Gly Gly
                485                 490                 495

Gly Ser Lys Arg
            500

<210> SEQ ID NO 26
<211> LENGTH: 17
<212> TYPE: PRT
<213> ORGANISM: Artificial Sequence
<220> FEATURE:
<223> OTHER INFORMATION: CelBss

<400> SEQUENCE: 26

Met Ile Trp Thr Leu Ala Pro Phe Val Ala Leu Leu Pro Leu Val Thr
1               5                   10                  15

Ala

<210> SEQ ID NO 27
<211> LENGTH: 423
<212> TYPE: PRT
<213> ORGANISM: Artificial Sequence
<220> FEATURE:
<223> OTHER INFORMATION: CelB

<400> SEQUENCE: 27
```

-continued

```
Met Ile Trp Thr Leu Ala Pro Phe Val Ala Leu Leu Pro Leu Val Thr
1               5                   10                  15

Ala Gln Gln Val Gly Thr Thr Ala Asp Ala His Pro Arg Leu Thr Thr
                20                  25                  30

Tyr Lys Cys Thr Ser Gln Asn Gly Cys Thr Arg Gln Asn Thr Ser Val
            35                  40                  45

Val Leu Asp Ala Ala Thr His Phe Ile His Lys Lys Gly Thr Gln Thr
50                  55                  60

Ser Cys Thr Asn Ser Asn Gly Leu Asp Thr Ser Ile Cys Pro Asp Lys
65                  70                  75                  80

Gln Thr Cys Ala Asp Asn Cys Val Val Asp Gly Ile Thr Asp Tyr Ala
                85                  90                  95

Ser Tyr Gly Val Gln Thr Lys Asn Asp Thr Leu Thr Leu His Gln Tyr
            100                 105                 110

Leu Gln Thr Gly Asn Glu Thr Lys Ser Val Ser Pro Arg Val Tyr Leu
            115                 120                 125

Leu Ala Glu Asp Gly Glu Asn Tyr Ser Met Leu Gln Leu Leu Asn Gln
130                 135                 140

Glu Phe Thr Phe Asp Val Asp Ala Ser Thr Leu Val Cys Gly Met Asn
145                 150                 155                 160

Gly Ala Leu Tyr Leu Ser Glu Met Glu Ala Ser Gly Gly Lys Ser Ser
                165                 170                 175

Leu Asn Gln Ala Gly Ala Lys Tyr Gly Thr Gly Tyr Cys Asp Ala Gln
            180                 185                 190

Cys Tyr Thr Thr Pro Trp Ile Asn Gly Glu Gly Asn Thr Glu Ser Val
            195                 200                 205

Gly Ser Cys Cys Gln Glu Met Asp Ile Trp Glu Ala Asn Ala Arg Ala
210                 215                 220

Thr Gly Leu Thr Pro His Pro Cys Asn Thr Thr Gly Leu Tyr Glu Cys
225                 230                 235                 240

Ser Gly Ser Gly Cys Gly Asp Ser Gly Val Cys Asp Lys Ser Gly Cys
                245                 250                 255

Gly Phe Asn Pro Tyr Gly Leu Gly Ala Lys Asp Tyr Tyr Gly Tyr Gly
            260                 265                 270

Leu Lys Val Asn Thr Asn Glu Thr Phe Thr Val Val Thr Gln Phe Leu
            275                 280                 285

Thr Ser Asp Asn Thr Thr Ser Gly Gln Leu Ser Glu Ile Arg Arg Leu
290                 295                 300

Tyr Ile Gln Asn Gly Gln Val Ile Gln Asn Ala Ala Val Thr Ser Gly
305                 310                 315                 320

Gly Lys Thr Val Asp Ser Ile Thr Lys Asp Phe Cys Ser Gly Glu Gly
                325                 330                 335

Ser Ala Phe Asn Arg Leu Gly Gly Leu Glu Glu Met Gly His Ala Leu
            340                 345                 350

Gly Arg Gly Met Val Leu Ala Leu Ser Val Trp Asn Asp Ala Gly Ser
            355                 360                 365

Phe Met Gln Trp Leu Asp Gly Gly Ser Ala Pro Cys Ser Ala Thr
370                 375                 380

Glu Gly Asp Pro Ala Leu Ile Glu Lys Leu Tyr Pro Asp Thr His Val
385                 390                 395                 400

Lys Phe Ser Lys Ile Arg Trp Gly Asp Ile Gly Ser Thr Tyr Arg His
                405                 410                 415
```

```
Gly Gly Gly Gly Ser Lys Arg
            420

<210> SEQ ID NO 28
<211> LENGTH: 27
<212> TYPE: PRT
<213> ORGANISM: Artificial Sequence
<220> FEATURE:
<223> OTHER INFORMATION: SKIK_CDHss

<400> SEQUENCE: 28

Met Ser Lys Ile Lys Lys Leu Val Asn Arg Leu Leu Ala Ser Phe Leu
1               5                   10                  15

Ser Ala Ser Thr Val Leu Gln Ser Cys Trp Ala
            20                  25

<210> SEQ ID NO 29
<211> LENGTH: 18
<212> TYPE: PRT
<213> ORGANISM: Artificial Sequence
<220> FEATURE:
<223> OTHER INFORMATION: AsAP1ss54

<400> SEQUENCE: 29

Met Arg Phe Leu Ser Ile Val Gly Ala Ala Leu Phe Ala Ser Ser Ala
1               5                   10                  15

Val Ala

<210> SEQ ID NO 30
<211> LENGTH: 24
<212> TYPE: PRT
<213> ORGANISM: Artificial Sequence
<220> FEATURE:
<223> OTHER INFORMATION: AsAP3ss72

<400> SEQUENCE: 30

Met His Ile Arg Thr Ala Ile Thr Ala Gly Ala Ala Leu Val Gln Thr
1               5                   10                  15

Ala Val Ala Ala Ser Val Gln Ala
            20

<210> SEQ ID NO 31
<211> LENGTH: 480
<212> TYPE: PRT
<213> ORGANISM: Bos taurus (bovine intestinal)

<400> SEQUENCE: 31

Leu Ile Pro Ala Glu Glu Asn Pro Ala Phe Trp Asn Arg Gln Ala
1               5                   10                  15

Ala Gln Ala Leu Asp Val Ala Lys Lys Leu Gln Pro Ile Gln Thr Ala
            20                  25                  30

Ala Lys Asn Val Ile Leu Phe Leu Gly Asp Gly Met Gly Val Pro Thr
        35                  40                  45

Val Thr Ala Thr Arg Ile Leu Lys Gly Gln Met Asn Gly Lys Leu Gly
    50                  55                  60

Pro Glu Thr Pro Leu Ala Met Asp Gln Phe Pro Tyr Val Ala Leu Ser
65                  70                  75                  80

Lys Thr Tyr Asn Val Asp Arg Gln Val Pro Asp Ser Ala Gly Thr Ala
                85                  90                  95

Thr Ala Tyr Leu Cys Gly Val Lys Gly Asn Tyr Arg Thr Ile Gly Val
            100                 105                 110
```

```
Ser Ala Ala Ala Arg Tyr Asn Gln Cys Asn Thr Thr Arg Gly Asn Glu
            115                 120                 125

Val Thr Ser Val Ile Asn Arg Ala Lys Lys Ala Gly Lys Ala Val Gly
130                 135                 140

Val Val Thr Thr Thr Arg Val Gln His Ala Ser Pro Ala Gly Ala Tyr
145                 150                 155                 160

Ala His Thr Val Asn Arg Asn Trp Tyr Ser Asp Ala Asp Leu Pro Ala
            165                 170                 175

Asp Ala Gln Lys Asn Gly Cys Gln Asp Ile Ala Ala Gln Leu Val Tyr
            180                 185                 190

Asn Met Asp Ile Asp Val Ile Leu Gly Gly Gly Arg Met Tyr Met Phe
            195                 200                 205

Pro Glu Gly Thr Pro Asp Pro Glu Tyr Pro Asp Asp Ala Ser Val Asn
210                 215                 220

Gly Val Arg Lys Asp Lys Gln Asn Leu Val Gln Glu Trp Gln Ala Lys
225                 230                 235                 240

His Gln Gly Ala Gln Tyr Val Trp Asn Arg Thr Ala Leu Leu Gln Ala
            245                 250                 255

Ala Asp Asp Ser Ser Val Thr His Leu Met Gly Leu Phe Glu Pro Ala
            260                 265                 270

Asp Met Lys Tyr Asn Val Gln Gln Asp His Thr Lys Asp Pro Thr Leu
            275                 280                 285

Ala Glu Met Thr Glu Ala Ala Leu Gln Val Leu Ser Arg Asn Pro Arg
            290                 295                 300

Gly Phe Tyr Leu Phe Val Glu Gly Gly Arg Ile Asp His Gly His His
305                 310                 315                 320

Asp Gly Lys Ala Tyr Met Ala Leu Thr Glu Ala Ile Met Phe Asp Asn
            325                 330                 335

Ala Ile Ala Lys Ala Asn Glu Leu Thr Ser Glu Leu Asp Thr Leu Ile
            340                 345                 350

Leu Val Thr Ala Asp His Ser His Val Phe Ser Phe Gly Gly Tyr Thr
            355                 360                 365

Leu Arg Gly Thr Ser Ile Phe Gly Leu Ala Pro Gly Lys Ala Leu Asp
370                 375                 380

Ser Lys Ser Tyr Thr Ser Ile Leu Tyr Gly Asn Gly Pro Gly Tyr Ala
385                 390                 395                 400

Leu Gly Gly Gly Ser Arg Pro Asp Val Asn Gly Ser Thr Ser Glu Glu
            405                 410                 415

Pro Ser Tyr Arg Gln Gln Ala Ala Val Pro Leu Ala Ser Glu Thr His
            420                 425                 430

Gly Gly Glu Asp Val Ala Val Phe Ala Arg Gly Pro Gln Ala His Leu
            435                 440                 445

Val His Gly Val Gln Glu Glu Thr Phe Val Ala His Ile Met Ala Phe
450                 455                 460

Ala Gly Cys Val Glu Pro Tyr Thr Asp Cys Asn Leu Pro Ala Pro Ala
465                 470                 475                 480

<210> SEQ ID NO 32
<211> LENGTH: 481
<212> TYPE: PRT
<213> ORGANISM: Bos taurus (bovine intestinal)

<400> SEQUENCE: 32

Phe Ile Pro Ala Glu Glu Glu Asp Pro Ala Phe Trp Asn Arg Gln Ala
1               5                   10                  15
```

```
Ala Gln Ala Leu Asp Val Ala Lys Lys Leu Gln Pro Ile Gln Thr Ala
            20                  25                  30

Ala Lys Asn Val Ile Leu Phe Leu Gly Asp Gly Met Gly Val Pro Thr
            35                  40                  45

Val Thr Ala Thr Arg Ile Leu Lys Gly Gln Met Asn Gly Lys Leu Gly
 50                  55                  60

Pro Glu Thr Pro Leu Ala Met Asp Gln Phe Pro Tyr Val Ala Leu Ser
 65                  70                  75                  80

Lys Thr Tyr Asn Val Asp Arg Gln Val Pro Asp Ser Ala Gly Thr Ala
                 85                  90                  95

Thr Ala Tyr Leu Cys Gly Val Lys Gly Asn Tyr Lys Thr Ile Gly Val
            100                 105                 110

Ser Ala Ala Ala Arg Tyr Asn Gln Cys Asn Thr Thr Ser Gly Asn Glu
            115                 120                 125

Val Thr Ser Val Met Asn Arg Ala Lys Lys Ala Gly Lys Ser Val Gly
130                 135                 140

Val Val Thr Thr Ser Arg Val Gln His Ala Ser Pro Ala Gly Ala Tyr
145                 150                 155                 160

Ala His Thr Val Asn Arg Asn Trp Tyr Ser Asp Ala Asp Leu Pro Ala
                165                 170                 175

Asp Ala Gln Thr Tyr Gly Cys Gln Asp Ile Ala Thr Gln Leu Val Asn
            180                 185                 190

Asn Met Asp Ile Asp Val Ile Leu Gly Gly Gly Arg Met Tyr Met Phe
            195                 200                 205

Pro Glu Gly Thr Pro Asp Pro Glu Tyr Pro Tyr Asp Val Asn Gln Thr
210                 215                 220

Gly Val Arg Lys Asp Lys Arg Asn Leu Val Gln Glu Trp Gln Ala Lys
225                 230                 235                 240

His Gln Gly Ala Gln Tyr Val Trp Asn Arg Thr Glu Leu Leu Gln Ala
                245                 250                 255

Ala Asn Asp Pro Ser Val Thr His Leu Met Gly Leu Phe Glu Pro Ala
            260                 265                 270

Asp Met Lys Tyr Asn Val Gln Gln Asp Pro Thr Lys Asp Pro Thr Leu
            275                 280                 285

Glu Glu Met Thr Glu Ala Ala Leu Gln Val Leu Ser Arg Asn Pro Gln
290                 295                 300

Gly Phe Tyr Leu Phe Val Glu Gly Gly Arg Ile Asp His Gly His His
305                 310                 315                 320

Glu Gly Lys Ala Tyr Met Ala Leu Thr Asp Thr Val Met Phe Asp Asn
                325                 330                 335

Ala Ile Ala Lys Ala Asn Glu Leu Thr Ser Glu Leu Asp Thr Leu Ile
            340                 345                 350

Leu Ala Thr Ala Asp His Ser His Val Phe Ser Phe Gly Gly Tyr Thr
            355                 360                 365

Leu Arg Gly Thr Ser Ile Phe Gly Leu Ala Pro Ser Lys Ala Ser Asp
            370                 375                 380

Asn Lys Ser Tyr Thr Ser Ile Leu Tyr Gly Asn Gly Pro Gly Tyr Val
385                 390                 395                 400

Leu Gly Gly Gly Leu Arg Pro Asp Val Asn Asp Ser Ile Ser Glu Asp
                405                 410                 415

Pro Ser Tyr Arg Gln Gln Ala Ala Val Pro Leu Ser Ser Glu Ser His
            420                 425                 430
```

```
Gly Gly Glu Asp Val Ala Val Phe Ala Arg Gly Pro Gln Ala His Leu
            435                 440                 445

Val His Gly Val Gln Glu Glu Thr Phe Val Ala His Val Met Ala Phe
    450                 455                 460

Ala Gly Cys Val Glu Pro Tyr Thr Asp Cys Asn Leu Pro Ala Pro Ser
465                 470                 475                 480

Gly

<210> SEQ ID NO 33
<211> LENGTH: 1440
<212> TYPE: DNA
<213> ORGANISM: Bos taurus (bovine intestinal)

<400> SEQUENCE: 33
ctcatcccag ctgaagagga aaacccggcc ttctggaaca ggcaggctgc ccaagctctg    60
gacgtggcca agaagctcca gcctatccaa acggccgcta agaacgtcat cctcttcttg   120
ggagatggca tgggcgtgcc aacagtcact gccactcgta tccttaaggg ccaaatgaac   180
ggaaagttgg gcccagagac tcctctggct atggaccagt tcccatacgt ggccctgtcg   240
aagacataca acgttgaccg tcaagtgccg gattccgctg aacagccac cgcttacctc   300 tgcggcgtca agggaaacta ccgcacaatc ggcgtttccg ctgccgctag gtacaaccag   360
tgtaacacca ctagaggaaa cgaggttacc tctgtgatca accgtgctaa gaaggctggc   420
aaggccgttg gcgtggtcac aaccactaga gtgcagcacg cttctcccgc cggtgcttac   480
gcccacaccg tcaaccgcaa ctggtacagc gacgccgatc tgcctgctga cgcccagaag   540
aacggctgcc aagacatcgc cgctcagttg gtctacaaca tggacatcga tgttatcctg   600
ggaggtggca ggatgtacat gttccccgag ggaactcccg accctgaata ccctgacgat   660
gcttccgtca acggtgttag aaaggataag cagaacctgg tccaggagtg gcaagctaag   720
caccagggag cccaatacgt ttggaaccgt acagctctgc tccaggccgc tgacgattcc   780
tctgtgaccc acttgatggg tctgttcgaa cccgctgaca tgaagtacaa cgtccagcaa   840
gaccacacta aagatcctac actggccgag atgactgaag ccgctctcca ggttttgtcc   900
cgtaaccccc gtggtttcta cctcttcgtg gagggaggtc gcatcgacca cggtcaccac   960
gacggcaagg cttacatggc tttgacagaa gctatcatgt tcgacaacgc tatcgccaag  1020
gctaacgagc tgacaagcga actcgacacc ctgatcctcg tgactgccga tcactcccac  1080
gtcttctctt tcggcggata caccctgagg ggcacttcaa tcttcggcct cgctcctgga  1140
aaggccttgg actctaagag ctacacctca atcctgtacg aaacggtcc cggctacgct  1200 ctcggtggcg gatcgaggcc tgacgtgaac ggttcaacta gtgaggaacc aagctacaga  1260
cagcaagccg ctgtcccgtt ggcctcagag actcacggtg gcgaagacgt tgctgtgttc  1320
gcccgtggtc cacaagctca cctggtgcac ggcgtccagg aagaaacctt cgtggcccac  1380
atcatggcct cgctggttg tgtcgagcct acaccgact gcaacctccc agccccagcc  1440

<210> SEQ ID NO 34
<211> LENGTH: 1443
<212> TYPE: DNA
<213> ORGANISM: Bos taurus (bovine intestinal)

<400> SEQUENCE: 34
ttcatcccag ctgaggaaga ggatcctgct ttctggaacc gtcaggctgc tcaggctctt    60
gacgttgcca agaagttgca gccaatccag accgccgcta agaatgtcat cctcttcctg   120
```

```
ggcgatggta tgggagtccc gaccgtgact gctacccgca tcctcaaggg ccagatgaat      180
ggaaagctcg gcccagaaac cccgctggct atggaccagt tcccttacgt ggccctgtcg      240
aagacttata acgttgatcg tcaagtccct gactctgctg gtactgctac cgcctacctt      300
tgcggtgtga agggaaatta taagaccatc ggcgtttccg ccgctgcccg gtataaccag      360
tgtaatacca cttctggtaa cgaggttact agcgtcatga atcgggctaa gaaggccggc      420
aagtctgttg gtgtcgtgac cacttcgcgc gtccagcatg cttcccctgc tggagcctac      480
gctcacaccg tcaaccgcaa ttggtatagc gatgctgacc tgcccgccga tgctcagacc      540
tacggctgcc aggacatcgc cactcagctc gtcaacaata tggatatcga cgtgatcctg      600
ggaggcggtc gtatgtatat gttccctgaa ggtacccctg atcccgagta ccctatgac      660 gtgaaccaga ctggagttcg gaaggacaag cgcaatcttg tgcaggaatg gcaggctaag      720
catcagggtg cccagtacgt tggaaccgc accgagctcc tgcaggctgc caatgatcca      780
tcggtcactc acctcatggg actgttcgaa ccggccgaca tgaagtataa cgtgcagcag      840
gatcctacta aggaccccac ccttgaagag atgaccgagc tgcccttca ggttttgtcc       900 cggaatccac agggcttcta cttgttcgtc gagggcggcc gcatcgatca tggacatcac      960
gagggcaagg cttatatggc cctcactgat accgttatgt tcgacaacgc catcgctaag     1020
gccaatgaac tcacttcgga gctggatacc cttatcttgg ctactgccga ccattcgcac     1080
gtcttctcct tcggtggata cactcttcgt ggtacctcca tcttcggatt ggctccttcc     1140
aaggcctctg acaacaagag ctacacctcg atcctgtatg caatggtcc tggatacgtc      1200 cttggcggtg gattgcgtcc cgatgtgaac gacagcatct cggaggatcc atcttatcgg     1260
cagcaggctg ccgtcccgtt gtcctctgaa agccatggcg gtgaggatgt ggctgttttc     1320
gctcgtggac cacaggctca tttggtgcac ggcgttcagg aagagacctt cgtcgcccac     1380
gtgatggctt ttgcggggttg cgttgagccc tatactgact gtaacttgcc agccccttcg     1440
ggt                                                                  1443

<210> SEQ ID NO 35
<211> LENGTH: 57
<212> TYPE: DNA
<213> ORGANISM: Bos taurus (bovine intestinal)

<400> SEQUENCE: 35
atgcaaggtg cttgtgtttt attacttctt ggtttacatt tacaattatc tttaggt         57

<210> SEQ ID NO 36
<211> LENGTH: 19
<212> TYPE: PRT
<213> ORGANISM: Bos taurus (bovine intestinal)

<400> SEQUENCE: 36

Met Gln Gly Ala Cys Val Leu Leu Leu Gly Leu His Leu Gln Leu
1               5                   10                  15

Ser Leu Gly

<210> SEQ ID NO 37
<211> LENGTH: 1509
<212> TYPE: DNA
<213> ORGANISM: Artificial Sequence
<220> FEATURE:
<223> OTHER INFORMATION: CDHss-bIAPII

<400> SEQUENCE: 37
```

-continued

```
atgaaacttg tcaaccgtct gctggcttcg ttcttgtccg catccaccgt tctccagtcg    60
tgctgggctc tcatcccagc tgaagaggaa aacccggcct tctggaacag gcaggctgcc   120
caagctctgg acgtggccaa gaagctccag cctatccaaa cggccgctaa gaacgtcatc   180
ctcttcttgg gagatggcat gggcgtgcca acagtcactg ccactcgtat ccttaagggc   240
caaatgaacg gaaagttggg cccagagact cctctggcta tggaccagtt cccatacgtg   300
gccctgtcga agacatacaa cgttgaccgt caagtgccgg attccgctgg aacagccacc   360
gcttacctct gcggcgtcaa gggaaactac cgcacaatcg gcgtttccgc tgccgctagg   420
tacaaccagt gtaacaccac tagaggaaac gaggttacct ctgtgatcaa ccgtgctaag   480
aaggctggca aggccgttgg cgtggtcaca accactagag tgcagcacgc ttctcccgcc   540
ggtgcttacg cccacaccgt caaccgcaac tggtacagcg acgccgatct gcctgctgac   600
gcccagaaga acggctgcca agacatcgcc gctcagttgg tctacaacat ggacatcgat   660
gttatcctgg gaggtggcag gatgtacatg ttccccgagg gaactcccga ccctgaatac   720
cctgacgatg cttccgtcaa cggtgttaga aaggataagc agaacctggt ccaggagtgg   780
caagctaagc accagggagc ccaatacgtt tggaaccgta cagctctgct ccaggccgct   840
gacgattcct ctgtgaccca cttgatgggt ctgttcgaac ccgctgacat gaagtacaac   900
gtccagcaag accacactaa agatcctaca ctggccgaga tgactgaagc cgctctccag   960
gttttgtccc gtaaccccg tggtttctac ctcttcgtgg agggaggtcg catcgaccac  1020
ggtcaccacg acggcaaggc ttacatggct ttgacagaag ctatcatgtt cgacaacgct  1080
atcgccaagc ctaacgagct gacaagcgaa ctcgacaccc tgatcctcgt gactgccgat  1140
cactcccacg tcttctcttt cggcggatac accctgaggg gcacttcaat cttcggcctc  1200
gctcctggaa aggccttgga ctctaagagc tacacctcaa tcctgtacgg aaacggtccc  1260
ggctacgctc tcggtggcgg atcgaggcct gacgtgaacg gttcaactag tgaggaacca  1320
agctacagac agcaagccgc tgtcccgttg gcctcagaga ctcacggtgg cgaagacgtt  1380
gctgtgttcg cccgtggtcc acaagctcac ctggtgcacg gcgtccagga gaaaccttc   1440
gtggcccaca tcatggcctt cgctggttgt gtcgagcctt acaccgactg caacctccca  1500
gccccagcc                                                          1509
```

<210> SEQ ID NO 38
<211> LENGTH: 28
<212> TYPE: DNA
<213> ORGANISM: Artificial Sequence
<220> FEATURE:
<223> OTHER INFORMATION: Primer Talp1F

<400> SEQUENCE: 38

```
gtaccaggag tacattggag agttctac                                       28
```

<210> SEQ ID NO 39
<211> LENGTH: 25
<212> TYPE: DNA
<213> ORGANISM: Artificial Sequence
<220> FEATURE:
<223> OTHER INFORMATION: Primer Ptef-1R

<400> SEQUENCE: 39

```
tttgaaggtg gtgcgaactt tgtag                                          25
```

<210> SEQ ID NO 40
<211> LENGTH: 30

<212> TYPE: DNA
<213> ORGANISM: Artificial Sequence
<220> FEATURE:
<223> OTHER INFORMATION: Primer Ptef-CIAPIIFw

<400> SEQUENCE: 40
cgcaccacct tcaaaatgaa acttgtcaac                               30

<210> SEQ ID NO 41
<211> LENGTH: 30
<212> TYPE: DNA
<213> ORGANISM: Artificial Sequence
<220> FEATURE:
<223> OTHER INFORMATION: Primer Talp-CIAPIIRv

<400> SEQUENCE: 41
atgtactcct ggtacctagg ctggggctgg                               30

<210> SEQ ID NO 42
<211> LENGTH: 30
<212> TYPE: DNA
<213> ORGANISM: Artificial Sequence
<220> FEATURE:
<223> OTHER INFORMATION: Primer delta 1Fw

<400> SEQUENCE: 42
aggtacaacc agtgtcagac cactagagga                               30

<210> SEQ ID NO 43
<211> LENGTH: 23
<212> TYPE: DNA
<213> ORGANISM: Artificial Sequence
<220> FEATURE:
<223> OTHER INFORMATION: Primer delta 1Rv

<400> SEQUENCE: 43
acactggttg tacctagcgg cag                                      23

<210> SEQ ID NO 44
<211> LENGTH: 30
<212> TYPE: DNA
<213> ORGANISM: Artificial Sequence
<220> FEATURE:
<223> OTHER INFORMATION: Primer delta 1kFw

<400> SEQUENCE: 44
aggtacaacc agtgtaagac cactagagga                               30

<210> SEQ ID NO 45
<211> LENGTH: 23
<212> TYPE: DNA
<213> ORGANISM: Artificial Sequence
<220> FEATURE:
<223> OTHER INFORMATION: Primer delta 1kRv

<400> SEQUENCE: 45
acactggttg tacctagcgg cag                                      23

<210> SEQ ID NO 46
<211> LENGTH: 30
<212> TYPE: DNA
<213> ORGANISM: Artificial Sequence
<220> FEATURE:
<223> OTHER INFORMATION: Primer delta 13Fw

<400> SEQUENCE: 46

```
tcgaggcctg acgtgcaggg ttcaactagt                                      30
```

<210> SEQ ID NO 47
<211> LENGTH: 24
<212> TYPE: DNA
<213> ORGANISM: Artificial Sequence
<220> FEATURE:
<223> OTHER INFORMATION: Primer delta 13Rv

<400> SEQUENCE: 47

```
cacgtcaggc ctcgatccgc cacc                                            24
```

<210> SEQ ID NO 48
<211> LENGTH: 30
<212> TYPE: DNA
<213> ORGANISM: Artificial Sequence
<220> FEATURE:
<223> OTHER INFORMATION: Primer delta 1k3Fw

<400> SEQUENCE: 48

```
tcgaggcctg acgtgcaggg ttcaactagt                                      30
```

<210> SEQ ID NO 49
<211> LENGTH: 24
<212> TYPE: DNA
<213> ORGANISM: Artificial Sequence
<220> FEATURE:
<223> OTHER INFORMATION: Primer delta 1k3Rv

<400> SEQUENCE: 49

```
cacgtcaggc ctcgatccgc cacc                                            24
```

<210> SEQ ID NO 50
<211> LENGTH: 1512
<212> TYPE: DNA
<213> ORGANISM: Artificial Sequence
<220> FEATURE:
<223> OTHER INFORMATION: DNA Construct delta 1

<400> SEQUENCE: 50

```
atgaaacttg tcaaccgtct gctggcttcg ttcttgtccg catccaccgt tctccagtcg     60
tgctgggctc tcatcccagc tgaagaggaa aacccggcct tctggaacag gcaggctgcc    120
caagctctgg acgtggccaa gaagctccag cctatccaaa cggccgctaa gaacgtcatc    180
ctcttcttgg agatggcat gggcgtgcca acagtcactg ccactcgtat ccttaagggc     240
caaatgaacg gaaagttggg cccagagact cctctggcta tggaccagtt cccatacgtg    300
gccctgtcga agacatacaa cgttgaccgt caagtgccgg attccgctgg aacagccacc    360
gcttacctct gcggcgtcaa gggaaactac cgcacaatcg gcgtttccgc tgccgctagg    420
tacaaccagt gtcagaccac tagaggaaac gaggttacct ctgtgatcaa ccgtgctaag    480
aaggctggca aggccgttgg cgtggtcaca accactagag tgcagcacgc ttctcccgcc    540
ggtgcttacg cccacaccgt caaccgcaac tggtacagcg acgccgatct gctgctgac    600
gcccagaaga acggctgcca agacatcgcc gctcagttgg tctacaacat ggacatcgat    660
gttatcctgg gagtggcag gatgtacatg ttccccgagg gaactcccga ccctgaatac    720
cctgacgatg cttccgtcaa cggtgttaga aaggataagc agaacctggt ccaggagtgg    780
caagctaagc accagggagc ccaatacgtt tggaaccgta cagctctgct ccaggccgct    840
gacgattcct ctgtgaccca cttgatgggt ctgttcgaac ccgctgacat gaagtacaac    900
gtccagcaag accacactaa agatcctaca ctggccgaga tgactgaagc cgctctccag    960
```

```
gttttgtccc gtaaccccg tggtttctac ctcttcgtgg agggaggtcg catcgaccac    1020
ggtcaccacg acggcaaggc ttacatggct ttgacagaag ctatcatgtt cgacaacgct    1080
atcgccaagg ctaacgagct gacaagcgaa ctcgacaccc tgatcctcgt gactgccgat    1140
cactcccacg tcttctcttt cggcggatac accctgaggg gcacttcaat cttcggcctc    1200
gctcctggaa aggccttgga ctctaagagc tacacctcaa tcctgtacgg aaacggtccc    1260
ggctacgctc tcggtggcgg atcgaggcct gacgtgaacg gttcaactag tgaggaacca    1320
agctacagac agcaagccgc tgtcccgttg gcctcagaga ctcacggtgg cgaagacgtt    1380
gctgtgttcg cccgtggtcc acaagctcac ctggtgcacg gcgtccagga agaaaccttc    1440
gtggcccaca tcatggcctt cgctggttgt gtcgagcctt acaccgactg caacctccca    1500
gccccagcct ag                                                        1512

<210> SEQ ID NO 51
<211> LENGTH: 1512
<212> TYPE: DNA
<213> ORGANISM: Artificial Sequence
<220> FEATURE:
<223> OTHER INFORMATION: DNA Construct delta 1k

<400> SEQUENCE: 51
atgaaacttg tcaaccgtct gctggcttcg ttcttgtccg catccaccgt tctccagtcg      60
tgctgggctc tcatcccagc tgaagaggaa aacccggcct ctggaacag gcaggctgcc     120 caagctctgg acgtggccaa gaagctccag cctatccaaa cggccgctaa gaacgtcatc     180
ctcttcttgg agatggcat gggcgtgcca acagtcactg ccactcgtat ccttaagggc     240
caaatgaacg gaaagttggg cccagagact cctctggcta tggaccagtt cccatacgtg     300
gccctgtcga agacatacaa cgttgaccgt caagtgccgg attccgctgg aacagccacc     360
gcttacctct cggcgtcaa gggaaactac cgcacaatcg cgtttccgc tgccgctagg     420 tacaaccagt gtaagaccac tagaggaaac gaggttacct ctgtgatcaa ccgtgctaag     480
aaggctggca aggccgttgg cgtggtcaca accactagag tgcagcacgc ttctcccgcc     540
ggtgcttacg cccacaccgt caaccgcaac tggtacagcg acgccgatct gctgctgac     600 gcccagaaga acggctgcca agacatcgcc gctcagttgg tctacaacat ggacatcgat     660
gttatcctgg gaggtggcag gatgtacatg ttccccgagg aactcccga ccctgaatac     720 cctgacgatg cttccgtcaa cggtgttaga aaggataagc agaacctggt ccaggagtgg     780
caagctaagc caccaggagc ccaatacgtt tggaaccgta cagctctgct ccaggccgct     840
gacgattcct ctgtgaccca cttgatgggt ctgttcgaac cgctgacat gaagtacaac     900 gtccagcaag accacactaa agatcctaca ctggccgaga tgactgaag cgctctccag     960 gttttgtccc gtaaccccg tggtttctac ctcttcgtgg agggaggtcg catcgaccac    1020
ggtcaccacg acggcaaggc ttacatggct ttgacagaag ctatcatgtt cgacaacgct    1080
atcgccaagg ctaacgagct gacaagcgaa ctcgacaccc tgatcctcgt gactgccgat    1140
cactcccacg tcttctcttt cggcggatac accctgaggg gcacttcaat cttcggcctc    1200
gctcctggaa aggccttgga ctctaagagc tacacctcaa tcctgtacgg aaacggtccc    1260
ggctacgctc tcggtggcgg atcgaggcct gacgtgaacg gttcaactag tgaggaacca    1320
agctacagac agcaagccgc tgtcccgttg gcctcagaga ctcacggtgg cgaagacgtt    1380
gctgtgttcg cccgtggtcc acaagctcac ctggtgcacg gcgtccagga agaaaccttc    1440
```

```
gtggcccaca tcatggcctt cgctggttgt gtcgagcctt acaccgactg caacctccca    1500
gccccagcct ag                                                        1512

<210> SEQ ID NO 52
<211> LENGTH: 1512
<212> TYPE: DNA
<213> ORGANISM: Artificial Sequence
<220> FEATURE:
<223> OTHER INFORMATION: DNA Construct delta 13

<400> SEQUENCE: 52
atgaaacttg tcaaccgtct gctggcttcg ttcttgtccg catccaccgt tctccagtcg      60
tgctgggctc tcatcccagc tgaagaggaa aacccggcct tctggaacag gcaggctgcc    120
caagctctgg acgtggccaa gaagctccag cctatccaaa cggccgctaa gaacgtcatc    180
ctcttcttgg gagatggcat gggcgtgcca acagtcactg ccactcgtat ccttaagggc    240
caaatgaacg gaaagttggg cccagagact cctctggcta tggaccagtt cccatacgtg    300
gccctgtcga agacatacaa cgttgaccgt caagtgccgg attccgctgg aacagccacc    360
gcttacctct gcggcgtcaa gggaaactac cgcacaatcg gcgtttccgc tgccgctagg    420
tacaaccagt gtcagaccac tagaggaaac gaggttacct ctgtgatcaa ccgtgctaag    480
aaggctggca aggccgttgg cgtggtcaca accactagag tgcagcacgc ttctcccgcc    540
ggtgcttacg cccacaccgt caaccgcaac tggtacagcg acgccgatct gcctgctgac    600
gcccagaaga acggctgcca agacatcgcc gctcagttgg tctacaacat ggacatcgat    660
gttatcctgg gaggtggcag gatgtacatg ttccccgagg gaactcccga ccctgaatac    720
cctgacgatg cttccgtcaa cggtgttaga aaggataagc agaacctggt ccaggagtgg    780
caagctaagc caggggagc ccaatacgtt tggaaccgta cagctctgct ccaggccgct    840
gacgattcct ctgtgaccca cttgatgggt ctgttcgaac ccgctgacat gaagtacaac    900
gtccagcaag accacactaa agatcctaca ctggccgaga tgactgaagc cgctctccag    960
gttttgtccc gtaaccccg tggtttctac ctcttcgtgg agggaggtcg catcgaccac    1020
ggtcaccacg acggcaaggc ttacatggct ttgacagaag ctatcatgtt cgacaacgct    1080
atcgccaagg ctaacgagct gacaagcgaa ctcgacaccc tgatcctcgt gactgccgat    1140
cactcccacg tcttctcttt cggcggatac accctgaggg gcacttcaat cttcggcctc    1200
gctcctggaa aggccttgga ctctaagagc tacacctcaa tcctgtacgg aaacggtccc    1260
ggctacgctc tcggtggcgg atcgaggcct gacgtgcagg gttcaactag tgaggaacca    1320
agctacagac agcaagccgc tgtcccgttg gcctcagaga ctcacggtgg cgaagacgtt    1380
gctgtgttcg cccgtggtcc acaagctcac ctggtgcacg cgtccagga agaaaccttc    1440 gtggcccaca tcatggcctt cgctggttgt gtcgagcctt acaccgactg caacctccca    1500
gccccagcct ag                                                        1512

<210> SEQ ID NO 53
<211> LENGTH: 1512
<212> TYPE: DNA
<213> ORGANISM: Artificial Sequence
<220> FEATURE:
<223> OTHER INFORMATION: DNA Construct delta 1k3

<400> SEQUENCE: 53
atgaaacttg tcaaccgtct gctggcttcg ttcttgtccg catccaccgt tctccagtcg      60
tgctgggctc tcatcccagc tgaagaggaa aacccggcct tctggaacag gcaggctgcc    120
```

```
caagctctgg acgtggccaa gaagctccag cctatccaaa cggccgctaa gaacgtcatc    180
ctcttcttgg gagatggcat gggcgtgcca acagtcactg ccactcgtat ccttaagggc    240
caaatgaacg gaaagttggg cccagagact cctctggcta tggaccagtt cccatacgtg    300
gccctgtcga agacatacaa cgttgaccgt caagtgccgg attccgctgg aacagccacc    360
gcttacctct gcggcgtcaa gggaaactac cgcacaatcg gcgtttccgc tgccgctagg    420
tacaaccagt gtaagaccac tagaggaaac gaggttacct ctgtgatcaa ccgtgctaag    480
aaggctggca aggccgttgg cgtggtcaca accactagag tgcagcacgc ttctcccgcc    540
ggtgcttacg cccacaccgt caaccgcaac tggtacagcg acgccgatct gcctgctgac    600
gcccagaaga acggctgcca agacatcgcc gctcagttgg tctacaacat ggacatcgat    660
gttatcctgg gaggtggcag gatgtacatg ttccccgagg gaactcccga ccctgaatac    720
cctgacgatg cttccgtcaa cggtgttaga aaggataagc agaacctggt ccaggagtgg    780
caagctaagc accagggagc ccaatacgtt tggaaccgta cagctctgct ccaggccgct    840
gacgattcct ctgtgaccca cttgatgggt ctgttcgaac ccgctgacat gaagtacaac    900
gtccagcaag accacactaa agatcctaca ctggccgaga tgactgaagc cgctctccag    960
gttttgtccc gtaaccccg tggtttctac ctcttcgtgg agggaggtcg catcgaccac    1020
ggtcaccacg acggcaaggc ttacatggct ttgacagaag ctatcatgtt cgacaacgct    1080
atcgccaagg ctaacgagct gacaagcgaa ctcgacaccc tgatcctcgt gactgccgat    1140
cactcccacg tcttctcttt cggcggatac accctgaggg gcacttcaat cttcggcctc    1200
gctcctggaa aggccttgga ctctaagagc tacacctcaa tcctgtacgg aaacggtccc    1260
ggctacgctc tcggtggcgg atcgaggcct gacgtgcagg gttcaactag tgaggaacca    1320
agctacagac agcaagccgc tgtcccgttg gcctcagaga ctcacggtgg cgaagacgtt    1380
gctgtgttcg cccgtggtcc acaagctcac ctggtgcacg cgtccagga agaaaccttc    1440
gtggcccaca tcatggcctt cgctggttgt gtcgagcctt acaccgactg caacctccca    1500
gccccagcct ag                                                        1512
```

<210> SEQ ID NO 54
<211> LENGTH: 503
<212> TYPE: PRT
<213> ORGANISM: Artificial Sequence
<220> FEATURE:
<223> OTHER INFORMATION: bIAPII delta 1

<400> SEQUENCE: 54

```
Met Lys Leu Val Asn Arg Leu Leu Ala Ser Phe Leu Ser Ala Ser Thr
1               5                  10                  15

Val Leu Gln Ser Cys Trp Ala Leu Ile Pro Ala Glu Glu Glu Asn Pro
            20                  25                  30

Ala Phe Trp Asn Arg Gln Ala Ala Gln Ala Leu Asp Val Ala Lys Lys
        35                  40                  45

Leu Gln Pro Ile Gln Thr Ala Ala Lys Asn Val Ile Leu Phe Leu Gly
    50                  55                  60

Asp Gly Met Gly Val Pro Thr Val Thr Ala Thr Arg Ile Leu Lys Gly
65                  70                  75                  80

Gln Met Asn Gly Lys Leu Gly Pro Glu Thr Pro Leu Ala Met Asp Gln
                85                  90                  95

Phe Pro Tyr Val Ala Leu Ser Lys Thr Tyr Asn Val Asp Arg Gln Val
            100                 105                 110
```

```
Pro Asp Ser Ala Gly Thr Ala Thr Ala Tyr Leu Cys Gly Val Lys Gly
        115                 120                 125

Asn Tyr Arg Thr Ile Gly Val Ser Ala Ala Arg Tyr Asn Gln Cys
    130                 135                 140

Gln Thr Thr Arg Gly Asn Glu Val Thr Ser Val Ile Asn Arg Ala Lys
145                 150                 155                 160

Lys Ala Gly Lys Ala Val Gly Val Val Thr Thr Thr Arg Val Gln His
                165                 170                 175

Ala Ser Pro Ala Gly Ala Tyr Ala His Thr Val Asn Arg Asn Trp Tyr
            180                 185                 190

Ser Asp Ala Asp Leu Pro Ala Asp Ala Gln Lys Asn Gly Cys Gln Asp
        195                 200                 205

Ile Ala Ala Gln Leu Val Tyr Asn Met Asp Ile Asp Val Ile Leu Gly
    210                 215                 220

Gly Gly Arg Met Tyr Met Phe Pro Glu Gly Thr Pro Asp Pro Glu Tyr
225                 230                 235                 240

Pro Asp Asp Ala Ser Val Asn Gly Val Arg Lys Asp Lys Gln Asn Leu
                245                 250                 255

Val Gln Glu Trp Gln Ala Lys His Gln Gly Ala Gln Tyr Val Trp Asn
            260                 265                 270

Arg Thr Ala Leu Leu Gln Ala Ala Asp Asp Ser Ser Val Thr His Leu
        275                 280                 285

Met Gly Leu Phe Glu Pro Ala Asp Met Lys Tyr Asn Val Gln Gln Asp
    290                 295                 300

His Thr Lys Asp Pro Thr Leu Ala Glu Met Thr Glu Ala Ala Leu Gln
305                 310                 315                 320

Val Leu Ser Arg Asn Pro Arg Gly Phe Tyr Leu Phe Val Glu Gly Gly
                325                 330                 335

Arg Ile Asp His Gly His His Asp Gly Lys Ala Tyr Met Ala Leu Thr
            340                 345                 350

Glu Ala Ile Met Phe Asp Asn Ala Ile Ala Lys Ala Asn Glu Leu Thr
        355                 360                 365

Ser Glu Leu Asp Thr Leu Ile Leu Val Thr Ala Asp His Ser His Val
370                 375                 380

Phe Ser Phe Gly Gly Tyr Thr Leu Arg Gly Thr Ser Ile Phe Gly Leu
385                 390                 395                 400

Ala Pro Gly Lys Ala Leu Asp Ser Lys Ser Tyr Thr Ser Ile Leu Tyr
                405                 410                 415

Gly Asn Gly Pro Gly Tyr Ala Leu Gly Gly Ser Arg Pro Asp Val
            420                 425                 430

Asn Gly Ser Thr Ser Glu Glu Pro Ser Tyr Arg Gln Gln Ala Ala Val
        435                 440                 445

Pro Leu Ala Ser Glu Thr His Gly Gly Glu Asp Val Ala Val Phe Ala
    450                 455                 460

Arg Gly Pro Gln Ala His Leu Val His Val Gly Val Gln Glu Glu Thr Phe
465                 470                 475                 480

Val Ala His Ile Met Ala Phe Ala Gly Cys Val Glu Pro Tyr Thr Asp
                485                 490                 495

Cys Asn Leu Pro Ala Pro Ala
            500

<210> SEQ ID NO 55
<211> LENGTH: 503
```

```
<212> TYPE: PRT
<213> ORGANISM: Artificial Sequence
<220> FEATURE:
<223> OTHER INFORMATION: bIAPII delta 1k

<400> SEQUENCE: 55

Met Lys Leu Val Asn Arg Leu Leu Ala Ser Phe Leu Ser Ala Ser Thr
1               5                   10                  15

Val Leu Gln Ser Cys Trp Ala Leu Ile Pro Ala Glu Glu Asn Pro
            20                  25                  30

Ala Phe Trp Asn Arg Gln Ala Ala Gln Ala Leu Asp Val Ala Lys Lys
            35                  40                  45

Leu Gln Pro Ile Gln Thr Ala Ala Lys Asn Val Ile Leu Phe Leu Gly
    50                  55                  60

Asp Gly Met Gly Val Pro Thr Val Thr Ala Thr Arg Ile Leu Lys Gly
65                  70                  75                  80

Gln Met Asn Gly Lys Leu Gly Pro Glu Thr Pro Leu Ala Met Asp Gln
                85                  90                  95

Phe Pro Tyr Val Ala Leu Ser Lys Thr Tyr Asn Val Asp Arg Gln Val
            100                 105                 110

Pro Asp Ser Ala Gly Thr Ala Thr Ala Tyr Leu Cys Gly Val Lys Gly
            115                 120                 125

Asn Tyr Arg Thr Ile Gly Val Ser Ala Ala Arg Tyr Asn Gln Cys
    130                 135                 140

Lys Thr Thr Arg Gly Asn Glu Val Thr Ser Val Ile Asn Arg Ala Lys
145                 150                 155                 160

Lys Ala Gly Lys Ala Val Gly Val Val Thr Thr Thr Arg Val Gln His
                165                 170                 175

Ala Ser Pro Ala Gly Ala Tyr Ala His Thr Val Asn Arg Asn Trp Tyr
            180                 185                 190

Ser Asp Ala Asp Leu Pro Ala Asp Ala Gln Lys Asn Gly Cys Gln Asp
            195                 200                 205

Ile Ala Ala Gln Leu Val Tyr Asn Met Asp Ile Asp Val Ile Leu Gly
    210                 215                 220

Gly Gly Arg Met Tyr Met Phe Pro Glu Gly Thr Pro Asp Pro Glu Tyr
225                 230                 235                 240

Pro Asp Asp Ala Ser Val Asn Gly Val Arg Lys Asp Lys Gln Asn Leu
            245                 250                 255

Val Gln Glu Trp Gln Ala Lys His Gln Gly Ala Gln Tyr Val Trp Asn
            260                 265                 270

Arg Thr Ala Leu Leu Gln Ala Ala Asp Asp Ser Ser Val Thr His Leu
        275                 280                 285

Met Gly Leu Phe Glu Pro Ala Asp Met Lys Tyr Asn Val Gln Gln Asp
    290                 295                 300

His Thr Lys Asp Pro Thr Leu Ala Glu Met Thr Glu Ala Ala Leu Gln
305                 310                 315                 320

Val Leu Ser Arg Asn Pro Arg Gly Phe Tyr Leu Phe Val Glu Gly Gly
            325                 330                 335

Arg Ile Asp His Gly His His Asp Gly Lys Ala Tyr Met Ala Leu Thr
            340                 345                 350

Glu Ala Ile Met Phe Asp Asn Ala Ile Ala Lys Ala Asn Glu Leu Thr
        355                 360                 365

Ser Glu Leu Asp Thr Leu Ile Leu Val Thr Ala Asp His Ser His Val
    370                 375                 380
```

```
Phe Ser Phe Gly Gly Tyr Thr Leu Arg Gly Thr Ser Ile Phe Gly Leu
385                 390                 395                 400

Ala Pro Gly Lys Ala Leu Asp Ser Lys Ser Tyr Thr Ser Ile Leu Tyr
                405                 410                 415

Gly Asn Gly Pro Gly Tyr Ala Leu Gly Gly Ser Arg Pro Asp Val
                420                 425                 430

Asn Gly Ser Thr Ser Glu Glu Pro Ser Tyr Arg Gln Gln Ala Ala Val
            435                 440                 445

Pro Leu Ala Ser Glu Thr His Gly Gly Glu Asp Val Ala Val Phe Ala
    450                 455                 460

Arg Gly Pro Gln Ala His Leu Val His Gly Val Gln Glu Glu Thr Phe
465                 470                 475                 480

Val Ala His Ile Met Ala Phe Ala Gly Cys Val Glu Pro Tyr Thr Asp
                485                 490                 495

Cys Asn Leu Pro Ala Pro Ala
                500
```

```
<210> SEQ ID NO 56
<211> LENGTH: 503
<212> TYPE: PRT
<213> ORGANISM: Artificial Sequence
<220> FEATURE:
<223> OTHER INFORMATION: bIAPII delta 13

<400> SEQUENCE: 56

Met Lys Leu Val Asn Arg Leu Leu Ala Ser Phe Leu Ser Ala Ser Thr
1               5                   10                  15

Val Leu Gln Ser Cys Trp Ala Leu Ile Pro Ala Glu Glu Glu Asn Pro
            20                  25                  30

Ala Phe Trp Asn Arg Gln Ala Ala Gln Ala Leu Asp Val Ala Lys Lys
        35                  40                  45

Leu Gln Pro Ile Gln Thr Ala Ala Lys Asn Val Ile Leu Phe Leu Gly
50                  55                  60

Asp Gly Met Gly Val Pro Thr Val Thr Ala Thr Arg Ile Leu Lys Gly
65                  70                  75                  80

Gln Met Asn Gly Lys Leu Gly Pro Glu Thr Pro Leu Ala Met Asp Gln
                85                  90                  95

Phe Pro Tyr Val Ala Leu Ser Lys Thr Tyr Asn Val Asp Arg Gln Val
            100                 105                 110

Pro Asp Ser Ala Gly Thr Ala Thr Ala Tyr Leu Cys Gly Val Lys Gly
        115                 120                 125

Asn Tyr Arg Thr Ile Gly Val Ser Ala Ala Ala Arg Tyr Asn Gln Cys
    130                 135                 140

Gln Thr Thr Arg Gly Asn Glu Val Thr Ser Val Ile Asn Arg Ala Lys
145                 150                 155                 160

Lys Ala Gly Lys Ala Val Gly Val Val Thr Thr Thr Arg Val Gln His
                165                 170                 175

Ala Ser Pro Ala Gly Ala Tyr Ala His Thr Val Asn Arg Asn Trp Tyr
            180                 185                 190

Ser Asp Ala Asp Leu Pro Ala Asp Ala Gln Lys Asn Gly Cys Gln Asp
        195                 200                 205

Ile Ala Ala Gln Leu Val Tyr Asn Met Asp Ile Asp Val Ile Leu Gly
    210                 215                 220

Gly Gly Arg Met Tyr Met Phe Pro Glu Gly Thr Pro Asp Pro Glu Tyr
225                 230                 235                 240
```

```
Pro Asp Asp Ala Ser Val Asn Gly Val Arg Lys Asp Lys Gln Asn Leu
            245                 250                 255

Val Gln Glu Trp Gln Ala Lys His Gln Gly Ala Gln Tyr Val Trp Asn
        260                 265                 270

Arg Thr Ala Leu Leu Gln Ala Ala Asp Asp Ser Ser Val Thr His Leu
            275                 280                 285

Met Gly Leu Phe Glu Pro Ala Asp Met Lys Tyr Asn Val Gln Gln Asp
        290                 295                 300

His Thr Lys Asp Pro Thr Leu Ala Glu Met Thr Glu Ala Ala Leu Gln
305                 310                 315                 320

Val Leu Ser Arg Asn Pro Arg Gly Phe Tyr Leu Phe Val Glu Gly Gly
            325                 330                 335

Arg Ile Asp His Gly His His Asp Gly Lys Ala Tyr Met Ala Leu Thr
            340                 345                 350

Glu Ala Ile Met Phe Asp Asn Ala Ile Ala Lys Ala Asn Glu Leu Thr
            355                 360                 365

Ser Glu Leu Asp Thr Leu Ile Leu Val Thr Ala Asp His Ser His Val
    370                 375                 380

Phe Ser Phe Gly Gly Tyr Thr Leu Arg Gly Thr Ser Ile Phe Gly Leu
385                 390                 395                 400

Ala Pro Gly Lys Ala Leu Asp Ser Lys Ser Tyr Thr Ser Ile Leu Tyr
            405                 410                 415

Gly Asn Gly Pro Gly Tyr Ala Leu Gly Gly Ser Arg Pro Asp Val
            420                 425                 430

Gln Gly Ser Thr Ser Glu Glu Pro Ser Tyr Arg Gln Gln Ala Ala Val
            435                 440                 445

Pro Leu Ala Ser Glu Thr His Gly Gly Glu Asp Val Ala Val Phe Ala
    450                 455                 460

Arg Gly Pro Gln Ala His Leu Val His Gly Val Gln Glu Glu Thr Phe
465                 470                 475                 480

Val Ala His Ile Met Ala Phe Ala Gly Cys Val Glu Pro Tyr Thr Asp
            485                 490                 495

Cys Asn Leu Pro Ala Pro Ala
            500

<210> SEQ ID NO 57
<211> LENGTH: 503
<212> TYPE: PRT
<213> ORGANISM: Artificial Sequence
<220> FEATURE:
<223> OTHER INFORMATION: bIAPII delta 1k3

<400> SEQUENCE: 57

Met Lys Leu Val Asn Arg Leu Leu Ala Ser Phe Leu Ser Ala Ser Thr
1               5                   10                  15

Val Leu Gln Ser Cys Trp Ala Leu Ile Pro Ala Glu Glu Asn Pro
            20                  25                  30

Ala Phe Trp Asn Arg Gln Ala Ala Gln Ala Leu Asp Val Ala Lys Lys
        35                  40                  45

Leu Gln Pro Ile Gln Thr Ala Ala Lys Asn Val Ile Leu Phe Leu Gly
    50                  55                  60

Asp Gly Met Gly Val Pro Thr Val Thr Ala Thr Arg Ile Leu Lys Gly
65                  70                  75                  80

Gln Met Asn Gly Lys Leu Gly Pro Glu Thr Pro Leu Ala Met Asp Gln
            85                  90                  95
```

```
Phe Pro Tyr Val Ala Leu Ser Lys Thr Tyr Asn Val Asp Arg Gln Val
                100                 105                 110

Pro Asp Ser Ala Gly Thr Ala Thr Ala Tyr Leu Cys Gly Val Lys Gly
            115                 120                 125

Asn Tyr Arg Thr Ile Gly Val Ser Ala Ala Arg Tyr Asn Gln Cys
    130                 135                 140

Lys Thr Thr Arg Gly Asn Glu Val Thr Ser Val Ile Asn Arg Ala Lys
145                 150                 155                 160

Lys Ala Gly Lys Ala Val Gly Val Val Thr Thr Thr Arg Val Gln His
                165                 170                 175

Ala Ser Pro Ala Gly Ala Tyr Ala His Thr Val Asn Arg Asn Trp Tyr
            180                 185                 190

Ser Asp Ala Asp Leu Pro Ala Asp Ala Gln Lys Asn Gly Cys Gln Asp
            195                 200                 205

Ile Ala Ala Gln Leu Val Tyr Asn Met Asp Ile Asp Val Ile Leu Gly
            210                 215                 220

Gly Gly Arg Met Tyr Met Phe Pro Glu Gly Thr Pro Asp Pro Glu Tyr
225                 230                 235                 240

Pro Asp Asp Ala Ser Val Asn Gly Val Arg Lys Asp Lys Gln Asn Leu
            245                 250                 255

Val Gln Glu Trp Gln Ala Lys His Gln Gly Ala Gln Tyr Val Trp Asn
            260                 265                 270

Arg Thr Ala Leu Leu Gln Ala Ala Asp Asp Ser Ser Val Thr His Leu
            275                 280                 285

Met Gly Leu Phe Glu Pro Ala Asp Met Lys Tyr Asn Val Gln Gln Asp
            290                 295                 300

His Thr Lys Asp Pro Thr Leu Ala Glu Met Thr Glu Ala Ala Leu Gln
305                 310                 315                 320

Val Leu Ser Arg Asn Pro Arg Gly Phe Tyr Leu Phe Val Glu Gly Gly
                325                 330                 335

Arg Ile Asp His Gly His His Asp Gly Lys Ala Tyr Met Ala Leu Thr
            340                 345                 350

Glu Ala Ile Met Phe Asp Asn Ala Ile Ala Lys Ala Asn Glu Leu Thr
            355                 360                 365

Ser Glu Leu Asp Thr Leu Ile Leu Val Thr Ala Asp His Ser His Val
            370                 375                 380

Phe Ser Phe Gly Gly Tyr Thr Leu Arg Gly Thr Ser Ile Phe Gly Leu
385                 390                 395                 400

Ala Pro Gly Lys Ala Leu Asp Ser Lys Ser Tyr Thr Ser Ile Leu Tyr
            405                 410                 415

Gly Asn Gly Pro Gly Tyr Ala Leu Gly Gly Gly Ser Arg Pro Asp Val
            420                 425                 430

Gln Gly Ser Thr Ser Glu Glu Pro Ser Tyr Arg Gln Gln Ala Ala Val
            435                 440                 445

Pro Leu Ala Ser Glu Thr His Gly Gly Glu Asp Val Ala Val Phe Ala
            450                 455                 460

Arg Gly Pro Gln Ala His Leu Val His Gly Val Gln Glu Glu Thr Phe
465                 470                 475                 480

Val Ala His Ile Met Ala Phe Ala Gly Cys Val Glu Pro Tyr Thr Asp
                485                 490                 495

Cys Asn Leu Pro Ala Pro Ala
            500
```

```
<210> SEQ ID NO 58
<211> LENGTH: 30
<212> TYPE: DNA
<213> ORGANISM: Artificial Sequence
<220> FEATURE:
<223> OTHER INFORMATION: Primer Ptef-CIAPIVFw

<400> SEQUENCE: 58
cgcaccacct tcaaaatgca gtgggcctgt                                   30

<210> SEQ ID NO 59
<211> LENGTH: 30
<212> TYPE: DNA
<213> ORGANISM: Artificial Sequence
<220> FEATURE:
<223> OTHER INFORMATION: Primer Talp-CIAPIVRv

<400> SEQUENCE: 59
atgtactcct ggtacctaac ccgaaggggc                                   30

<210> SEQ ID NO 60
<211> LENGTH: 1500
<212> TYPE: DNA
<213> ORGANISM: Artificial Sequence
<220> FEATURE:
<223> OTHER INFORMATION: bIAPIV

<400> SEQUENCE: 60
atgcagtggg cctgtgtgct gctgctgctg ggcctgtggc tacagctctc cctcaccttc     60
atcccagctg aggaagagga tcctgctttc tggaaccgtc aggctgctca ggctcttgac    120
gttgccaaga agttgcagcc aatccagacc gccgctaaga atgtcatcct cttcctgggc    180
gatggtatgg gagtcccgac cgtgactgct cccgcatcc tcaagggcca gatgaatgga    240
aagctcggcc cagaaacccc gctggctatg accagttcc cttacgtggc cctgtcgaag    300
acttataacg ttgatcgtca gtccctgac tctgctggta ctgctaccgc ctaccttttgc    360 ggtgtgaagg gaaattataa gaccatcggc gttttcgccg ctgcccggta taaccagtgt    420
aataccactt ctggtaacga ggttactagc gtcatgaatc gggctaagaa ggccggcaag    480
tctgttggtg tcgtgaccac ttcgcgcgtc cagcatgctt ccctgctgg agcctacgct    540 cacaccgtca accgcaattg gtatagcgat gctgacctgc cgccgatgc tcagacctac    600 ggctgccagg acatcgccac tcagctcgtc aacaatatgg atatcgacgt gatcctggga    660
ggcggtcgta tgtatatgtt ccctgaaggt accctgatc ccgagtaccc ctatgacgtg    720
aaccagactg gagttcggaa ggacaagcgc atcttgtgc aggaatggca ggctaagcat    780
cagggtgccc agtacgtttg gaaccgcacc gagctcctgc aggctgccaa tgatccatcg    840
gtcactcacc tcatgggact gttcgaaccg gccgacatga gtataacgt gcagcaggat    900 cctactaagg accccaccct tgaagagatg accgaggctg cccttcaggt tttgtcccgg    960
aatccacagg gcttctactt gttcgtcgag ggcggccgca tcgatcatgg acatcacgag   1020
ggcaaggctt atatggccct cactgatacc gttatgttcg acaacgccat cgctaaggcc   1080
aatgaactca cttcggagct ggatacccttt atcttggcta ctgccgacca ttcgcacgtc   1140
ttctccttcg gtggatacac tcttcgtggt acctccatct tcggattggc tccttccaag   1200
gcctctgaca caagagcta cacctcgatc ctgtatggca atggtcctgg atacgtcctt   1260
ggcggtggat tgcgtcccga tgtgaacgac agcatctcgg aggatccatc ttatcggcag   1320
caggctgccg tcccgttgtc ctctgaaagc catggcggtg aggatgtggc tgttttcgct   1380
```

```
cgtggaccac aggctcattt ggtgcacggc gttcaggaag agaccttcgt cgcccacgtg    1440
atggcttttg cgggttgcgt tgagccctat actgactgta acttgccagc cccttcgggt    1500
```

<210> SEQ ID NO 61
<211> LENGTH: 7
<212> TYPE: PRT
<213> ORGANISM: Artificial Sequence
<220> FEATURE:
<223> OTHER INFORMATION: Linker Kex

<400> SEQUENCE: 61

Gly Gly Gly Gly Ser Lys Arg
1               5

<210> SEQ ID NO 62
<211> LENGTH: 7
<212> TYPE: PRT
<213> ORGANISM: Artificial Sequence
<220> FEATURE:
<223> OTHER INFORMATION: Linker Kexmut1

<400> SEQUENCE: 62

Gly Gly Gly Arg His Lys Arg
1               5

<210> SEQ ID NO 63
<211> LENGTH: 7
<212> TYPE: PRT
<213> ORGANISM: Artificial Sequence
<220> FEATURE:
<223> OTHER INFORMATION: Linker Kexmut2

<400> SEQUENCE: 63

Gly Gly Gly Pro His Lys Arg
1               5

<210> SEQ ID NO 64
<211> LENGTH: 9
<212> TYPE: PRT
<213> ORGANISM: Artificial Sequence
<220> FEATURE:
<223> OTHER INFORMATION: Linker Kexmut3

<400> SEQUENCE: 64

Gly Gly Gly Gln Arg Leu Val Lys Arg
1               5

<210> SEQ ID NO 65
<211> LENGTH: 9
<212> TYPE: PRT
<213> ORGANISM: Artificial Sequence
<220> FEATURE:
<223> OTHER INFORMATION: Linker Kexmut4

<400> SEQUENCE: 65

Gly Gly Gly Val Ala Val Glu Lys Arg
1               5

<210> SEQ ID NO 66
<211> LENGTH: 21
<212> TYPE: DNA
<213> ORGANISM: Artificial Sequence
<220> FEATURE:
<223> OTHER INFORMATION: Linker Kex

<400> SEQUENCE: 66
ggcggtggag gctctaagcg c                                                21

<210> SEQ ID NO 67
<211> LENGTH: 21
<212> TYPE: DNA
<213> ORGANISM: Artificial Sequence
<220> FEATURE:
<223> OTHER INFORMATION: Linker Kexmut1

<400> SEQUENCE: 67
ggcggtggac gccataagcg c                                                21

<210> SEQ ID NO 68
<211> LENGTH: 21
<212> TYPE: DNA
<213> ORGANISM: Artificial Sequence
<220> FEATURE:
<223> OTHER INFORMATION: Linker Kexmut2

<400> SEQUENCE: 68
ggcggtggac cccataagcg c                                                21

<210> SEQ ID NO 69
<211> LENGTH: 27
<212> TYPE: DNA
<213> ORGANISM: Artificial Sequence
<220> FEATURE:
<223> OTHER INFORMATION: Linker Kexmut3

<400> SEQUENCE: 69
ggcggtggac aacgcctggt caagcgc                                          27

<210> SEQ ID NO 70
<211> LENGTH: 27
<212> TYPE: DNA
<213> ORGANISM: Artificial Sequence
<220> FEATURE:
<223> OTHER INFORMATION: Linker Kexmut4

<400> SEQUENCE: 70
ggcggtggag tcgcagtcga aaagcgc                                          27

<210> SEQ ID NO 71
<211> LENGTH: 25
<212> TYPE: DNA
<213> ORGANISM: Artificial Sequence
<220> FEATURE:
<223> OTHER INFORMATION: Primer Kex Fw

<400> SEQUENCE: 71
ggcggtggag gctctaagcg cttca                                            25

<210> SEQ ID NO 72
<211> LENGTH: 30
<212> TYPE: DNA
<213> ORGANISM: Artificial Sequence
<220> FEATURE:
<223> OTHER INFORMATION: Primer Cytbb rev

<400> SEQUENCE: 72
agagcctcca ccgccaccgt cagggacagg                                       30

<210> SEQ ID NO 73
<211> LENGTH: 26
<212> TYPE: DNA
<213> ORGANISM: Artificial Sequence

```
<220> FEATURE:
<223> OTHER INFORMATION: Primer bIAPIV-1F

<400> SEQUENCE: 73
ttcatcccag ctgaggaaga ggatcc                                          26

<210> SEQ ID NO 74
<211> LENGTH: 30
<212> TYPE: DNA
<213> ORGANISM: Artificial Sequence
<220> FEATURE:
<223> OTHER INFORMATION: Primer CDHssrev

<400> SEQUENCE: 74
ctcagctggg atgaaagccc agcatgactg                                      30

<210> SEQ ID NO 75
<211> LENGTH: 45
<212> TYPE: DNA
<213> ORGANISM: Artificial Sequence
<220> FEATURE:
<223> OTHER INFORMATION: Primer SKIK_Fw

<400> SEQUENCE: 75
cgcaccacct tcaaaatgtc caagatcaag aagctcgtta accgt                     45

<210> SEQ ID NO 76
<211> LENGTH: 25
<212> TYPE: DNA
<213> ORGANISM: Artificial Sequence
<220> FEATURE:
<223> OTHER INFORMATION: Primer Ptef-1F

<400> SEQUENCE: 76
tttgaaggtg gtgcgaactt tgtag                                           25

<210> SEQ ID NO 77
<211> LENGTH: 36
<212> TYPE: DNA
<213> ORGANISM: Artificial Sequence
<220> FEATURE:
<223> OTHER INFORMATION: Primer Kexmut1F

<400> SEQUENCE: 77
gacggtggcg gtggacgcca taagcgcttc atccca                               36

<210> SEQ ID NO 78
<211> LENGTH: 36
<212> TYPE: DNA
<213> ORGANISM: Artificial Sequence
<220> FEATURE:
<223> OTHER INFORMATION: Primer Kexmut2F

<400> SEQUENCE: 78
gacggtggcg gtggacccca taagcgcttc atccca                               36

<210> SEQ ID NO 79
<211> LENGTH: 42
<212> TYPE: DNA
<213> ORGANISM: Artificial Sequence
<220> FEATURE:
<223> OTHER INFORMATION: Primer Kexmut3F

<400> SEQUENCE: 79
gacggtggcg gtggacaacg cctggtcaag cgcttcatcc ca                        42
```

<210> SEQ ID NO 80
<211> LENGTH: 42
<212> TYPE: DNA
<213> ORGANISM: Artificial Sequence
<220> FEATURE:
<223> OTHER INFORMATION: Primer Kexmut4F

<400> SEQUENCE: 80
gacggtggcg gtggagtcgc agtcgaaaag cgcttcatcc ca            42

<210> SEQ ID NO 81
<211> LENGTH: 20
<212> TYPE: DNA
<213> ORGANISM: Artificial Sequence
<220> FEATURE:
<223> OTHER INFORMATION: Primer KexmutRv

<400> SEQUENCE: 81
tccaccgcca ccgtcaggga                                      20

<210> SEQ ID NO 82
<211> LENGTH: 57
<212> TYPE: DNA
<213> ORGANISM: Artificial Sequence
<220> FEATURE:
<223> OTHER INFORMATION: Primer KexmutF

<400> SEQUENCE: 82
aactttcttt tttccctcaa tgccattgct ggcgctgtcg cgttcatccc agctgag    57

<210> SEQ ID NO 83
<211> LENGTH: 39
<212> TYPE: DNA
<213> ORGANISM: Artificial Sequence
<220> FEATURE:
<223> OTHER INFORMATION: Primer GlaBssRv

<400> SEQUENCE: 83
ggaaaaaaga aagttgttcc gcattttgaa ggtggtgcg                39

<210> SEQ ID NO 84
<211> LENGTH: 30
<212> TYPE: DNA
<213> ORGANISM: Artificial Sequence
<220> FEATURE:
<223> OTHER INFORMATION: Primer CelBssF

<400> SEQUENCE: 84
ccactggtaa cggctttcat cccagctgag                          30

<210> SEQ ID NO 85
<211> LENGTH: 25
<212> TYPE: DNA
<213> ORGANISM: Artificial Sequence
<220> FEATURE:
<223> OTHER INFORMATION: Primer CelBssRv

<400> SEQUENCE: 85
agccgttacc agtggcagga gtgcc                               25

<210> SEQ ID NO 86
<211> LENGTH: 50
<212> TYPE: DNA
<213> ORGANISM: Artificial Sequence
<220> FEATURE:
<223> OTHER INFORMATION: Primer AsAP1ss54F

<400> SEQUENCE: 86

```
taggtgcggc gctcttcgct tccagcgctg ttgccttcat cccagctgag         50
```

<210> SEQ ID NO 87
<211> LENGTH: 49
<212> TYPE: DNA
<213> ORGANISM: Artificial Sequence
<220> FEATURE:
<223> OTHER INFORMATION: Primer AsAP1ss54R

<400> SEQUENCE: 87

```
agagcgccgc acctacaatt gagaggaacc tcattttgaa ggtggtgcg          49
```

<210> SEQ ID NO 88
<211> LENGTH: 53
<212> TYPE: DNA
<213> ORGANISM: Artificial Sequence
<220> FEATURE:
<223> OTHER INFORMATION: Primer AsAP3ss72F

<400> SEQUENCE: 88

```
cccttgtcca gactgcagtt gcagcttctg ttcaggcatt catcccagct gag     53
```

<210> SEQ ID NO 89
<211> LENGTH: 64
<212> TYPE: DNA
<213> ORGANISM: Artificial Sequence
<220> FEATURE:
<223> OTHER INFORMATION: Primer AsAP3ss72R

<400> SEQUENCE: 89

```
cagtctggac aagggccgcg cccgcggtga tggcagtgcg atatgcatt ttgaaggtgg   60
tgcg                                                              64
```

<210> SEQ ID NO 90
<211> LENGTH: 1500
<212> TYPE: DNA
<213> ORGANISM: Artificial Sequence
<220> FEATURE:
<223> OTHER INFORMATION: bIAPIV

<400> SEQUENCE: 90

```
atgcagtggg cctgtgtgct gctgctgctg ggcctgtggc tacagctctc cctcaccttc    60
atcccagctg aggaagagga tcctgctttc tggaaccgtc aggctgctca ggctcttgac   120
gttgccaaga agttgcagcc aatccagacc gccgctaaga atgtcatcct cttcctgggc   180
gatggtatgg gagtcccgac cgtgactgct acccgcatcc tcaagggcca gatgaatgga   240
aagctcggcc cagaaacccc gctggctatg accagttcc cttacgtggc cctgtcgaag   300
acttataacg ttgatcgtca agtccctgac tctgctggta ctgctaccgc taccttgc   360
ggtgtgaagg gaaattataa gaccatcggc gtttccgccg ctgcccggta taaccagtgt   420
aataccactt ctggtaacga ggttactagc gtcatgaatc gggctaagaa ggccggcaag   480
tctgttggtg tcgtgaccac ttcgcgcgtc cagcatgctt ccctgctgg agcctacgct   540
cacaccgtca accgcaattg gtatagcgat gctgacctgc cgccgatgc tcagacctac   600
ggctgccagg acatcgccac tcagctcgtc aacaatatgg atatcgacgt gatcctggga   660
ggcggtcgta tgtatatgtt ccctgaaggt acccctgatc ccgagtaccc ctatgacgtg   720
aaccagactg gagttcggaa ggacaagcgc aatcttgtgc aggaatggca ggctaagcat   780
```

| | |
|---|---|
| cagggtgccc agtacgtttg aaccgcacc gagctcctgc aggctgccaa tgatccatcg | 840 |
| gtcactcacc tcatgggact gttcgaaccg gccgacatga agtataacgt gcagcaggat | 900 |
| cctactaagg accccaccct gaagagatg accgaggctg cccttcaggt tttgtcccgg | 960 |
| aatccacagg gcttctactt gttcgtcgag ggcggccgca tcgatcatgg acatcacgag | 1020 |
| ggcaaggctt atatggccct cactgatacc gttatgttcg acaacgccat cgctaaggcc | 1080 |
| aatgaactca cttcggagct ggataccctt atcttggcta ctgccgacca ttcgcacgtc | 1140 |
| ttctccttcg gtggatacac tcttcgtggt acctccatct tcggattggc tccttccaag | 1200 |
| gcctctgaca caagagcta cacctcgatc ctgtatggca atggtcctgg atacgtcctt | 1260 |
| ggcggtggat tgcgtcccga tgtgaacgac agcatctcgg aggatccatc ttatcggcag | 1320 |
| caggctgccg tcccgttgtc ctctgaaagc catggcggtg aggatgtggc tgttttcgct | 1380 |
| cgtggaccac aggctcattt ggtgcacggc gttcaggaag agaccttcgt cgcccacgtg | 1440 |
| atggcttttg cgggttgcgt tgagccctat actgactgta acttgccagc cccttcgggt | 1500 |

<210> SEQ ID NO 91
<211> LENGTH: 1569
<212> TYPE: DNA
<213> ORGANISM: Artificial Sequence
<220> FEATURE:
<223> OTHER INFORMATION: CDHss_bAPIV

<400> SEQUENCE: 91

| | |
|---|---|
| atgaagctcg ttaaccgttt gctcgcttca ttcctgtcag cgagcaccgg tgagtggtgg | 60 |
| cctatcgagc taatgttgct tctcttcgtc tgacttttct tggcagtgtt gcagtcatgc | 120 |
| tgggctttca tcccagctga ggaagaggat cctgctttct ggaaccgtca ggctgctcag | 180 |
| gctcttgacg ttgccaagaa gttgcagcca atccagaccg ccgctaagaa tgtcatcctc | 240 |
| ttcctgggcg atggtatggg agtcccgacc gtgactgcta cccgcatcct caagggccag | 300 |
| atgaatggaa agctcggccc agaaaccccg ctggctatgg accagttccc ttacgtggcc | 360 |
| ctgtcgaaga cttataacgt tgatcgtcaa gtccctgact ctgctggtac tgctaccgcc | 420 |
| tacctttgcg gtgtgaaggg aaattataag accatcggcg tttccgccgc tgcccggtat | 480 |
| aaccagtgta ataccacttc tggtaacgag gttactagcg tcatgaatcg ggctaagaag | 540 |
| gccggcaagt ctgttggtgt cgtgaccact tcgcgcgtcc agcatgcttc ccctgctgga | 600 |
| gcctacgctc acaccgtcaa ccgcaattgg tatagcgatg ctgacctgcc cgccgatgct | 660 |
| cagacctacg gctgccagga catcgccact cagctcgtca acaatatgga tatcgacgtg | 720 |
| atcctgggag gcggtcgtat gtatatgttc cctgaaggta cccctgatcc cgagtacccc | 780 |
| tatgacgtga accagactgg agttcggaag gacaagcgca atcttgtgca ggaatggcag | 840 |
| gctaagcatc agggtgccca gtacgtttgg aaccgcaccg agctcctgca ggctgccaat | 900 |
| gatccatcgg tcactcacct catgggactg ttcgaaccgg ccgacatgaa gtataacgtg | 960 |
| cagcaggatc ctactaagga ccccaccctt gaagagatga ccgaggctgc ccttcaggtt | 1020 |
| ttgtcccgga atccacaggg cttctacttg ttcgtcgagg gcggccgcat cgatcatgga | 1080 |
| catcacgagg gcaaggctta tatggccctc actgataccg ttatgttcga caacgccatc | 1140 |
| gctaaggcca atgaactcac ttcggagctg ataccctta tcttggctac tgccgaccat | 1200 |
| tcgcacgtct tctccttcgg tggatacact cttcgtggta cctccatctt cggattggct | 1260 |
| ccttccaagg cctctgacaa caagagctac acctcgatcc tgtatggcaa tggtcctgga | 1320 |
| tacgtccttg gcggtggatt gcgtcccgat gtgaacgaca gcatctcgga ggatccatct | 1380 |

| | |
|---|---|
| tatcggcagc aggctgccgt cccgttgtcc tctgaaagcc atggcggtga ggatgtggct | 1440 |
| gttttcgctc gtggaccaca ggctcatttg gtgcacggcg ttcaggaaga gaccttcgtc | 1500 |
| gcccacgtga tggcttttgc gggttgcgtt gagccctata ctgactgtaa cttgccagcc | 1560 |
| ccttcgggt | 1569 |

<210> SEQ ID NO 92
<211> LENGTH: 2336
<212> TYPE: DNA
<213> ORGANISM: Artificial Sequence
<220> FEATURE:
<223> OTHER INFORMATION: CDHcytbkex_bAPIV

<400> SEQUENCE: 92

| | |
|---|---|
| atgaagctcg ttaaccgttt gctcgcttca ttcctgtcag cgagcaccgg tgagtggtgg | 60 |
| cctatcgagc taatgttgct tctcttcgtc tgacttttct tggcagtgtt gcagtcatgc | 120 |
| tgggctcagt ccggcacacc ggttgcctac acggatactg agacgggcat cacgtttgac | 180 |
| acgtggtcgg tacctgctgg tacgggtacg ggtggtctcg tcttcggtgt agccctgccg | 240 |
| ggttcggcat tgaccaccga tgcgacggag tttatcggtt acctggtgag gatctcgagc | 300 |
| taatcatgac cgctctgaag tggcgctaaa cgttctaatg tttcaagcaa tgtgcgtccc | 360 |
| aaaatgcctc gtccgctggc tggtgtggca tttccttggg tggtggcatg aacaacaatc | 420 |
| tcttgttctt ggcctatccg tacgaggata ccatcttgac ctccctgcga ttcggctcgg | 480 |
| gctatagcat gcccggggtc tataccggca atgccaacgt cacccagatt tcttcaagca | 540 |
| tcaatgccac tcactttacg ttgcttttcc gttgcgagaa ttgtctgacc tgggaccaag | 600 |
| atggtcaaac cggaaacgcg accacaagca agggtaggtt agtcctggga tgggcacagt | 660 |
| ctacggagag cccgtcgaac ccgtcctgtc cggacaatat cagcctggcg cagcacgaca | 720 |
| accagggtat tatctcagcc actctggatg agaatgcagc cagtgagtcc tacgaggact | 780 |
| gggtcaagtt ggctaataag actgttcccg gggactgctc cggtgacggt ggtggcggca | 840 |
| acgagccgac tcctgtccct gtccctgacg gtggcggtgg aggctctaag cgcttcatcc | 900 |
| cagctgagga agaggatcct gctttctgga ccgtcaggc tgctcaggct cttgacgttg | 960 |
| ccaagaagtt gcagccaatc cagaccgccg ctaagaatgt catcctcttc ctgggcgatg | 1020 |
| gtatgggagt cccgaccgtg actgctaccc gcatcctcaa gggccagatg aatggaaagc | 1080 |
| tcggcccaga aaccccgctg gctatggacc agttcccctta cgtggccctg tcgaagactt | 1140 |
| ataacgttga tcgtcaagtc cctgactctg ctggtactgc taccgcctac ctttgcggtg | 1200 |
| tgaagggaaa ttataagacc atcggcgttt ccgccgctgc ccggtataac cagtgtaata | 1260 |
| ccacttctgg taacgaggtt actagcgtca tgaatcgggc taagaaggcc ggcaagtctg | 1320 |
| ttggtgtcgt gaccacttcg cgcgtccagc atgcttcccc tgctggagcc tacgctcaca | 1380 |
| ccgtcaaccg caattggtat agcgatgctg acctgcccgc cgatgctcag acctacggct | 1440 |
| gccaggacat cgccactcag ctcgtcaaca atatggatat cgacgtgatc ctgggaggcg | 1500 |
| gtcgtatgta tatgttccct gaaggtaccc ctgatcccga gtaccctat gacgtgaacc | 1560 |
| agactggagt tcggaaggac aagcgcaatc ttgtgcagga atggcaggct aagcatcagg | 1620 |
| gtgcccagta cgtttggaac cgcaccgagc tcctgcaggc tgccaatgat ccatcggtca | 1680 |
| ctcacctcat gggactgttc gaaccggccg acatgaagta taacgtgcag caggatccta | 1740 |
| ctaaggaccc caccccttgaa gagatgaccg aggctgccct tcaggttttg tcccggaatc | 1800 |

```
cacagggctt ctacttgttc gtcgagggcg gccgcatcga tcatggacat cacgagggca    1860
aggcttatat ggccctcact gataccgtta tgttcgacaa cgccatcgct aaggccaatg    1920
aactcacttc ggagctggat acccttatct tggctactgc cgaccattcg cacgtcttct    1980
ccttcggtgg atacactctt cgtggtacct ccatcttcgg attggctcct tccaaggcct    2040
ctgacaacaa gagctacacc tcgatcctgt atggcaatgg tcctggatac gtccttggcg    2100
gtggattgcg tcccgatgtg aacgacagca tctcggagga tccatcttat cggcagcagg    2160
ctgccgtccc gttgtcctct gaaagccatg gcggtgagga tgtggctgtt ttcgctcgtg    2220
gaccacaggc tcatttggtg cacggcgttc aggaagagac cttcgtcgcc cacgtgatgg    2280
cttttgcggg ttgcgttgag ccctatactg actgtaactt gccagcccct tcgggt       2336

<210> SEQ ID NO 93
<211> LENGTH: 2336
<212> TYPE: DNA
<213> ORGANISM: Artificial Sequence
<220> FEATURE:
<223> OTHER INFORMATION: CDHcytbKexmut1_bAPIV

<400> SEQUENCE: 93
atgaagctcg ttaaccgttt gctcgcttca ttcctgtcag cgagcaccgg tgagtggtgg      60
cctatcgagc taatgttgct tctcttcgtc tgacttttct tggcagtgtt gcagtcatgc     120
tgggctcagt ccggcacacc ggttgcctac acgatactg agacgggcat cacgtttgac     180
acgtggtcgg tacctgctgg tacgggtacg ggtggtctcg tcttcggtgt agccctgccg     240
ggttcggcat tgaccaccga tgcgacggag tttatcggtt acctggtgag gatctcgagc     300
taatcatgac cgctctgaag tggcgctaaa cgttctaatg tttcaagcaa tgtgcgtccc     360
aaaatgcctc gtccgctggc tggtgtggca tttccttggg tggtggcatg aacaacaatc     420
tcttgttctt ggcctatccg tacgaggata ccatcttgac ctccctgcga ttcggctcgg     480
gctatagcat gccgggggtc tataccggca atgccaacgt cacccagatt tcttcaagca     540
tcaatgccac tcactttacg ttgcttttcc gttgcgagaa ttgtctgacc tgggaccaag     600
atggtcaaac cggaaacgcg accacaagca agggtaggtt agtcctggga tgggcacagt     660
ctacggagag cccgtcgaac ccgtcctgtc cggacaatat cagcctggcg cagcacgaca     720
accagggtat tatctcagcc actctggatg agaatgcagc cagtgagtcc tacgaggact     780
gggtcaagtt ggctaataag actgttcccg gggactgctc cggtgacggt ggtggcggca     840
acgagccgac tcctgtccct gtccctgacg gtggcggtgg acgccataag cgcttcatcc     900
cagctgagga agaggatcct gctttctgga accgtcaggc tgctcaggct cttgacgttg     960
ccaagaagtt gcagccaatc cagaccgccg ctaagaatgt catcctcttc ctgggcgatg    1020
gtatgggagt cccgaccgtg actgctaccc gcatcctcaa gggccagatg aatggaaagc    1080
tcggcccaga aaccccgctg gctatggacc agttccctta cgtggccctg tcgaagactt    1140
ataacgttga tcgtcaagtc cctgactctg ctggtactgc taccgcctac ctttgcggtg    1200
tgaagggaaa ttataagacc atcggcgttt ccgccgctgc ccggtataac cagtgtaata    1260
ccacttctgg taacgaggtt actagcgtca tgaatcgggc taagaaggcc ggcaagtctg    1320
ttggtgtcgt gaccacttcg cgcgtccagc atgcttcccc tgctggagcc tacgctcaca    1380
ccgtcaaccg caattggtat agcgatgctg acctgcccgc cgatgctcag acctacggct    1440
gccaggacat cgccactcag ctcgtcaaca atatggatat cgacgtgatc ctgggaggcg    1500
gtcgtatgta tatgttccct gaaggtaccc ctgatcccga gtaccctat gacgtgaacc    1560
```

```
agactggagt tcggaaggac aagcgcaatc ttgtgcagga atggcaggct aagcatcagg    1620
gtgcccagta cgtttggaac cgcaccgagc tcctgcaggt tgccaatgat ccatcggtca    1680
ctcacctcat gggactgttc gaaccggccg acatgaagta taacgtgcag caggatccta    1740
ctaaggaccc caccctttgaa gagatgaccg aggctgccct tcaggttttg tcccggaatc   1800
```
*(Note: verify line 1800)*

```
cacagggctt ctacttgttc gtcgagggcg ccgcatcga tcatggacat cacgagggca     1860
aggcttatat ggccctcact gataccgtta tgttcgacaa cgccatcgct aaggccaatg    1920
aactcacttc ggagctggat acccttatct ggctactgc cgaccattcg cacgtcttct    1980
ccttcggtgg atacactctt cgtggtacct ccatcttcgg attggctcct tccaaggcct   2040
ctgacaacaa gagctacacc tcgatcctgt atggcaatgg tcctggatac gtccttggcg   2100
gtggattgcg tcccgatgtg aacgacagca ctctcggagga tccatcttat cggcagcagg  2160
ctgccgtccc gttgtcctct gaaagccatg gcggtgagga tgtggctgtt ttcgctcgtg   2220
gaccacaggc tcatttggtg cacggcgttc aggaagagac cttcgtcgcc cacgtgatgg   2280
cttttgcggg ttgcgttgag ccctatactg actgtaactt gccagcccct tcgggt       2336
```

<210> SEQ ID NO 94
<211> LENGTH: 2336
<212> TYPE: DNA
<213> ORGANISM: Artificial Sequence
<220> FEATURE:
<223> OTHER INFORMATION: CDHcytbKexmut2_bAPIV

<400> SEQUENCE: 94

```
atgaagctcg ttaaccgttt gctcgcttca ttcctgtcag cgagcaccgg tgagtggtgg      60
cctatcgagc taatgttgct tctcttcgtc tgactttcct tggcagtgtt gcagtcatgc    120
tgggctcagt ccggcacacc ggttgcctac acggatactg agacgggcat cacgtttgac    180
acgtggtcgg tacctgctgg tacgggtacg ggtggtctcg tcttcggtgt agccctgccg    240
ggttcggcat tgaccaccga tgcgacggag tttatcggtt acctggtgag gatctcgagc    300
taatcatgac cgctctgaag tggcgctaaa cgttctaatg tttcaagcaa tgtgcgtccc    360
aaaatgcctc gtccgctggc tggtgtggca tttccttggg tggtgcatg aacaacaatc     420 tcttgttctt ggcctatccg tacgaggata ccatcttgac ctccctgcga ttcggctcgg    480
gctatagcat gccgggggtc tataccggca atgccaacgt cacccagatt tcttcaagca    540
tcaatgccac tcactttacg ttgcttttcc gttgcgagaa ttgtctgacc tgggaccaag    600
atggtcaaac cggaaacgcg accacaagca agggtaggtt agtcctggga tgggcacagt    660
ctacggagag cccgtcgaac ccgtcctgtc cggacaatat cagcctggcg cagcacgaca    720
accagggtat tatctcagcc actctggatg agaatgcagc cagtgagtcc tacgaggact    780
gggtcaagtt ggctaataag actgttcccg gggactgctc cggtgacggt ggtggcggca    840
acgagccgac tcctgtccct gtccctgacg gtggcgtgg acccgataag cgcttcatcc     900
cagctgagga agaggatcct gctttctgga accgtcaggc tgctcaggct cttgacgttg    960
ccaagaagtt gcagccaatc cagaccgccg ctaagaatgt catcctcttc ctgggcgatg   1020
gtatgggagt cccgaccgtg actgctaccc gcatcctcaa gggccagatg aatggaaagc   1080
tcggcccaga aaccccgctg gctatggacc agttccctta cgtggccctg tcgaagactt   1140
ataacgttga tcgtcaagtc cctgactctg ctggtactgc taccgcctac ctttgcggtg   1200
tgaagggaaa ttataagacc atcggcgttt ccgccgctgc ccggtataac cagtgtaata   1260
```

| | |
|---|---|
| ccacttctgg taacgaggtt actagcgtca tgaatcgggc taagaaggcc ggcaagtctg | 1320 |
| ttggtgtcgt gaccacttcg cgcgtccagc atgcttcccc tgctggagcc tacgctcaca | 1380 |
| ccgtcaaccg caattggtat agcgatgctg acctgcccgc cgatgctcag acctacggct | 1440 |
| gccaggacat cgccactcag ctcgtcaaca atatggatat cgacgtgatc ctgggaggcg | 1500 |
| gtcgtatgta tatgttccct gaaggtaccc ctgatcccga gtaccctat gacgtgaacc | 1560 |
| agactggagt tcggaaggac aagcgcaatc ttgtgcagga atggcaggct aagcatcagg | 1620 |
| gtgcccagta cgtttggaac cgcaccgagc tcctgcaggc tgccaatgat ccatcggtca | 1680 |
| ctcacctcat gggactgttc gaaccggccg acatgaagta taacgtgcag caggatccta | 1740 |
| ctaaggaccc caccccttgaa gagatgaccg aggctgccct tcaggttttg tcccggaatc | 1800 |
| cacagggctt ctacttgttc gtcgagggcg gccgcatcga tcatggacat cacgagggca | 1860 |
| aggcttatat ggccctcact gataccgtta tgttcgacaa cgccatcgct aaggccaatg | 1920 |
| aactcacttc ggagctggat acccttatct tggctactgc cgaccattcg cacgtcttct | 1980 |
| ccttcggtgg atacactctt cgtggtacct ccatcttcgg attggctcct tccaaggcct | 2040 |
| ctgacaacaa gagctacacc tcgatcctgt atggcaatgg tcctggatac gtccttggcg | 2100 |
| gtggattgcg tcccgatgtg aacgacagca tctcggagga tccatcttat cggcagcagg | 2160 |
| ctgccgtccc gttgtcctct gaaagccatg gcggtgagga tgtggctgtt ttcgctcgtg | 2220 |
| gaccacaggc tcatttggtg cacggcgttc aggaagagac cttcgtcgcc cacgtgatgg | 2280 |
| cttttgcggg ttgcgttgag ccctatactg actgtaactt gccagcccct tcgggt | 2336 |

<210> SEQ ID NO 95
<211> LENGTH: 2342
<212> TYPE: DNA
<213> ORGANISM: Artificial Sequence
<220> FEATURE:
<223> OTHER INFORMATION: CDHcytbKexmut3_bAPIV

<400> SEQUENCE: 95

| | |
|---|---|
| atgaagctcg ttaaccgttt gctcgcttca ttcctgtcag cgagcaccgg tgagtggtgg | 60 |
| cctatcgagc taatgttgct tctcttcgtc tgacttttct tggcagtgtt gcagtcatgc | 120 |
| tgggctcagt ccggcacacc ggttgcctac acggatactg agacgggcat cacgtttgac | 180 |
| acgtggtcgg tacctgctgg tacgggtacg ggtggtctcg tcttcggtgt agccctgccg | 240 |
| ggttcggcat tgaccaccga tgcgacggag tttatcggtt acctggtgag gatctcgagc | 300 |
| taatcatgac cgctctgaag tggcgctaaa cgttctaatg tttcaagcaa tgtgcgtccc | 360 |
| aaaatgcctc gtccgctggc tggtgtggca tttccttggg tggtggcatg aacaacaatc | 420 |
| tcttgttctt ggcctatccg tacgaggata ccatcttgac ctcccgtgcga ttcggctcgg | 480 |
| gctatagcat gcccggggtc tataccggca atgccaacgt cacccagatt tcttcaagca | 540 |
| tcaatgccac tcactttacg ttgcttttcc gttgcgagaa ttgtctgacc tgggaccaag | 600 |
| atggtcaaac cggaaacgcg accacaagca agggtaggtt agtcctggga tgggcacagt | 660 |
| ctacggagag cccgtcgaac ccgtcctgtc cggacaatat cagcctggcg cagcacgaca | 720 |
| accagggtat tatctcagcc actctggatg agaatgcagc cagtgagtcc tacgaggact | 780 |
| gggtcaagtt ggctaataag actgttcccg gggactgctc cggtgacggt ggtggcggca | 840 |
| acgagccgac tcctgtccct gtccctgacg gtggcggtgg acaacgcctg gtcaagcgct | 900 |
| tcatcccagc tgaggaagag gatcctgctt tctggaaccg tcaggctgct caggctcttg | 960 |
| acgttgccaa gaagttgcag ccaatccaga ccgccgctaa gaatgtcatc ctcttcctgg | 1020 |

```
gcgatggtat gggagtcccg accgtgactg ctacccgcat cctcaagggc cagatgaatg    1080
gaaagctcgg cccagaaacc ccgctggcta tggaccagtt cccttacgtg gccctgtcga    1140
agacttataa cgttgatcgt caagtccctg actctgctgg tactgctacc gcctaccttt    1200
gcggtgtgaa gggaaattat aagaccatcg gcgtttccgc cgctgcccgg tataaccagt    1260
gtaataccac ttctggtaac gaggttacta gcgtcatgaa tcgggctaag aaggccggca    1320
agtctgttgg tgtcgtgacc acttcgcgcg tccagcatgc ttcccctgct ggagcctacg    1380
ctcacaccgt caaccgcaat tggtatagcg atgctgacct gcccgccgat gctcagacct    1440
acggctgcca ggacatcgcc actcagctcg tcaacaatat ggatatcgac gtgatcctgg    1500
gaggcggtcg tatgtatatg ttccctgaag gtaccctga tcccgagtac ccctatgacg    1560
tgaaccagac tggagttcgg aaggacaagc gcaatcttgt gcaggaatgg caggctaagc    1620
atcagggtgc ccagtacgtt tggaaccgca ccgagctcct gcaggctgcc aatgatccat    1680
cggtcactca cctcatggga ctgttcgaac cggccgacat gaagtataac gtgcagcagg    1740
atcctactaa ggaccccacc cttgaagaga tgaccgaggc tgcccttcag gttttgtccc    1800
ggaatccaca gggcttctac ttgttcgtcg agggcggccg catcgatcat ggacatcacg    1860
agggcaaggc ttatatggcc ctcactgata ccgttatgtt cgacaacgcc atcgctaagg    1920
ccaatgaact cacttcggag ctggataccc ttatcttggc tactgccgac cattcgcacg    1980
tcttctcctt cggtggatac actcttcgtg gtacctccat cttcggattg gctccttcca    2040
aggcctctga caacaagagc tacacctcga tcctgtatgg caatggtcct ggatacgtcc    2100
ttggcggtgg attgcgtccc gatgtgaacg acagcatctc ggaggatcca tcttatcggc    2160
agcaggctgc cgtcccgttg tcctctgaaa gccatggcgg tgaggatgtg gctgttttcg    2220
ctcgtggacc acaggctcat ttggtgcacg gcgttcagga agagaccttc gtcgcccacg    2280
tgatggcttt gcgggttgc gttgagccct atactgactg taacttgcca gcccttcgg    2340 gt                                                                    2342
```

<210> SEQ ID NO 96
<211> LENGTH: 2342
<212> TYPE: DNA
<213> ORGANISM: Artificial Sequence
<220> FEATURE:
<223> OTHER INFORMATION: CDHcytbKexmut4_bAPIV

<400> SEQUENCE: 96

```
atgaagctcg ttaaccgttt gctcgcttca ttcctgtcag cgagcaccgg tgagtggtgg     60
cctatcgagc taatgttgct tctcttcgtc tgacttttct tggcagtgtt gcagtcatgc    120
tgggctcagt ccggcacacc ggttgcctac acggatactg agacgggcat cacgtttgac    180
acgtggtcgg tacctgctgg tacgggtacg ggtggtctcg tcttcggtgt agccctgccg    240
ggttcggcat tgaccaccga tgcgacggag tttatcggtt acctggtgag gatctcgagc    300
taatcatgac cgctctgaag tggcgctaaa cgttctaatg tttcaagcaa tgtgcgtccc    360
aaaatgcctc gtccgctggc tggtgtggca tttccttggg tggtggcatg aacaacaatc    420
tcttgttctt ggcctatccg tacgaggata ccatcttgac ctccctgcga ttcggctcgg    480
gctatagcat gcccggggtc tataccggca atgccaacgt cacccagatt tcttcaagca    540
tcaatgccac tcactttacg ttgcttttcc gttgcgagaa ttgtctgacc tgggaccaag    600
atggtcaaac cggaaacgcg accacaagca agggtaggtt agtcctggga tgggcacagt    660
```

| | |
|---|---|
| ctacggagag cccgtcgaac ccgtcctgtc cggacaatat cagcctggcg cagcacgaca | 720 |
| accagggtat tatctcagcc actctggatg agaatgcagc cagtgagtcc tacgaggact | 780 |
| gggtcaagtt ggctaataag actgttcccg gggactgctc cggtgacggt ggtggcggca | 840 |
| acgagccgac tcctgtccct gtccctgacg gtggcggtgg agtcgcagtc gaaaagcgct | 900 |
| tcatcccagc tgaggaagag gatcctgctt tctggaaccg tcaggctgct caggctcttg | 960 |
| acgttgccaa gaagttgcag ccaatccaga ccgccgctaa gaatgtcatc ctcttcctgg | 1020 |
| gcgatggtat gggagtcccg accgtgactg ctacccgcat cctcaagggc cagatgaatg | 1080 |
| gaaagctcgg cccagaaacc ccgctggcta tggaccagtt cccttacgtg ccctgtcga | 1140 |
| agacttataa cgttgatcgt caagtccctg actctgctgg tactgctacc gcctaccttt | 1200 |
| gcggtgtgaa gggaaattat aagaccatcg gcgtttccgc cgctgccgg tataaccagt | 1260 |
| gtaataccac ttctggtaac gaggttacta gcgtcatgaa tcgggctaag aaggccggca | 1320 |
| agtctgttgg tgtcgtgacc acttcgcgcg tccagcatgc ttcccctgct ggagcctacg | 1380 |
| ctcacaccgt caaccgcaat tggtatagcg atgctgacct gcccgccgat gctcagacct | 1440 |
| acggctgcca ggacatcgcc actcagctcg tcaacaatat ggatatcgac gtgatcctgg | 1500 |
| gaggcggtcg tatgtatatg ttccctgaag gtaccccctga tcccgagtac ccctatgacg | 1560 |
| tgaaccagac tggagttcgg aaggacaagc gcaatcttgt gcaggaatgg caggctaagc | 1620 |
| atcagggtgc ccagtacgtt tggaaccgca ccgagctcct gcaggctgcc aatgatccat | 1680 |
| cggtcactca cctcatggga ctgttcgaac cggccgacat gaagtataac gtgcagcagg | 1740 |
| atcctactaa ggaccccacc cttgaagaga tgaccgaggc tgcccttcag gttttgtccc | 1800 |
| ggaatccaca gggcttctac ttgttcgtcg agggcggccg catcgatcat ggacatcacg | 1860 |
| agggcaaggc ttatatggcc ctcactgata ccgttatgtt cgacaacgcc atcgctaagg | 1920 |
| ccaatgaact cacttcggag ctggataccc ttatcttggc tactgccgac cattcgcacg | 1980 |
| tcttctcctt cggtggatac actcttcgtg gtacctccat cttcggattg ctccttcca | 2040 |
| aggcctctga caacaagagc tacacctcga tcctgtatgg caatggtcct ggatacgtcc | 2100 |
| ttggcggtgg attgcgtccc gatgtgaacg acagcatctc ggaggatcca tcttatcggc | 2160 |
| agcaggctgc cgtcccgttg tcctctgaaa gccatggcgg tgaggatgtg ctgttttcg | 2220 |
| ctcgtggacc acaggctcat ttggtgcacg gcgttcagga agagaccttc gtcgcccacg | 2280 |
| tgatggcttt tgcggggttgc gttgagccct atactgactg taacttgcca gccccttcgg | 2340 |
| gt | 2342 |

<210> SEQ ID NO 97
<211> LENGTH: 4344
<212> TYPE: DNA
<213> ORGANISM: Artificial Sequence
<220> FEATURE:
<223> OTHER INFORMATION: CDHall_bIAPIV

<400> SEQUENCE: 97

| | |
|---|---|
| atgaagctcg ttaaccgttt gctcgcttca ttcctgtcag cgagcaccgg tgagtggtgg | 60 |
| cctatcgagc taatgttgct tctcttcgtc tgacttttct tggcagtgtt gcagtcatgc | 120 |
| tgggctcagt ccggcacacc ggttgcctac acggatactg agacgggcat cacgtttgac | 180 |
| acgtggtcgg tacctgctgg tacgggtacg ggtggtctcg tcttcggtgt agccctgccg | 240 |
| ggttcggcat tgaccaccga tcgacggag tttatcggtt acctggtgag gatctcgagc | 300 |
| taatcatgac cgctctgaag tggcgctaaa cgttctaatg tttcaagcaa tgtgcgtccc | 360 |

```
aaaatgcctc gtccgctggc tggtgtggca tttccttggg tggtggcatg aacaacaatc      420
tcttgttctt ggcctatccg tacgaggata ccatcttgac ctccctgcga ttcggctcgg      480
gctatagcat gcccggggtc tataccggca atgccaacgt cacccagatt tcttcaagca      540
tcaatgccac tcactttacg ttgcttttcc gttgcgagaa ttgtctgacc tgggaccaag      600
atggtcaaac cggaaacgcg accacaagca agggtaggtt agtcctggga tgggcacagt      660
ctacggagag cccgtcgaac ccgtcctgtc cggacaatat cagcctggcg cagcacgaca      720
accagggtat tatctcagcc actctggatg agaatgcagc cagtgagtcc tacgaggact      780
gggtcaagtt ggctaataag actgttcccg gggactgctc cggtgacggt ggtggcggca      840
acgagccgac tcctgtccct gtccctgacg gtgctacata cgactatatt gtcgtcggtg      900
gaggtgccgg gggtatccct gtcgccgatc ggctgagtga ggctggacac agtgttctcc      960
tgatcgagaa aggtcctcct tcctcgggac gctggggtgg caccatgaag cccagctggc     1020
tggatgatac caacctgacg cgatttgatg tccctgggct gtgcaaccag atctgggtcg     1080
actccaacgg tatcgcctgc agtgacaccg atcagatggc aggttgtgtg ctgggtggag     1140
gcaccgccgt caacgcagga ttgtggtgga aggtaagccg tgcccagatg ccatgttcgg     1200
atccatcact gacaatgtcc agccaaatcc cgttgactgg gactacaact tccccgaggg     1260
atggcagtcg tccgacatgc aggctgccgc ggaccgcgtg ttctcgcgga tccctggaac     1320
cacaaccccc tccaccgatg gaaagcttta ttaccaacaa ggagccgata tactgttaaa     1380
tggcttgcaa tccgccggat ggtcatccgt caccctcaac gatgtcccgg cccagaaaac     1440
caagaccttt ggccacgcac cattcatgtt ctctggaggt gagcgcggag ggcccatggg     1500
gacgtatctg gtgtcggcga gcagagagaga taattttgcc cgctggtcga acacgactgt     1560
gaagagggtt gttcgtgaag gcggacgtat caccggagtt gaggtcgagg cgaccctcga     1620
tggtggctac gcgggtaccg tcaatgtaac tgccaatacg ggtcgagtca ttctttctgc     1680
aggaactttt ggaacgccca aggtccttat gagaagtacg cttcgttgga tgatattgtt     1740
agggagttat tgctaatggc gtataggtgg tatcggcccg aaggaccagc tgtccatcgt     1800
gaagagctca actgatggag agacaatgat tgccgaatct gagtggatcg aacttccggt     1860
tggcgagaac ttggtcgatc atgtcaatgt gagtgccaag tggaccgggg aggctactac     1920
tatgctaata ggatgcttac agactgatgt tgtggtgacc cacctgatg ttgtcttcta      1980 tgatttcaaa gcggcataca agaccccat cgagagtgat gcgacgagct atctgagtat       2040
gtagtaatgc ttcgaaggac agtccagcac taacttgcgt agacgatcgc accgggattt     2100
tcgcccaggc tgcgcctaac attggtccta tgtaagttgc ccgtctacca aacacgtcat     2160
ggtactaacg cctgtagaat cttcgacgaa gtcaccggct ctgatggcat taaacgacag     2220
atacagtgga ctgctcgtgt ggaaggcggc cacgacacgc ctgacggacg tacgttgact     2280
cctaagtgaa agattagtgc aatatattaa ccgtgctgta gacgccatga ccatcagcca     2340 ataccctcggc cgcggctcaa cctcgcgtgg ccgcatgacc attaccgcag gactggacac     2400
ggtggtctcg acgctgccat tcctacggga cgagagcgac gttaatgctg taatccaggg     2460
aatccagaac ctgaagatgg ccctgaacgg gacaggattt acctggaact accctgctcg     2520
gaacacttcc attgccgagt ttgtcaatac tgtgagtgct gatttctgga aggatgttcg     2580
acgtaactga cactgataga tgccaatcac tgccggaaca cgccgagcta atcactggat     2640
gggtgagtta tgaatctgct ttttaaaatt tcgtcgctaa ttgttatagg aacctgcaaa     2700
```

| | |
|---|---:|
| ataggtacag atgatggccg tactggaggt agcgccgttg ttgatttgaa tacgaaggtc | 2760 |
| tatgaacgg acaacctgtt cgtcgtggat gctagtatct tcccgggtat gatcacgtcc | 2820 |
| aatccttcgg cttacattgt tacggtcgcg gagcatgcag ctgaaaagat tcttgcgctg | 2880 |
| ggcggtggag gctctaagcg cttcatccca gctgaggaag aggatcctgc tttctggaac | 2940 |
| cgtcaggctg ctcaggctct tgacgttgcc aagaagttgc agccaatcca gaccgccgct | 3000 |
| aagaatgtca tcctcttcct gggcgatggt atgggagtcc cgaccgtgac tgctacccgc | 3060 |
| atcctcaagg gccagatgaa tggaaagctc ggcccagaaa ccccgctggc tatggaccag | 3120 |
| ttcccttacg tggccctgtc gaagacttat aacgttgatc gtcaagtccc tgactctgct | 3180 |
| ggtactgcta ccgcctacct tgcggtgtg aagggaaatt ataagaccat cggcgtttcc | 3240 |
| gccgctgccc ggtataacca gtgtaatacc acttctggta acgaggttac tagcgtcatg | 3300 |
| aatcgggcta agaaggccgg caagtctgtt ggtgtcgtga ccacttcgcg cgtccagcat | 3360 |
| gcttcccctg ctggagccta cgctcacacc gtcaaccgca attggtatag cgatgctgac | 3420 |
| ctgcccgccg atgctcagac ctacggctgc caggacatcg ccactcagct cgtcaacaat | 3480 |
| atggatatcg acgtgatcct gggaggcggt cgtatgtata tgttccctga aggtaccct | 3540 |
| gatcccgagt acccctatga cgtgaaccag actggagttc ggaaggacaa gcgcaatctt | 3600 |
| gtgcaggaat ggcaggctaa gcatcagggt gcccagtacg tttggaaccg caccgagctc | 3660 |
| ctgcaggctg ccaatgatcc atcggtcact cacctcatgg gactgttcga accggccgac | 3720 |
| atgaagtata cgtgcagca ggatcctact aaggacccca cccttgaaga gatgaccgag | 3780 |
| gctgcccttc aggttttgtc ccggaatcca cagggcttct acttgttcgt cgagggcggc | 3840 |
| cgcatcgatc atggacatca cgagggcaag gcttatatgg ccctcactga taccgttatg | 3900 |
| ttcgacaacg ccatcgctaa ggccaatgaa ctcacttcgg agctggatac ccttatcttg | 3960 |
| gctactgccg accattcgca cgtcttctcc ttcggtggat acactcttcg tggtacctcc | 4020 |
| atcttcggat tggctccttc caaggcctct gacaacaaga gctacacctc gatcctgtat | 4080 |
| ggcaatggtc ctggatacgt ccttggcggt ggattgcgtc ccgatgtgaa cgacagcatc | 4140 |
| tcggaggatc catcttatcg gcagcaggct gccgtcccgt tgtcctctga aagccatggc | 4200 |
| ggtgaggatg tggctgtttt cgctcgtgga ccacaggctc atttggtgca cggcgttcag | 4260 |
| gaagagacct tcgtcgccca cgtgatggct tttgcgggtt cgttgagcc ctatactgac | 4320 |
| tgtaacttgc cagccccttc gggt | 4344 |

<210> SEQ ID NO 98
<211> LENGTH: 1494
<212> TYPE: DNA
<213> ORGANISM: Artificial Sequence
<220> FEATURE:
<223> OTHER INFORMATION: GlaBss_bIAPIV

<400> SEQUENCE: 98

| | |
|---|---:|
| atgcggaaca actttctttt tcccctcaat gccattgctg gcgctgtcgc gttcatccca | 60 |
| gctgaggaag aggatcctgc tttctggaac cgtcaggctg ctcaggctct tgacgttgcc | 120 |
| aagaagttgc agccaatcca gaccgccgct aagaatgtca tcctcttcct gggcgatggt | 180 |
| atgggagtcc cgaccgtgac tgctacccgc atcctcaagg gccagatgaa tggaaagctc | 240 |
| ggcccagaaa ccccgctggc tatggaccag ttcccttacg tggccctgtc gaagacttat | 300 |
| aacgttgatc gtcaagtccc tgactctgct ggtactgcta ccgcctacct tgcggtgtg | 360 |
| aagggaaatt ataagaccat cggcgtttcc gccgctgccc ggtataacca gtgtaatacc | 420 |

```
acttctggta acgaggttac tagcgtcatg aatcgggcta agaaggccgg caagtctgtt      480
ggtgtcgtga ccacttcgcg cgtccagcat gcttcccctg ctggagccta cgctcacacc      540
gtcaaccgca attggtatag cgatgctgac ctgcccgccg atgctcagac ctacggctgc      600
caggacatcg ccactcagct cgtcaacaat atggatatcg acgtgatcct gggaggcggt      660
cgtatgtata tgttccctga aggtacccct gatcccgagt accctatga cgtgaaccag       720 actggagttc ggaaggacaa gcgcaatctt gtgcaggaat ggcaggctaa gcatcagggt      780
gcccagtacg tttggaaccg caccgagctc ctgcaggctg ccaatgatcc atcggtcact      840
cacctcatgg gactgttcga accggccgac atgaagtata acgtgcagca ggatcctact      900
aaggacccca cccttgaaga gatgaccgag gctgcccttc aggttttgtc ccggaatcca      960
cagggcttct acttgttcgt cgagggcggc cgcatcgatc atggacatca cgagggcaag     1020
gcttatatgg ccctcactga taccgttatg ttcgacaacg ccatcgctaa ggccaatgaa     1080
ctcacttcgg agctggatac ccttatcttg gctactgccg accattcgca cgtcttctcc     1140
ttcggtggat acactcttcg tggtacctcc atcttcggat tggctccttc caaggcctct     1200
gacaacaaga gctacacctc gatcctgtat ggcaatggtc ctggatacgt ccttggcggt     1260
ggattgcgtc ccgatgtgaa cgacagcatc tcggaggatc catcttatcg gcagcaggct     1320
gccgtcccgt tgtcctctga aagccatggc ggtgaggatg tggctgtttt cgctcgtgga     1380
ccacaggctc atttggtgca cggcgttcag gaagagacct tcgtcgccca cgtgatggct     1440
tttgcgggtt gcgttgagcc ctatactgac tgtaacttgc cagccccttc gggt           1494
```

<210> SEQ ID NO 99
<211> LENGTH: 1494
<212> TYPE: DNA
<213> ORGANISM: Artificial Sequence
<220> FEATURE:
<223> OTHER INFORMATION: CelBss_bIAPIV

<400> SEQUENCE: 99

```
atgatctgga cactcgctcc ctttgtggca ctcctgccac tggtaacggc tttcatccca       60
gctgaggaag aggatcctgc tttctggaac cgtcaggctg ctcaggctct tgacgttgcc      120
aagaagttgc agccaatcca gaccgccgct aagaatgtca tcctcttcct gggcgatggt      180
atgggagtcc cgaccgtgac tgctacccgc atcctcaagg ccagatgaa tggaaagctc       240 ggcccagaaa ccccgctggc tatggaccag ttcccttacg tggccctgtc gaagacttat      300
aacgttgatc gtcaagtccc tgactctgct ggtactgcta ccgcctacct tgcggtgtg       360 aagggaaatt ataagaccat cggcgtttcc gccgctgccc ggtataacca gtgtaatacc      420
acttctggta acgaggttac tagcgtcatg aatcgggcta agaaggccgg caagtctgtt      480
ggtgtcgtga ccacttcgcg cgtccagcat gcttcccctg ctggagccta cgctcacacc      540
gtcaaccgca attggtatag cgatgctgac ctgcccgccg atgctcagac ctacggctgc      600
caggacatcg ccactcagct cgtcaacaat atggatatcg acgtgatcct gggaggcggt      660
cgtatgtata tgttccctga aggtacccct gatcccgagt accctatga cgtgaaccag       720 actggagttc ggaaggacaa gcgcaatctt gtgcaggaat ggcaggctaa gcatcagggt      780
gcccagtacg tttggaaccg caccgagctc ctgcaggctg ccaatgatcc atcggtcact      840
cacctcatgg gactgttcga accggccgac atgaagtata acgtgcagca ggatcctact      900
aaggacccca cccttgaaga gatgaccgag gctgcccttc aggttttgtc ccggaatcca      960
```

| | |
|---|---|
| cagggcttct acttgttcgt cgagggcggc cgcatcgatc atggacatca cgagggcaag | 1020 |
| gcttatatgg ccctcactga taccgttatg ttcgacaacg ccatcgctaa ggccaatgaa | 1080 |
| ctcacttcgg agctggatac ccttatcttg gctactgccg accattcgca cgtcttctcc | 1140 |
| ttcggtggat acactcttcg tggtacctcc atcttcggat ggctccttc caaggcctct | 1200 |
| gacaacaaga gctacacctc gatcctgtat ggcaatggtc ctggatacgt ccttggcggt | 1260 |
| ggattgcgtc ccgatgtgaa cgacagcatc tcggaggatc catcttatcg gcagcaggct | 1320 |
| gccgtcccgt tgtcctctga aagccatggc ggtgaggatg tggctgtttt cgctcgtgga | 1380 |
| ccacaggctc atttggtgca cggcgttcag gaagagacct tcgtcgccca cgtgatggct | 1440 |
| tttgcgggtt gcgttgagcc ctatactgac tgtaacttgc cagcccttc gggt | 1494 |

<210> SEQ ID NO 100
<211> LENGTH: 2712
<212> TYPE: DNA
<213> ORGANISM: Artificial Sequence
<220> FEATURE:
<223> OTHER INFORMATION: CelB_bIAPIV

<400> SEQUENCE: 100

| | |
|---|---|
| atgatctgga cactcgctcc ctttgtggca ctcctgccac tggtaacggc tcaacaggtg | 60 |
| ggaactacag cggacgccca tcccagactc accacgtata aatgtacttc acagaacggc | 120 |
| tgcacgaggc agaacacctc agtcgtcctt gatgcagcaa cccatttat ccacaaaaaa | 180 |
| ggaacacaaa catcctgcac caacagcaac ggcttggaca cttccatttg tccggacaaa | 240 |
| cagacctgcg cggacaactg tgtcgttgat gggatcacgg actacgctag ctacggcgtc | 300 |
| cagacgaaga atgacacatt gacccttcac caatatctgc aaactggcaa tgaaacaaag | 360 |
| tccgtgtcac cgcgtgtcta cctcctcgct gaagacggag agaactattc catgctgcaa | 420 |
| ctcctgaatc aggaattcac cttcgatgtc gacgcctcta ccctcgtctg cggcatgaat | 480 |
| ggtgctctat atctctctga atggaggct tcgggcggaa agagttccct aaatcaagcg | 540 |
| ggagccaaat acggaaccgg ttactgtgat gcccaatgct acaccacgcc ttggatcaac | 600 |
| ggcgaaggca acaccgagag tgtcggctcc tgctgtcagg aaatggatat tgggaagcc | 660 |
| aacgcccgag caacagggct tacaccgcac ccttgcaaca caaccggttt gtacgagtgc | 720 |
| agcggctcgg gatgcggaga ctccggggtc tgtgacaagt ccggctgtgg attcaaccca | 780 |
| tatggcctag gtgcaaagga ctactacggt tacggcctca aggtcaacac caacgagaca | 840 |
| ttcacggtcg taacccagtt cctcacaagc gataacacga catcgggcca gctcagcgaa | 900 |
| atccgccgtc tctacatcca gaacggccag gttattcaaa atgctgccgt cacctcagga | 960 |
| ggaaaaactg tcgactcaat cacaaaggat ttctgcagcg tgaaggaag tgccttcaac | 1020 |
| cgacttggcg gcctcgagga atgggccac gccttgggcc gcggcatggt tcttgcgctc | 1080 |
| agtgtctgga cgacgcagg ctcattcatg caatggcttg atggggcag cgcaggaccg | 1140 |
| tgcagcgcga cggagggaga cccggcgttg atcgagaagt tgtatccgga tactcatgtg | 1200 |
| aagttttcca agatccggtg gggagatatt ggatctacct acaggcatgg cggtggaggc | 1260 |
| tctaagcgct tcatcccagc tgaggaagag gatcctgctt tctggaaccg tcaggctgct | 1320 |
| caggctcttg acgttgccaa gaagttgcag ccaatccaga ccgccgctaa gaatgtcatc | 1380 |
| ctcttcctgg gcgatggtat gggagtcccg accgtgactg ctaccgcat cctcaagggc | 1440 |
| cagatgaatg gaaagctcgg cccagaaacc ccgctggcta tggaccagtt cccttacgtg | 1500 |
| gccctgtcga agacttataa cgttgatcgt caagtccctg actctgctgg tactgctacc | 1560 |

-continued

```
gcctaccttt gcggtgtgaa gggaaattat aagaccatcg gcgtttccgc cgctgcccgg    1620
tataaccagt gtaataccac ttctggtaac gaggttacta cgtcatgaa tcgggctaag    1680 aaggccggca gtctgttgg tgtcgtgacc acttcgcgcg tccagcatgc ttcccctgct    1740
ggagcctacg ctcacaccgt caaccgcaat tggtatagcg atgctgacct gcccgccgat    1800
gctcagacct acggctgcca ggacatcgcc actcagctcg tcaacaatat ggatatcgac    1860
gtgatcctgg gaggcggtcg tatgtatatg ttccctgaag taccccctga tcccgagtac    1920
ccctatgacg tgaaccagac tggagttcgg aaggacaagc gcaatcttgt gcaggaatgg    1980
caggctaagc atcagggtgc ccagtacgtt tggaaccgca ccgagctcct gcaggctgcc    2040
aatgatccat cggtcactca cctcatggga ctgttcgaac cggccgacat gaagtataac    2100
gtgcagcagg atcctactaa ggaccccacc cttgaagaga tgaccgaggc tgcccttcag    2160
gttttgtccc ggaatccaca gggcttctac ttgttcgtcg agggcggccg catcgatcat    2220
ggacatcacg agggcaaggc ttatatggcc ctcactgata ccgttatgtt cgacaacgcc    2280
atcgctaagg ccaatgaact cacttcggag ctggataccc ttatcttggc tactgccgac    2340
cattcgcacg tcttctcctt cggtggatac actcttcgtg gtacctccat cttcggattg    2400
gctccttcca aggcctctga caacaagagc tacacctcga tcctgtatgg caatggtcct    2460
ggatacgtcc ttggcggtgg attgcgtccc gatgtgaacg acagcatctc ggaggatcca    2520
tcttatcggc agcaggctgc cgtcccgttg tcctctgaaa gccatggcgg tgaggatgtg    2580
gctgttttcg ctcgtggacc acaggctcat ttggtgcacg gcgttcagga agagaccttc    2640
gtcgcccacg tgatggcttt tgcggggtgc gttgagccct atactgactg taacttgcca    2700
gccccttcgg gt    2712
```

<210> SEQ ID NO 101
<211> LENGTH: 1581
<212> TYPE: DNA
<213> ORGANISM: Artificial Sequence
<220> FEATURE:
<223> OTHER INFORMATION: SKIK_CDHss_bIAPIV

<400> SEQUENCE: 101

```
atgtccaaga tcaagaagct cgttaaccgt ttgctcgctt cattcctgtc agcgagcacc      60
ggtgagtggt ggcctatcga gctaatgttg cttctcttcg tctgactttt cttggcagtg     120
ttgcagtcat gctgggcttt catcccagct gaggaagagg atcctgcttt ctggaaccgt     180
caggctgctc aggctcttga cgttgccaag aagttgcagc caatccagac cgccgctaag     240
aatgtcatcc tcttcctggg cgatggtatg ggagtcccga ccgtgactgc taccgcatc      300 ctcaagggcc agatgaatgg aaagctcggc ccagaaaccc cgctggctat ggaccagttc     360
ccttacgtgg ccctgtcgaa gacttataac gttgatcgtc aagtccctga ctctgctggt     420
actgctaccg cctacctttg cggtgtgaag ggaaattata agaccatcgg cgtttccgcc     480
gctgcccggt ataaccagtg taataccact tctggtaacg aggttactag cgtcatgaat     540
cgggctaaga aggccggcaa gtctgttggt gtcgtgacca cttcgcgcgt ccagcatgct     600
tcccctgctg agcctacgc tcacaccgtc aaccgcaatt ggtatagcga tgctgacctg     660
cccgccgatg ctcagaccta cggctgccag gacatcgcca ctcagctcgt caacaatatg     720
gatatcgacg tgatcctggg aggcggtcgt atgtatatgt tccctgaagg taccccctgat    780 cccgagtacc cctatgacgt gaaccagact ggagttcgga aggacaagcg caatcttgtg    840
```

```
caggaatggc aggctaagca tcagggtgcc cagtacgttt ggaaccgcac cgagctcctg    900
caggctgcca atgatccatc ggtcactcac ctcatgggac tgttcgaacc ggccgacatg    960
aagtataacg tgcagcagga tcctactaag accccaccc ttgaagagat gaccgaggct   1020
gcccttcagg ttttgtcccg gaatccacag ggcttctact tgttcgtcga gggcggccgc   1080
atcgatcatg gacatcacga gggcaaggct tatatggccc tcactgatac cgttatgttc   1140
gacaacgcca tcgctaaggc caatgaactc acttcggagc tggataccct tatcttggct   1200
actgccgacc attcgcacgt cttctccttc ggtggataca ctcttcgtgg tacctccatc   1260
ttcggattgg ctccttccaa ggcctctgac aacaagagct acacctcgat cctgtatggc   1320
aatggtcctg gatacgtcct ggcggtgga ttgcgtcccg atgtgaacga cagcatctcg   1380
gaggatccat cttatcggca gcaggctgcc gtcccgttgt cctctgaaag ccatggcggt   1440
gaggatgtgg ctgttttcgc tcgtggacca caggctcatt tggtgcacgg cgttcaggaa   1500
gagaccttcg tcgcccacgt gatggctttt gcgggttgcg ttgagcccta tactgactgt   1560
aacttgccag ccccttcggg t                                             1581

<210> SEQ ID NO 102
<211> LENGTH: 1497
<212> TYPE: DNA
<213> ORGANISM: Artificial Sequence
<220> FEATURE:
<223> OTHER INFORMATION: AsAP1ss54_bIAPIV

<400> SEQUENCE: 102
atgaggttcc tctcaattgt aggtgcggcg ctcttcgctt ccagcgctgt tgccttcatc     60
ccagctgagg aagaggatcc tgctttctgg aaccgtcagg ctgctcaggc tcttgacgtt    120
gccaagaagt tgcagccaat ccagaccgcc gctaagaatg tcatcctctt cctgggcgat    180
ggtatgggag tcccgaccgt gactgctacc cgcatcctca agggccagat gaatggaaag    240
ctcggcccag aaaccccgct ggctatggac cagttccctt acgtggccct gtcgaagact    300
tataacgttg atcgtcaagt ccctgactct gctggtactg ctaccgccta cctttgcggt    360
gtgaagggaa attataagac catcggcgtt tccgccgctg cccggtataa ccagtgtaat    420
accacttctg gtaacgaggt tactagcgtc atgaatcggg ctaagaaggc cggcaagtct    480
gttggtgtcg tgaccacttc gcgcgtccag catgcttccc ctgctggagc ctacgctcac    540
accgtcaacc gcaattggta tagcgatgct gacctgcccg ccgatgctca gacctacggc    600
tgccaggaca tcgccactca gctcgtcaac aatatggata tcgacgtgat cctgggaggc    660
ggtcgtatgt atatgttccc tgaaggtacc cctgatcccg agtaccccta tgacgtgaac    720
cagactggag ttcggaagga caagcgcaat cttgtgcagg aatggcaggc taagcatcag    780 ggtgccagt acgtttggaa ccgcaccgag ctcctgcagg ctgccaatga tccatcggtc    840
actcacctca tgggactgtt cgaaccggcc gacatgaagt ataacgtgca gcaggatcct    900
actaaggacc ccacccttga agagatgacc gaggctgccc ttcaggtttt gtcccggaat    960
ccacagggct tctacttgtt cgtcgagggc ggccgcatcg atcatggaca tcacgagggc   1020
aaggcttata tggccctcac tgataccgtt atgttcgaca cgccatcgc taaggccaat   1080 gaactcactt cggagctgga taccttatc ttggctactg ccgaccattc gcacgtcttc   1140
tccttcggtg gatacactct tcgtggtacc tccatcttcg gattggctcc ttccaaggcc   1200
tctgacaaca agagctacac ctcgatcctg tatggcaatg gtcctggata cgtccttggc   1260
ggtggattgc gtcccgatgt gaacgacagc atctcggagg atccatctta tcggcagcag   1320
```

```
gctgccgtcc cgttgtcctc tgaaagccat ggcggtgagg atgtggctgt tttcgctcgt   1380
ggaccacagg ctcatttggt gcacggcgtt caggaagaga ccttcgtcgc ccacgtgatg   1440
gcttttgcgg gttgcgttga gccctatact gactgtaact tgccagcccc ttcgggt     1497
```

<210> SEQ ID NO 103
<211> LENGTH: 1515
<212> TYPE: DNA
<213> ORGANISM: Artificial Sequence
<220> FEATURE:
<223> OTHER INFORMATION: AsAP3ss72_bIAPIV

<400> SEQUENCE: 103

```
atgcatatcc gcactgccat caccgcgggc gcggcccttg tccagactgc agttgcagct    60
tctgttcagg cattcatccc agctgaggaa gaggatcctg ctttctggaa ccgtcaggct   120
gctcaggctc ttgacgttgc caagaagttg cagccaatcc agaccgccgc taagaatgtc   180
atcctcttcc tggcgatgg tatgggagtc ccgaccgtga ctgctacccg catcctcaag   240
ggccagatga atggaaagct cggcccagaa accccgctgg ctatggacca gttcccttac   300
gtggccctgt cgaagactta taacgttgat cgtcaagtcc ctgactctgc tggtactgct   360
accgcctacc tttgcggtgt gaagggaaat tataagacca tcggcgtttc cgccgctgcc   420
cggtataacc agtgtaatac cacttctggt aacgaggtta ctagcgtcat gaatcgggct   480
aagaaggccg gcaagtctgt tggtgtcgtg accacttcgc gcgtccagca tgcttcccct   540
gctggagcct acgctcacac cgtcaaccgc aattggtata gcgatgctga cctgcccgcc   600
gatgctcaga cctacggctg ccaggacatc gccactcagc tcgtcaacaa tatggatatc   660
gacgtgatcc tgggaggcgg tcgtatgtat atgttccctg aaggtacccc tgatcccgag   720
tacccctatg acgtgaacca gactggagtt cggaaggaca agcgcaatct tgtgcaggaa   780
tggcaggcta agcatcaggg tgcccagtac gtttggaacc gcaccgagct cctgcaggct   840
gccaatgatc catcggtcac tcacctcatg ggactgttcg aaccggccga catgaagtat   900
aacgtgcagc aggatcctac taaggacccc acccttgaag agatgaccga ggctgccctt   960
caggttttgt cccggaatcc acagggcttc tacttgttcg tcgagggcgg ccgcatcgat  1020
catggacatc acgagggcaa ggcttatatg gccctcactg ataccgttat gttcgacaac  1080
gccatcgcta aggccaatga actcacttcg gagctggata cccttatctt ggctactgcc  1140
gaccattcgc acgtcttctc cttcggtgga tacactcttc gtggtacctc catcttcgga  1200
ttggctcctt ccaaggcctc tgacaacaag agctacacct cgatcctgta tggcaatggt  1260
cctggatacg tccttggcgg tggattgcgt cccgatgtga acgacagcat ctcggaggat  1320
ccatcttatc ggcagcaggc tgccgtcccg ttgtcctctg aaagccatgg cggtgaggat  1380
gtggctgttt cgctcgtgg accacaggct catttggtgc acggcgttca ggaagagacc  1440
ttcgtcgccc acgtgatggc ttttgcgggt tgcgttgagc cctatactga ctgtaacttg  1500
ccagcccctt cgggt                                                   1515
```

<210> SEQ ID NO 104
<211> LENGTH: 500
<212> TYPE: PRT
<213> ORGANISM: Artificial Sequence
<220> FEATURE:
<223> OTHER INFORMATION: bIAPIV

<400> SEQUENCE: 104

```
Met Gln Trp Ala Cys Val Leu Leu Leu Gly Leu Trp Leu Gln Leu
1               5                   10                  15

Ser Leu Thr Phe Ile Pro Ala Glu Glu Asp Pro Ala Phe Trp Asn
                20                  25                  30

Arg Gln Ala Ala Gln Ala Leu Asp Val Ala Lys Lys Leu Gln Pro Ile
            35                  40                  45

Gln Thr Ala Ala Lys Asn Val Ile Leu Phe Leu Gly Asp Gly Met Gly
        50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Lys Thr
        115                 120                 125

Ile Gly Val Ser Ala Ala Arg Tyr Asn Gln Cys Asn Thr Thr Ser
130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Thr Tyr Gly Cys Gln Asp Ile Ala Thr Gln
        195                 200                 205

Leu Val Asn Asn Met Asp Ile Asp Val Ile Leu Gly Gly Gly Arg Met
210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                245                 250                 255

Gln Ala Lys His Gln Gly Ala Gln Tyr Val Trp Asn Arg Thr Glu Leu
            260                 265                 270

Leu Gln Ala Ala Asn Asp Pro Ser Val Thr His Leu Met Gly Leu Phe
        275                 280                 285

Glu Pro Ala Asp Met Lys Tyr Asn Val Gln Gln Asp Pro Thr Lys Asp
        290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
                325                 330                 335

Gly His His Glu Gly Lys Ala Tyr Met Ala Leu Thr Asp Thr Val Met
            340                 345                 350

Phe Asp Asn Ala Ile Ala Lys Ala Asn Glu Leu Thr Ser Glu Leu Asp
        355                 360                 365

Thr Leu Ile Leu Ala Thr Ala Asp His Ser His Val Phe Ser Phe Gly
        370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
                405                 410                 415

Gly Tyr Val Leu Gly Gly Gly Leu Arg Pro Asp Val Asn Asp Ser Ile
```

```
            420                 425                 430
Ser Glu Asp Pro Ser Tyr Arg Gln Gln Ala Ala Val Pro Leu Ser Ser
            435                 440                 445

Glu Ser His Gly Gly Glu Asp Val Ala Val Phe Ala Arg Gly Pro Gln
    450                 455                 460

Ala His Leu Val His Gly Val Gln Glu Thr Phe Val Ala His Val
465                 470                 475                 480

Met Ala Phe Ala Gly Cys Val Glu Pro Tyr Thr Asp Cys Asn Leu Pro
                485                 490                 495

Ala Pro Ser Gly
            500

<210> SEQ ID NO 105
<211> LENGTH: 504
<212> TYPE: PRT
<213> ORGANISM: Artificial Sequence
<220> FEATURE:
<223> OTHER INFORMATION: CDHss_bAPIV

<400> SEQUENCE: 105

Met Lys Leu Val Asn Arg Leu Leu Ala Ser Phe Leu Ser Ala Ser Thr
1               5                   10                  15

Val Leu Gln Ser Cys Trp Ala Phe Ile Pro Ala Glu Glu Asp Pro
            20                  25                  30

Ala Phe Trp Asn Arg Gln Ala Ala Gln Ala Leu Asp Val Ala Lys Lys
        35                  40                  45

Leu Gln Pro Ile Gln Thr Ala Ala Lys Asn Val Ile Leu Phe Leu Gly
    50                  55                  60

Asp Gly Met Gly Val Pro Thr Val Thr Ala Thr Arg Ile Leu Lys Gly
65                  70                  75                  80

Gln Met Asn Gly Lys Leu Gly Pro Glu Thr Pro Leu Ala Met Asp Gln
                85                  90                  95

Phe Pro Tyr Val Ala Leu Ser Lys Thr Tyr Asn Val Asp Arg Gln Val
            100                 105                 110

Pro Asp Ser Ala Gly Thr Ala Thr Ala Tyr Leu Cys Gly Val Lys Gly
        115                 120                 125

Asn Tyr Lys Thr Ile Gly Val Ser Ala Ala Arg Tyr Asn Gln Cys
    130                 135                 140

Asn Thr Thr Ser Gly Asn Glu Val Thr Ser Val Met Asn Arg Ala Lys
145                 150                 155                 160

Lys Ala Gly Lys Ser Val Gly Val Val Thr Thr Ser Arg Val Gln His
                165                 170                 175

Ala Ser Pro Ala Gly Ala Tyr Ala His Thr Val Asn Arg Asn Trp Tyr
            180                 185                 190

Ser Asp Ala Asp Leu Pro Ala Asp Ala Gln Thr Tyr Gly Cys Gln Asp
        195                 200                 205

Ile Ala Thr Gln Leu Val Asn Asn Met Asp Ile Asp Val Ile Leu Gly
    210                 215                 220

Gly Gly Arg Met Tyr Met Phe Pro Glu Gly Thr Pro Asp Pro Glu Tyr
225                 230                 235                 240

Pro Tyr Asp Val Asn Gln Thr Gly Val Arg Lys Asp Lys Arg Asn Leu
                245                 250                 255

Val Gln Glu Trp Gln Ala Lys His Gln Gly Ala Gln Tyr Val Trp Asn
            260                 265                 270

Arg Thr Glu Leu Leu Gln Ala Ala Asn Asp Pro Ser Val Thr His Leu
```

-continued

```
                    275                 280                 285
Met Gly Leu Phe Glu Pro Ala Asp Met Lys Tyr Asn Val Gln Gln Asp
            290                 295                 300

Pro Thr Lys Asp Pro Thr Leu Glu Glu Met Thr Glu Ala Ala Leu Gln
305                 310                 315                 320

Val Leu Ser Arg Asn Pro Gln Gly Phe Tyr Leu Phe Val Glu Gly Gly
                    325                 330                 335

Arg Ile Asp His Gly His His Glu Gly Lys Ala Tyr Met Ala Leu Thr
                340                 345                 350

Asp Thr Val Met Phe Asp Asn Ala Ile Ala Lys Ala Asn Glu Leu Thr
                355                 360                 365

Ser Glu Leu Asp Thr Leu Ile Leu Ala Thr Ala Asp His Ser His Val
            370                 375                 380

Phe Ser Phe Gly Gly Tyr Thr Leu Arg Gly Thr Ser Ile Phe Gly Leu
385                 390                 395                 400

Ala Pro Ser Lys Ala Ser Asp Asn Lys Ser Tyr Thr Ser Ile Leu Tyr
                    405                 410                 415

Gly Asn Gly Pro Gly Tyr Val Leu Gly Gly Gly Leu Arg Pro Asp Val
                420                 425                 430

Asn Asp Ser Ile Ser Glu Asp Pro Ser Tyr Arg Gln Gln Ala Ala Val
            435                 440                 445

Pro Leu Ser Ser Glu Ser His Gly Gly Glu Asp Val Ala Val Phe Ala
450                 455                 460

Arg Gly Pro Gln Ala His Leu Val His Gly Val Gln Glu Glu Thr Phe
465                 470                 475                 480

Val Ala His Val Met Ala Phe Ala Gly Cys Val Glu Pro Tyr Thr Asp
                    485                 490                 495

Cys Asn Leu Pro Ala Pro Ser Gly
                500
```

<210> SEQ ID NO 106
<211> LENGTH: 739
<212> TYPE: PRT
<213> ORGANISM: Artificial Sequence
<220> FEATURE:
<223> OTHER INFORMATION: CDHcytbkex_bAPIV

<400> SEQUENCE: 106

```
Met Lys Leu Val Asn Arg Leu Leu Ala Ser Phe Leu Ser Ala Ser Thr
1               5                   10                  15

Val Leu Gln Ser Cys Trp Ala Gln Ser Gly Thr Pro Val Ala Tyr Thr
                20                  25                  30

Asp Thr Glu Thr Gly Ile Thr Phe Asp Thr Trp Ser Val Pro Ala Gly
            35                  40                  45

Thr Gly Thr Gly Gly Leu Val Phe Gly Val Ala Leu Pro Gly Ser Ala
        50                  55                  60

Leu Thr Thr Asp Ala Thr Glu Phe Ile Gly Tyr Leu Gln Cys Ala Ser
65                  70                  75                  80

Gln Asn Ala Ser Ser Ala Gly Trp Cys Gly Ile Ser Leu Gly Gly Gly
                    85                  90                  95

Met Asn Asn Asn Leu Leu Phe Leu Ala Tyr Pro Tyr Glu Asp Thr Ile
                100                 105                 110

Leu Thr Ser Leu Arg Phe Gly Ser Gly Tyr Ser Met Pro Gly Val Tyr
            115                 120                 125

Thr Gly Asn Ala Asn Val Thr Gln Ile Ser Ser Ser Ile Asn Ala Thr
```

```
            130                 135                 140
His Phe Thr Leu Leu Phe Arg Cys Glu Asn Cys Leu Thr Trp Asp Gln
145                 150                 155                 160

Asp Gly Gln Thr Gly Asn Ala Thr Thr Ser Lys Gly Arg Leu Val Leu
                165                 170                 175

Gly Trp Ala Gln Ser Thr Glu Ser Pro Ser Asn Pro Ser Cys Pro Asp
            180                 185                 190

Asn Ile Ser Leu Ala Gln His Asp Asn Gln Gly Ile Ile Ser Ala Thr
        195                 200                 205

Leu Asp Glu Asn Ala Ala Ser Glu Ser Tyr Glu Asp Trp Val Lys Leu
    210                 215                 220

Ala Asn Lys Thr Val Pro Gly Asp Cys Ser Gly Asp Gly Gly Gly
225                 230                 235                 240

Asn Glu Pro Thr Pro Val Pro Val Pro Asp Gly Gly Gly Gly Ser
                245                 250                 255

Lys Arg Phe Ile Pro Ala Glu Glu Asp Pro Ala Phe Trp Asn Arg
            260                 265                 270

Gln Ala Ala Gln Ala Leu Asp Val Ala Lys Lys Leu Gln Pro Ile Gln
        275                 280                 285

Thr Ala Ala Lys Asn Val Ile Leu Phe Leu Gly Asp Gly Met Gly Val
    290                 295                 300

Pro Thr Val Thr Ala Thr Arg Ile Leu Lys Gly Gln Met Asn Gly Lys
305                 310                 315                 320

Leu Gly Pro Glu Thr Pro Leu Ala Met Asp Gln Phe Pro Tyr Val Ala
                325                 330                 335

Leu Ser Lys Thr Tyr Asn Val Asp Arg Gln Val Pro Asp Ser Ala Gly
            340                 345                 350

Thr Ala Thr Ala Tyr Leu Cys Gly Val Lys Gly Asn Tyr Lys Thr Ile
        355                 360                 365

Gly Val Ser Ala Ala Arg Tyr Asn Gln Cys Asn Thr Thr Ser Gly
    370                 375                 380

Asn Glu Val Thr Ser Val Met Asn Arg Ala Lys Lys Ala Gly Lys Ser
385                 390                 395                 400

Val Gly Val Val Thr Thr Ser Arg Val Gln His Ala Ser Pro Ala Gly
                405                 410                 415

Ala Tyr Ala His Thr Val Asn Arg Asn Trp Tyr Ser Asp Ala Asp Leu
            420                 425                 430

Pro Ala Asp Ala Gln Thr Tyr Gly Cys Gln Asp Ile Ala Thr Gln Leu
        435                 440                 445

Val Asn Asn Met Asp Ile Asp Val Ile Leu Gly Gly Gly Arg Met Tyr
    450                 455                 460

Met Phe Pro Glu Gly Thr Pro Asp Pro Glu Tyr Pro Tyr Asp Val Asn
465                 470                 475                 480

Gln Thr Gly Val Arg Lys Asp Lys Arg Asn Leu Val Gln Glu Trp Gln
                485                 490                 495

Ala Lys His Gln Gly Ala Gln Tyr Val Trp Asn Arg Thr Glu Leu Leu
            500                 505                 510

Gln Ala Ala Asn Asp Pro Ser Val Thr His Leu Met Gly Leu Phe Glu
        515                 520                 525

Pro Ala Asp Met Lys Tyr Asn Val Gln Gln Asp Pro Thr Lys Asp Pro
    530                 535                 540

Thr Leu Glu Glu Met Thr Glu Ala Ala Leu Gln Val Leu Ser Arg Asn
545                 550                 555                 560
```

```
Pro Gln Gly Phe Tyr Leu Phe Val Glu Gly Arg Ile Asp His Gly
                565                 570                 575

His His Glu Gly Lys Ala Tyr Met Ala Leu Thr Asp Thr Val Met Phe
            580                 585                 590

Asp Asn Ala Ile Ala Lys Ala Asn Glu Leu Thr Ser Glu Leu Asp Thr
                595                 600                 605

Leu Ile Leu Ala Thr Ala Asp His Ser His Val Phe Ser Phe Gly Gly
    610                 615                 620

Tyr Thr Leu Arg Gly Thr Ser Ile Phe Gly Leu Ala Pro Ser Lys Ala
625                 630                 635                 640

Ser Asp Asn Lys Ser Tyr Thr Ser Ile Leu Tyr Gly Asn Gly Pro Gly
                645                 650                 655

Tyr Val Leu Gly Gly Gly Leu Arg Pro Asp Val Asn Asp Ser Ile Ser
                660                 665                 670

Glu Asp Pro Ser Tyr Arg Gln Gln Ala Ala Val Pro Leu Ser Ser Glu
                675                 680                 685

Ser His Gly Gly Glu Asp Val Ala Val Phe Ala Arg Gly Pro Gln Ala
    690                 695                 700

His Leu Val His Gly Val Gln Glu Glu Thr Phe Val Ala His Val Met
705                 710                 715                 720

Ala Phe Ala Gly Cys Val Glu Pro Tyr Thr Asp Cys Asn Leu Pro Ala
                725                 730                 735

Pro Ser Gly

<210> SEQ ID NO 107
<211> LENGTH: 739
<212> TYPE: PRT
<213> ORGANISM: Artificial Sequence
<220> FEATURE:
<223> OTHER INFORMATION: CDHcytbKexmut1_bAPIV

<400> SEQUENCE: 107

Met Lys Leu Val Asn Arg Leu Leu Ala Ser Phe Leu Ser Ala Ser Thr
1               5                   10                  15

Val Leu Gln Ser Cys Trp Ala Gln Ser Gly Thr Pro Val Ala Tyr Thr
                20                  25                  30

Asp Thr Glu Thr Gly Ile Thr Phe Asp Thr Trp Ser Val Pro Ala Gly
            35                  40                  45

Thr Gly Thr Gly Gly Leu Val Phe Gly Val Ala Leu Pro Gly Ser Ala
    50                  55                  60

Leu Thr Thr Asp Ala Thr Glu Phe Ile Gly Tyr Leu Gln Cys Ala Ser
65                  70                  75                  80

Gln Asn Ala Ser Ser Ala Gly Trp Cys Gly Ile Ser Leu Gly Gly Gly
                85                  90                  95

Met Asn Asn Asn Leu Leu Phe Leu Ala Tyr Pro Tyr Glu Asp Thr Ile
                100                 105                 110

Leu Thr Ser Leu Arg Phe Gly Ser Gly Tyr Ser Met Pro Gly Val Tyr
            115                 120                 125

Thr Gly Asn Ala Asn Val Thr Gln Ile Ser Ser Ile Asn Ala Thr
    130                 135                 140

His Phe Thr Leu Leu Phe Arg Cys Glu Asn Cys Leu Thr Trp Asp Gln
145                 150                 155                 160

Asp Gly Gln Thr Gly Asn Ala Thr Thr Ser Lys Gly Arg Leu Val Leu
                165                 170                 175
```

-continued

Gly Trp Ala Gln Ser Thr Glu Ser Pro Ser Asn Pro Ser Cys Pro Asp
            180                 185                 190

Asn Ile Ser Leu Ala Gln His Asp Asn Gln Gly Ile Ile Ser Ala Thr
        195                 200                 205

Leu Asp Glu Asn Ala Ala Ser Glu Ser Tyr Glu Asp Trp Val Lys Leu
    210                 215                 220

Ala Asn Lys Thr Val Pro Gly Asp Cys Ser Gly Asp Gly Gly Gly
225                 230                 235                 240

Asn Glu Pro Thr Pro Val Pro Val Pro Asp Gly Gly Gly Arg His
                245                 250                 255

Lys Arg Phe Ile Pro Ala Glu Glu Asp Pro Ala Phe Trp Asn Arg
            260                 265                 270

Gln Ala Ala Gln Ala Leu Asp Val Ala Lys Lys Leu Gln Pro Ile Gln
            275                 280                 285

Thr Ala Ala Lys Asn Val Ile Leu Phe Leu Gly Asp Gly Met Gly Val
        290                 295                 300

Pro Thr Val Thr Ala Thr Arg Ile Leu Lys Gly Gln Met Asn Gly Lys
305                 310                 315                 320

Leu Gly Pro Glu Thr Pro Leu Ala Met Asp Gln Phe Pro Tyr Val Ala
            325                 330                 335

Leu Ser Lys Thr Tyr Asn Val Asp Arg Gln Val Pro Asp Ser Ala Gly
            340                 345                 350

Thr Ala Thr Ala Tyr Leu Cys Gly Val Lys Gly Asn Tyr Lys Thr Ile
            355                 360                 365

Gly Val Ser Ala Ala Arg Tyr Asn Gln Cys Asn Thr Thr Ser Gly
    370                 375                 380

Asn Glu Val Thr Ser Val Met Asn Arg Ala Lys Lys Ala Gly Lys Ser
385                 390                 395                 400

Val Gly Val Val Thr Thr Ser Arg Val Gln His Ala Ser Pro Ala Gly
                405                 410                 415

Ala Tyr Ala His Thr Val Asn Arg Asn Trp Tyr Ser Asp Ala Asp Leu
            420                 425                 430

Pro Ala Asp Ala Gln Thr Tyr Gly Cys Gln Asp Ile Ala Thr Gln Leu
            435                 440                 445

Val Asn Asn Met Asp Ile Asp Val Ile Leu Gly Gly Gly Arg Met Tyr
    450                 455                 460

Met Phe Pro Glu Gly Thr Pro Asp Pro Glu Tyr Pro Tyr Asp Val Asn
465                 470                 475                 480

Gln Thr Gly Val Arg Lys Asp Lys Arg Asn Leu Val Gln Glu Trp Gln
                485                 490                 495

Ala Lys His Gln Gly Ala Gln Tyr Val Trp Asn Arg Thr Glu Leu Leu
            500                 505                 510

Gln Ala Ala Asn Asp Pro Ser Val Thr His Leu Met Gly Leu Phe Glu
        515                 520                 525

Pro Ala Asp Met Lys Tyr Asn Val Gln Gln Asp Pro Thr Lys Asp Pro
    530                 535                 540

Thr Leu Glu Glu Met Thr Glu Ala Ala Leu Gln Val Leu Ser Arg Asn
545                 550                 555                 560

Pro Gln Gly Phe Tyr Leu Phe Val Glu Gly Gly Arg Ile Asp His Gly
                565                 570                 575

His His Glu Gly Lys Ala Tyr Met Ala Leu Thr Asp Thr Val Met Phe
            580                 585                 590

Asp Asn Ala Ile Ala Lys Ala Asn Glu Leu Thr Ser Glu Leu Asp Thr

```
                595                 600                 605
Leu Ile Leu Ala Thr Ala Asp His Ser His Val Phe Ser Phe Gly Gly
        610                 615                 620

Tyr Thr Leu Arg Gly Thr Ser Ile Phe Gly Leu Ala Pro Ser Lys Ala
625                 630                 635                 640

Ser Asp Asn Lys Ser Tyr Thr Ser Ile Leu Tyr Gly Asn Gly Pro Gly
                645                 650                 655

Tyr Val Leu Gly Gly Leu Arg Pro Asp Val Asn Asp Ser Ile Ser
        660                 665                 670

Glu Asp Pro Ser Tyr Arg Gln Gln Ala Ala Val Pro Leu Ser Ser Glu
                675                 680                 685

Ser His Gly Gly Glu Asp Val Ala Val Phe Ala Arg Gly Pro Gln Ala
        690                 695                 700

His Leu Val His Gly Val Gln Glu Glu Thr Phe Val Ala His Val Met
705                 710                 715                 720

Ala Phe Ala Gly Cys Val Glu Pro Tyr Thr Asp Cys Asn Leu Pro Ala
                725                 730                 735

Pro Ser Gly

<210> SEQ ID NO 108
<211> LENGTH: 739
<212> TYPE: PRT
<213> ORGANISM: Artificial Sequence
<220> FEATURE:
<223> OTHER INFORMATION: CDHcytbKexmut2_bAPIV

<400> SEQUENCE: 108

Met Lys Leu Val Asn Arg Leu Leu Ala Ser Phe Leu Ser Ala Ser Thr
1               5                   10                  15

Val Leu Gln Ser Cys Trp Ala Gln Ser Gly Thr Pro Val Ala Tyr Thr
            20                  25                  30

Asp Thr Glu Thr Gly Ile Thr Phe Asp Thr Trp Ser Val Pro Ala Gly
        35                  40                  45

Thr Gly Thr Gly Gly Leu Val Phe Gly Val Ala Leu Pro Gly Ser Ala
    50                  55                  60

Leu Thr Thr Asp Ala Thr Glu Phe Ile Gly Tyr Leu Gln Cys Ala Ser
65                  70                  75                  80

Gln Asn Ala Ser Ser Ala Gly Trp Cys Gly Ile Ser Leu Gly Gly Gly
                85                  90                  95

Met Asn Asn Asn Leu Leu Phe Leu Ala Tyr Pro Tyr Glu Asp Thr Ile
            100                 105                 110

Leu Thr Ser Leu Arg Phe Gly Ser Gly Tyr Ser Met Pro Gly Val Tyr
        115                 120                 125

Thr Gly Asn Ala Asn Val Thr Gln Ile Ser Ser Ser Ile Asn Ala Thr
    130                 135                 140

His Phe Thr Leu Leu Phe Arg Cys Glu Asn Cys Leu Thr Trp Asp Gln
145                 150                 155                 160

Asp Gly Gln Thr Gly Asn Ala Thr Thr Ser Lys Gly Arg Leu Val Leu
                165                 170                 175

Gly Trp Ala Gln Ser Thr Glu Ser Pro Ser Asn Pro Ser Cys Pro Asp
            180                 185                 190

Asn Ile Ser Leu Ala Gln His Asp Asn Gln Gly Ile Ile Ser Ala Thr
        195                 200                 205

Leu Asp Glu Asn Ala Ala Ser Glu Ser Tyr Glu Asp Trp Val Lys Leu
    210                 215                 220
```

```
Ala Asn Lys Thr Val Pro Gly Asp Cys Ser Gly Asp Gly Gly Gly
225                 230                 235                 240

Asn Glu Pro Thr Pro Val Pro Val Pro Asp Gly Gly Gly Pro His
            245                 250                 255

Lys Arg Phe Ile Pro Ala Glu Glu Asp Pro Ala Phe Trp Asn Arg
            260                 265                 270

Gln Ala Ala Gln Ala Leu Asp Val Ala Lys Lys Leu Gln Pro Ile Gln
        275                 280                 285

Thr Ala Ala Lys Asn Val Ile Leu Phe Leu Gly Asp Gly Met Gly Val
        290                 295                 300

Pro Thr Val Thr Ala Thr Arg Ile Leu Lys Gly Gln Met Asn Gly Lys
305                 310                 315                 320

Leu Gly Pro Glu Thr Pro Leu Ala Met Asp Gln Phe Pro Tyr Val Ala
                325                 330                 335

Leu Ser Lys Thr Tyr Asn Val Asp Arg Gln Val Pro Asp Ser Ala Gly
            340                 345                 350

Thr Ala Thr Ala Tyr Leu Cys Gly Val Lys Gly Asn Tyr Lys Thr Ile
            355                 360                 365

Gly Val Ser Ala Ala Ala Arg Tyr Asn Gln Cys Asn Thr Thr Ser Gly
370                 375                 380

Asn Glu Val Thr Ser Val Met Asn Arg Ala Lys Lys Ala Gly Lys Ser
385                 390                 395                 400

Val Gly Val Val Thr Thr Ser Arg Val Gln His Ala Ser Pro Ala Gly
                405                 410                 415

Ala Tyr Ala His Thr Val Asn Arg Asn Trp Tyr Ser Asp Ala Asp Leu
                420                 425                 430

Pro Ala Asp Ala Gln Thr Tyr Gly Cys Gln Asp Ile Ala Thr Gln Leu
            435                 440                 445

Val Asn Asn Met Asp Ile Asp Val Ile Leu Gly Gly Gly Arg Met Tyr
450                 455                 460

Met Phe Pro Glu Gly Thr Pro Asp Pro Glu Tyr Pro Tyr Asp Val Asn
465                 470                 475                 480

Gln Thr Gly Val Arg Lys Asp Lys Arg Asn Leu Val Gln Glu Trp Gln
                485                 490                 495

Ala Lys His Gln Gly Ala Gln Tyr Val Trp Asn Arg Thr Glu Leu Leu
            500                 505                 510

Gln Ala Ala Asn Asp Pro Ser Val Thr His Leu Met Gly Leu Phe Glu
            515                 520                 525

Pro Ala Asp Met Lys Tyr Asn Val Gln Gln Asp Pro Thr Lys Asp Pro
            530                 535                 540

Thr Leu Glu Glu Met Thr Glu Ala Ala Leu Gln Val Leu Ser Arg Asn
545                 550                 555                 560

Pro Gln Gly Phe Tyr Leu Phe Val Glu Gly Gly Arg Ile Asp His Gly
                565                 570                 575

His His Glu Gly Lys Ala Tyr Met Ala Leu Thr Asp Thr Val Met Phe
            580                 585                 590

Asp Asn Ala Ile Ala Lys Ala Asn Glu Leu Thr Ser Glu Leu Asp Thr
            595                 600                 605

Leu Ile Leu Ala Thr Ala Asp His Ser His Val Phe Ser Phe Gly Gly
            610                 615                 620

Tyr Thr Leu Arg Gly Thr Ser Ile Phe Gly Leu Ala Pro Ser Lys Ala
625                 630                 635                 640
```

-continued

```
Ser Asp Asn Lys Ser Tyr Thr Ser Ile Leu Tyr Gly Asn Gly Pro Gly
            645                 650                 655

Tyr Val Leu Gly Gly Leu Arg Pro Asp Val Asn Asp Ser Ile Ser
        660                 665                 670

Glu Asp Pro Ser Tyr Arg Gln Gln Ala Ala Val Pro Leu Ser Ser Glu
        675                 680                 685

Ser His Gly Gly Glu Asp Val Ala Val Phe Ala Arg Gly Pro Gln Ala
        690                 695                 700

His Leu Val His Gly Val Gln Glu Glu Thr Phe Val Ala His Val Met
705                 710                 715                 720

Ala Phe Ala Gly Cys Val Glu Pro Tyr Thr Asp Cys Asn Leu Pro Ala
                725                 730                 735

Pro Ser Gly

<210> SEQ ID NO 109
<211> LENGTH: 741
<212> TYPE: PRT
<213> ORGANISM: Artificial Sequence
<220> FEATURE:
<223> OTHER INFORMATION: CDHcytbKexmut3_bAPIV

<400> SEQUENCE: 109

Met Lys Leu Val Asn Arg Leu Leu Ala Ser Phe Leu Ser Ala Ser Thr
1               5                   10                  15

Val Leu Gln Ser Cys Trp Ala Gln Ser Gly Thr Pro Val Ala Tyr Thr
            20                  25                  30

Asp Thr Glu Thr Gly Ile Thr Phe Asp Thr Trp Ser Val Pro Ala Gly
        35                  40                  45

Thr Gly Thr Gly Gly Leu Val Phe Gly Val Ala Leu Pro Gly Ser Ala
    50                  55                  60

Leu Thr Thr Asp Ala Thr Glu Phe Ile Gly Tyr Leu Gln Cys Ala Ser
65              70                  75                  80

Gln Asn Ala Ser Ser Ala Gly Trp Cys Gly Ile Ser Leu Gly Gly Gly
                85                  90                  95

Met Asn Asn Asn Leu Leu Phe Leu Ala Tyr Pro Tyr Glu Asp Thr Ile
            100                 105                 110

Leu Thr Ser Leu Arg Phe Gly Ser Gly Tyr Ser Met Pro Gly Val Tyr
        115                 120                 125

Thr Gly Asn Ala Asn Val Thr Gln Ile Ser Ser Ser Ile Asn Ala Thr
    130                 135                 140

His Phe Thr Leu Leu Phe Arg Cys Glu Asn Cys Leu Thr Trp Asp Gln
145                 150                 155                 160

Asp Gly Gln Thr Gly Asn Ala Thr Thr Ser Lys Gly Arg Leu Val Leu
                165                 170                 175

Gly Trp Ala Gln Ser Thr Glu Ser Pro Ser Asn Pro Ser Cys Pro Asp
            180                 185                 190

Asn Ile Ser Leu Ala Gln His Asp Asn Gln Gly Ile Ile Ser Ala Thr
        195                 200                 205

Leu Asp Glu Asn Ala Ala Ser Glu Ser Tyr Glu Asp Trp Val Lys Leu
    210                 215                 220

Ala Asn Lys Thr Val Pro Gly Asp Cys Ser Gly Asp Gly Gly Gly Gly
225                 230                 235                 240

Asn Glu Pro Thr Pro Val Pro Val Pro Asp Gly Gly Gly Gly Gln Arg
                245                 250                 255

Leu Val Lys Arg Phe Ile Pro Ala Glu Glu Glu Asp Pro Ala Phe Trp
```

```
                260                 265                 270
        Asn Arg Gln Ala Ala Gln Ala Leu Asp Val Ala Lys Lys Leu Gln Pro
                    275                 280                 285

Ile Gln Thr Ala Ala Lys Asn Val Ile Leu Phe Leu Gly Asp Gly Met
                290                 295                 300

Gly Val Pro Thr Val Thr Ala Thr Arg Ile Leu Lys Gly Gln Met Asn
        305                 310                 315                 320

Gly Lys Leu Gly Pro Glu Thr Pro Leu Ala Met Asp Gln Phe Pro Tyr
                        325                 330                 335

Val Ala Leu Ser Lys Thr Tyr Asn Val Asp Arg Gln Val Pro Asp Ser
                    340                 345                 350

Ala Gly Thr Ala Thr Ala Tyr Leu Cys Gly Val Lys Gly Asn Tyr Lys
                355                 360                 365

Thr Ile Gly Val Ser Ala Ala Arg Tyr Asn Gln Cys Asn Thr Thr
            370                 375                 380

Ser Gly Asn Glu Val Thr Ser Val Met Asn Arg Ala Lys Lys Ala Gly
        385                 390                 395                 400

Lys Ser Val Gly Val Val Thr Thr Ser Arg Val Gln His Ala Ser Pro
                        405                 410                 415

Ala Gly Ala Tyr Ala His Thr Val Asn Arg Asn Trp Tyr Ser Asp Ala
                    420                 425                 430

Asp Leu Pro Ala Asp Ala Gln Thr Tyr Gly Cys Gln Asp Ile Ala Thr
                435                 440                 445

Gln Leu Val Asn Asn Met Asp Ile Asp Val Ile Leu Gly Gly Gly Arg
            450                 455                 460

Met Tyr Met Phe Pro Glu Gly Thr Pro Asp Pro Glu Tyr Pro Tyr Asp
        465                 470                 475                 480

Val Asn Gln Thr Gly Val Arg Lys Asp Lys Arg Asn Leu Val Gln Glu
                        485                 490                 495

Trp Gln Ala Lys His Gln Gly Ala Gln Tyr Val Trp Asn Arg Thr Glu
                    500                 505                 510

Leu Leu Gln Ala Ala Asn Asp Pro Ser Val Thr His Leu Met Gly Leu
                515                 520                 525

Phe Glu Pro Ala Asp Met Lys Tyr Asn Val Gln Gln Asp Pro Thr Lys
            530                 535                 540

Asp Pro Thr Leu Glu Glu Met Thr Glu Ala Ala Leu Gln Val Leu Ser
        545                 550                 555                 560

Arg Asn Pro Gln Gly Phe Tyr Leu Phe Val Glu Gly Gly Arg Ile Asp
                        565                 570                 575

His Gly His His Glu Gly Lys Ala Tyr Met Ala Leu Thr Asp Thr Val
                    580                 585                 590

Met Phe Asp Asn Ala Ile Ala Lys Ala Asn Glu Leu Thr Ser Glu Leu
                595                 600                 605

Asp Thr Leu Ile Leu Ala Thr Ala Asp His Ser His Val Phe Ser Phe
            610                 615                 620

Gly Gly Tyr Thr Leu Arg Gly Thr Ser Ile Phe Gly Leu Ala Pro Ser
        625                 630                 635                 640

Lys Ala Ser Asp Asn Lys Ser Tyr Thr Ser Ile Leu Tyr Gly Asn Gly
                        645                 650                 655

Pro Gly Tyr Val Leu Gly Gly Leu Arg Pro Asp Val Asn Asp Ser
                    660                 665                 670

Ile Ser Glu Asp Pro Ser Tyr Arg Gln Gln Ala Ala Val Pro Leu Ser
                675                 680                 685
```

```
Ser Glu Ser His Gly Gly Glu Asp Val Ala Val Phe Ala Arg Gly Pro
    690                 695                 700

Gln Ala His Leu Val His Gly Val Gln Glu Thr Phe Val Ala His
705             710                 715                 720

Val Met Ala Phe Ala Gly Cys Val Glu Pro Tyr Thr Asp Cys Asn Leu
                725                 730                 735

Pro Ala Pro Ser Gly
            740

<210> SEQ ID NO 110
<211> LENGTH: 741
<212> TYPE: PRT
<213> ORGANISM: Artificial Sequence
<220> FEATURE:
<223> OTHER INFORMATION: CDHcytbKexmut4_bAPIV

<400> SEQUENCE: 110

Met Lys Leu Val Asn Arg Leu Leu Ala Ser Phe Leu Ser Ala Ser Thr
1               5                   10                  15

Val Leu Gln Ser Cys Trp Ala Gln Ser Gly Thr Pro Val Ala Tyr Thr
            20                  25                  30

Asp Thr Glu Thr Gly Ile Thr Phe Asp Thr Trp Ser Val Pro Ala Gly
        35                  40                  45

Thr Gly Thr Gly Gly Leu Val Phe Gly Val Ala Leu Pro Gly Ser Ala
    50                  55                  60

Leu Thr Thr Asp Ala Thr Glu Phe Ile Gly Tyr Leu Gln Cys Ala Ser
65              70                  75                  80

Gln Asn Ala Ser Ser Ala Gly Trp Cys Gly Ile Ser Leu Gly Gly Gly
                85                  90                  95

Met Asn Asn Asn Leu Leu Phe Leu Ala Tyr Pro Tyr Glu Asp Thr Ile
            100                 105                 110

Leu Thr Ser Leu Arg Phe Gly Ser Gly Tyr Ser Met Pro Gly Val Tyr
        115                 120                 125

Thr Gly Asn Ala Asn Val Thr Gln Ile Ser Ser Ile Asn Ala Thr
    130                 135                 140

His Phe Thr Leu Leu Phe Arg Cys Glu Asn Cys Leu Thr Trp Asp Gln
145             150                 155                 160

Asp Gly Gln Thr Gly Asn Ala Thr Thr Ser Lys Gly Arg Leu Val Leu
                165                 170                 175

Gly Trp Ala Gln Ser Thr Glu Ser Pro Ser Asn Pro Ser Cys Pro Asp
            180                 185                 190

Asn Ile Ser Leu Ala Gln His Asp Asn Gln Gly Ile Ile Ser Ala Thr
        195                 200                 205

Leu Asp Glu Asn Ala Ala Ser Glu Ser Tyr Glu Asp Trp Val Lys Leu
    210                 215                 220

Ala Asn Lys Thr Val Pro Gly Asp Cys Ser Gly Asp Gly Gly Gly
225             230                 235                 240

Asn Glu Pro Thr Pro Val Pro Val Pro Asp Gly Gly Gly Val Ala
                245                 250                 255

Val Glu Lys Arg Phe Ile Pro Ala Glu Glu Asp Pro Ala Phe Trp
            260                 265                 270

Asn Arg Gln Ala Ala Gln Ala Leu Asp Val Ala Lys Lys Leu Gln Pro
        275                 280                 285

Ile Gln Thr Ala Ala Lys Asn Val Ile Leu Phe Leu Gly Asp Gly Met
    290                 295                 300
```

-continued

```
Gly Val Pro Thr Val Thr Ala Thr Arg Ile Leu Lys Gly Gln Met Asn
305                 310                 315                 320
Gly Lys Leu Gly Pro Glu Thr Pro Leu Ala Met Asp Gln Phe Pro Tyr
                325                 330                 335
Val Ala Leu Ser Lys Thr Tyr Asn Val Asp Arg Gln Val Pro Asp Ser
            340                 345                 350
Ala Gly Thr Ala Thr Ala Tyr Leu Cys Gly Val Lys Gly Asn Tyr Lys
        355                 360                 365
Thr Ile Gly Val Ser Ala Ala Arg Tyr Asn Gln Cys Asn Thr Thr
370                 375                 380
Ser Gly Asn Glu Val Thr Ser Val Met Asn Arg Ala Lys Lys Ala Gly
385                 390                 395                 400
Lys Ser Val Gly Val Thr Thr Ser Arg Val Gln His Ala Ser Pro
                405                 410                 415
Ala Gly Ala Tyr Ala His Thr Val Asn Arg Asn Trp Tyr Ser Asp Ala
            420                 425                 430
Asp Leu Pro Ala Asp Ala Gln Thr Tyr Gly Cys Gln Asp Ile Ala Thr
        435                 440                 445
Gln Leu Val Asn Asn Met Asp Ile Asp Val Ile Leu Gly Gly Arg
450                 455                 460
Met Tyr Met Phe Pro Glu Gly Thr Pro Asp Pro Glu Tyr Pro Tyr Asp
465                 470                 475                 480
Val Asn Gln Thr Gly Val Arg Lys Asp Lys Arg Asn Leu Val Gln Glu
                485                 490                 495
Trp Gln Ala Lys His Gln Gly Ala Gln Tyr Val Trp Asn Arg Thr Glu
            500                 505                 510
Leu Leu Gln Ala Ala Asn Asp Pro Ser Val Thr His Leu Met Gly Leu
        515                 520                 525
Phe Glu Pro Ala Asp Met Lys Tyr Asn Val Gln Gln Asp Pro Thr Lys
        530                 535                 540
Asp Pro Thr Leu Glu Glu Met Thr Glu Ala Ala Leu Gln Val Leu Ser
545                 550                 555                 560
Arg Asn Pro Gln Gly Phe Tyr Leu Phe Val Glu Gly Gly Arg Ile Asp
                565                 570                 575
His Gly His His Glu Gly Lys Ala Tyr Met Ala Leu Thr Asp Thr Val
            580                 585                 590
Met Phe Asp Asn Ala Ile Ala Lys Ala Asn Glu Leu Thr Ser Glu Leu
        595                 600                 605
Asp Thr Leu Ile Leu Ala Thr Ala Asp His Ser His Val Phe Ser Phe
610                 615                 620
Gly Gly Tyr Thr Leu Arg Gly Thr Ser Ile Phe Gly Leu Ala Pro Ser
625                 630                 635                 640
Lys Ala Ser Asp Asn Lys Ser Tyr Thr Ser Ile Leu Tyr Gly Asn Gly
                645                 650                 655
Pro Gly Tyr Val Leu Gly Gly Leu Arg Pro Asp Val Asn Asp Ser
            660                 665                 670
Ile Ser Glu Asp Pro Ser Tyr Arg Gln Gln Ala Ala Val Pro Leu Ser
        675                 680                 685
Ser Glu Ser His Gly Gly Glu Asp Val Ala Val Phe Ala Arg Gly Pro
        690                 695                 700
Gln Ala His Leu Val His Gly Val Gln Glu Glu Thr Phe Val Ala His
705                 710                 715                 720
```

```
Val Met Ala Phe Ala Gly Cys Val Glu Pro Tyr Thr Asp Cys Asn Leu
                725                 730                 735
Pro Ala Pro Ser Gly
            740

<210> SEQ ID NO 111
<211> LENGTH: 1277
<212> TYPE: PRT
<213> ORGANISM: Artificial Sequence
<220> FEATURE:
<223> OTHER INFORMATION: CDHall_bIAPIV

<400> SEQUENCE: 111

Met Lys Leu Val Asn Arg Leu Leu Ala Ser Phe Leu Ala Ser Thr
1               5                   10                  15

Val Leu Gln Ser Cys Trp Ala Gln Ser Gly Thr Pro Val Ala Tyr Thr
                20                  25                  30

Asp Thr Glu Thr Gly Ile Thr Phe Asp Thr Trp Ser Val Pro Ala Gly
                35                  40                  45

Thr Gly Thr Gly Gly Leu Val Phe Gly Val Ala Leu Pro Gly Ser Ala
            50                  55                  60

Leu Thr Thr Asp Ala Thr Glu Phe Ile Gly Tyr Leu Gln Cys Ala Ser
65                  70                  75                  80

Gln Asn Ala Ser Ser Ala Gly Trp Cys Gly Ile Ser Leu Gly Gly
                85                  90                  95

Met Asn Asn Asn Leu Leu Phe Leu Ala Tyr Pro Tyr Glu Asp Thr Ile
                100                 105                 110

Leu Thr Ser Leu Arg Phe Gly Ser Gly Tyr Ser Met Pro Gly Val Tyr
                115                 120                 125

Thr Gly Asn Ala Asn Val Thr Gln Ile Ser Ser Ile Asn Ala Thr
            130                 135                 140

His Phe Thr Leu Leu Phe Arg Cys Glu Asn Cys Leu Thr Trp Asp Gln
145                 150                 155                 160

Asp Gly Gln Thr Gly Asn Ala Thr Thr Ser Lys Gly Arg Leu Val Leu
                165                 170                 175

Gly Trp Ala Gln Ser Thr Glu Ser Pro Ser Asn Pro Ser Cys Pro Asp
                180                 185                 190

Asn Ile Ser Leu Ala Gln His Asp Asn Gln Gly Ile Ile Ser Ala Thr
                195                 200                 205

Leu Asp Glu Asn Ala Ala Ser Glu Ser Tyr Glu Asp Trp Val Lys Leu
            210                 215                 220

Ala Asn Lys Thr Val Pro Gly Asp Cys Ser Gly Asp Gly Gly Gly
225                 230                 235                 240

Asn Glu Pro Thr Pro Val Pro Val Pro Asp Gly Ala Thr Tyr Asp Tyr
                245                 250                 255

Ile Val Val Gly Gly Gly Ala Gly Gly Ile Pro Val Ala Asp Arg Leu
                260                 265                 270

Ser Glu Ala Gly His Ser Val Leu Leu Ile Glu Lys Gly Pro Pro Ser
                275                 280                 285

Ser Gly Arg Trp Gly Gly Thr Met Lys Pro Ser Trp Leu Asp Asp Thr
            290                 295                 300

Asn Leu Thr Arg Phe Asp Val Pro Gly Leu Cys Asn Gln Ile Trp Val
305                 310                 315                 320

Asp Ser Asn Gly Ile Ala Cys Ser Asp Thr Asp Gln Met Ala Gly Cys
                325                 330                 335
```

```
Val Leu Gly Gly Gly Thr Ala Val Asn Ala Gly Leu Trp Trp Lys Pro
                340                 345                 350

Asn Pro Val Asp Trp Asp Tyr Asn Phe Pro Glu Gly Trp Gln Ser Ser
            355                 360                 365

Asp Met Gln Ala Ala Ala Asp Arg Val Phe Ser Arg Ile Pro Gly Thr
    370                 375                 380

Thr Thr Pro Ser Thr Asp Gly Lys Leu Tyr Tyr Gln Gln Gly Ala Asp
385                 390                 395                 400

Ile Leu Leu Asn Gly Leu Gln Ser Ala Gly Trp Ser Ser Val Thr Leu
                405                 410                 415

Asn Asp Val Pro Ala Gln Lys Thr Lys Thr Phe Gly His Ala Pro Phe
            420                 425                 430

Met Phe Ser Gly Gly Glu Arg Gly Gly Pro Met Gly Thr Tyr Leu Val
    435                 440                 445

Ser Ala Ser Glu Arg Asp Asn Phe Ala Arg Trp Ser Asn Thr Thr Val
        450                 455                 460

Lys Arg Val Val Arg Glu Gly Gly Arg Ile Thr Gly Val Glu Val Glu
465                 470                 475                 480

Ala Thr Leu Asp Gly Gly Tyr Ala Gly Thr Val Asn Val Thr Ala Asn
                485                 490                 495

Thr Gly Arg Val Ile Leu Ser Ala Gly Thr Phe Gly Thr Pro Lys Val
            500                 505                 510

Leu Met Arg Ser Gly Ile Gly Pro Lys Asp Gln Leu Ser Ile Val Lys
    515                 520                 525

Ser Ser Thr Asp Gly Glu Thr Met Ile Ala Glu Ser Glu Trp Ile Glu
530                 535                 540

Leu Pro Val Gly Glu Asn Leu Val Asp His Val Asn Thr Asp Val Val
545                 550                 555                 560

Val Thr His Pro Asp Val Val Phe Tyr Asp Phe Lys Ala Ala Tyr Lys
                565                 570                 575

Thr Pro Ile Glu Ser Asp Ala Thr Ser Tyr Leu Asn Asp Arg Thr Gly
            580                 585                 590

Ile Phe Ala Gln Ala Ala Pro Asn Ile Gly Pro Ile Ile Phe Asp Glu
    595                 600                 605

Val Thr Gly Ser Asp Gly Ile Lys Arg Gln Ile Gln Trp Thr Ala Arg
    610                 615                 620

Val Glu Gly Gly His Asp Thr Pro Asp Gly His Ala Met Thr Ile Ser
625                 630                 635                 640

Gln Tyr Leu Gly Arg Gly Ser Thr Ser Arg Gly Arg Met Thr Ile Thr
                645                 650                 655

Ala Gly Leu Asp Thr Val Val Ser Thr Leu Pro Phe Leu Arg Asp Glu
            660                 665                 670

Ser Asp Val Asn Ala Val Ile Gln Gly Ile Gln Asn Leu Lys Met Ala
    675                 680                 685

Leu Asn Gly Thr Gly Phe Thr Trp Asn Tyr Pro Ala Arg Asn Thr Ser
    690                 695                 700

Ile Ala Glu Phe Val Asn Thr Met Pro Ile Thr Ala Gly Thr Arg Arg
705                 710                 715                 720

Ala Asn His Trp Met Gly Thr Cys Lys Ile Gly Thr Asp Asp Gly Arg
                725                 730                 735

Thr Gly Gly Ser Ala Val Val Asp Leu Asn Thr Lys Val Tyr Gly Thr
            740                 745                 750

Asp Asn Leu Phe Val Val Asp Ala Ser Ile Phe Pro Gly Met Ile Thr
```

-continued

```
            755                 760                 765
Ser Asn Pro Ser Ala Tyr Ile Val Thr Val Ala Glu His Ala Ala Glu
            770                 775                 780
Lys Ile Leu Ala Leu Gly Gly Gly Ser Lys Arg Phe Ile Pro Ala
785                 790                 795                 800
Glu Glu Glu Asp Pro Ala Phe Trp Asn Arg Gln Ala Ala Gln Ala Leu
                        805                 810                 815
Asp Val Ala Lys Lys Leu Gln Pro Ile Gln Thr Ala Ala Lys Asn Val
            820                 825                 830
Ile Leu Phe Leu Gly Asp Gly Met Gly Val Pro Thr Val Thr Ala Thr
                835                 840                 845
Arg Ile Leu Lys Gly Gln Met Asn Gly Lys Leu Gly Pro Glu Thr Pro
                850                 855                 860
Leu Ala Met Asp Gln Phe Pro Tyr Val Ala Leu Ser Lys Thr Tyr Asn
865                 870                 875                 880
Val Asp Arg Gln Val Pro Asp Ser Ala Gly Thr Ala Thr Ala Tyr Leu
                        885                 890                 895
Cys Gly Val Lys Gly Asn Tyr Lys Thr Ile Gly Val Ser Ala Ala Ala
                    900                 905                 910
Arg Tyr Asn Gln Cys Asn Thr Thr Ser Gly Asn Glu Val Thr Ser Val
                915                 920                 925
Met Asn Arg Ala Lys Lys Ala Gly Lys Ser Val Gly Val Val Thr Thr
            930                 935                 940
Ser Arg Val Gln His Ala Ser Pro Ala Gly Ala Tyr Ala His Thr Val
945                 950                 955                 960
Asn Arg Asn Trp Tyr Ser Asp Ala Asp Leu Pro Ala Asp Ala Gln Thr
                    965                 970                 975
Tyr Gly Cys Gln Asp Ile Ala Thr Gln Leu Val Asn Asn Met Asp Ile
                980                 985                 990
Asp Val Ile Leu Gly Gly Gly Arg Met Tyr Met Phe Pro Glu Gly Thr
                995                 1000                1005
Pro Asp Pro Glu Tyr Pro Tyr Asp Val Asn Gln Thr Gly Val Arg
            1010                1015                1020
Lys Asp Lys Arg Asn Leu Val Gln Glu Trp Gln Ala Lys His Gln
            1025                1030                1035
Gly Ala Gln Tyr Val Trp Asn Arg Thr Glu Leu Leu Gln Ala Ala
            1040                1045                1050
Asn Asp Pro Ser Val Thr His Leu Met Gly Leu Phe Glu Pro Ala
            1055                1060                1065
Asp Met Lys Tyr Asn Val Gln Gln Asp Pro Thr Lys Asp Pro Thr
            1070                1075                1080
Leu Glu Glu Met Thr Glu Ala Ala Leu Gln Val Leu Ser Arg Asn
            1085                1090                1095
Pro Gln Gly Phe Tyr Leu Phe Val Glu Gly Gly Arg Ile Asp His
            1100                1105                1110
Gly His His Glu Gly Lys Ala Tyr Met Ala Leu Thr Asp Thr Val
            1115                1120                1125
Met Phe Asp Asn Ala Ile Ala Lys Ala Asn Glu Leu Thr Ser Glu
            1130                1135                1140
Leu Asp Thr Leu Ile Leu Ala Thr Ala Asp His Ser His Val Phe
            1145                1150                1155
Ser Phe Gly Gly Tyr Thr Leu Arg Gly Thr Ser Ile Phe Gly Leu
            1160                1165                1170
```

Ala Pro Ser Lys Ala Ser Asp Asn Lys Ser Tyr Thr Ser Ile Leu
1175                1180                1185

Tyr Gly Asn Gly Pro Gly Tyr Val Leu Gly Gly Gly Leu Arg Pro
    1190                1195                1200

Asp Val Asn Asp Ser Ile Ser Glu Asp Pro Ser Tyr Arg Gln Gln
1205                1210                1215

Ala Ala Val Pro Leu Ser Ser Glu Ser His Gly Gly Glu Asp Val
1220                1225                1230

Ala Val Phe Ala Arg Gly Pro Gln Ala His Leu Val His Gly Val
1235                1240                1245

Gln Glu Glu Thr Phe Val Ala His Val Met Ala Phe Ala Gly Cys
1250                1255                1260

Val Glu Pro Tyr Thr Asp Cys Asn Leu Pro Ala Pro Ser Gly
1265                1270                1275

<210> SEQ ID NO 112
<211> LENGTH: 498
<212> TYPE: PRT
<213> ORGANISM: Artificial Sequence
<220> FEATURE:
<223> OTHER INFORMATION: GlaBss_bIAPIV

<400> SEQUENCE: 112

Met Arg Asn Asn Phe Leu Phe Ser Leu Asn Ala Ile Ala Gly Ala Val
1               5                   10                  15

Ala Phe Ile Pro Ala Glu Glu Glu Asp Pro Ala Phe Trp Asn Arg Gln
                20                  25                  30

Ala Ala Gln Ala Leu Asp Val Ala Lys Lys Leu Gln Pro Ile Gln Thr
            35                  40                  45

Ala Ala Lys Asn Val Ile Leu Phe Leu Gly Asp Gly Met Gly Val Pro
        50                  55                  60

Thr Val Thr Ala Thr Arg Ile Leu Lys Gly Gln Met Asn Gly Lys Leu
65                  70                  75                  80

Gly Pro Glu Thr Pro Leu Ala Met Asp Gln Phe Pro Tyr Val Ala Leu
                85                  90                  95

Ser Lys Thr Tyr Asn Val Asp Arg Gln Val Pro Asp Ser Ala Gly Thr
                100                 105                 110

Ala Thr Ala Tyr Leu Cys Gly Val Lys Gly Asn Tyr Lys Thr Ile Gly
            115                 120                 125

Val Ser Ala Ala Ala Arg Tyr Asn Gln Cys Asn Thr Thr Ser Gly Asn
        130                 135                 140

Glu Val Thr Ser Val Met Asn Arg Ala Lys Lys Ala Gly Lys Ser Val
145                 150                 155                 160

Gly Val Val Thr Thr Ser Arg Val Gln His Ala Ser Pro Ala Gly Ala
                165                 170                 175

Tyr Ala His Thr Val Asn Arg Asn Trp Tyr Ser Asp Ala Asp Leu Pro
            180                 185                 190

Ala Asp Ala Gln Thr Tyr Gly Cys Gln Asp Ile Ala Thr Gln Leu Val
        195                 200                 205

Asn Asn Met Asp Ile Asp Val Ile Leu Gly Gly Gly Arg Met Tyr Met
    210                 215                 220

Phe Pro Glu Gly Thr Pro Asp Pro Glu Tyr Pro Tyr Asp Val Asn Gln
225                 230                 235                 240

Thr Gly Val Arg Lys Asp Lys Arg Asn Leu Val Gln Glu Trp Gln Ala
                245                 250                 255

Lys His Gln Gly Ala Gln Tyr Val Trp Asn Arg Thr Glu Leu Leu Gln
        260                 265                 270

Ala Ala Asn Asp Pro Ser Val Thr His Leu Met Gly Leu Phe Glu Pro
        275                 280                 285

Ala Asp Met Lys Tyr Asn Val Gln Gln Asp Pro Thr Lys Asp Pro Thr
290                 295                 300

Leu Glu Glu Met Thr Glu Ala Ala Leu Gln Val Leu Ser Arg Asn Pro
305                 310                 315                 320

Gln Gly Phe Tyr Leu Phe Val Glu Gly Gly Arg Ile Asp His Gly His
                325                 330                 335

His Glu Gly Lys Ala Tyr Met Ala Leu Thr Asp Thr Val Met Phe Asp
            340                 345                 350

Asn Ala Ile Ala Lys Ala Asn Glu Leu Thr Ser Glu Leu Asp Thr Leu
        355                 360                 365

Ile Leu Ala Thr Ala Asp His Ser His Val Phe Ser Phe Gly Gly Tyr
    370                 375                 380

Thr Leu Arg Gly Thr Ser Ile Phe Gly Leu Ala Pro Ser Lys Ala Ser
385                 390                 395                 400

Asp Asn Lys Ser Tyr Thr Ser Ile Leu Tyr Gly Asn Gly Pro Gly Tyr
                405                 410                 415

Val Leu Gly Gly Gly Leu Arg Pro Asp Val Asn Asp Ser Ile Ser Glu
            420                 425                 430

Asp Pro Ser Tyr Arg Gln Gln Ala Ala Val Pro Leu Ser Ser Glu Ser
        435                 440                 445

His Gly Gly Glu Asp Val Ala Val Phe Ala Arg Gly Pro Gln Ala His
    450                 455                 460

Leu Val His Gly Val Gln Glu Glu Thr Phe Val Ala His Val Met Ala
465                 470                 475                 480

Phe Ala Gly Cys Val Glu Pro Tyr Thr Asp Cys Asn Leu Pro Ala Pro
                485                 490                 495

Ser Gly

<210> SEQ ID NO 113
<211> LENGTH: 498
<212> TYPE: PRT
<213> ORGANISM: Artificial Sequence
<220> FEATURE:
<223> OTHER INFORMATION: CelBss_bIAPIV

<400> SEQUENCE: 113

Met Ile Trp Thr Leu Ala Pro Phe Val Ala Leu Leu Pro Leu Val Thr
1               5                   10                  15

Ala Phe Ile Pro Ala Glu Glu Glu Asp Pro Ala Phe Trp Asn Arg Gln
            20                  25                  30

Ala Ala Gln Ala Leu Asp Val Ala Lys Lys Leu Gln Pro Ile Gln Thr
        35                  40                  45

Ala Ala Lys Asn Val Ile Leu Phe Leu Gly Asp Gly Met Gly Val Pro
    50                  55                  60

Thr Val Thr Ala Thr Arg Ile Leu Lys Gly Gln Met Asn Gly Lys Leu
65                  70                  75                  80

Gly Pro Glu Thr Pro Leu Ala Met Asp Gln Phe Pro Tyr Val Ala Leu
                85                  90                  95

Ser Lys Thr Tyr Asn Val Asp Arg Gln Val Pro Asp Ser Ala Gly Thr
            100                 105                 110

Ala Thr Ala Tyr Leu Cys Gly Val Lys Gly Asn Tyr Lys Thr Ile Gly
            115                 120                 125

Val Ser Ala Ala Ala Arg Tyr Asn Gln Cys Asn Thr Thr Ser Gly Asn
130                 135                 140

Glu Val Thr Ser Val Met Asn Arg Ala Lys Lys Ala Gly Lys Ser Val
145                 150                 155                 160

Gly Val Val Thr Thr Ser Arg Val Gln His Ala Ser Pro Ala Gly Ala
                165                 170                 175

Tyr Ala His Thr Val Asn Arg Asn Trp Tyr Ser Asp Ala Asp Leu Pro
            180                 185                 190

Ala Asp Ala Gln Thr Tyr Gly Cys Gln Asp Ile Ala Thr Gln Leu Val
        195                 200                 205

Asn Asn Met Asp Ile Asp Val Ile Leu Gly Gly Arg Met Tyr Met
210                 215                 220

Phe Pro Glu Gly Thr Pro Asp Pro Glu Tyr Pro Tyr Asp Val Asn Gln
225                 230                 235                 240

Thr Gly Val Arg Lys Asp Lys Arg Asn Leu Val Gln Glu Trp Gln Ala
                245                 250                 255

Lys His Gln Gly Ala Gln Tyr Val Trp Asn Arg Thr Glu Leu Leu Gln
            260                 265                 270

Ala Ala Asn Asp Pro Ser Val Thr His Leu Met Gly Leu Phe Glu Pro
        275                 280                 285

Ala Asp Met Lys Tyr Asn Val Gln Gln Asp Pro Thr Lys Asp Pro Thr
    290                 295                 300

Leu Glu Glu Met Thr Glu Ala Ala Leu Gln Val Leu Ser Arg Asn Pro
305                 310                 315                 320

Gln Gly Phe Tyr Leu Phe Val Glu Gly Gly Arg Ile Asp His Gly His
                325                 330                 335

His Glu Gly Lys Ala Tyr Met Ala Leu Thr Asp Thr Val Met Phe Asp
            340                 345                 350

Asn Ala Ile Ala Lys Ala Asn Glu Leu Thr Ser Glu Leu Asp Thr Leu
        355                 360                 365

Ile Leu Ala Thr Ala Asp His Ser His Val Phe Ser Phe Gly Gly Tyr
    370                 375                 380

Thr Leu Arg Gly Thr Ser Ile Phe Gly Leu Ala Pro Ser Lys Ala Ser
385                 390                 395                 400

Asp Asn Lys Ser Tyr Thr Ser Ile Leu Tyr Gly Asn Gly Pro Gly Tyr
                405                 410                 415

Val Leu Gly Gly Gly Leu Arg Pro Asp Val Asn Asp Ser Ile Ser Glu
            420                 425                 430

Asp Pro Ser Tyr Arg Gln Gln Ala Ala Val Pro Leu Ser Ser Glu Ser
        435                 440                 445

His Gly Gly Glu Asp Val Ala Val Phe Ala Arg Gly Pro Gln Ala His
    450                 455                 460

Leu Val His Gly Val Gln Glu Glu Thr Phe Val Ala His Val Met Ala
465                 470                 475                 480

Phe Ala Gly Cys Val Glu Pro Tyr Thr Asp Cys Asn Leu Pro Ala Pro
                485                 490                 495

Ser Gly

<210> SEQ ID NO 114
<211> LENGTH: 904
<212> TYPE: PRT
<213> ORGANISM: Artificial Sequence
<220> FEATURE:
<223> OTHER INFORMATION: CelB_bIAPIV

<400> SEQUENCE: 114

```
Met Ile Trp Thr Leu Ala Pro Phe Val Ala Leu Leu Pro Leu Val Thr
1               5                   10                  15

Ala Gln Gln Val Gly Thr Thr Ala Asp Ala His Pro Arg Leu Thr Thr
            20                  25                  30

Tyr Lys Cys Thr Ser Gln Asn Gly Cys Thr Arg Gln Asn Thr Ser Val
        35                  40                  45

Val Leu Asp Ala Ala Thr His Phe Ile His Lys Lys Gly Thr Gln Thr
    50                  55                  60

Ser Cys Thr Asn Ser Asn Gly Leu Asp Thr Ser Ile Cys Pro Asp Lys
65                  70                  75                  80

Gln Thr Cys Ala Asp Asn Cys Val Val Asp Gly Ile Thr Asp Tyr Ala
                85                  90                  95

Ser Tyr Gly Val Gln Thr Lys Asn Asp Thr Leu Thr Leu His Gln Tyr
            100                 105                 110

Leu Gln Thr Gly Asn Glu Thr Lys Ser Val Ser Pro Arg Val Tyr Leu
        115                 120                 125

Leu Ala Glu Asp Gly Glu Asn Tyr Ser Met Leu Gln Leu Leu Asn Gln
    130                 135                 140

Glu Phe Thr Phe Asp Val Asp Ala Ser Thr Leu Val Cys Gly Met Asn
145                 150                 155                 160

Gly Ala Leu Tyr Leu Ser Glu Met Glu Ala Ser Gly Gly Lys Ser Ser
                165                 170                 175

Leu Asn Gln Ala Gly Ala Lys Tyr Gly Thr Gly Tyr Cys Asp Ala Gln
            180                 185                 190

Cys Tyr Thr Thr Pro Trp Ile Asn Gly Glu Gly Asn Thr Glu Ser Val
        195                 200                 205

Gly Ser Cys Cys Gln Glu Met Asp Ile Trp Glu Ala Asn Ala Arg Ala
    210                 215                 220

Thr Gly Leu Thr Pro His Pro Cys Asn Thr Thr Gly Leu Tyr Glu Cys
225                 230                 235                 240

Ser Gly Ser Gly Cys Gly Asp Ser Gly Val Cys Asp Lys Ser Gly Cys
                245                 250                 255

Gly Phe Asn Pro Tyr Gly Leu Gly Ala Lys Asp Tyr Tyr Gly Tyr Gly
            260                 265                 270

Leu Lys Val Asn Thr Asn Glu Thr Phe Thr Val Val Thr Gln Phe Leu
        275                 280                 285

Thr Ser Asp Asn Thr Thr Ser Gly Gln Leu Ser Glu Ile Arg Arg Leu
    290                 295                 300

Tyr Ile Gln Asn Gly Gln Val Ile Gln Asn Ala Ala Val Thr Ser Gly
305                 310                 315                 320

Gly Lys Thr Val Asp Ser Ile Thr Lys Asp Phe Cys Ser Gly Glu Gly
                325                 330                 335

Ser Ala Phe Asn Arg Leu Gly Gly Leu Glu Glu Met Gly His Ala Leu
            340                 345                 350

Gly Arg Gly Met Val Leu Ala Leu Ser Val Trp Asn Asp Ala Gly Ser
        355                 360                 365

Phe Met Gln Trp Leu Asp Gly Gly Ser Ala Gly Pro Cys Ser Ala Thr
    370                 375                 380

Glu Gly Asp Pro Ala Leu Ile Glu Lys Leu Tyr Pro Asp Thr His Val
385                 390                 395                 400
```

```
Lys Phe Ser Lys Ile Arg Trp Gly Asp Ile Gly Ser Thr Tyr Arg His
            405                 410                 415
Gly Gly Gly Gly Ser Lys Arg Phe Ile Pro Ala Glu Glu Glu Asp Pro
            420                 425                 430
Ala Phe Trp Asn Arg Gln Ala Ala Gln Ala Leu Asp Val Ala Lys Lys
            435                 440                 445
Leu Gln Pro Ile Gln Thr Ala Ala Lys Asn Val Ile Leu Phe Leu Gly
        450                 455                 460
Asp Gly Met Gly Val Pro Thr Val Thr Ala Thr Arg Ile Leu Lys Gly
465                 470                 475                 480
Gln Met Asn Gly Lys Leu Gly Pro Glu Thr Pro Leu Ala Met Asp Gln
            485                 490                 495
Phe Pro Tyr Val Ala Leu Ser Lys Thr Tyr Asn Val Asp Arg Gln Val
            500                 505                 510
Pro Asp Ser Ala Gly Thr Ala Thr Ala Tyr Leu Cys Gly Val Lys Gly
        515                 520                 525
Asn Tyr Lys Thr Ile Gly Val Ser Ala Ala Ala Arg Tyr Asn Gln Cys
        530                 535                 540
Asn Thr Thr Ser Gly Asn Glu Val Thr Ser Val Met Asn Arg Ala Lys
545                 550                 555                 560
Lys Ala Gly Lys Ser Val Gly Val Val Thr Thr Ser Arg Val Gln His
            565                 570                 575
Ala Ser Pro Ala Gly Ala Tyr Ala His Thr Val Asn Arg Asn Trp Tyr
            580                 585                 590
Ser Asp Ala Asp Leu Pro Ala Asp Ala Gln Thr Tyr Gly Cys Gln Asp
            595                 600                 605
Ile Ala Thr Gln Leu Val Asn Asn Met Asp Ile Asp Val Ile Leu Gly
        610                 615                 620
Gly Gly Arg Met Tyr Met Phe Pro Glu Gly Thr Pro Asp Pro Glu Tyr
625                 630                 635                 640
Pro Tyr Asp Val Asn Gln Thr Gly Val Arg Lys Asp Lys Arg Asn Leu
            645                 650                 655
Val Gln Glu Trp Gln Ala Lys His Gln Gly Ala Gln Tyr Val Trp Asn
            660                 665                 670
Arg Thr Glu Leu Leu Gln Ala Ala Asn Asp Pro Ser Val Thr His Leu
        675                 680                 685
Met Gly Leu Phe Glu Pro Ala Asp Met Lys Tyr Asn Val Gln Gln Asp
        690                 695                 700
Pro Thr Lys Asp Pro Thr Leu Glu Glu Met Thr Glu Ala Ala Leu Gln
705                 710                 715                 720
Val Leu Ser Arg Asn Pro Gln Gly Phe Tyr Leu Phe Val Glu Gly Gly
            725                 730                 735
Arg Ile Asp His Gly His His Glu Gly Lys Ala Tyr Met Ala Leu Thr
            740                 745                 750
Asp Thr Val Met Phe Asp Asn Ala Ile Ala Lys Ala Asn Glu Leu Thr
        755                 760                 765
Ser Glu Leu Asp Thr Leu Ile Leu Ala Thr Ala Asp His Ser His Val
        770                 775                 780
Phe Ser Phe Gly Gly Tyr Thr Leu Arg Gly Thr Ser Ile Phe Gly Leu
785                 790                 795                 800
Ala Pro Ser Lys Ala Ser Asp Asn Lys Ser Tyr Thr Ser Ile Leu Tyr
            805                 810                 815
```

```
Gly Asn Gly Pro Gly Tyr Val Leu Gly Gly Leu Arg Pro Asp Val
            820                 825                 830

Asn Asp Ser Ile Ser Glu Asp Pro Ser Tyr Arg Gln Gln Ala Ala Val
835                 840                 845

Pro Leu Ser Ser Glu Ser His Gly Gly Glu Asp Val Ala Val Phe Ala
            850                 855                 860

Arg Gly Pro Gln Ala His Leu Val His Gly Val Gln Glu Glu Thr Phe
865                 870                 875                 880

Val Ala His Val Met Ala Phe Ala Gly Cys Val Glu Pro Tyr Thr Asp
                885                 890                 895

Cys Asn Leu Pro Ala Pro Ser Gly
            900
```

<210> SEQ ID NO 115
<211> LENGTH: 508
<212> TYPE: PRT
<213> ORGANISM: Artificial Sequence
<220> FEATURE:
<223> OTHER INFORMATION: SKIK_CDHss_bIAPIV

<400> SEQUENCE: 115

```
Met Ser Lys Ile Lys Lys Leu Val Asn Arg Leu Leu Ala Ser Phe Leu
1               5                   10                  15

Ser Ala Ser Thr Val Leu Gln Ser Cys Trp Ala Phe Ile Pro Ala Glu
            20                  25                  30

Glu Glu Asp Pro Ala Phe Trp Asn Arg Gln Ala Ala Gln Ala Leu Asp
        35                  40                  45

Val Ala Lys Lys Leu Gln Pro Ile Gln Thr Ala Ala Lys Asn Val Ile
    50                  55                  60

Leu Phe Leu Gly Asp Gly Met Gly Val Pro Thr Val Thr Ala Thr Arg
65                  70                  75                  80

Ile Leu Lys Gly Gln Met Asn Gly Lys Leu Gly Pro Glu Thr Pro Leu
                85                  90                  95

Ala Met Asp Gln Phe Pro Tyr Val Ala Leu Ser Lys Thr Tyr Asn Val
            100                 105                 110

Asp Arg Gln Val Pro Asp Ser Ala Gly Thr Ala Thr Ala Tyr Leu Cys
        115                 120                 125

Gly Val Lys Gly Asn Tyr Lys Thr Ile Gly Val Ser Ala Ala Ala Arg
    130                 135                 140

Tyr Asn Gln Cys Asn Thr Thr Ser Gly Asn Glu Val Thr Ser Val Met
145                 150                 155                 160

Asn Arg Ala Lys Lys Ala Gly Lys Ser Val Gly Val Val Thr Thr Ser
                165                 170                 175

Arg Val Gln His Ala Ser Pro Ala Gly Ala Tyr Ala His Thr Val Asn
            180                 185                 190

Arg Asn Trp Tyr Ser Asp Ala Asp Leu Pro Ala Asp Ala Gln Thr Tyr
        195                 200                 205

Gly Cys Gln Asp Ile Ala Thr Gln Leu Val Asn Asn Met Asp Ile Asp
    210                 215                 220

Val Ile Leu Gly Gly Gly Arg Met Tyr Met Phe Pro Glu Gly Thr Pro
225                 230                 235                 240

Asp Pro Glu Tyr Pro Tyr Asp Val Asn Gln Thr Gly Val Arg Lys Asp
                245                 250                 255

Lys Arg Asn Leu Val Gln Glu Trp Gln Ala Lys His Gln Gly Ala Gln
            260                 265                 270
```

```
Tyr Val Trp Asn Arg Thr Glu Leu Gln Ala Ala Asn Asp Pro Ser
            275                 280                 285

Val Thr His Leu Met Gly Leu Phe Glu Pro Ala Asp Met Lys Tyr Asn
290                 295                 300

Val Gln Gln Asp Pro Thr Lys Asp Pro Thr Leu Glu Glu Met Thr Glu
305                 310                 315                 320

Ala Ala Leu Gln Val Leu Ser Arg Asn Pro Gln Gly Phe Tyr Leu Phe
            325                 330                 335

Val Glu Gly Gly Arg Ile Asp His Gly His His Glu Gly Lys Ala Tyr
                340                 345                 350

Met Ala Leu Thr Asp Thr Val Met Phe Asp Asn Ala Ile Ala Lys Ala
            355                 360                 365

Asn Glu Leu Thr Ser Glu Leu Asp Thr Leu Ile Leu Ala Thr Ala Asp
370                 375                 380

His Ser His Val Phe Ser Phe Gly Gly Tyr Thr Leu Arg Gly Thr Ser
385                 390                 395                 400

Ile Phe Gly Leu Ala Pro Ser Lys Ala Ser Asp Asn Lys Ser Tyr Thr
            405                 410                 415

Ser Ile Leu Tyr Gly Asn Gly Pro Gly Tyr Val Leu Gly Gly Gly Leu
            420                 425                 430

Arg Pro Asp Val Asn Asp Ser Ile Ser Glu Asp Pro Ser Tyr Arg Gln
            435                 440                 445

Gln Ala Ala Val Pro Leu Ser Ser Glu Ser His Gly Gly Glu Asp Val
            450                 455                 460

Ala Val Phe Ala Arg Gly Pro Gln Ala His Leu Val His Gly Val Gln
465                 470                 475                 480

Glu Glu Thr Phe Val Ala His Val Met Ala Phe Ala Gly Cys Val Glu
                485                 490                 495

Pro Tyr Thr Asp Cys Asn Leu Pro Ala Pro Ser Gly
            500                 505

<210> SEQ ID NO 116
<211> LENGTH: 499
<212> TYPE: PRT
<213> ORGANISM: Artificial Sequence
<220> FEATURE:
<223> OTHER INFORMATION: AsAP1ss54_bIAPIV

<400> SEQUENCE: 116

Met Arg Phe Leu Ser Ile Val Gly Ala Ala Leu Phe Ala Ser Ser Ala
1               5                   10                  15

Val Ala Phe Ile Pro Ala Glu Glu Asp Pro Ala Phe Trp Asn Arg
                20                  25                  30

Gln Ala Ala Gln Ala Leu Asp Val Ala Lys Lys Leu Gln Pro Ile Gln
            35                  40                  45

Thr Ala Ala Lys Asn Val Ile Leu Phe Leu Gly Asp Gly Met Gly Val
50                  55                  60

Pro Thr Val Thr Ala Thr Arg Ile Leu Lys Gly Gln Met Asn Gly Lys
65                  70                  75                  80

Leu Gly Pro Glu Thr Pro Leu Ala Met Asp Gln Phe Pro Tyr Val Ala
                85                  90                  95

Leu Ser Lys Thr Tyr Asn Val Asp Arg Gln Val Pro Asp Ser Ala Gly
            100                 105                 110

Thr Ala Thr Ala Tyr Leu Cys Gly Val Lys Gly Asn Tyr Lys Thr Ile
            115                 120                 125
```

Gly Val Ser Ala Ala Ala Arg Tyr Asn Gln Cys Asn Thr Thr Ser Gly
    130                 135                 140

Asn Glu Val Thr Ser Val Met Asn Arg Ala Lys Lys Ala Gly Lys Ser
145                 150                 155                 160

Val Gly Val Val Thr Thr Ser Arg Val Gln His Ala Ser Pro Ala Gly
                165                 170                 175

Ala Tyr Ala His Thr Val Asn Arg Asn Trp Tyr Ser Asp Ala Asp Leu
            180                 185                 190

Pro Ala Asp Ala Gln Thr Tyr Gly Cys Gln Asp Ile Ala Thr Gln Leu
        195                 200                 205

Val Asn Asn Met Asp Ile Asp Val Ile Leu Gly Gly Gly Arg Met Tyr
210                 215                 220

Met Phe Pro Glu Gly Thr Pro Asp Pro Glu Tyr Pro Tyr Asp Val Asn
225                 230                 235                 240

Gln Thr Gly Val Arg Lys Asp Lys Arg Asn Leu Val Gln Glu Trp Gln
                245                 250                 255

Ala Lys His Gln Gly Ala Gln Tyr Val Trp Asn Arg Thr Glu Leu Leu
            260                 265                 270

Gln Ala Ala Asn Asp Pro Ser Val Thr His Leu Met Gly Leu Phe Glu
        275                 280                 285

Pro Ala Asp Met Lys Tyr Asn Val Gln Gln Asp Pro Thr Lys Asp Pro
290                 295                 300

Thr Leu Glu Glu Met Thr Glu Ala Ala Leu Gln Val Leu Ser Arg Asn
305                 310                 315                 320

Pro Gln Gly Phe Tyr Leu Phe Val Glu Gly Gly Arg Ile Asp His Gly
                325                 330                 335

His His Glu Gly Lys Ala Tyr Met Ala Leu Thr Asp Thr Val Met Phe
            340                 345                 350

Asp Asn Ala Ile Ala Lys Ala Asn Glu Leu Thr Ser Glu Leu Asp Thr
        355                 360                 365

Leu Ile Leu Ala Thr Ala Asp His Ser His Val Phe Ser Phe Gly Gly
370                 375                 380

Tyr Thr Leu Arg Gly Thr Ser Ile Phe Gly Leu Ala Pro Ser Lys Ala
385                 390                 395                 400

Ser Asp Asn Lys Ser Tyr Thr Ser Ile Leu Tyr Gly Asn Gly Pro Gly
                405                 410                 415

Tyr Val Leu Gly Gly Leu Arg Pro Asp Val Asn Asp Ser Ile Ser
            420                 425                 430

Glu Asp Pro Ser Tyr Arg Gln Gln Ala Ala Val Pro Leu Ser Ser Glu
        435                 440                 445

Ser His Gly Gly Glu Asp Val Ala Val Phe Ala Arg Gly Pro Gln Ala
450                 455                 460

His Leu Val His Gly Val Gln Glu Glu Thr Phe Val Ala His Val Met
465                 470                 475                 480

Ala Phe Ala Gly Cys Val Glu Pro Tyr Thr Asp Cys Asn Leu Pro Ala
                485                 490                 495

Pro Ser Gly

<210> SEQ ID NO 117
<211> LENGTH: 505
<212> TYPE: PRT
<213> ORGANISM: Artificial Sequence
<220> FEATURE:
<223> OTHER INFORMATION: AsAP3ss72_bIAPIV

<400> SEQUENCE: 117

```
Met His Ile Arg Thr Ala Ile Thr Ala Gly Ala Ala Leu Val Gln Thr
1               5                   10                  15

Ala Val Ala Ala Ser Val Gln Ala Phe Ile Pro Ala Glu Glu Glu Asp
            20                  25                  30

Pro Ala Phe Trp Asn Arg Gln Ala Gln Ala Leu Asp Val Ala Lys
        35                  40                  45

Lys Leu Gln Pro Ile Gln Thr Ala Ala Lys Asn Val Ile Leu Phe Leu
    50                  55                  60

Gly Asp Gly Met Gly Val Pro Thr Val Thr Ala Thr Arg Ile Leu Lys
65                  70                  75                  80

Gly Gln Met Asn Gly Lys Leu Gly Pro Glu Thr Pro Leu Ala Met Asp
                85                  90                  95

Gln Phe Pro Tyr Val Ala Leu Ser Lys Thr Tyr Asn Val Asp Arg Gln
            100                 105                 110

Val Pro Asp Ser Ala Gly Thr Ala Thr Ala Tyr Leu Cys Gly Val Lys
        115                 120                 125

Gly Asn Tyr Lys Thr Ile Gly Val Ser Ala Ala Arg Tyr Asn Gln
130                 135                 140

Cys Asn Thr Thr Ser Gly Asn Glu Val Thr Ser Val Met Asn Arg Ala
145                 150                 155                 160

Lys Lys Ala Gly Lys Ser Val Gly Val Val Thr Thr Ser Arg Val Gln
                165                 170                 175

His Ala Ser Pro Ala Gly Ala Tyr Ala His Thr Val Asn Arg Asn Trp
            180                 185                 190

Tyr Ser Asp Ala Asp Leu Pro Ala Asp Ala Gln Thr Tyr Gly Cys Gln
        195                 200                 205

Asp Ile Ala Thr Gln Leu Val Asn Asn Met Asp Ile Asp Val Ile Leu
210                 215                 220

Gly Gly Gly Arg Met Tyr Met Phe Pro Glu Gly Thr Pro Asp Pro Glu
225                 230                 235                 240

Tyr Pro Tyr Asp Val Asn Gln Thr Gly Val Arg Lys Asp Lys Arg Asn
                245                 250                 255

Leu Val Gln Glu Trp Gln Ala Lys His Gln Gly Ala Gln Tyr Val Trp
            260                 265                 270

Asn Arg Thr Glu Leu Leu Gln Ala Ala Asn Asp Pro Ser Val Thr His
        275                 280                 285

Leu Met Gly Leu Phe Glu Pro Ala Asp Met Lys Tyr Asn Val Gln Gln
290                 295                 300

Asp Pro Thr Lys Asp Pro Thr Leu Glu Glu Met Thr Glu Ala Ala Leu
305                 310                 315                 320

Gln Val Leu Ser Arg Asn Pro Gln Gly Phe Tyr Leu Phe Val Glu Gly
                325                 330                 335

Gly Arg Ile Asp His Gly His His Glu Gly Lys Ala Tyr Met Ala Leu
            340                 345                 350

Thr Asp Thr Val Met Phe Asp Asn Ala Ile Ala Lys Ala Asn Glu Leu
        355                 360                 365

Thr Ser Glu Leu Asp Thr Leu Ile Leu Ala Thr Ala Asp His Ser His
370                 375                 380

Val Phe Ser Phe Gly Gly Tyr Thr Leu Arg Gly Thr Ser Ile Phe Gly
385                 390                 395                 400

Leu Ala Pro Ser Lys Ala Ser Asp Asn Lys Ser Tyr Thr Ser Ile Leu
                405                 410                 415
```

```
Tyr Gly Asn Gly Pro Gly Tyr Val Leu Gly Gly Gly Leu Arg Pro Asp
            420                 425                 430

Val Asn Asp Ser Ile Ser Glu Asp Pro Ser Tyr Arg Gln Gln Ala Ala
        435                 440                 445

Val Pro Leu Ser Ser Glu Ser His Gly Gly Glu Asp Val Ala Val Phe
    450                 455                 460

Ala Arg Gly Pro Gln Ala His Leu Val His Gly Val Gln Glu Thr
465                 470                 475                 480

Phe Val Ala His Val Met Ala Phe Ala Gly Cys Val Glu Pro Tyr Thr
                485                 490                 495

Asp Cys Asn Leu Pro Ala Pro Ser Gly
            500                 505

<210> SEQ ID NO 118
<211> LENGTH: 69
<212> TYPE: DNA
<213> ORGANISM: Artificial Sequence
<220> FEATURE:
<223> OTHER INFORMATION: CDHss without intron

<400> SEQUENCE: 118
atgaaacttg tcaaccgtct gctggcttcg ttcttgtccg catccaccgt tctccagtcg      60
tgctgggct                                                             69
```